(12) United States Patent
Habashita et al.

(10) Patent No.: US 7,285,680 B2
(45) Date of Patent: Oct. 23, 2007

(54) β-ALANINE DERIVATIVES AND THE USE THEREOF

(75) Inventors: Hiromu Habashita, Mishima-gun (JP); Masahiko Terakado, Mishima-gun (JP); Shinji Nakade, Mishima-gun (JP); Takuya Seko, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 166 days.

(21) Appl. No.: 10/515,653

(22) PCT Filed: May 28, 2003

(86) PCT No.: PCT/JP03/06678

§ 371 (c)(1), (2), (4) Date: Nov. 24, 2004

(87) PCT Pub. No.: WO03/099765

PCT Pub. Date: Dec. 4, 2003

(65) Prior Publication Data
US 2005/0256160 A1   Nov. 17, 2005

(30) Foreign Application Priority Data
May 28, 2002   (JP)   ............... 2002-153592

(51) Int. Cl.
C07C 233/83  (2006.01)
C07C 311/46  (2006.01)
C07D 209/16  (2006.01)
C07D 213/40  (2006.01)
C07D 217/06  (2006.01)
C07D 307/52  (2006.01)

(52) U.S. Cl. ............... 564/152; 564/155; 564/156; 564/161; 564/163; 562/400; 562/405; 562/465; 562/492

(58) Field of Classification Search ............... 564/152, 564/155, 156, 161, 153; 562/400, 405, 465, 562/492
See application file for complete search history.

(56) References Cited

FOREIGN PATENT DOCUMENTS

| | | |
|---|---|---|
| EP | 1 550 461 A | 7/2005 |
| JP | 2002-212070 A | 7/2002 |
| WO | WO 01/60819 A1 | 8/2001 |
| WO | WO 01/71022 A2 | 9/2001 |
| WO | WO 02/092068 A1 | 11/2002 |

Primary Examiner—Johann Richter
Assistant Examiner—Yevgeny Valenrod
(74) Attorney, Agent, or Firm—Sughrue Mion, PLLC

(57) ABSTRACT

A compound of the general formula (I)

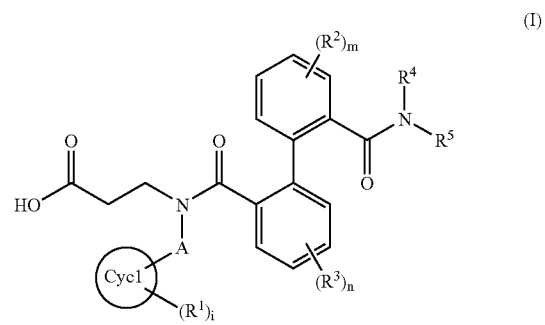

(wherein the symbols are as defined in the description), or a prodrug or a salt thereof.

This compound engages in LPA receptor bonding and antagonism and hence is useful in the prevention and/or treatment of urinary system disease (symptom with prostatic hypertrophy or neurogenic bladder dysfunction disease, symptom to be caused by spinal cord neoplasm, nucleous hernia, spinal canal stenosis or diabetes, lower urinary tract symptom (for example, occlusion disease of lower urinary tract), inflammatory disease of lower urinary tract, polyuria), carcinoma association disease (solid tumor, solid tumor metastasis, angiofibroma, myeloma, multiple myeloma, Kaposi's sarcoma, leucemia and carcinomatous infiltration transition), proliferative disease (disorder with aberrant angiogenesis, artery obstruction and pulmonary fibrosis), inflammation/immune system disease (psoriasis, nephropathy, hepatitis and pneumonitis symptom), disease by secretion fault (Sjogren syndrome) or brain association disease (brain infarction, cerebral apoplexy and brain or peripheral neuropathy).

5 Claims, No Drawings

β-ALANINE DERIVATIVES AND THE USE THEREOF

TECHNICAL FIELD

The present invention relates to a β-alanine derivatives having antagonisitic activity against lysophosphatidic acid receptor (especially EDG-2 receptor) which is useful as medicament, a process for producting the same and the use thereof.

More specifically, the present invention relates to:
(1) a β-alanine derivative represented by formula (I)

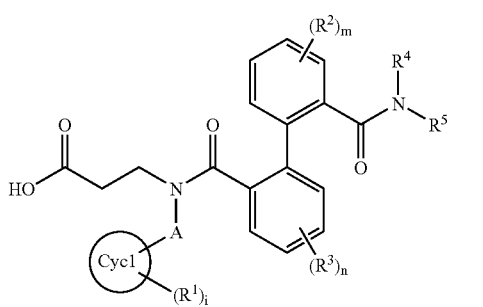

(in the formula, all symbols have the same meanings as those which will be mentioned later), a prodrug thereof, and a non-toxic salt thereof,
(2) a process for producing the same and
(3) a pharmaceutical agent containing the same as an active ingredient.

BACKGROUND OF THE INVENTION

It is known that various lipid mediators such as eicosanoid and platelet activating factor (PAF) are produced by the activity of phospholipase from cell membranes.

Lysophosphatidic acid (hereinafter abbreviated as LPA) represented by

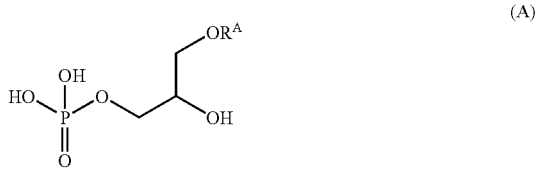

(wherein $R^A$ is acyl, alkenyl or alkyl) is a lipid which is produced from cell membranes, acts as a mediator for signal transduction and delivers various signals into cells. LPA that exists naturally is L-α-LPA.

Recently, the existence of three subtypes of LPA receptor has been disclosed and it is gradually proved that their physiological activities are via LPA receptor. Three subtypes of LPA receptor are called EDG (Endothelial differentiation gene)-2, 4 and 7, respectively, and form part of EDG receptor family as well as EDG-1, 3, 5, 6 and 8 that are sphingosine-1-phosphate receptor. EDG-2 is called LPA1 or VZG (Ventricular zone gene)-1, too (*Mol Pharmacol* 2000 December; 58(6) : 1188-96). LPA receptor to which LPA binds delivers signals into cells via G-protein coupled to the receptor. Gs, Gi, Gq are known as G-proteins that can bind to LPA receptor, and the receptors are said to relate to the response to the action of increase or, adversely, decrease of cell growth. Furthermore, since MAP-kinase systems operate in the downstreams of G-proteins, it has been known that LPA receptors deliver various signals.

Since localization of LPA receptors is different between their subtypes although they exist widely in living body, it is considered that the role of each receptor is different by the organ. The increase of blood pressure in rats, and the contraction of colon in rats and ileum in guinea pigs have been known as the pharmacological activity caused by LPA (*J. Pharm. Pharmacol.* 1991, 43, 774, *J. Pharm. Pharmacol.* 1982, 34, 514). In addition, the effect of LPA on urethral contraction is set forth in WO02/062389 specification and the suppressive effect of LPA on secretion of pancreatic juice is set forth in WO03/007991 specification.

In addition, concerning to the relationship between LPA and carcinoma, until now it is known that LPA enhances the proliferation of the epithelial cancer cells originated from prostate gland (*J Cellular Physiol.* 1998 174, 261) and ovarian cancer cells (*J. Urol.* 2000, 163, 1027).

In addition, it is known that LPA is related to the function of growth of various cells such as airway smooth muscle cells (*Am. J. Physiol. Lung Cell Mol. Physiol.*, 2002, 282(1) : L91), fibroblast (*Mol. Cell Biol.,* 1998, 18(12) : 7119), mesangial cells (*Clin. Science* 1999, 96, 431), hepatocyte, liver stellate cells (*Biochem. Biophys. Res. Commun.,* 1998, 248, 436), vasucular smooth muscle cells (*Am. J. Physiol.,* 1994, 267 (Cell Physiol. 36) : C204), vascular endothelial cells (*Am. J. Physiol. Cell Physiol.,* 2000, 278(3) : C612), glia cells/Schwann cells (*Proc. Natl. Acad. Sci. USA,* 1999, 96, 5233), adipocytes (*J. Clin. Invest.,* 1998, 101, 1431) as well as cancer cells. In addition, it is known that LPA is related to the function of chemotaxis of inflammatory cells as well as cancer cells besides cell growth (*Biochem Biophys Res Commun.,* 1993, 15;193(2), 497). Moreover proliferation and cytokine-secreting activity in response to LPA of immune cells (*J. Imuunol.* 1999, 162, 2049), platelet aggregation activity to LPA (*Biochem. Biophys. Res. Commun.,* 1981, 99, 391) are known. Besides, from analysis of knockout mouse of EDG-2 which is one of the LPA receptor, EDG-2 is concerned to be related to the brain function (Proc. Natl. Acad. Sci. USA, 2000, 97, 13384).

From these evidences, it is thought that drug antagonizing to LPA receptor is useful for prevention and/or treatment of diseases such as various kinds of disease namely urinary system disease, carcinoma-associated disease, proliferative disease, inflammation/immune system disease, disease by secretory dysfunction or brain-associated disease.

For example, for urinary system disease, symptom with prostatic hypertrophy or neurogenic bladder dysfunction disease (such as dysuria (micturation initiation delay, extension between on urination, urinary stream very small, intermission micturation, two steps of micturation), pollakiuria, night urination, urodynia), symptom to be caused by cerebrovascular disorder, Parkinson disease, cerebral oncosis, a multiple sclerosis, Shy-Drager symptom, spinal cord neoplasm, nucleous hernia, spinal canal stenosis, diabetes, etc. (such as dysuria (micturation initiation delay, extension between on urination, urinary stream very small, intermission micturation, two steps of miction), pollakiuria, night urination, urodynia), lower urinary tract symptom (for example, occlusion disease of lower urinary tract), inflammatory disease of lower urinary tract (such as infection), polyuria are thought about.

For example, for carcinoma-related disease, solid tumor, solid tumor metastasis, angiofibroma, myeloma, multiple myeloma, Kaposi's sarcoma, leucemia are given. In solid tumor, mammary cancer, lung cancer, gastric cancer, carcinoma oesophagi, colon rectal cancer, liver cancer, ovarian cancer, theca cell tumor, androblastoma, cervix cancer, endometrial carcinoma, prostate cancer, kidney cancer, carcinoma cutaneum, osteosarcoma, pancreas cancer, urinary tract carcinoma, thyroid cancer, cerebral oncosis are given. In addition, it is thought that carcinomatous infiltration transition is suppressed by LPA receptor antagonist.

For example, for proliferative disease, the disease with aberrant angiogenesis are given (for example, re-arctation, diabetic retinopathy, angiogenesis-related glaucoma, crystalline lens fiber multiplication symptom, thyroid gland hyperplasia (including Basedow's goiter), lung inflammation, nephrotic syndrome and osteoporosis), and also artery obstruction, pulmonary fibrosis are given.

For example, for inflammation/immune system disease, psoriasis, nephropathy (for example, IgA nephropathy), nephritis by other inflammation/immunopathy, hepatitis, pneumonitis symptom are given.

For example, for disease by secretory dysfunction, secretory dysfunction by autonomic nervous system dysfunction is given, for example, Sjogren syndrome is given.

For example, for brain-related disease, brain infarction, cerebral apoplexy, brain or peripheral neuropathy are given.

In the specification of WO01/60819, it is described that the compound represented by formula (B)

(B)

[wherein $R^{1B}$ represents optionally substituted by alkyl, aryl, heterocyclic radical, alkyloxy, aryloxy, alkylthio, arylthio or halogen atom, $R^{2B}$ represents optionally substituted by alkyl, aryl, heterocyclic radical, alkyloxy, aryloxy or halogen atom, $R^{3B}$ represents hydrogen atom, lower alkyl or alkyl substituted by halogen atom, $R^{4B}$ represents a radical selected from (a) optionally substituted by phenyl, aryl or heterocyclic radical, (b) substituted or non-substituted alkyl or (c) substituted or non-substituted alkenyl, $X^B$ represents oxygen atom or sulfur atom. With the proviso that, $R^{3B}$ and $R^{4B}$ may form a five- to ten-membered cyclic structure together with a carbon atom to which they bind, and when $R^{3B}$ is a hydrogen atom, $R^{4B}$ represents a group other than methyl.]

or a salt thereof have the LPA receptor antagonistic activity.

DISCLOSURE OF THE INVENTION

The inventors of the present invention have carried out intensive studies for finding compounds which specifically binds to LPA receptors and exerts antagonistic activity and, as a result, they have found that β-alanine derivatives represented by formula (I) achieve the problem to accomplish the present invention. The present invention can become various kinds of treatment of disease medicine by showing antagonism in LPA receptor. For example, the novel compound which may be prevention and/or therapeutic agent such as the urinary system disease that does not influence blood pressure is provided. The β-alanine derivative represented by formula (I) of the present invention is the novel compound which is not known till now.

The present invention relates to:

(1) A β-alanine derivative represented by formula (I):

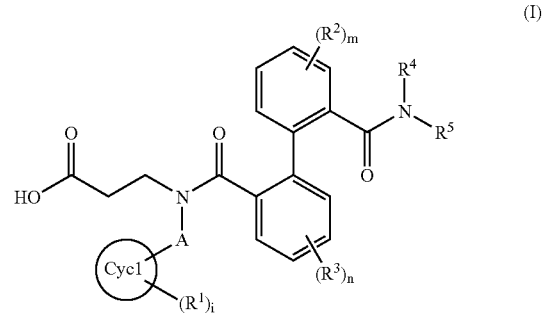

(I)

wherein A represents (1) C1~6 alkylene, (2) C2~6 alkenylene, or (3) C2~6 alkynylene wherein A may be substituted by 1-3 of C1~4 alkyl;

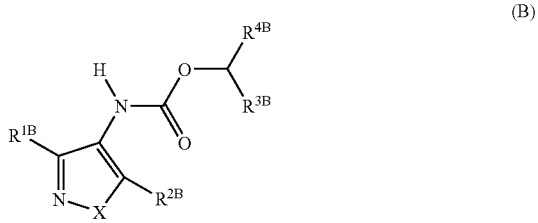

represents (1) C3~15 carbocyclic ring, or (2) 3-15 membered heterocyclic ring containing 1-4 of nitrogen atom(s), 1-2 of oxygen atom(s) and/or 1-2 of sulfur atom(s);

$R^1$ represents (1) C1~4 alkyl, (2) a halogen atom, (3) cyano, (4) trihalomethyl, (5) —$OR^6$, (6) —$SR^7$, (7) —$NR^8R^9$, (8) nitro, (9) —$COOR^{10}$, (10) —$CONR^{11}R^{12}$, (11) —$NR^{13}COR^{14}$, (12) —$SO_2NR^{15}R^{16}$, (13) —$NR^{17}SO_2R^{18}$, (14) —$S(O)R^{19}$ or (15) —$SO_2R^{20}$;

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ each independently represents (1) a hydrogen atom or (2) C1~4 alkyl;

$R^2$ and $R^3$ each independently represents (1) C1~4 alkyl, (2) C1~4 alkoxy or (3) a halogen atom;

$R^4$ and $R^5$ each independently represents (1) a hydrogen atom, (2) C1~4 alkyl, (3) C2~4 alkenyl, (4) C2~4 alkynyl, (5) C1~4 alkyl substituted by —$OR^{21}$, (6) C1~4 alkyl substituted by —$NR^{22}R^{23}$ or (7)

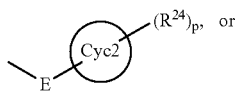

R⁴ and R⁵ taken together with nitrogen atom to which they are attached represents 3-15 membered mono-, bi- or tricyclic heterocyclic ring wherein the heterocyclic ring contains at least one nitrogen atom and may be substituted by C1~14 alkyl substituted by —OR²⁵;

$R^{21}$, $R^{22}$, $R^{23}$ and $R^{25}$ each independently represents (1) a hydrogen atom, (2) C1~4 alkyl, (3) C2~6 acyl or (4) trihaloacetyl;

E represents (1) single bond, (2) C1~6 alkylene, (3) C2~6 alkenylene or (4) C2~6 alkynylene wherein E may be substituted by C1~4 alkyl substituted by 1-3 of group(s) selected from (1) C1~4 alkyl and (2) —OR²⁶;

$R^{26}$ represents (1) a hydrogen atom, (2) C1~4 alkyl, (3) C2~6 acyl or (4) trihaloacetyl;

represents (1) C3~15 carbocyclic ring or (2) 3-15 membered heterocyclic ring containing 1-4 of nitrogen atom(s), 1-2 of oxygen atom(s) and/or 1-2 of sulfur atom(s);

$R^{24}$ represents (1) C1~4 alkyl, (2) a halogen atom, (3) cyano, (4) trihalomethyl, (5) —OR²⁷, (6) —SR²⁸, (7) —NR²⁹R³⁰, (8) nitro, (9) —COOR³¹, (10) —CONR³²R³³, (11) —NR³⁴COR³⁵, (12) —SO₂NR³⁶R³⁷, (13) —NR³⁸SO₂R³⁹, (14) —S(O)R⁴⁰ or (15) —SO₂R⁴¹;

$R^{27}$, $R^{28}$, $R^{29}$, $R^{30}$, $R^{31}$, $R^{32}$, $R^{33}$ $R^{34}$, $R^{35}$, $R^{36}$, $R^{37}$, $R^{38}$, $R^{39}$, $R^{40}$ and $R^{41}$ each independently represents (1) a hydrogen atom or (2) C1~4 alkyl;

i represents 0 or an integer of 1~5;
m represents 0 or an integer of 1~4;
n represents 0 or an integer of 1~4;
p represents 0 or an integer of 1~5;
wherein when i is 2 or more, plural R¹ are the same or different; when m is 2 or more, plural R² are the same or different; when n is 2 or more, plural R³ are the same or different; when p is 2 or more, plural R²⁴ are the same or different, or a prodrug thereof or a salt thereof, (2) The prodrug according to above-mentioned (1) represented by formula (IA):

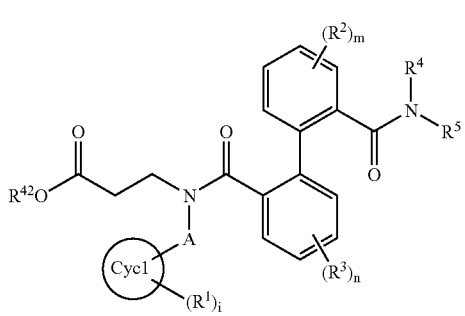

(IA)

wherein R⁴² represents (1) C1~8 alkyl or (2) C1~8 alkyl substituted by 1-2 of hydroxyl or amino, and the other symbols are the same meaning as defined in above-mentioned (1), (3) The prodrug according to above-mentioned (1) represented by formula (IB):

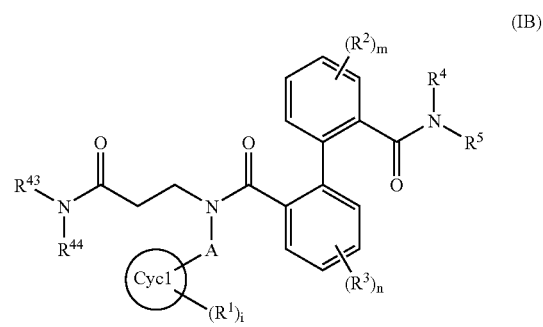

(IB)

wherein R⁴³ and R⁴⁴ each independently represents (1) a hydrogen atom, (2) C1~8 alkyl or (3) C1~8 alkyl substituted by 1-2 of hydroxyl or amino, and other symbols are the same meaning as defined in above-mentioned (1), (4) The prodrug according to above-mentioned (1) represented by formula (IC):

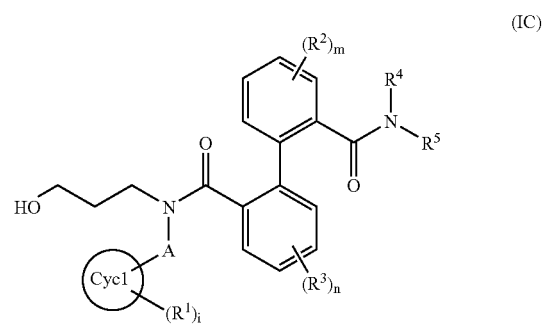

(IC)

wherein all other symbols are the same meaning as defined in above-mentioned (1), (5) A pharmaceutical composition comprising the compound according to above-mentioned (1), or a prodrug thereof or a salt thereof, (6) The pharmaceutical composition according to above-mentioned (5), which is a LPA receptor antagonist, (7) The pharmaceutical composition according to above-mentioned (6), wherein the LPA receptor is an EDG-2 receptor, (8) The pharmaceutical composition according to above-mentioned (7), which is an agent for prevention and/or treatment for urinary system disease, (9) The pharmaceutical composition according to above-mentioned (7), which is an agent for prevention and/or treatment for disease associated with carcinoma, proliferative disease, inflammation/immune system disease, disease by secretion fault or disease associated with brain,

(10) A method for prevention and/or treatment of diseases caused by EDG-2, which comprises administering an effective amount of the compound according to above-mentioned (1), or a prodrug thereof or a salt thereof to a mammal,

(11) The method for prevention and/or treatment according to above-mentioned (10), wherein the disease caused by EDG-2 is urinary system disease,

(12) The method for prevention and/or treatment according to above-mentioned (10), wherein the disease caused by EDG-2 is disease associated with carcinoma, proliferative disease, inflammation/immune system disease, disease by secretion fault or disease associated with brain,

(13) Use of the compound according to above-mentioned (1), a prodrug thereof or a salt thereof for the manufacture of an agent for prevention and/or treatment of diseases caused by EDG-2,

(14) The use according to above-mentioned (13), wherein the disease caused by EDG-2 is urinary system disease,

(15) The use according to above-mentioned (13), wherein the disease caused by EDG-2 is disease associated with carcinoma, proliferative disease, inflammation/immune system disease, disease by secretion fault or disease associated with brain,

(16) An agent for prevention and/or treatment of urinary system disease comprising a combination of LPA receptor antagonist containing the compound according to above-mentioned (1) or a prodrug thereof or a salt thereof as an active ingredient and one or two more agent(s) selected from other LPA receptor antagonist, α1 blocking agent, anticholinergic agent, 5α-reductase inhibitor and/or anti-androgenic agent; and

(17) A preparation of the compound according to above-mentioned (1) or prodrug thereof or salt thereof.

DETAILED DESCRIPTION OF THE INVENTION

In the present specification, C1-4 alkyl means methyl, ethyl, propyl, butyl and isomers thereof.

In the present specification, C1-8 alkyl means methyl, ethyl, propyl, butyl, pentyl, hexyl, heptyl, octyl and isomers thereof.

In the present specification, C2-4 alkenyl means ethenyl, propenyl, butenyl and isomers thereof.

In the present specification, C2-4 alkynyl means ethynyl, propynyl, butynyl and isomers thereof.

In the present specification, C1-4 alkoxy means methoxy, ethoxy, propoxy, butoxy and isomers thereof.

In the present specification, C1-6 alkylene means methylene, ethylene, triethylene, tetraethylene, pentaethylene, hexaethylene and isomers thereof.

In the present specification, C2-6 alkenylene means ethenylene, propenylene, butenylene, pentenylene, hexenylene and isomers thereof.

In the present specification, C2-6 alkynylene means ethynylene, propynylene, butynylene, pentynylene, hexynylene and the isomer thereof.

In the present specification, C2-6 acyl means ethanoyl, propanoyl, butanoyl, pentanoyl, hexanoyl and isomers thereof.

In the present specification, a halogen atom means such as a fluorine, chlorine, bromine and iodine atom.

In the present specification, trihalomethyl means methyl which is substituted with three halogen atoms, such as trifluoromethyl, trichloromethyl, tribromomethyl, and tri-iodomethyl.

In the present specification, trihaloacetyl means acethyl which is substituted with three halogen atoms, such as trifluoroacetyl, trichloroacetyl, tribromoacetyl and tri-iodoacetyl.

In the present specification, C3-15 carbocyclic ring includes C3-15 mono-, bi- or tricyclic unsaturated carbocyclic ring, partially saturated or fully saturated carbocyclic ring, bicyclic carbocyclic ring having spiro bond or bicyclic bridged carbocyclic ring; for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane and noradamantane.

In the present specification, 3-15 membered heterocyclic ring containing 1-4 of nitrogen atom(s), 1-2 of oxygen atom(s) and/or 1-2 of sulfur atom(s) includes 3-15 membered mono-, bi- or tricyclic unsaturated heterocyclic ring, partially saturated or fully saturated heterocyclic ring containing hetero atom(s) selected from 1-4 of nitrogen atom(s), 1-2 of oxygen atom(s) and/or 1-2 of sulfur atom(s); for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane and benzodithiane.

In the present specification, 3-15 membered mono-, bi- or tricyclic heterocyclic ring which is represented by $R^4$ and $R^5$ taken together with nitrogen atom to which they are attached includes 3-15 membered mono-, bi- or tricyclic unsaturated heterocyclic ring, partially saturated or fully saturated heterocyclic ring containing at least one nitrogen atom; for example, pyrrole, imidazole, triazole, tetrazole, pyrazole, indole, isoindole, indazole, purine, benzimidazole, benzazepine, benzodiazepine, benzotriazole, carbazole, β-carboline, 1,2,3,4-tetrahydro-β-carboline, phenothiazine, phenoxazine, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), dihydrofurazan, tetrahydrofurazan, dihydrooxadiazole, tetrahydrooxadiazole (oxadiazolidine), tetrahydrooxazine, dihydrooxadiazine, tetrahydrooxadiazine, perhydrooxazepine, tetrahydrooxadiazepine, perhydrooxadiazepine, dihydrothiadiazole, tetrahydrothiadiazole (thiadiazolidine), tetrahydrothiazine, dihydrothiadiazine, tetrahydrothiadiazine, perhydrothiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, tetrahydrobenzoxazepine, dihydrocarbazole, tetrahydrocarbazole, perhydrocarbazole, dihydroacridine and perhydroacridine.

Unless otherwise specifically mentioned, all isomers are included in the present specification. For example, alkyl, alkenyl, alkynyl, alkoxy, alkylene, alkenylene and alkynylene include linear and branched ones. Moreover, all of isomers due to double bond, ring and fused ring (E-, Z-, cis- and trans-substances), isomers due to presence of asymmetric carbon, etc. (R-, S-, α- and β-substances, enantiomer and diastereomer), optically active substances having optical rotation (D-, L-, d- and l-substances), polar substances by chromatographic separation (high-polar substance and low-polar substance), equilibrium compounds, rotational isomers, a mixture thereof in any proportion and a racemic mixture are included in the present invention.

Unless otherwise specifically mentioned in the present specification, a symbol $\ldots\ldots^{\backslash\backslash\backslash\backslash}$ means a bond to the opposite side of the paper (i.e., α-configuration), means a bond to this side of the paper (i.e., β-configuration) and means a mixture of α- and β-configurations as will be obvious for persons skilled in the art.

The compounds of the present invention are converted to non-toxic salts by known methods. With regard to the non-toxic salts, those which are pharmaceutically acceptable and soluble in water are preferred. Examples of appropriate salts are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl)methylamine, lysine, arginine and N-methyl-D-glucamine) and acid addition salt (such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate)). The salt of the compound of the present invention also includes solvates and also solvates with the above-mentioned alkaline (earth) metal salt, ammonium salt, organic amine salt and acid addition salt.

The solvate is preferably non-toxic and water-soluble. Examples of an appropriate solvate are solvates with water and with alcoholic solvent (such as ethanol).

A prodrug of the present invention is not limited in particular, but the compound which is improved against bioavailability and permeability of biomembrane is preferable. Since the compound represented by formula (I) of the present invention has carboxyl group, it includes the compound which is converted to carboxyl group by cleaving in vivo or by oxidation in vivo.

The compound which is converted to carboxyl group by cleaving in vivo include, for example, carboxylic ester derivertives represented by formula (IA) or carboxamide derivatives represented by formula (IB).

The compound which is converted to carboxyl group by oxidation in vivo includes, for example, alcohol derivertives represented by formula (IC).

In formula (I), A is preferably C1-6 alkylene, more preferably methylene, ethylene, trimethylene or tetramethylene.

In formula (I),

is preferably C5-10 carbocyclic ring or 5-10 membered heterocyclic ring containing 1-4 of nitrogen atom(s), 1-2 of oxygen atom(s) and/or 1-2 of sulfur atom(s) and, more preferably benzene, naphthalene, tetrahydronaphthalene, indene, cyclohexane, pyridine, piperidine, quinoline, tetrahydroquinoline, pyrrole, pyrrolidine, indole, indoline, furan, benzofuran, thiophene or benzothiophene.

In formula (1), $R^1$ is preferably C1-4 alkyl, halogen atom, $—OR^6$, $—SR^7$, $—NR^8R^9$, nitro, $—COOR^{10}$, $—CONR^{11}R^{12}$, $—NR^{13}COR^{14}$, $—SO_2NR^{15}R^{16}$ or $—NR^{17}SO_2R^{18}$ and, more preferably methyl, ethyl, propyl, butyl, fluorine atom, chlorine atom, hydroxy, methoxy, ethoxy, propoxy, aminosulfonyl or dimethylaminosulfonyl.

In formula (I), $R^2$ or $R^3$ are preferably C1-4 alkyl or C1-4 alkoxy.

$R^4$ and $R^5$ are preferably hydrogen atom, C1-4 alkyl, C2-4 alkenyl, C1-4 alkyl substituted by $—OR^{21}$, C1-4 alkyl substituted by $—NR^{22}R^{23}$ or

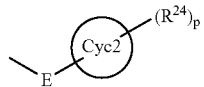

and, more preferably hydrogen atom, C1-4 alkyl, allyl, hydroxymentyl, 2-hydroxyethyl, 2-(dimethylamino)ethyl or

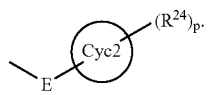

In formula (I), 3-15 membered mono-, bi- or tricyclic heterocyclic ring which is represented by $R^4$ and $R^5$ taken together with nitrogen atom to which they are attached is preferably aziridine, azetidine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrooxazine, perhydrooxazepine, tetrahydrothiazine, perhydrothiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, tetrahydrobenzoxazepine, dihydrocarbazole, tetrahydrocarbazole, perhydrocarbazole, dihydroacridine, perhydroacridine, carbazole, β-carboline, 1,2,3,4-tetrahydro-β-carboline, phenothiazine and phenoxazine.

In formula (I), E is preferably C1-6 alkylene or C2-6-alkenylene and, more preferably methylene, ethylene, trimethylene or tetramethylene.

In formula (I),

is preferably C5-10 carbocyclic ring or 5-10 membered heterocyclic ring containing 1-4 of nitrogen atom(s), 1-2 of oxygen atom(s) and/or 1-2 of sulfur atom(s) and, more preferably benzene, naphthalene, tetrahydronaphthalene, indene, cyclohexane, pyridine, piperidine, quinoline, tetrahydroquinoline, pyrrole, pyrrolidine, indole, indoline, furan, benzofuran, thiophene or benzothiophene.

In formula (I), $R^{24}$ is preferably C1-4 alkyl, halogen atom, $-OR^{27}$, $-SR^{28}$, $-NR^{29}R^{30}$, nitro, $-COOR^{31}$, $-CONR^{32}R^{33}$, $-NR^{34}COR^{35}$, $-SO_2NR^{36}R^{37}$ or $-NR^{38}SO_2R^{39}$ and, more preferably, methyl, ethyl, propyl, butyl, fluorine atom, chlorine atom, hydroxy, methoxy, ethoxy, propoxy, aminosulfonyl or dimethylaminosulfonyl.

i is preferably 0 or an integer of 1-3.

m is preferably 0 or an integer of 1-2.

n is preferably 0 or an integer of 1-2.

p is preferably 0 or an integer of 1-3.

Among the compounds of the present invention represented by formula (I), preferred compounds are compound represented by formula (I-A-1):

(I-A-1)

(wherein all symbols have the same meanings as described above), formula (I-A-2):

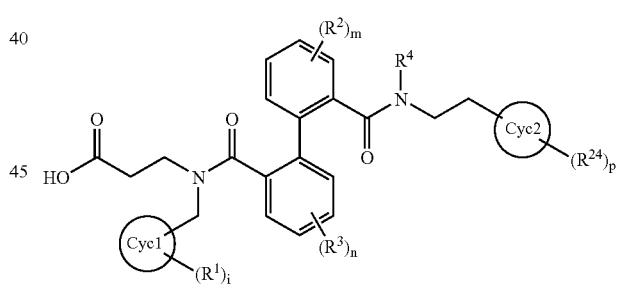

(I-A-2)

(wherein all symbols have the same meanings as described above), formula (I-A-3):

(I-A-3)

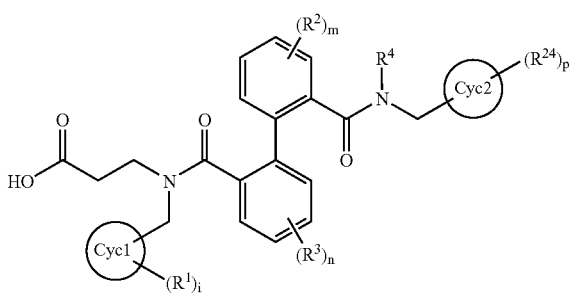

(wherein all symbols have the same meanings as described above), formula (I-A-4):

(I-A-4)

(wherein all symbols have the same meanings as described above), formula (I-A-5):

(I-A-5)

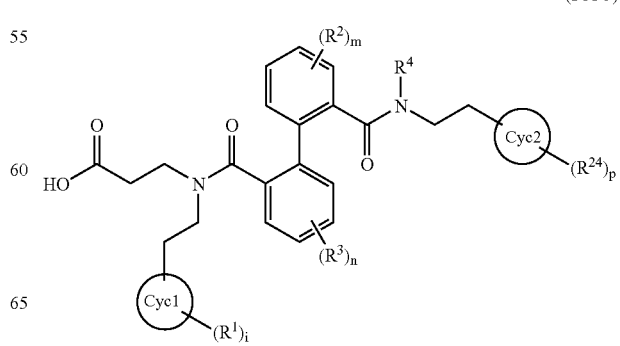

(wherein all symbols have the same meanings as described above), formula (I-A-6):

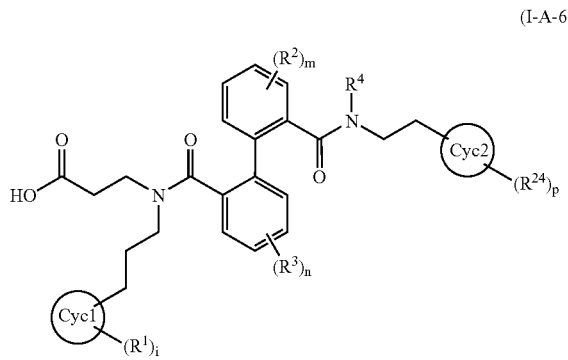

(wherein all symbols have the same meanings as described above), prodrug thereof and non-toxic salt thereof.

Concrete compounds of the present invention include compounds shown in Examples, prodrug thereof and non-toxic salts thereof.

Processes for the Preparation of the Compound of the Present Invention:

The compounds of the present invention represented by formula (I), formula (IA), formula (IB) and formula (IC) can be prepared by the following processes and the processes shown in Examples.

The compound represented by formula (I) can be produced subjecting the compound represented by formula (II)

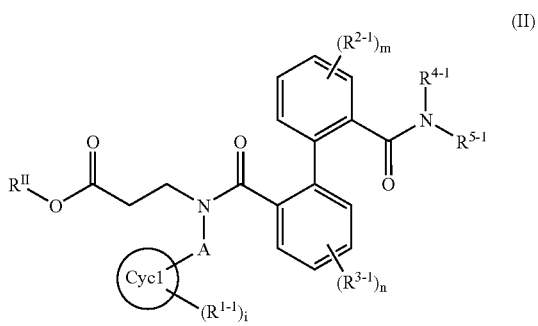

(wherein $R^{II}$ is protective group of carboxyl, $R^{1-1}$, $R^{2-1}$, $R^{3-1}$, $R^{4-1}$, and $R^{5-1}$ are the same meanings as $R^1$, $R^2$, $R^3$, $R^4$ and $R^5$ respectively, hydroxyl, amino or thiol in the group represented by $R^{1-1}$, $R^{2-1}$, $R^{3-1}$, $R^{4-1}$ and $R^{5-1}$ is protected if necessary; and other symbols have the same meaning as defined above) to deprotection of protective group of carboxyl followed by subjecting to deprotection, if necessary.

The protective group for carboxyl includes such as methyl, ethyl, allyl, t-butyl, trichloroethyl, benzyl (Bn), phenacyl, p-methoxybenzyl, trityl, 2-chlorotrityl, and solid-phase support which those structures linked and the like.

Deprotection reaction of carboxyl has been well known and its examples are as follows.

(1) Hydrolysis with an alkali,
(2) a deprotection reaction under an acidic condition,
(3) a deprotection reaction by hydrogenolysis,
(4) a deprotection reaction using metal and
(5) a deprotection reaction using organic metal.

Those methods will be specifically illustrated as follows.

(1) A deprotection reaction using an alkali is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane).

(2) A deprotection reaction under an acidic condition is carried out, for example, at the temperature of 0 to 100° C. in an organic acid (such as acetic acid, trifluoroacetic acid, methanesulfonic acid and p-tosylic acid), an inorganic acid (hydrochloric acid and sulfuric acid) or a mixture thereof (such as hydrogen bromide/acetic acid) in an organic solvent (such as dichloromethane, chloroform, dioxane, ethyl acetate and anisole).

(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel), in a solvent (such as an ether type (e.g., tetrahydrofuran, dioxane, dimethoxyethane and diethyl ether), an alcohol type (e.g., methanol and ethanol), a benzene type (e.g., benzene and toluene), a ketone type (e.g., acetone and methyl ethyl ketone), a nitrile type (e.g., acetonitrile), an amide type (such as dimethylformamide), water, ethyl acetate, acetic acid or a mixed solvent comprising two or more thereof).

(4) A deprotection reaction using metal is carried out, for example, at the temperature of 0 to 40° C., with or without ultrasonic wave in the presence of powdery zinc in an acidic solvent (such as buffer of acetic acid of pH 4.2 to 7.2 or mixture of the buffer and an organic solvent such as tetrahydrofuran).

(5) A deprotection reaction using a metal complex is carried out, for example, at the temperature of 0 to 40° C. using a metal complex such as tetrakistriphenylphosphine palladium (0), bis(triphenylphosphine)palladium (II) dichloride, palladium (II) acetate and tris(triphenylphosphine) rhodium (I) chloride) in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Besides the above-mentioned method, for example, a deprotection reaction may be carried out by a method mentioned in "T. W Greene, *Protective Groups in Organic Synthesis*, Wiley, New York, 1999".

As persons skilled in the art can easily understand that the aimed compound of the present invention is able to be easily produced by using appropriate ones among those deprotection reactions.

The deprotection reaction of the protective group can be done by the following methods.

The protective group for hydroxyl includes such as methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc) and 2,2,2-trichloroethoxycarbonyl (Troc) and the like.

The protective group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl)ethoxymethyl (SEM) and the like.

The protective group of thiol includes such as benzyl, methoxybenzyl, methoxymethyl (MOM), 2-tetrahydropyranyl (THP), diphenylmethyl and acetyl (Ac) and the like.

With regard to the protective group for hydroxyl, for amino and for thiol, there is no particular limitation to the above ones so far as it is a group which is able to be easily and selectively detached. For example, a deprotection reaction may be carried out by a method mentioned in "T. W. Greene, *Protective Groups in Organic Synthesis*, Wiley, New York, 1999".

Deprotection reaction of a protective group for hydroxyl, amino or thiol is known and its examples are as follows.

(1) a hydrolyzing reaction with an alkali;
(2) a deprotection reaction under an acidic condition;
(3) a deprotection reaction by hydrogenolysis;
(4) a deprotection reaction of silyl;
(5) a deprotection reaction using metal; and
(6) a deprotection reaction using an organic metal.

Those methods will be specifically illustrated as follows.

A deprotection reaction using an alkali is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane).

(2) A deprotection reaction under an acidic condition is carried out, for example, at the temperature of 0 to 100° C. in an organic acid (such as acetic acid, trifluoroacetic acid, methanesulfonic acid and p-tosylic acid), an inorganic acid (hydrochloric acid and sulfuric acid) or a mixture thereof (such as hydrogen bromide/acetic acid) in an organic solvent (such as dichloromethane, chloroform, dioxane, ethyl acetate and anisole).

(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst [such as palladium-carbon, palladium black, palladium hydroxide, platinum oxide and Raney nickel) in a solvent (such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].

(4) A deprotection reaction of silyl is carried out, for example, at the temperature of 0 to 40° C. using tetrabutylammonium fluoride in an organic solvent miscible with water (such as tetrahydrofuran and acetonitrile).

(5) A deprotection reaction using metal is carried out, for example, at the temperature of 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction using a metal complex is carried out, for example, at the temperature of 0 to 40° C. using a metal complex such as tetrakistriphenylphosphine palladium (0), bis(triphenylphosphine)palladium (II) dichloride, palladium (II) acetate and tris(triphenylphosphine) rhodium (I) chloride) in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Besides the above-mentioned method, for example, a deprotection reaction may be carried out by a method mentioned in "T. W Greene, *Protective Groups in Organic Synthesis*, Wiley, New York, 1999".

As persons skilled in the art can easily understand that the aimed compound of the present invention is able to be easily produced by using appropriate ones among those deprotection reactions.

The compound represented by formula (IA) is able to be produced subjecting the compound represented by formula (IIA)

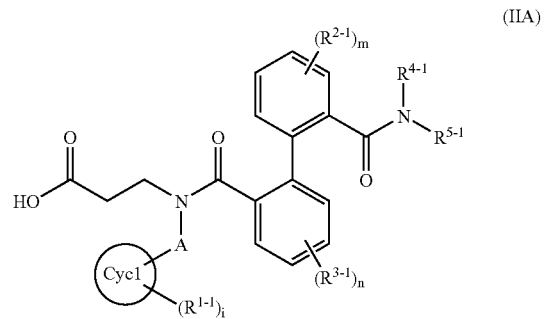

(IIA)

(wherein all symbols have the same meaning as defined above) to an esterification reaction with formula (IIB)

$$R^{42-1}\text{—OH} \quad (IIB)$$

(wherein $R^{42-1}$ is the same meaning as $R^{42}$, hydroxyl or amino in the group represented by $R^{42-1}$ is protected if necessary; and other symbols have the same meaning as defined above) followed, by subjecting to deprotection, if necessary.

Esterification reaction has been known and its examples are
(1) a process using an acid halide,
(2) a process using a mixed acid anhydride and
(3) a process using a condensing agent.

Such processes will be specifically illustrated as follows.

(1) A process using an acid halide is carried out, for example, in such a manner that carboxylic acid reacts with an agent for producing an acid halide (such as oxalyl chloride and thionyl chloride) in an organic solvent (such as chloroform, dichloromethane, diethyl ether and tetrahydrofuran) or without solvent at −20° C. to refluxing temperature and the resulting acid halide reacts with an alcohol in the presence of a base (such as pyridine, triethylamine, dimethylaniline, dimethylaminopyridine and diisopropylethylamine) in an inert organic solvent (such as chloroform, dichloromethane, diethyl ether and tetrahydrofuran) at the temperature of 0 to 40° C. It is also possible to conduct the reaction with an acid halide at 0 to 40° C. in an organic solvent (such as dioxane and tetrahydrofuran) using an aqueous solution of alkali (such as aqueous solution of sodium bicarbonate and an aqueous solution of sodium hydroxide).

(2) A process using a mixed acid anhydride is carried out, for example, in such a manner that carboxylic acid is made to react with an acid halide (such as pivaloyl chloride, tosyl chloride or mesyl chloride) or with an acid derivative (such as ethyl chloroformate and isobutyl chloroformate) at 0 to 40° C. in an organic solvent (such as chloroform, dichloromethane, diethyl ether and tetrahydrofuran) or without a solvent in the presence of a base (such as pyridine, triethylamine, dimethylaniline, dimethylaminopyridine and diisopropylethylamine) and the resulting mixed acid anhydride is made to react with an alcohol at 0 to 40° C. in an organic solvent (such as chloroform, dichloromethane, diethyl ether and tetrahydrofuran).

(3) A process using a condensing agent is carried out, for example, in such a manner that carboxylic acid and an alcohol are subjected to a reaction at 0 to 40° C. with or without 1-hydroxybenztriazole (HOBt) using a condensing agent (such as 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide and 1-propanephosphonic acid cyclic anhydride (PPA), etc.) in the presence or absence of a base (such as pyridine, triethylamine, dimethylanilin and dimethylaminopyridine) in an organic solvent (such as chloroform, dichloromethane, dimethylformamide, diethyl ether and tetrahydrofuran) or without a solvent.

It is preferred that all of the reactions (1), (2) and (3) are carried out in an atmosphere of inert gas (such as argon and nitrogen) under an anhydrous condition.

A deprotection reaction of hydroxyl, amino or thiol is able to be carried out by the same methods as those mentioned above.

The compound represented by formula (IA) is also able to be produced subjecting the compound represented by formula (IIC)

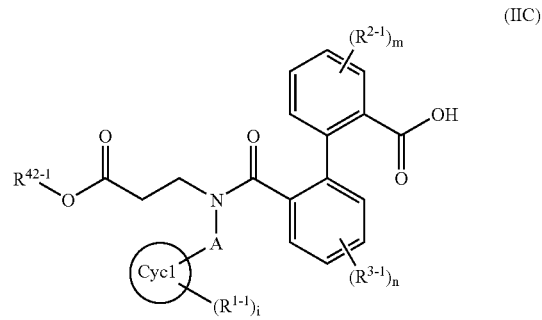

(IIC)

(wherein all symbols have the same meaning as defined above) to an amidation reaction with formula (IID)

(IID)

(wherein all symbols have the same meaning as defined above) followed, by subjecting to deprotection, if necessary.

Amidation reaction has been known and its examples are
(1) a process using an acid halide,
(2) a process using a mixed acid anhydride and
(3) a process using a condensing agent.

Such processes will be specifically illustrated as follows.

(1) A process using an acid halide is carried out, for example, in such a manner that carboxylic acid reacts with an agent for producing an acid halide (such as oxalyl chloride and thionyl chloride) in an organic solvent (such as chloroform, dichloromethane, diethyl ether and tetrahydrofuran) or without solvent at −20° C. to refluxing temperature and the resulting acid halide reacts with an amine in the presence of a base (such as pyridine, triethylamine, dimethylaniline, dimethylaminopyridine and diisopropylethylamine) in an inert organic solvent (such as chloroform, dichloromethane, diethyl ether and tetrahydrofuran) at the temperature of 0 to 40° C. It is also possible to conduct the reaction with an acid halide at 0 to 40° C. in an organic solvent (such as dioxane and tetrahydrofuran) using an aqueous solution of alkali (such as aqueous solution of sodium bicarbonate and an aqueous solution of sodium hydroxide).

(2) A process using a mixed acid anhydride is carried out, for example, in such a manner that carboxylic acid is made to react with an acid halide (such as pivaloyl chloride, tosyl chloride or mesyl chloride) or with an acid derivative (such as ethyl chloroformate and isobutyl chloroformate) at 0 to 40° C. in an organic solvent (such as chloroform, dichloromethane, diethyl ether and tetrahydrofuran) or without a solvent in the presence of a base (such as pyridine, triethylamine, dimethylaniline, dimethylaminopyridine and diisopropylethylamine) and the resulting mixed acid anhydride is made to react with an amine at 0 to 40° C. in an organic solvent (such as chloroform, dichloromethane, diethyl ether and tetrahydrofuran).

(3) A process using a condensing agent is carried out, for example, in such a manner that carboxylic acid and an amine are subjected to a reaction at 0 to 40° C. with or without 1-hydroxybenztriazole (HOBt) using a condensing agent (such as 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide and 1-propanephosphonic acid cyclic anhydride (PPA), etc.) in the presence or absence of a base (such as pyridine, triethylamine, dimethylanilin and dimethylaminopyridine) in an organic solvent (such as chloroform, dichloromethane, dimethylformamide, diethyl ether and tetrahydrofuran) or without a solvent.

It is preferred that all of the reactions (1), (2) and (3) are carried out in an atmosphere of inert gas (such as argon and nitrogen) under an anhydrous condition.

A deprotection reaction of hydroxyl or amino is able to be carried out by the same methods as those mentioned above.

The compound represented by formula (IB) is able to be produced subjecting the compound represented by formula (IIA) to an amidation reaction with a compound represented by formula (IIE)

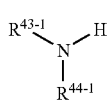

(IIE)

(wherein $R^{43-1}$ and $R^{44-1}$ have the same meanings as $R^{43}$ and $R^{44}$, respectively, and hydroxyl or amino in the group represented by $R^{43-1}$ and $R^{44-1}$ is protected, if necessary; and other symbols have the same meaning as defined above) followed by subjecting to deprotection, if necessary.

Amidation reaction is able to be carried out by the same methods as those mentioned above.

A deprotection reaction of hydroxyl, amino or thiol is able to be carried out by the same methods as those mentioned above.

The compound represented by formula (IC) is able to be produced subjecting the compound represented by formula (IIA) to reduction reaction followed by subjecting to deprotection, if necessary.

The reduction reaction has been known and it is carried out, for example, in such a manner that (1) carboxylic acid is made to react with an acid halide (such as oxalyl chloride, thionyl chloride), with an acid anhydride (such as acetic anhydride) or with an acid derivatives (such as ethyl chloroformate, isobutyl chloroformate) at −20 to 60 degrees in an organic solvent (such as chloroform, dichloromethane, diethylether, tetrahydrofuran) or without a solvent in the presence of a base (such as pyridine, triethylamine, dimethylaniline, dimethylaminopyridine, diisopropylethylamine, N-methylmorpholine) and the resulting compound is made to react with reducing agent (such as sodium borohydride, tetrabutylammonium borohydride, calsium borohydride) at 0 to 60 degrees in a solvent (such as methanol, tetrahydrofuran, water) or (2) carboxylic acid is made to react with a reducing agent (such as diborane, borane-pyridine complex, borane-methyl sulfide complex, diisobutyl aluminium hydride) at −80 to 0 degrees in an organic solvent (such as tetrahydrofuran, toluene).

A deprotection reaction of hydroxyl, amino or thiol is able to be carried out by the same methods as those mentioned above.

Compounds represented by formulae (II), (IIA) and (IIC) have been known per se or are able to be easily produced by known methods.

For example, the compounds represented by formulae (II), (IIA) and (IIC) are able to be produced by the process shown in the following reaction step formula 1.

In the reaction step, X represents a leaving group (leaving group represents such as a halogen atom, mesyloxy and tosyloxy) and other symbols have the same meanings as those defined above.

Reaction Step Formula 1

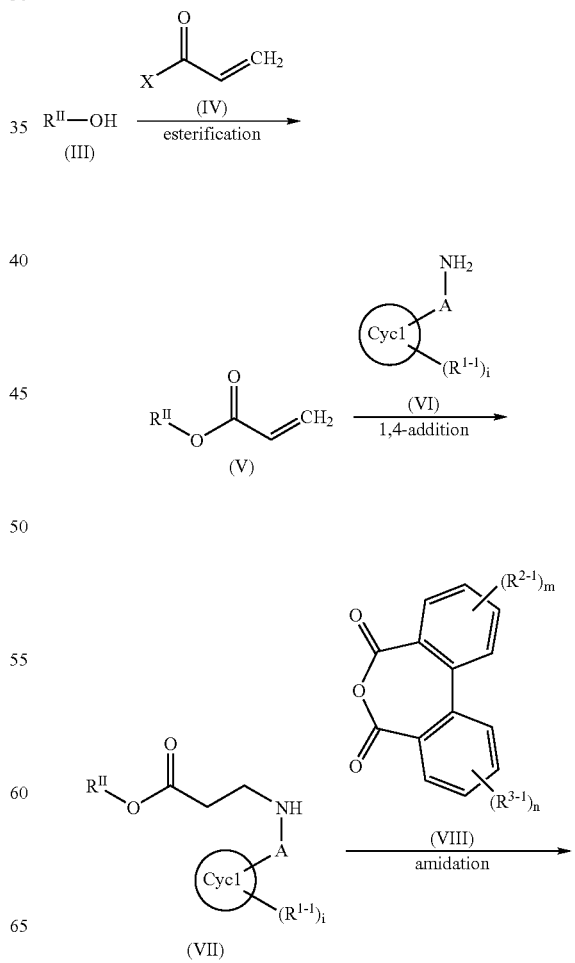

-continued

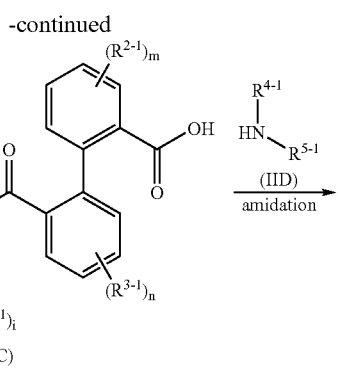

(IIC)

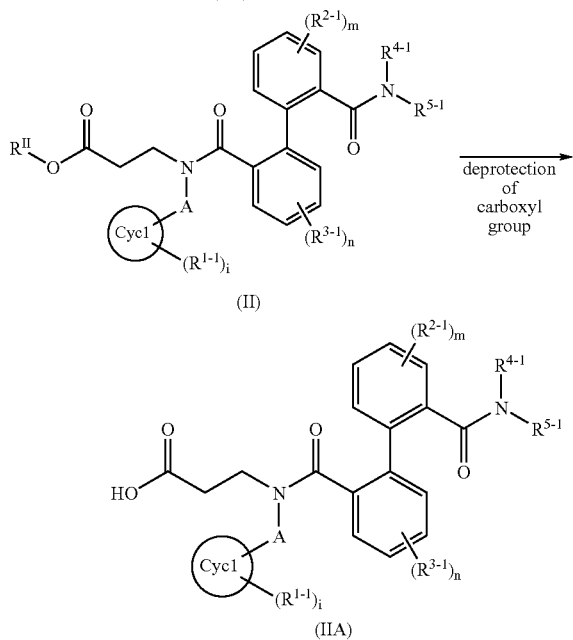

In the above reaction step formula 1, the compounds represented by formulae (III), (IV), (VI), (VIII) and (IID) used as starting materials have been known or able to be easily produced by known methods.

In each of the reactions mentioned in the present specification, the reaction product is able to be purified by a conventional purifying method such as distillation under ordinary pressure, or high performance liquid chromatography, thin-layer chromatography or column chromatography using silica gel or magnesium silicate and recrystallization. Purification may be carried out for each reaction or after completion of some reactions.

[Toxicity]

Toxicity of the compound of the present invention represented by formula (I) is sufficiently low and it was confirmed to be sufficiently safe to be used as pharmaceuticals.

INDUSTRIAL APPLICABILITY

[Application to Pharmaceuticals]

Since the compounds of the present invention represented by formula (I) be antagonistic to LPA receptors, they are believed to be useful for prevention and/or treatment of diseases such as various kinds of disease namely urinary system disease, carcinoma association disease, proliferative disease, inflammation/immune system disease, disease by secretion fault or brain association disease.

For example, for urinary system disease, symptom with prostatic hypertrophy or neurogenic bladder dysfunction disease (such as dysuria (miction initiation delay, extension between on urination, urinary stream very small, intermission miction, two steps of miction), pollakiuria, night urination, urodynia), symptom to be caused by cerebrovascular disorder, Parkinson disease, cerebral oncosis, a multiple sclerosis, Shy-Drager symptom, spinal cord neoplasm, nucleous hernia, spinal canal stenosis, diabetes, etc. (such as dysuria (miction initiation delay, extension between on urination, urinary stream very small, intermission miction, two steps of miction), pollakiuria, night urination, urodynia), lower urinary tract symptom (for example, occlusion disease of lower urinary tract), inflammatory disease of lower urinary tract (such as infection), polyuria are thought about.

For example, for carcinoma-related disease, solid tumor, solid tumor metastasis, angiofibroma, myeloma, multiple myeloma, Kaposi's sarcoma, leucemia are given. In solid tumor, mammary cancer, lung cancer, gastric cancer, carcinoma oesophagi, colon rectal cancer, liver cancer, ovarian cancer, theca cell tumor, androblastoma, cervix cancer, endometrial carcinoma, prostate cancer, kidney cancer, carcinoma cutaneum, osteosarcoma, pancreas cancer, urinary tract carcinoma, thyroid cancer, cerebral oncosis are given. In addition, it is thought that carcinomatous infiltration transition is suppressed by LPA receptor antagonist.

For example, for proliferative disease, disorder with aberrant angiogenesis (for example, re-arctation, diabetic retinopathy, angiogenesis-related glaucoma, crystalline lens fiber multiplication symptom, thyroid gland hyperplasia (including Basedow's goiter), lung inflammation, nephrotic syndrome and osteoporosis), artery obstruction, pulmonary fibrosis are given.

For example, for inflammation/immune system disease, psoriasis, nephropathy (for example, IgA nephropathy), nephritis by other inflammation/immunopathy, hepatitis, pneumonitis symptom are given.

For example, for disease by secretion fault, secretion fault by autonomic nervous system anomaly is given, for example, for secretion fault by autonomic nervous system anomaly, Sjogren syndrome is given.

For example, for brain-related disease, brain infarction, cerebral apoplexy, brain or peripheral neuropathy are given.

The compound of the present invention represented by formula (I), prodrug thereof or non-toxic salt thereof may be administered as a combined preparation by combining with other pharmaceuticals for the purpose of 1) supplementing and/or enhancing of prevention and/or treatment effect of the compound, 2) improvement in pharmacokinetics and absorption and reduction of dose of the compound and/or 3) reduction of side effect of the compound.

The combined preparation of the compound of the present invention represented by formula (I) with other pharmaceuticals may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of the present invention represented by formula (I) may be firstly administered followed by administering the other pharmaceutical or the other pharmaceutical may be administered firstly followed by administering the compound of the present invention represented by formula (I). Methods for each of the administration are the same or different.

There is no particular limitation for the diseases showing prevention and/or treatment effect by the above-mentioned combined preparation, so far as it is a disease in which the prevention and/or treatment effect of the compound of present invention represented by formula (I) are supplemented and/or enhanced.

The other pharmaceutical for supplementing and/or enhancing the prevention and/or treatment effect of the compound of the present invention represented by formula (I) for urinary system disease includes other urologic disease therapeutic agent such as other LPA receptor antagonist, α1 blocking agent, anticholinergic agent, 5α-reductase inhibitor and/or anti-androgenic agent. But anticholinergic agent is used only by case without prostatic hypertrophy. It is mainly used by remedy of pollakiuria or anischuria of case without prostatic hypertrophy.

The other pharmaceutical for supplementing and/or enhancing the prevention and/or treatment effect of the compound of the present invention represented by formula (I) for carcinoma disease region includes such as other carcinoma treatment of disease agent.

The other LPA receptor antagonist includes such as methyl 3-({4-[4-({[1-(2-chlorophenyl)ethoxy]carbonyl}amino)-3-methyl-5-isoxazolyl]benzyl}sulfanyl) propanoate.

The α1 blocking agent includes such as terazosin hydrochloride, Bunazosin Hydrochloride, urapidil, tamsulosin hydrochloride, doxazosin mesilate, prazosin hydrochloride, indolamine, naftopidil, alfuzosin hydrochloride and AIO-8507L.

The anticholinergic agent includes such as oxybutinin hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin and YM-905.

The 5α-reductase inhibitor includes such as finasteride and GI-998745.

The anti-androgenic agent includes such as oxendolone, osaterone acetate and bicalutamide.

The other carcinoma treatment of disease agent includes alkylating agent (such as nitrogen mustard N-oxide hydrochloride, cyclophosphamide, ifosfamide, melphalan, thiotepa, carboquone, busulfan), nitrosourea derivative (such as nimustine hydrochloride, ranimustine), an antimetabolite (such as methotrexate, mercaptopurine, 6-mercaptopurinboside, fluorouracil, tegafur, UFT, carmofur, doxifluridine, cytarabine, enocitabine), anticancer antibiotics (such as actionmycin D, mitomycin C, daunorubicin hydrochloride, doxorubicin hydrochloride, aclarubicin hydrochloride, neocarzinostatin, pirarubicin, epirubicin, idarubicin, chromomycin A3, bleomycin, peplomycin sulfate), plant alkaloid (such as vinblastine sulfate, vincristine sulfate, vindesine sulfate), hormone (such as estramustine phosphate sodium, mepitiostane, epitiostanol, tamoxifen citrate, diethylstilbestrol phosphate, medroxyprogesterone acetate), immunopotentiation agent (such as lentinan, picibanil, krestin, shizophyllan, ubenimex, interferon), others (such as L-asparaginase, procarbazine hydrochloride, mitoxantrone hydrochloride, cisplatin, carboplatin).

There is no particular limitation for the ratio by weight of the compound represented by formula (I) to other pharmaceuticals.

With regard to other pharmaceuticals, any two or more may be compounded and administered.

With regard to other pharmaceuticals which supplement and/or enhance the prevention and/or treatment effect of the compound represented by formula (I), not only that which has been found up to now but also that which will be found in future on the basis of the above-mentioned mechanism are included.

When the compound represented by formula (I) which are used in the present invention, or concomitant drug combined the compound represented by formula (I) with other drugs are used for the above-described purpose, it is usually administered systemically or topically via an oral or parenteral route.

The dose of these compounds depends on the age, weight and symptom of the patient, the remedial value, the administration method, the treatment time, etc. In practice, however, these compounds are administered orally once or several times per day each in an amount of from 0.01 mg to 1000 mg, preferably 0.1 mg to 500 mg or more preferably 0.1 mg to 300 mg per adult, parenterally once or several times per day each in an amount of from 0.01 mg to 500 mg, preferably 0.1 mg to 100 mg or more preferably 0.1 mg to 50 mg per adult or continuously administered into vein for 1 hour to 24 hours per day.

It goes without saying that the dose of these compounds may be less than the aforementioned value or may need to exceed the aforementioned range because the dose varies under various conditions as mentioned above.

When the compound represented by formula (I) which are used in the present invention, or concomitant drug combined the compound represented by formula (I) with other drugs is administered, they are used in the form of solid or liquid agent for oral administration, injection, agent for external application, suppository, dye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch), binder (e.g., hydroxypropyl cellulose, polyvinyl pyrrolidone, magnesium metasilicoaluminate), disintegrant (e.g., calcium fibrinoglycolate), glidant (e.g., magnesium stearate), stabilizer, dissolution aid (e.g., glutamic acid, aspartic acid) or the like. The solid agent may be coated with a coating agent (e.g., white sugar, gelatin, hydroxypropyl cellulose, hydroxypropyl methyl cellulose phthalate) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof). Furthermore, such a liquid agent may comprise a wetting agent, a suspending agent, an emulsifier, a sweetening agent, a flavor, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are titurated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester), wax (e.g., beeswax, whale wax, ceresin), surface active agent (e.g., polyoxyethylenealkyletherphosphoric acid ester), higher alcohol (e.g., cetanol, stearyl alcohol, setostearyl alcohol), silicon oil (e.g., dimethyl polysiloxane), hydrocarbon (e.g., hydrophilic petrolatum, white petrolatum, purified lanolin, liquid paraffin), glycol (e.g., ethylene glycol, diethylene glycol, propylene glycol, polyethylene glycol, macrogol), vegetable oil (e.g., castor oil, olive oil, sesame oil, turpentine oil), water, absorption accelerator and rash preventive may be used singly or in admixture of two or more thereof. The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol), gelling agent (e.g., carboxymethyl cellulose, hydroxyethyl cellulose, hydroxypropyl cellulose, ethyl cellulose), neutralizing agent (e.g., triethanolamine, diisopropanolamine), surface active agent (e.g., polyethylene glycol monostearate), gum, water, absorption accelerator, and rash preventive are used singly or in admixture of two or more thereof. The gel base may further comprise a humectant, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol), higher alcohol (e.g., 2-hexyl decanol, cetanol), emulsifier (e.g., polyoxyethylene alkyl ether, aliphatic acid ester), water, absorption accelerator, and rash preventive are used singly or in admixture of two or more thereof. The cream base may further comprise a humectant, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose), wetting agent (e.g., urea, glycerin, propylene glycol), filler (e.g., kaolin, zinc oxide, talc, calcium, magnesium), water, dissolution aid, tackifier, and rash preventive may be used singly or in admixture of two or more thereof. The wet compress base may further comprise a humectant, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a humectant, an antioxidant, a perfume, etc.

The liniment is prepared by any known or commonly used formulation. For example, one or more active materials are dissolved, suspended or emulsified in water, alcohol (e.g., ethanol, polyethylene glycol), higher aliphatic acid, glycerin, soap, emulsifier, suspending agent, etc., singly or in combination of two or more thereof, to prepare such a liniment. The liniment may further comprise a humectant, an antioxidant, a perfume, etc.

The nebula, inhalant and spray each may comprise a stabilizer such as sodium hydrogensulfite and a buffer capable of providing isotonicity such as isotonic agent (e.g., sodium chloride, sodium citrate, citric acid). For the process for the preparation of spray, reference can be made to U.S. Pat. Nos. 2,868,691 and 3,095,355.

The injection for parenteral administration may be in the form of solution, suspension, emulsion or solid injection to be dissolved or suspended in a solvent in use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination. The injection may further comprise a stabilizer, a dissolution aid (e.g., glutamic acid, aspartic acid, Polysolvate 80 (trade name)), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvent before use.

The eye drops for parenteral administration may be in the form of liquid, suspension, emulsion or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic process. Alternatively, an aseptic solid agent such as freeze-dried product which has previously been prepared may be rendered aseptic or dissolved in an aseptic distilled water for injection or other solvent before use.

The inhalant for parenteral administration may be in the form of aerosol, powder for inhalation or liquid for inhalation. The liquid for inhalation may be dissolved or suspended in water or other proper medium in use.

These inhalants are prepared by an known method.

For example, the liquid for inhalation is prepared from materials properly selected from preservatives (e.g., benzalconium chloride, Paraben), colorants, buffering agents (e.g., sodium phosphate, sodium acetate), isotonic agents (e.g., sodium chloride, concentrated glycerin), thickening agents (e.g., carboxyvinyl polymer), absorption accelerators, etc. as necessary.

The powder for inhalation is prepared from materials properly selected from glidants (e.g., stearic acid and salt thereof), binders (e.g., starch, dextrin), vehicles (e.g., lactose, cellulose), colorants, preservatives (e.g., benzalconium chloride, Paraben), absorption accelerators, etc., if necessary.

In order to administer the liquid for inhalation, a sprayer (e.g., atomizer, nebulizer) is normally used. In order to administer the powder for inhalation, a powder inhaler is normally used.

Other examples of the composition for oral administration include sublingual medication for sublingual administration, suppository for rectal administration and pessary for vaginal administration prepared by an ordinary formulation comprising one or more active materials.

Referring to the local administration of the compound represented by formula (I) of the present invention, medicament may be locally administered to site of disease. The form of medicament is not limited to its administration method. The medicament may be in the form of injection which is administered to intramuscular, subcutaneous or articular site, solid agent (such as embedding agent, pellet and powder) or ointment.

The extended-release preparation of the compound represented by formula (I) is not limited to its form so far as medicament can be continuously administered to site of disease. The extended-release preparation may be in the form of, e.g., extended-release injection (e.g., microcapsuled preparation, microspheric preparation, nanospheric preparation), embedding preparation (e.g., film-like preparation) or the like.

The microcapsuled preparation, microspheric preparation and nanospheric preparation of the invention each are particulate pharmaceutical composition with an in vivo degradable polymer comprising the compound represented by formula (I) of the present invention, or concomitant drug combined the compound represented by formula (I) of the present invention with other drugs as active components.

Examples of the in vivo degradable polymer of the invention include aliphatic acid ester polymers and copolymers thereof, polyacrylic acid esters, polyhydroxybutyric acids, polyalkylene oxalates, polyorthoesters, polycarbonates, and polyaminoacids. These compounds may be used singly or in admixture of two or more thereof. Examples of the aliphatic acid ester polymers and copolymers thereof include polylactic acid, polyglycolic acid, polycitric acid, polymalic acid, and lactic acid-glycolic acid copolymer. These compounds may be used singly or in admixture of two or more thereof. Besides these compounds, poly-$\alpha$-cyanoacrylic acid esters, poly-$\beta$-hydroxybutyric acids, polytrimethyleneoxates, polyorthoesters, polyorthocarbonates, polyethylene carbonates, poly-$\gamma$-benzyl-L-glutamic acids and poly-L-alanines may be used singly or in admixture of two or more thereof. Preferred among these compounds are polylactic acids, polyglycolic acids and lactic acid-glycolic acid copolymers, more preferably lactic acid-glycolic acid copolymers.

The average molecular weight of these in vivo degradable polymers to be used in the invention is preferably from about 2,000 to 800,000, more preferably from about 5,000 to 200,000. For example, the polylactic acid preferably has a weight-average molecular weight of from about 5,000 to 100,000, more preferably from about 6,000 to 50,000. The polylactic acid can be synthesized according to any known preparation method per se. In the lactic acid-glycolic cid copolymer, the composition ratio of the lactic acid to the glycolic acid is preferably from about 100/0 to 50/50 (w/w), particularly from about 90/10 to 50/50. The weight-average molecular weight of the lactic acid-glycolic acid copolymer is preferably from about 5,000 to 100,000, more preferably from about 10,000 to 80,000. The lactic acid-glycolic acid copolymer can be synthesized according to any known preparation method per se.

The term "weight-average molecular weight" as used herein is meant to indicate molecular weight in polystyrene equivalence determined by gel permeation chromatography (GPC).

The aforementioned in vivo degradable polymer may be changed depending on the intensity of pharmacological activity of the compound represented by formula (I) which are used in the present invention, or concomitant drug combined the compound represented by formula (I) with other drugs and the desired medicines to be released so far as the aforementioned aims of the invention are accomplished. For example, the in vivo degradable polymer may be used in an amount of from about 0.2 to 10,000 times, preferably from about 1 to 1,000 times, more preferably from about 1 to 100 times (by weight) that of the physiologically active material.

BEST MODE FOR CARRYING OUT THE INVENTION

The following reference examples and examples illustrate the present invention, but do not limit the present invention.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

3-(2-(4-ethoxyphenyl)ethyl)aminopropanoic acid ethyl ester hydrochloride 4-ethoxyphenethylamine (2.2 g) and ethyl acrylate (1.5 g) were dissolved in ethanol (25 ml) and the mixture was stirred at room temperature for 3 days. The ethanol was removed under reduced pressure. To the obtained residue was added 4N Hydrogen chloride in ethyl acetate. The solvent was removed under reduced pressure. The obtained residue was washed with diisopropyl ether to give the title compound (4.0 g) having the following physical data.

TLC:Rf 0.89 (chloroform:methanol=9:1); NMR(DMSO-$d_6$):δ 9.10 (brs, 2H), 7.16 (d, J=8.7 Hz, 2H), 6.87 (d, J=8.7 Hz, 2H), 4.11 (q, J=7.2 Hz, 2H), 3.99 (q, J=7.2 Hz, 2H), 3.40-3.00 (m, 4H), 3.00-2.85 (m, 2H), 2.79 (t, J=7.5 Hz, 2H), 1.31 (t, J=7.2 Hz, 3H), 1.21 (t, J=7.2 Hz, 3H).

REFERENCE EXAMPLE 2

3-(N-((2-(2-carboxyphenyl)phenyl)carbonyl)-N-(2-(4-ethoxyphenyl)ethyl)amino)propanoic acid ethyl ester The compound (600 mg) prepared in Reference example 1, diphenic anhydride (538 mg) and trietylamine (0.85 ml) were dissolved in methylene chloride (10 ml). The mixture was stirred at room temperature overnight. The reaction mixture was added to a mixture of ethyl acetate and 1N hydrochloric acid. The aqueous layer was extracted with ethyl acetate. These organic layers were combined and then washed with a saturated aqueous solution of sodium bicarbonate and a saturated aqueous solution of sodium chloride, and dried over anhydrous sodium sulfate. The solvent was removed to give the title compound (837 mg) having the following physical data.

TLC:Rf 0.50 (chloroform:methanol=9:1);
NMR(DMSO-$d_6$):δ 7.90-7.15 (m, 8H), 7.00-6.70 (m, 4H), 4.00-3.90 (m, 4H), 3.80-3.00 (m, 4H), 2.60-2.00 (m, 4H), 1.35-1.05 (m, 6H).

EXAMPLE 1

3-(N-((2-(2-((pyridin-3-ylmethylamino)carbonyl)phenyl)phenyl)carbonyl)-N-(2-(4-ethoxyphenyl)ethyl)amino)propanoic acid ethyl ester The compound (150 mg) prepared in Reference example 2, 3-picolylamine (50 mg) and 1-ethyl-3-[3-(dimethylamino)propyl]carbodiimide hydrochloride (180 mg) were dissolved in methylene chloride (5 ml). The mixture was stirred at room temperature overnight. The reaction mixture was added to a mixture of ethyl acetate and 1N hydrochloric acid. The aqueous layer was extracted with ethyl acetate. These organic layer were combined, washed with a saturated aqueous solution of sodium chloride, and dried over anhydrous sodium sulfate. The solvent was removed and the obtained residue was purified by column chromatography on silica gel (chloroform:ethyl acetate=1:2) to give the compound (147 mg) of the present invention having the following physical data.

TLC:Rf 0.20 (chloroform:ethyl acetate=3:2); NMR (DMSO-$d_6$):δ 9.00-8.10 (m, 2H), 7.60-6.75 (m, 17H), 4.40-3.90 (m, 4H), 3.80-3.10 (m, 4H), 2.80-2.05 (m, 4H), 1.40-1.30 (m, 3H), 1.20-1.10 (m, 3H).

EXAMPLE 1(1)~(4)

The following compounds of the present invention were obtained in the same procedures as a series of reactions of Reference example 1→Reference example 2 using corresponding amine instead of 4-ethoxyphenethylamine followed by the same manner as in Example 1 using corresponding amine.

EXAMPLE 1(1)

3-(N-((2-(2-((pyridin-3-ylmethylamino)carbonyl)phenyl)phenyl)carbonyl)-N-(2-(4-methoxyphenyl)ethyl)amino)propanoic acid ethyl ester TLC:Rf 0.14 (chloroform:ethyl acetate=1:1).

EXAMPLE 1(2)

3-(N-((2-(2-(benzyaminocarbonyl)phenyl)phenyl)carbonyl)-N-(2-(4-ethoxyphenyl)ethyl)amino)propanoic acid ethyl ester TLC:Rf 0.91 (methylene chloride:methanol=9:1); NMR (DMSO-$d_6$):δ 9.10-8.60 (m, 1H), 7.60-6.70 (m, 17H), 4.40-3.80 (m, 6H), 3.80-3.00 (m, 4H), 2.80-2.00 (m, 4H), 1.40-1.20 (m, 3H), 1.20-1.10 (m, 3H).

EXAMPLE 1(3)

3-(N-((2-(2-(methylaminocarbonyl)phenyl)phenyl)carbonyl)-N-(2-(4-ethoxyphenyl)ethyl)amino)propanoic acid ethyl ester TLC:Rf 0.62 (methylene chloride:ethyl acetate=2:1); MASS (APCI, Pos., 40V): 503 (M+H)$^+$.

EXAMPLE 1(4)

3-(N-((2-(2-(benzylaminocarbonyl)phenyl)phenyl)carbonyl)-N-(2-phenylethylamino))propanoic acid ethyl ester TLC:Rf 0.73 (methylene chloride:ethyl acetate=4:1); MASS (APCI, Pos., 40V): 535 (M+H)$^+$.

EXAMPLE 2

3-(N-((2-(2-((pyridin-3-ylmethylamino)carbonyl)phenyl)phenyl)carbonyl)-N-(2-(4-ethoxyphenyl)ethyl)amino)propanoic acid The compound (110 mg) prepared in Example 1 and 1N aqueous solution of sodium hydroxide (0.5 ml) were dissolved in a mixture of ethanol (1 ml) and tetrahydrofuran (2 ml). The mixture was stirred at room temperature overnight. The reaction mixture was added to a mixture of ethyl acetate and 1N hydrochloric acid. The aqueous layer was extracted with ethyl acetate. These organic layers were combined, washed with a saturated aqueous solution of sodium chloride and dried over anhydrous sodium sulfate. The solvent was removed to give the compound (77 mg) of the present invention having the following physical data.

TLC:Rf 0.36 (chloroform:methanol=9:1); NMR(DMSO-$d_6$):δ 9.00-8.30 (m, 2H), 7.60-6.70 (m, 15H), 4.60-4.10 (m, 2H), 4.00-3.90 (m, 2H), 3.90-3.00 (m, 4H), 2.80-2.65 (m, 2H), 2.20-2.00 (m, 2H), 1.40-1.20 (m, 3H).

EXAMPLE 2(1)~(4)

The following compounds of the present invention were obtained in the same manner as in Example 2 using the compounds prepared in Example 1(1)~(4) instead of the compound prepared in Example 1.

EXAMPLE 2(1)

3-(N-((2-(2-((pyridin-3-ylmethylamino)carbonyl)phenyl)phenyl)carbonyl)-N-(2-(4-methoxyphenyl)ethyl)amino)propanoic acid TLC:Rf 0.56 (chloroform:methanol=9:1); NMR(DMSO-$d_6$, 100 degrees):δ 8.55 (brs, 1H), 8.48 (dd, J=1.2, 4.8 Hz, 1H), 8.30 (s, 1H), 7.60-6.95 (m, 12H), 6.81 (d, J=8.7 Hz, 2H), 4.30-4.20 (m, 2H), 3.73 (s, 3H), 3.50 (t, J=7.5 Hz, 2H), 3.42 (t, J=7.5 Hz, 2H), 2.80-2.60 (m, 2H), 2.20-2.10 (m, 2H).

EXAMPLE 2(2)

3-(N-((2-(2-(benzylaminocarbonyl)phenyl)phenyl)carbonyl)-N-(2-(4-ethoxyphenyl)ethyl)amino)propanoic acid TLC:Rf 0.67 (chloroform:methanol=9:1); NMR(DMSO-$d_6$):δ 9.10-8.60 (m, 1H), 7.60-6.70 (m, 17H), 4.40-3.80 (m, 4H), 3.80-3.00 (m, 4H), 2.80-1.90 (m, 4H), 1.40-1.20 (m, 3H).

EXAMPLE 2(3)

3-(N-((2-(2-(methylaminocarbonyl)phenyl)phenyl)carbonyl)-N-(2-(4-ethoxyphenyl)ethyl)amino)propanoic acid TLC:Rf 0.53 (chloroform:methanol=9:1); NMR(DMSO-$d_6$):δ 8.50-8.00 (m, 1H), 7.60-6.70 (m, 12H), 4.00-3.90 (m, 2H), 3.80-3.00 (m, 4H), 2.80-2.00 (m, 7H). 1.40-1.30 (m, 3H).

EXAMPLE 2(4)

3-(N-((2-(2-(benzylaminocarbonyl)phenyl)phenyl)carbonyl)-N-(2-phenylethyl)amino)propanoic acid TLC:Rf 0.47 (chloroform:methanol=9:1); MASS (APCI, Neg., 40V): 505 (M−H)⁻.

REFERENCE EXAMPLE 3

Polymer-supported Acrylic Acid Ester

To a suspension of a polystyrene-supported Wang resin (Argonaut, catalogue number: 800296) (1.06 mmol/g, 10.0 g) in methylene chloride (100 ml) was added N,N-diisopropylethylamine (9.17 ml) and acryloyl chloride (2.58 ml) at −78 degrees under an atomosphere of argon. The mixture was stirred at room temperature for 16 hours. The resin was filtered off from the reaction mixture and washed with methylene chloride (150 ml×4) and N-methyl-2-pyrrolidone (100 ml×3) to give polymer-supported acrylic acid ester.

REFERENCE EXAMPLE 4 polymer-supported 3-(2-(2,5-dimethoxyphenyl)ethyl)aminopropanoic acid ester

To a solution of the compound prepared in Reference example 3 in N-methyl-2-pyrrolidone (100 ml) was added 2,5-dimethoxyphenethylamine (9.60 g). The mixture was stirred at room temperature for 26 hours. The resin was filtered off from the reaction mixture and washed with N-methyl-2-pyrrolidone (100 ml×3) and methylene chloride (100 ml×4). The obtained resin was dried under reduced pressure to give polymer-supported 3-(2-(2,5-dimethoxyphenyl)ethyl)aminopropanoic acid ester (13.70 g).

REFERENCE EXAMPLE 5 polymer-supported 3-(N-((2-(2-carboxyphenyl)phenyl)carbonyl)-N-(2-(2,5-dimethoxyphenyl)ethyl)amino)propanoic acid ester To a suspension of the compound (4.00 g) prepared in Reference example 4 in N-methyl-2-pyrrolidone (40 ml) was added diphenic anhydride (6.93 g). The mixture was stirred at room temperature for 16 hours. The resin was filtered off from the reaction mixture and washed with N,N-dimethylformamide (50 ml×5) to give polymer-supported 3-(N-((2-(2-carboxyphenyl)phenyl)carbonyl)-N-(2-(2,5-dimethoxyphenyl)ethyl)amino)propanoic acid ester.

REFERENCE EXAMPLE 6 polymer-supported 3-(N-((2-(2-((4-chlorobenzylamino)carbonyl)phenyl)phenyl)carbonyl)-N-(2-(2,5-dimethoxyphenyl)ethyl)amino)propanoic acid ester To a solution of the compound prepared in Reference example 5 in N,N-dimethylformamide (40 ml) were added 4-chlorobenzylamine (3.76 ml), 1-hydroxybenzotriazole monohydrate (4.73 g) and N,N-diisopropylcarbodiimide (4.84 ml). The mixture was stirred at room temperature for 16 hours. The resin was filtered off from the reaction mixture and washed with N,N-dimethylformamide (50 ml×3), methylene chloride (50 ml×3), methanol (50 ml×2) and methylene chloride (50 ml×2) successively to give polymer-supported 3-(N-((2-(2-((4-chlorobenzylamino)carbonyl)phenyl)phenyl)carbonyl)-N-(2-(2,5-dimethoxyphenyl)ethyl)amino)propanoic acid ester

EXAMPLE 3

3-(N-((2-(2-((4-chlorobenzylamino)carbonyl)phenyl)phenyl)carbonyl)-N-(2-(2,5-dimethoxyphenyl)ethyl)amino)propanoic acid The compound prepared in Reference example 6 was suspended in a mixed solvent of trifluoroacetic acid and water (9:1, 40 ml). The mixture was stirred at room temperature for 1 hour. The reaction mixture was filtered. The resin was washed with the mixed solvent of trifluoroacetic acid and water (9:1, 40 ml). The filtrates were combined and then concentrated. The residue was azeotroped with toluene (20 ml×2). The obtained residue was purified by column chromatography on silica gel (ethyl acetate:methanol:acetic acid=100:1:0.1) to give the compound (1.106 g) of the present invention having the following physical data.

TLC:Rf 0.27 (ethyl acetate:methanol:acetic acid=100:1:0.1); NMR(DMSO-$d_6$):δ 12.22 (s, 1H), 9.00-8.60 (m, 1H), 7.60-7.30 (m, 5H), 7.30-7.00 (m, 4H), 6.97 (m, 1H), 6.90-6.40 (m, 5H), 4.45-4.25 (m, 1H), 4.23-3.90 (m, 1H), 3.80-3.10 (m, 11H), 2.78 (m, 1H), 2.49 (m, 1H), 2.08 (m, 1H).

EXAMPLE 3(1)

3-(N-((2-(2-((pyridin-3-ylmethylamino)carbonyl)phenyl)phenyl)carbonyl)-N-(2-(2,5-dimethoxyphenyl)ethyl)amino)propanoic acid The compound of the present invention having the following physical data was obtained by the same procedures as a series of reactions of Reference example 6→Example 3 using 3-pyridylmetnylamine instead of 4-chlorobenzylamine, if necessary, by converting to corresponding salts by conventional method.

Free Form:

TLC:Rf 0.57 (chloroform:methanol:acetic acid=9:1:0.5); NMR(CD$_3$OD):δ 8.61 (m, 1H), 8.34 (br, 1H), 7.73 (m, 2H), 7.64-7.54 (m, 1H), 7.54-7.38 (m, 2H), 7.38-7.20 (m, 2H), 7.16-7.02 (m, 2H), 6.86-6.74 (m, 2H), 6.74-6.60 (m, 2H), 4.58 (d, J=15.3 Hz, 1H), 4.18 (d, J=15.3 Hz, 1H), 3.90-3.70 (m, 1H), 3.72 (s, 3H), 3.53 (s, 3H), 3.65-3.35 (m, 2H), 2.88 (m, 2H), 2.80-2.40 (br, 2H), 2.22 (t, J=7.2 Hz, 2H).

Hydrochloride:

TLC:Rf 0.18 (ethyl acetate:methanol:acetic acid=90:9:0.2); NMR(DMSO-$d_6$):δ 9.20-8.90 (m, 1H), 8.79 (m, 1H), 8.70-8.30 (m, 1H), 8.10-7.70 (m, 2H), 7.60-6.60 (m, 1H), 4.70-4.45 (m, 1H), 4.35-4.10 (m, 1H), 3.80-3.10 (m, 11H), 2.85-2.60 (m, 1H), 2.55-2.30 (m, 1H), 2.25-1.95 (m, 1H).

REFERENCE EXAMPLE 7

Polymer-supported Acrylic Acid Ester

Lantern PS-Wang (trademark) (Mimotopes, code number: SPPSLHMP) (16.0 μmol/Lantern, 1000 pieces) was added to methylene chloride (198 ml) under an atmosphere of argon. To the mixture were added N,N-diisopropylethylamine (77.9 ml) and acryloyl chloride (24.4 ml) at −78 degrees. The reaction mixture was stirred at room temperature for 15 hours. The solid-phase support was filtered off from the reaction mixture, washed with methylene chloride (150 ml×5) and subjected to air-drying to give polymer-supported acrylic acid ester.

REFERENCE EXAMPLE 8

Polymer-supported 3-benzylaminopropanoic Acid Ester

To a solution of benzylamine in N-methyl-2-pyrrolidone (1.0 M, 15 ml) was added the compound prepared in Reference example 7 (45 pieces, 0.72 mmol). The mixture was stirred at room temperature for 16 hours. The solid-phase support was filtered off from the reaction mixture and washed with N-methyl-2-pyrrolidone (20 ml×4) to give polymer-supported 3-benzylaminopropanoic acid ester.

REFERENCE EXAMPLE 9 polymer-supported 3-(N-((2-(2-carboxyphenyl)phenyl)carbonyl)-N-(benzyl)amino)propanoic acid ester The compound prepared in Reference example 8 (1350 pieces, 21.6 mmol) was added N-methyl-2-pyrrolidone (500 ml). To the mixture was added diphenic anhydride (48.4 g). The mixture was stirred at 50 degrees for 60 hours. The solid-phase support was filtered off from the reaction mixture, washed with N,N-dimethylformamide (500 ml×4) and methylene chloride (500 ml×3), and subjected to air-drying to give polymer-supported 3-(N-((2-(2-carboxyphenyl)phenyl)carbonyl)-N-(benzyl)amino)propanoic acid ester.

REFERENCE EXAMPLE 10 polymer-supported 3-(N-((2-(2-((3-methylbenzylamino)carbonyl)phenyl)phenyl)carbonyl)-N-(benzyl)amino)propanoic acid ester The compound prepared in Reference example 9 (30 pieces, 0.48 mmol) was added to N,N-dimethylformamide (10 ml). To the mixture were added 3-methylbenzylamine (2.40 mmol), 1-hydroxybenzotriazole monohydrate (368 mg) and N,N-diisopropylcarbodiimide (0.376 ml). The mixture was stirred at room temperature for 16 hours. The solid-phase support was filtered off from the reaction mixture, washed with N,N-dimethylformamide (10 ml×3) and methylene chloride (10 ml×3), and subjected to air-drying to give polymer-supported 3-(N-((2-(2-((3-methylbenzylamino)carbonyl)phenyl)phenyl)carbonyl)-N-(benzyl)amino)propanoic acid ester.

EXAMPLE 4

3-(N-((2-(2-((3-methylbenzylamino)carbonyl)phenyl)phenyl)carbonyl)-N-(benzyl)amino)propanoic acid The compound (1 piece, 0.016 mmol) prepared in Reference example 10 was added to trifluoroacetic acid (0.5 ml) and treated at room temperature for 1 hour. The solid-phase support was taken out, and washed with trifluoroacetic acid (0.5 ml). The washed solution was combined and then concentrated to give under reduced pressure to give the compound of the present invention having the following physical data. The analysis condition of high performance liquid chromatography (HPLC) is shown below.
column: Xterra (trademark) MS $C_{18}$, 4.6×50 mm I.D., 5 μm, 100 Å;
flow rate: 3 mL/min;

Solvent
A solution: 0.1% aqueous solution of trifluoroacetic acid;
B solution: 0.1% trifluoroacetic acid in acetonitrile.

The mixture ratio of A and B was fixed in 95/5 for 0.5 minutes from starting of measurement. The mixture ratio of A and B was linearly changed to 0/100 for 2.5 minutes. The mixture ratio of A and B was fixed in 0/100 for 0.5 minutes. The mixture ratio of A and B was linearly changed to 95/5 for 0.1 minute.

HPLC retention time: 3.84 minutes; MASS data (ESI, Pos., 20V): 507 $(M+H)^+$.

EXAMPLE 4(1)~(1154)

The compounds of the present invention having the following physical data were obtained by the same procedures as a series of reactions of Reference example 8→Reference example 9 using corresponding amine instead of benzylamine followed by the same procedures as a series of reactions of Reference example 10→Example 4 using corresponding amine instead of 3-methylbenzylamine. The analysis condition of high performance liquid chromatography (HPLC) is shown below.

HPLC Condition A
column: Xterra (trademark) MS $C_{18}$, 4.6×50 mm I.D., 5 μm, 100 Å;
flow rate: 3 mL/min;

Solvent
A solution: 0.1% aqueous solution of trifluoroacetic acid;
B solution: 0.1% trifluoroacetic acid in acetonitrile.

The mixture ratio of A and B was fixed in 95/5 for 0.5 minutes from starting of measurement. The mixture ratio of A and B was linearly changed to 0/100 for 2.5 minutes. The mixture ratio of A and B was fixed in 0/100 for 0.5 minutes. The mixture ratio of A and B was linearly changed to 95/5 for 0.1 minute.

HPLC Condition B
column: Phenomenex Max-RP, 2×50 mm I.D., 4 μm, 80 Å;
flow rate: 250 μL/min;

Solvent
A solution: 0.05% aqueous solution of formic acid;
B solution: 0.05% formic acid in acetonitrile.

The mixture ratio of A and B was fixed in 95/5 at the time of a measurement start. The mixture ratio of A and B was linearly changed to 20/80 for 3.5 minutes. The mixture ratio of A and B was linearly changed to 10/90 for 0.5 minutes. The mixture ratio of A and B was fixed in 10/90 for 0.8 minutes. The mixture ratio of A and B was linearly changed to 95/5 for 1 minute.

EXAMPLE 4(1)

3-(N-((2-(2-((1,2,3,4-tetrahydro-1-naphthylamino)carbonyl)phenyl)phenyl)carbonyl)-N-(2-(1H-indol-3-yl)ethyl)amino)propanoic acid HPLC measurement condition: A HPLC retention time: 3.89 minutes; MASS data (ESI, Pos., 20V): 586 $(M+H)^+$.

EXAMPLE 4(2)

3-(N-((2-(2-((2-furylmethylamino)carbonyl)phenyl)phenyl)carbonyl)-N-(2-(1H-indol-3-yl)ethyl)amino)propanoic acid HPLC measurement condition: A HPLC retention time: 3.64 minutes; MASS data (ESI, Pos., 20V): 536 $(M+H)^+$.

EXAMPLE 4(3)

3-(N-((2-(2-((1-indaneamino)carbonyl)phenyl)phenyl)carbonyl)-N-(2-(1H-indol-3-yl)ethyl)amino)propanoic acid HPLC measurement condition: A HPLC retention time: 3.82 minutes; MASS data (ESI, Pos., 20V): 572 $(M+H)^+$.

EXAMPLE 4(4)

3-(N-((2-(2-((1-naphthylmethylamino)carbonyl)phenyl)phenyl)carbonyl)-N-(2-(1H-indol-3-yl)ethyl)amino)propanoic acid HPLC measurement condition: A HPLC retention time: 3.89 minutes; MASS data (ESI, Pos., 20V): 596 $(M+H)^+$, 214.

EXAMPLE 4(5)

3-(N-((2-(2-((1,2,3,4-tetrahydro-β-carbolin-2-yl)carbonyl)phenyl)phenyl)carbonyl)-N-(2-(1H-indol-3-yl)ethyl)amino)propanoic acid HPLC measurement condition: A HPLC retention time: 3.84 minutes; MASS data (ESI, Pos., 20V): 611 $(M+H)^+$.

EXAMPLE 4(6)

3-(N-((2-(2-((pyridin-2-ylmethylamino)carbonyl)phenyl)phenyl)carbonyl)-N-(2-(1H-indol-3-yl)ethyl)amino)propanoic acid HPLC measurement condition: A HPLC retention time: 3.23 minutes; MASS data (ESI, Pos., 20V): 547 $(M+H)^+$.

EXAMPLE 4(7)

3-(N-((2-(2-((pyridin-3-ylmethylamino)carbonyl)
phenyl)phenyl)carbonyl)-N-(2-(1H-indol-3-yl)ethyl)
amino)propanoic acid HPLC measurement condition: A HPLC retention time: 3.18 minutes; MASS data (ESI, Pos., 20V): 547 (M+H)$^+$.

EXAMPLE 4(8)

3-(N-((2-(2-((pyridin-4-ylmethylamino)carbonyl)
phenyl)phenyl)carbonyl)-N-(2-(1H-indol-3-yl)ethyl)
amino)propanoic acid HPLC measurement condition: A HPLC retention time: 3.14 minutes; MASS data (ESI, Pos., 20V): 547 (M+H)$^+$, 439.

EXAMPLE 4(9)

3-(N-((2-(2-((1,2,3,4-tetrahydroisoquinolin-2-yl)
carbonyl)phenyl)phenyl)carbonyl)-N-(2-(1H-indol-
3-yl)ethyl)amino)propanoic acid HPLC measurement condition: A HPLC retention time: 3.78 minutes; MASS data (ESI, Pos., 20V): 572 (M+H)$^+$.

EXAMPLE 4(10)

3-(N-((2-(2-((α-methylbenzylamino)carbonyl)phe-
nyl)phenyl)carbonyl)-N-(2-(1H-indol-3-yl)ethyl)
amino)propanoic acid HPLC measurement condition: A HPLC retention time: 3.80 minutes; MASS data (ESI, Pos., 20V): 560 (M+H)$^+$.

EXAMPLE 4(11)

3-(N-((2-(2-((benzylamino)carbonyl)phenyl)phenyl)
carbonyl)-N-(2-(1H-indol-3-yl)ethyl)amino)pro-
panoic acid HPLC measurement condition: A HPLC retention time: 3.73 minutes; MASS data (ESI, Pos., 20V): 546 (M+H)$^+$.

EXAMPLE 4(12)

3-(N-((2-(2-((2-methoxybenzylamino)carbonyl)phe-
nyl)phenyl)carbonyl)-N-(2-(1H-indol-3-yl)ethyl)
amino)propanoic acid HPLC measurement condition: A HPLC retention time: 3.75 minutes; MASS data (ESI, Pos., 20V): 576 (M+H)$^+$.

EXAMPLE 4(13)

3-(N-((2-(2-((2-methylbenzylamino)carbonyl)phe-
nyl)phenyl)carbonyl)-N-(2-(1H-indol-3-yl)ethyl)
amino)propanoic acid HPLC measurement condition: A HPLC retention time: 3.80 minutes; MASS data (ESI, Pos., 20V): 560 (M+H)$^+$.

EXAMPLE 4(14)

3-(N-((2-(2-((3-methoxybenzylamino)carbonyl)phe-
nyl)phenyl)carbonyl)-N-(2-(1H-indol-3-yl)ethyl)
amino)propanoic acid HPLC measurement condition: A HPLC retention time: 3.73 minutes; MASS data (ESI, Pos., 20V): 576 (M+H)$^+$.

EXAMPLE 4(15)

3-(N-((2-(2-((4-chlorobenzylamino)carbonyl)phenyl)
phenyl)carbonyl)-N-(2-(1H-indol-3-yl)ethyl)amino)
propanoic acid HPLC measurement condition: A HPLC retention time: 3.86 minutes; MASS data (ESI, Pos., 20V): 580 (M+H)$^+$, 214.

EXAMPLE 4(16)

3-(N-((2-(2-((4-methoxybenzylamino)carbonyl)phe-
nyl)phenyl)carbonyl)-N-(2-(1H-indol-3-yl)ethyl)
amino)propanoic acid HPLC measurement condition: A HPLC retention time: 3.71 minutes; MASS data (ESI, Pos., 20V): 576 (M+H)$^+$.

EXAMPLE 4(17)

3-(N-((2-(2-((4-methylbenzylamino)carbonyl)phe-
nyl)phenyl)carbonyl)-N-(2-(1H-indol-3-yl)ethyl)
amino)propanoic acid HPLC measurement condition: A HPLC retention time: 3.82 minutes; MASS data (ESI, Pos., 20V): 560 (M+H)$^+$.

EXAMPLE 4(18)

3-(N-((2-(2-((N-methyl-N-benzylamino)carbonyl)
phenyl)phenyl)carbonyl)-N-(2-(1H-indol-3-yl)ethyl)
amino)propanoic acid HPLC measurement condition: A HPLC retention time: 3.77 minutes; MASS data (ESI, Pos., 20V): 560 (M+H)$^+$.

EXAMPLE 4(19)

3-(N-((2-(2-((N-isopropyl-N-benzylamino)carbonyl)
phenyl)phenyl)carbonyl)-N-(2-(1H-indol-3-yl)ethyl)
amino)propanoic acid HPLC measurement condition: A HPLC retention time: 3.91 minutes; MASS data (ESI, Pos., 20V): 588 (M+H)$^+$.

EXAMPLE 4(20)

3-(N-((2-(2-((N-ethyl-N-benzylamino)carbonyl)phe-
nyl)phenyl)carbonyl)-N-(2-(1H-indol-3-yl)ethyl)
amino)propanoic acid HPLC measurement condition: A HPLC retention time: 3.84 minutes; MASS data (ESI, Pos., 20V): 574 (M+H)$^+$, 360.

EXAMPLE 4(21)

3-(N-((2-(2-((N-butyl-N-benzylamino)carbonyl)phenyl)phenyl)carbonyl)-N-(2-(1H-indol-3-yl)ethyl)amino)propanoic acid HPLC measurement condition: A HPLC retention time: 4.02 minutes; MASS data (ESI, Pos., 20V): 602 (M+H)$^+$, 388, 214.

EXAMPLE 4(22)

3-(N-((2-(2-((4-(tert-butyl)benzylamino)carbonyl)phenyl)phenyl)carbonyl)-N-(2-(1H-indol-3-yl)ethyl)amino)propanoic acid HPLC measurement condition: A HPLC retention time: 4.02 minutes; MASS data (ESI, Pos., 20V): 602 (M+H)$^+$.

EXAMPLE 4(23)

3-(N-((2-(2-(((5-methyl-2-furyl)methylamino)carbonyl)phenyl)phenyl)carbonyl)-N-(2-(1H-indol-3-yl)ethyl)amino)propanoic acid HPLC measurement condition: A HPLC retention time: 3.71 minutes; MASS data (ESI, Pos., 20V): 550 (M+H)$^+$, 214.

EXAMPLE 4(24)

3-(N-((2-(2-((1-phenyl-3-trifluoroacetoxypropylamino)carbonyl)phenyl)phenyl)carbonyl)-N-(2-(1H-indol-3-yl)ethyl)amino)propanoic acid HPLC measurement condition: A HPLC retention time: 3.98 minutes; MASS data (ESI, Pos., 20V): 686 (M+H)$^+$.

EXAMPLE 4(25)

3-(N-((2-(2-((2-fluorobenzylamino)carbonyl)phenyl)phenyl)carbonyl)-N-(2-(1H-indol-3-yl)ethyl)amino)propanoic acid HPLC measurement condition: A HPLC retention time: 3.77 minutes; MASS data (ESI, Pos., 20V): 564 (M+H)$^+$.

EXAMPLE 4(26)

3-(N-((2-(2-((3-fluorobenzylamino)carbonyl)phenyl)phenyl)carbonyl)-N-(2-(1H-indol-3-yl)ethyl)amino)propanoic acid HPLC measurement condition: A HPLC retention time: 3.77 minutes; MASS data (ESI, Pos., 20V): 564 (M+H)$^+$.

EXAMPLE 4(27)

3-(N-((2-(2-((2,5-difluorobenzylamino)carbonyl)phenyl)phenyl)carbonyl)-N-(2-(1H-indol-3-yl)ethyl)amino)propanoic acid HPLC measurement condition: A HPLC retention time: 3.79 minutes; MASS data (ESI, Pos., 20V): 582 (M+H)$^+$.

EXAMPLE 4(28)

3-(N-((2-(2-(((1R)-1-phenyl-2-hydroxyethylamino)carbonyl)phenyl)phenyl)carbonyl)-N-(2-(1H-indol-3-yl)ethyl)amino)propanoic acid HPLC measurement condition: A HPLC retention time: 3.58 minutes; MASS data (ESI, Pos., 20V): 576 (M+H)$^+$.

EXAMPLE 4(29)

3-(N-((2-(2-((2-chlorobenzylamino)carbonyl)phenyl)phenyl)carbonyl)-N-(2-(1H-indol-3-yl)ethyl)amino)propanoic acid HPLC measurement condition: A HPLC retention time: 3.84 minutes; MASS data (ESI, Pos., 20V): 580 (M+H)$^+$.

EXAMPLE 4(30)

3-(N-((2-(2-((4-fluorobenzylamino)carbonyl)phenyl)phenyl)carbonyl)-N-(2-(1H-indol-3-yl)ethyl)amino)propanoic acid HPLC measurement condition: A HPLC retention time: 3.75 minutes; MASS data (ESI, Pos., 20V): 564 (M+H)$^+$.

EXAMPLE 4(31)

3-(N-((2-(2-((allylamino)carbonyl)phenyl)phenyl)carbonyl)-N-(2-(1H-indo-1-3-yl)ethyl)amino)propanoic acid HPLC measurement condition: A HPLC retention time: 3.56 minutes; MASS data (ESI, Pos., 20V): 496 (M+H)$^+$.

EXAMPLE 4(32)

3-(N-((2-(2-((2,6-difluorobenzylamino)carbonyl)phenyl)phenyl)carbonyl)-N-(2-(1H-indol-3-yl)ethyl)amino)propanoic acid HPLC measurement condition: A HPLC retention time: 3.71 minutes; MASS data (ESI, Pos., 20V): 582 (M+H)$^+$.

EXAMPLE 4(33)

3-(N-((2-(2-((3-chlorobenzylamino)carbonyl)phenyl)phenyl)carbonyl)-N-(2-(1H-indol-3-yl)ethyl)amino)propanoic acid HPLC measurement condition: A HPLC retention time: 3.86 minutes; MASS data (ESI, Pos., 20V): 580 (M+H)$^+$.

EXAMPLE 4(34)

3-(N-((2-(2-(((1S)-1-phenyl-2-hydroxyethylamino)carbonyl)phenyl)phenyl)carbonyl)-N-(2-(1H-indol-3-yl)ethyl)amino)propanoic acid HPLC measurement condition: A HPLC retention time: 3.58 minutes; MASS data (ESI, Pos., 20V): 576 (M+H)$^+$.

EXAMPLE 4(35)

3-(N-((2-(2-(((1R)-1-(4-methylphenyl)ethylamino)carbonyl)phenyl)phenyl)carbonyl)-N-(2-(1H-indol-3-yl)ethyl)amino)propanoic acid HPLC measurement condition: A HPLC retention time: 3.88 minutes; MASS data (ESI, Pos., 20V): 574 (M+H)+.

EXAMPLE 4(36)

3-(N-((2-(2-((1-(4-fluorophenyl)ethylamino)carbonyl)phenyl)phenyl)carbonyl)-N-(2-(1H-indol-3-yl)ethyl)amino)propanoic acid HPLC measurement condition: A HPLC retention time: 3.82 minutes; MASS data (ESI, Pos., 20V): 578 (M+H)+.

EXAMPLE 4(37)

3-(N-((2-(2-((2-thienylmethylamino)carbonyl)phenyl)phenyl)carbonyl)-N-(2-(H-indol-3-yl)ethyl)amino)propanoic acid HPLC measurement condition: A HPLC retention time: 3.71 minutes; MASS data (ESI, Pos., 20V): 552 (M+H)+, 214.

EXAMPLE 4(38)

3-(N-((2-(2-(((3S)-3-hydroxymethyl-1,2,3,4-tetrahydroisoquinolin-2-yl)carbonyl)phenyl)phenyl)carbonyl)-N-(2-(1H-indol-3-yl)ethyl)amino)propanoic acid HPLC measurement condition: A HPLC retention time: 3.48 minutes; MASS data (ESI, Pos., 20V): 602 (M+H)+; HPLC retention time: 3.62 minutes; MASS data (ESI, Pos., 20V): 602 (M+H)+, 498.

EXAMPLE 4(39)

3-(N-((2-(2-((3-methylbenzylamino)carbonyl)phenyl)phenyl)carbonyl)-N-(2-(1H-indol-3-yl)ethyl)amino)propanoic acid HPLC measurement condition: A HPLC retention time: 3.82 minutes; MASS data (ESI, Pos., 20V): 560 (M+H)+.

EXAMPLE 4(40)

3-(N-((2-(2-((3,5-difluorobenzylamino)carbonyl)phenyl)phenyl)carbonyl)-N-(2-(1H-indol-3-yl)ethyl)amino)propanoic acid HPLC measurement condition: A HPLC retention time: 3.82 minutes; MASS data (ESI, Pos., 20V): 582 (M+H)+.

EXAMPLE 4(41)

3-(N-((2-(2-((N-methyl-N-(6-methylpyridin-2-yl)methylamino)carbonyl)phenyl)phenyl)carbonyl)-N-(2-(1H-indol-3-yl)ethyl)amino)propanoic acid HPLC measurement condition: A HPLC retention time: 3.22 minutes; MASS data (ESI, Pos., 20V): 575 (M+H)+.

EXAMPLE 4(42)

3-(N-((2-(2-((N-(2-(N,N-dimethylamino)ethyl)-N-benzylamino)carbonyl)phenyl)phenyl)carbonyl)-N-(2-(1H-indol-3-yl)ethyl)amino)propanoic acid HPLC measurement condition: A HPLC retention time: 3.44 minutes; MASS data (ESI, Pos., 20V): 617 (M+H)+.

EXAMPLE 4(43)

3-(N-((2-(2-((2-phenylethylamino)carbonyl)phenyl)phenyl)carbonyl)-N-(2-(1H-indol-3-yl)ethyl)amino)propanoic acid HPLC measurement condition: A HPLC retention time: 3.78 minutes; MASS data (ESI, Pos., 20V): 560 (M+H)+.

EXAMPLE 4(44)

3-(N-((2-(2-((1,2,3,4-tetrahydro-1-naphthylamino)carbonyl)phenyl)phenyl)carbonyl)-N-(2-(2,3-dimethoxyphenyl)ethyl)amino)propanoic acid HPLC measurement condition: A HPLC retention time: 3.95 minutes; MASS data (ESI, Pos., 20V): 607 (M+H)+.

EXAMPLE 4(45)

3-(N-((2-(2-((N-benzyl-N-(2-hydroxyethyl)amino)carbonyl)phenyl)phenyl)carbonyl)-N-(2-(2,3-dimethoxyphenyl)ethyl)amino)propanoic acid HPLC measurement condition: A HPLC retention time: 3.64 minutes; MASS data (ESI, Pos., 20V): 611 (M+H)+.

EXAMPLE 4(46)

3-(N-((2-(2-((2-furylmethylamino)carbonyl)phenyl)phenyl)carbonyl)-N-(2-(2,3-dimethoxyphenyl)ethyl)amino)propanoic acid HPLC measurement condition: A HPLC retention time: 3.69 minutes; MASS data (ESI, Pos., 20V): 557 (M+H)+.

EXAMPLE 4(47)

3-(N-((2-(2-((1-indaneamino)carbonyl)phenyl)phenyl)carbonyl)-N-(2-(2,3-dimethoxyphenyl)ethyl)amino)propanoic acid HPLC measurement condition: A HPLC retention time: 3.89 minutes; MASS data (ESI, Pos., 20V): 593 (M+H)+.

EXAMPLE 4(48)

3-(N-((2-(2-((1-naphthylmethylamino)carbonyl)phenyl)phenyl)carbonyl)-N-(2-(2,3-dimethoxyphenyl)ethyl)amino)propanoic acid HPLC measurement condition: A HPLC retention time: 3.95 minutes; MASS data (ESI, Pos., 20V): 617 (M+H)+.

EXAMPLE 4(49)

3-(N-((2-(2-((pyridin-2-ylmethylamino)carbonyl)
phenyl)phenyl)carbonyl)-N-(2-(2,3-dimethoxyphe-
nyl)ethyl)amino)propanoic acid HPLC measurement condition: A HPLC retention time: 3.23 minutes; MASS data (ESI, Pos., 20V): 568 (M+H)$^+$.

EXAMPLE 4(50)

3-(N-((2-(2-((pyridin-3-ylmethylamino)carbonyl)
phenyl)phenyl)carbonyl)-N-(2-(2,3-dimethoxyphe-
nyl)ethyl)amino)propanoic acid HPLC measurement condition: A HPLC retention time: 3.18 minutes; MASS data (ESI, Pos., 20V): 568 (M+H)$^+$.

EXAMPLE 4(51)

3-(N-((2-(2-((1,2,3,4-tetrahydroisoquinolin-2-yl)
carbonyl)phenyl)phenyl)carbonyl)-N-(2-(2,3-
dimethoxyphenyl)ethyl)amino)propanoic acid HPLC measurement condition: A HPLC retention time: 3.84 minutes; MASS data (ESI, Pos., 20V): 593 (M+H)$^+$.

EXAMPLE 4(52)

3-(N-((2-(2-((α-methylbenzylamino)carbonyl)phe-
nyl)phenyl)carbonyl)-N-(2-(2,3-dimethoxyphenyl)
ethyl)amino)propanoic acid HPLC measurement condition: A HPLC retention time: 3.86 minutes; MASS data (ESI, Pos., 20V): 581 (M+H)$^+$.

EXAMPLE 4(53)

3-(N-((2-(2-((benzylamino)carbonyl)phenyl)phenyl)
carbonyl)-N-(2-(2,3-dimethoxyphenyl)ethyl)amino)
propanoic acid HPLC measurement condition: A HPLC retention time: 3.80 minutes; MASS data (ESI, Pos., 20V): 567 (M+H)$^+$.

EXAMPLE 4(54)

3-(N-((2-(2-((2-methoxybenzylamino)carbonyl)phe-
nyl)phenyl)carbonyl)-N-(2-(2,3-dimethoxyphenyl)
ethyl)amino)propanoic acid HPLC measurement condition: A HPLC retention time: 3.80 minutes; MASS data (ESI, Pos., 20V): 597 (M+H)$^+$.

EXAMPLE 4(55)

3-(N-((2-(2-((2-methylbenzylamino)carbonyl)phe-
nyl)phenyl)carbonyl)-N-(2-(2,3-dimethoxyphenyl)
ethyl)amino)propanoic acid HPLC measurement condition: A HPLC retention time: 3.86 minutes; MASS data (ESI, Pos., 20V): 581 (M+H)$^+$.

EXAMPLE 4(56)

3-(N-((2-(2-((3-methoxybenzylamino)carbonyl)phe-
nyl)phenyl)carbonyl)-N-(2-(2,3-dimethoxyphenyl)
ethyl)amino)propanoic acid HPLC measurement condition: A HPLC retention time: 3.77 minutes; MASS data (ESI, Pos., 20V): 597 (M+H)$^+$.

EXAMPLE 4(57)

3-(N-((2-(2-((4-chlorobenzylamino)carbonyl)phenyl)
phenyl)carbonyl)-N-(2-(2,3-dimethoxyphenyl)ethyl)
amino)propanoic acid HPLC measurement condition: A HPLC retention time: 3.93 minutes; MASS data (ESI, Pos., 20V): 601 (M+H)$^+$.

EXAMPLE 4(58)

3-(N-((2-(2-((4-methoxybenzylamino)carbonyl)phe-
nyl)phenyl)carbonyl)-N-(2-(2,3-dimethoxyphenyl)
ethyl)amino)propanoic acid HPLC measurement condition: A HPLC retention time: 3.77 minutes; MASS data (ESI, Pos., 20V): 597 (M+H)$^+$.

EXAMPLE 4(59)

3-(N-((2-(2-((4-methylbenzylamino)carbonyl)phe-
nyl)phenyl)carbonyl)-N-(2-(2,3-dimethoxyphenyl)
ethyl)amino)propanoic acid HPLC measurement condition: A HPLC retention time: 3.88 minutes; MASS data (ESI, Pos., 20V): 581 (M+H)$^+$.

EXAMPLE 4(60)

3-(N-((2-(2-((N-methyl-N-benzylamino)carbonyl)
phenyl)phenyl)carbonyl)-N-(2-(2,3-dimethoxyphe-
nyl)ethyl)amino)propanoic acid HPLC measurement condition: A HPLC retention time: 3.82 minutes; MASS data (ESI, Pos., 20V): 581 (M+H)$^+$.

EXAMPLE 4(61)

3-(N-((2-(2-((N-ethyl-N-benzylamino)carbonyl)phe-
nyl)phenyl)carbonyl)-N-(2-(2,3-dimethoxyphenyl)
ethyl)amino)propanoic acid HPLC measurement condition: A HPLC retention time: 3.89 minutes; MASS data (ESI, Pos., 20V): 595 (M+H)$^+$.

EXAMPLE 4(62)

3-(N-((2-(2-((N-butyl-N-benzylamino)carbonyl)
phenyl)phenyl)carbonyl)-N-(2-(2,3-dimethoxyphe-
nyl)ethyl)amino)propanoic acid HPLC measurement condition: A HPLC retention time: 4.08 minutes; MASS data (ESI, Pos., 20V): 623 (M+H)$^+$.

EXAMPLE 4(63)

3-(N-((2-(2-((4-(tert-butyl)benzylamino)carbonyl)phenyl)phenyl)carbonyl)-N-(2-(2,3-dimethoxyphenyl)ethyl)amino)propanoic acid HPLC measurement condition: A HPLC retention time: 4.11 minutes; MASS data (ESI, Pos., 20V): 623 (M+H)$^+$.

EXAMPLE 4(64)

3-(N-((2-(2-(((5-methyl-2-furyl)methylamino)carbonyl)phenyl)phenyl)carbonyl)-N-(2-(2,3-dimethoxyphenyl)ethyl)amino)propanoic acid HPLC measurement condition: A HPLC retention time: 3.77 minutes; MASS data (ESI, Pos., 20V): 571 (M+H)$^+$.

EXAMPLE 4(65)

3-(N-((2-(2-((1-phenyl-3-trifluoroacetoxypropylamino)carbonyl)phenyl)phenyl)carbonyl)-N-(2-(2,3-dimethoxyphenyl)ethyl)amino)propanoic acid HPLC measurement condition: A HPLC retention time: 4.05 minutes; MASS data (ESI, Pos., 20V): 707 (M+H)$^+$.

EXAMPLE 4(66)

3-(N-((2-(2-((2-fluorobenzylamino)carbonyl)phenyl)phenyl)carbonyl)-N-(2-(2,3-dimethoxyphenyl)ethyl)amino)propanoic acid HPLC measurement condition: A HPLC retention time: 3.80 minutes; MASS data (ESI, Pos., 20V): 585 (M+H)$^+$.

EXAMPLE 4(67)

3-(N-((2-(2-((3-fluorobenzylamino)carbonyl)phenyl)phenyl)carbonyl)-N-(2-(2,3-dimethoxyphenyl)ethyl)amino)propanoic acid HPLC measurement condition: A HPLC retention time: 3.82 minutes; MASS data (ESI, Pos., 20V): 585 (M+H)$^+$.

EXAMPLE 4(68)

3-(N-((2-(2-((2,5-difluorobenzylamino)carbonyl)phenyl)phenyl)carbonyl)-N-(2-(2,3-dimethoxyphenyl)ethyl)amino)propanoic acid HPLC measurement condition: A HPLC retention time: 3.84 minutes; MASS data (ESI, Pos., 20V): 603 (M+H)$^+$.

EXAMPLE 4(69)

3-(N-((2-(2-(((1R)-1-phenyl-2-hydroxyethylamino)carbonyl)phenyl)phenyl)carbonyl)-N-(2-(2,3-dimethoxyphenyl)ethyl)amino)propanoic acid HPLC measurement condition: A HPLC retention time: 3.62 minutes; MASS data (ESI, Pos., 20V): 597 (M+H)$^+$.

EXAMPLE 4(70)

3-(N-((2-(2-((2-chlorobenzylamino)carbonyl)phenyl)phenyl)carbonyl)-N-(2-(2,3-dimethoxyphenyl)ethyl)amino)propanoic acid HPLC measurement condition: A HPLC retention time: 3.89 minutes; MASS data (ESI, Pos., 20V): 601 (M+H)$^+$.

EXAMPLE 4(71)

3-(N-((2-(2-((4-fluorobenzylamino)carbonyl)phenyl)phenyl)carbonyl)-N-(2-(2,3-dimethoxyphenyl)ethyl)amino)propanoic acid HPLC measurement condition: A HPLC retention time: 3.80 minutes; MASS data (ESI, Pos., 20V): 585 (M+H)$^+$.

EXAMPLE 4(72)

3-(N-((2-(2-((allylamino)carbonyl)phenyl)phenyl)carbonyl)-N-(2-(2,3-dimethoxyphenyl)ethyl)amino)propanoic acid HPLC measurement condition: A HPLC retention time: 3.62 minutes; MASS data (ESI, Pos., 20V): 517 (M+H)$^+$.

EXAMPLE 4(73)

3-(N-((2-(2-((2,6-difluorobenzylamino)carbonyl)phenyl)phenyl)carbonyl)-N-(2-(2,3-dimethoxyphenyl)ethyl)amino)propanoic acid HPLC measurement condition: A HPLC retention time: 3.77 minutes; MASS data (ESI, Pos., 20V): 603 (M+H)$^+$.

EXAMPLE 4(74)

3-(N-((2-(2-((3-chlorobenzylamino)carbonyl)phenyl)phenyl)carbonyl)-N-(2-(2,3-dimethoxyphenyl)ethyl)amino)propanoic acid HPLC measurement condition: A HPLC retention time: 3.93 minutes; MASS data (ESI, Pos., 20V): 601 (M+H)$^+$.

EXAMPLE 4(75)

3-(N-((2-(2-(((1S)-1-phenyl-2-hydroxyethylamino)carbonyl)phenyl)phenyl)carbonyl)-N-(2-(2,3-dimethoxyphenyl)ethyl)amino)propanoic acid HPLC measurement condition: A HPLC retention time: 3.62 minutes; MASS data (ESI, Pos., 20V): 597 (M+H)$^+$.

EXAMPLE 4(76)

3-(N-((2-(2-(((1R)-1-(4-methylphenyl)ethylamino)carbonyl)phenyl)phenyl)carbonyl)-N-(2-(2,3-dimethoxyphenyl)ethyl)amino)propanoic acid HPLC measurement condition: A HPLC retention time: 3.93 minutes; MASS data (ESI, Pos., 20V): 595 (M+H)$^+$.

EXAMPLE 4(77)

3-(N-((2-(2-((1-(4-fluorophenyl)ethylamino)carbonyl)phenyl)phenyl)carbonyl)-N-(2-(2,3-dimethoxyphenyl)ethyl)amino)propanoic acid HPLC measurement condition: A HPLC retention time: 3.89 minutes; MASS data (ESI, Pos., 20V): 599 (M+H)$^+$.

EXAMPLE 4(78)

3-(N-((2-(2-((2-thienylmethylamino)carbonyl)phenyl)phenyl)carbonyl)-N-(2-(2,3-dimethoxyphenyl)ethyl)amino)propanoic acid HPLC measurement condition: A HPLC retention time: 3.75 minutes; MASS data (ESI, Pos., 20V): 573 (M+H)$^+$.

EXAMPLE 4(79)

3-(N-((2-(2-(((3S)-3-hydroxymethyl-1,2,3,4-tetrahydroisoquinolin-2-yl)carbonyl)phenyl)phenyl)carbonyl)-N-(2-(2,3-dimethoxyphenyl)ethyl)amino)propanoic acid HPLC measurement condition: A HPLC retention time: 3.67 minutes; MASS data (ESI, Pos., 20V): 623 (M+H)$^+$.

EXAMPLE 4(80)

3-(N-((2-(2-((3-methylbenzylamino)carbonyl)phenyl)phenyl)carbonyl)-N-(2-(2,3-dimethoxyphenyl)ethyl)amino)propanoic acid HPLC measurement condition: A HPLC retention time: 3.88 minutes; MASS data (ESI, Pos., 20V): 581 (M+H)$^+$.

EXAMPLE 4(81)

3-(N-((2-(2-((3,5-difluorobenzylamino)carbonyl)phenyl)phenyl)carbonyl)-N-(2-(2,3-dimethoxyphenyl)ethyl)amino)propanoic acid HPLC measurement condition: A HPLC retention time: 3.89 minutes; MASS data (ESI, Pos., 20V): 603 (M+H)$^+$.

EXAMPLE 4(82)

3-(N-((2-(2-((N-methyl-N-(6-methylpyridin-2-yl)methylamino)carbonyl)phenyl)phenyl)carbonyl)-N-(2-(2,3-dimethoxyphenyl)ethyl)amino)propanoic acid HPLC measurement condition: A HPLC retention time: 3.22 minutes; MASS data (ESI, Pos., 20V): 596 (M+H)$^+$.

EXAMPLE 4(83)

3-(N-((2-(2-((N-(2-(N,N-dimethylamino)ethyl)-N-benzylamino)carbonyl)phenyl)phenyl)carbonyl)-N-(2-(2,3-dimethoxyphenyl)ethyl)amino)propanoic acid HPLC measurement condition: A HPLC retention time: 3.45 minutes; MASS data (ESI, Pos., 20V): 638 (M+H)$^+$.

EXAMPLE 4(84)

3-(N-((2-(2-((2-phenylethylamino)carbonyl)phenyl)phenyl)carbonyl)-N-(2-(2,3-dimethoxyphenyl)ethyl)amino)propanoic acid HPLC measurement condition: A HPLC retention time: 3.86 minutes; MASS data (ESI, Pos., 20V): 581 (M+H)$^+$.

EXAMPLE 4(85)

3-(N-((2-(2-((1,2,3,4-tetrahydro-1-naphthylamino)carbonyl)phenyl)phenyl)carbonyl)-N-(2-(pyridin-3-yl)ethyl)amino)propanoic acid HPLC measurement condition: A HPLC retention time: 3.22 minutes; MASS data (ESI, Pos., 20V): 548 (M+H)$^+$.

EXAMPLE 4(86)

3-(N-((2-(2-((N-benzyl-N-(2-hydroxyethyl)amino)carbonyl)phenyl)phenyl)carbonyl)-N-(2-(pyridin-3-yl)ethyl)amino)propanoic acid HPLC measurement condition: A HPLC retention time: 3.03 minutes; MASS data (ESI, Pos., 20V): 552 (M+H)$^+$.

EXAMPLE 4(87)

3-(N-((2-(2-((2-furylmethylamino)carbonyl)phenyl)phenyl)carbonyl)-N-(2-(pyridin-3-yl)ethyl)amino)propanoic acid HPLC measurement condition: A HPLC retention time: 3.00 minutes; MASS data (ESI, Pos., 20V): 498 (M+H)$^+$.

EXAMPLE 4(88)

3-(N-((2-(2-((1-indaneamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 534 (M+H)$^+$.

EXAMPLE 4(89)

3-(N-((2-(2-((1-naphthylmethylamino)carbonyl)phenyl)phenyl)carbonyl)-N-(2-(pyridin-3-yl)ethyl)amino)propanoic acid HPLC measurement condition: A HPLC retention time: 3.25 minutes; MASS data (ESI, Pos., 20V): 558 (M+H)$^+$.

EXAMPLE 4(90)

3-(N-((2-(2-((pyridin-2-ylmethylamino)carbonyl)phenyl)phenyl)carbonyl)-N-(2-(pyridin-3-yl)ethyl)amino)propanoic acid HPLC measurement condition: A HPLC retention time: 2.72 minutes; MASS data (ESI, Pos., 20V): 509 (M+H)$^+$, 255.

EXAMPLE 4(91)

3-(N-((2-(2-((pyridin-3-ylmethylamino)carbonyl)phenyl)phenyl)carbonyl)-N-(2-(pyridin-3-yl)ethyl)amino)propanoic acid HPLC measurement condition: A HPLC retention time: 2.68 minutes; MASS data (ESI, Pos., 20V): 509 (M+H)$^+$, 255.

EXAMPLE 4(92)

3-(N-((2-(2-((1,2,3,4-tetrahydroisoquinolin-2-yl)carbonyl)phenyl)phenyl)carbonyl)-N-(2-(pyridin-3-yl)ethyl)amino)propanoic acid HPLC measurement condition: A HPLC retention time: 3.20 minutes; MASS data (ESI, Pos., 20V): 534 (M+H)$^+$.

EXAMPLE 4(93)

3-(N-((2-(2-((α-methylbenzylamino)carbonyl)phenyl)phenyl)carbonyl)-N-(2-(pyridin-3-yl)ethyl)amino)propanoic acid HPLC measurement condition: A HPLC retention time: 3.14 minutes; MASS data (ESI, Pos., 20V): 522 (M+H)$^+$.

EXAMPLE 4(94)

3-(N-((2-(2-((benzylamino)carbonyl)phenyl)phenyl)carbonyl)-N-(2-(pyridin-3-yl)ethyl)amino)propanoic acid HPLC measurement condition: A HPLC retention time: 3.11 minutes; MASS data (ESI, Pos., 20V): 508 (M+H)$^+$.

EXAMPLE 4(95)

3-(N-((2-(2-((2-methoxybenzylamino)carbonyl)phenyl)phenyl)carbonyl)-N-(2-(pyridin-3-yl)ethyl)amino)propanoic acid HPLC measurement condition: A HPLC retention time: 3.12 minutes; MASS data (ESI, Pos., 20V): 538 (M+H)$^+$.

EXAMPLE 4(96)

3-(N-((2-(2-((2-methylbenzylamino)carbonyl)phenyl)phenyl)carbonyl)-N-(2-(pyridin-3-yl)ethyl)amino)propanoic acid HPLC measurement condition: A HPLC retention time: 3.14 minutes; MASS data (ESI, Pos., 20V): 522 (M+H)$^+$.

EXAMPLE 4(97)

3-(N-((2-(2-((4-chlorobenzylamino)carbonyl)phenyl)phenyl)carbonyl)-N-(2-(pyridin-3-yl)ethyl)amino)propanoic acid HPLC measurement condition: A HPLC retention time: 3.22 minutes; MASS data (ESI, Pos., 20V): 542 (M+H)$^+$.

EXAMPLE 4(98)

3-(N-((2-(2-((4-methoxybenzylamino)carbonyl)phenyl)phenyl)carbonyl)-N-(2-(pyridin-3-yl)ethyl)amino)propanoic acid HPLC measurement condition: A HPLC retention time: 3.09 minutes; MASS data (ESI, Pos., 20V): 538 (M+H)$^+$.

EXAMPLE 4(99)

3-(N-((2-(2-((4-methylbenzylamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 522 (M+H)$^+$.

EXAMPLE 4(100)

3-(N-((2-(2-((N-methyl-N-benzylamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 522 (M+H)$^+$.

EXAMPLE 4(101)

3-(N-((2-(2-((N-ethyl-N-benzylamino)carbonyl)phenyl)phenyl)carbonyl)-N-(2-(pyridin-3-yl)ethyl)amino)propanoic acid HPLC measurement condition: A HPLC retention time: 3.25 minutes; MASS data (ESI, Pos., 20V): 536 (M+H)$^+$.

EXAMPLE 4(102)

3-(N-((2-(2-((N-butyl-N-benzylamino)carbonyl)phenyl)phenyl)carbonyl)-N-(2-(pyridin-3-yl)ethyl)amino)propanoic acid HPLC measurement condition: A HPLC retention time: 3.40 minutes; MASS data (ESI, Pos., 20V): 564 (M+H)$^+$.

EXAMPLE 4(103)

3-(N-((2-(2-((4-(tert-butyl)benzylamino)carbonyl)phenyl)phenyl)carbonyl)-N-(2-(pyridin-3-yl)ethyl)amino)propanoic acid HPLC measurement condition: A HPLC retention time: 3.38 minutes; MASS data (ESI, Pos., 20V): 564 (M+H)$^+$.

EXAMPLE 4(104)

3-(N-((2-(2-((3-fluorobenzylamino)carbonyl)phenyl)phenyl)carbonyl)-N-(2-(pyridin-3-yl)ethyl)amino)propanoic acid HPLC measurement condition: A HPLC retention time: 3.12 minutes; MASS data (ESI, Pos., 20V): 526 (M+H)$^+$.

EXAMPLE 4(105)

3-(N-((2-(2-((2,5-difluorobenzylamino)carbonyl)phenyl)phenyl)carbonyl)-N-(2-(pyridin-3-yl)ethyl)amino)propanoic acid HPLC measurement condition: A HPLC retention time: 3.14 minutes; MASS data (ESI, Pos., 20V): 544 (M+H)+.

EXAMPLE 4(106)

3-(N-((2-(2-(((1R)-1-phenyl-2-hydroxyethylamino)carbonyl)phenyl)phenyl)carbonyl)-N-(2-(pyridin-3-yl)ethyl)amino)propanoic acid HPLC measurement condition: A HPLC retention time: 3.00 minutes; MASS data (ESI, Pos., 20V): 538 (M+H)+.

EXAMPLE 4(107)

3-(N-((2-(2-((2-chlorobenzylamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 542 (M+H)+.

EXAMPLE 4(108)

3-(N-((2-(2-((4-fluorobenzylamino)carbonyl)phenyl)phenyl)carbonyl)-N-(2-(pyridin-3-yl)ethyl)amino)propanoic acid HPLC measurement condition: A HPLC retention time: 3.11 minutes; MASS data (ESI, Pos., 20V): 526 (M+H)+.

EXAMPLE 4(109)

3-(N-((2-(2-((allylamino)carbonyl)phenyl)phenyl)carbonyl)-N-(2-(pyridin-3-yl)ethyl)amino)propanoic acid HPLC measurement condition: A HPLC retention time: 2.92 minutes; MASS data (ESI, Pos., 20V): 458 (M+H)+.

EXAMPLE 4(110)

3-(N-((2-(2-((2,6-difluorobenzylamino)carbonyl)phenyl)phenyl)carbonyl)-N-(2-(pyridin-3-yl)ethyl)amino)propanoic acid HPLC measurement condition: A HPLC retention time: 3.11 minutes; MASS data (ESI, Pos., 20V): 544 (M+H)+.

EXAMPLE 4(111)

3-(N-((2-(2-((3-chlorobenzylamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 542 (M+H)+.

EXAMPLE 4(112)

3-(N-((2-(2-(((1S)-1-phenyl-2-hydroxyethylamino)carbonyl)phenyl)phenyl)carbonyl)-N-(2-(pyridin-3-yl)ethyl)amino)propanoic acid HPLC measurement condition: A HPLC retention time: 2.98 minutes; MASS data (ESI, Pos., 20V): 538 (M+H)+.

EXAMPLE 4(113)

3-(N-((2-(2-(((1R)-1-(4-methyl phenyl)ethylamino)carbonyl)phenyl)phenyl)carbonyl)-N-(2-(pyridin-3-yl)ethyl)amino)propanoic acid HPLC measurement condition: A HPLC retention time: 3.23 minutes; MASS data (ESI, Pos., 20V): 536 (M+H)+.

EXAMPLE 4(114)

3-(N-((2-(2-((1-(4-fluorophenyl)ethylamino)carbonyl)phenyl)phenyl)carbonyl)-N-(2-(pyridin-3-yl)ethyl)amino)propanoic acid HPLC measurement condition: A HPLC retention time: 3.20 minutes; MASS data (ESI, Pos., 20V): 540 (M+H)+.

EXAMPLE 4(115)

3-(N-((2-(2-((2-thienylmethylamino)carbonyl)phenyl)phenyl)carbonyl)-N-(2-(pyridin-3-yl)ethyl)amino)propanoic acid HPLC measurement condition: A HPLC retention time: 3.07 minutes; MASS data (ESI, Pos., 20V): 514 (M+H)+.

EXAMPLE 4(116)

3-(N-((2-(2-(((3S)-3-hydroxymethyl-1,2,3,4-tetrahydroisoquinolin-2-yl)carbonyl)phenyl)phenyl)carbonyl)-N-(2-(pyridin-3-yl)ethyl)amino)propanoic acid HPLC measurement condition: A HPLC retention time: 3.07 minutes; MASS data (ESI, Pos., 20V): 564 (M+H)+, 283.

EXAMPLE 4(117)

3-(N-((2-(2-((3-methylbenzylamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 522 (M+H)+.

EXAMPLE 4(118)

3-(N-((2-(2-((3,5-difluorobenzylamino)carbonyl)phenyl)phenyl)carbonyl)-N-(2-(pyridin-3-yl)ethyl)amino)propanoic acid HPLC measurement condition: A HPLC retention time: 3.18 minutes; MASS data (ESI, Pos., 20V): 544 (M+H)+.

EXAMPLE 4(119)

3-(N-((2-(2-((N-methyl-N-(6-methylpyridin-2-yl) methylamino)carbonyl)phenyl)phenyl)carbonyl)-N-(2-(pyridin-3-yl)ethyl)amino)propanoic acid HPLC measurement condition: A HPLC retention time: 2.74 minutes; MASS data (ESI, Pos., 20V): 537 (M+H)$^+$, 432, 269.

EXAMPLE 4(120)

3-(N-((2-(2-((N-(2-(N,N-dimethylamino)ethyl)-N-benzylamino)carbonyl)phenyl)phenyl)carbonyl)-N-(2-(pyridin-3-yl)ethyl)amino)propanoic acid HPLC measurement condition: A HPLC retention time: 2.92 minutes; MASS data (ESI, Pos., 20V): 579 (M+H)$^+$, 290, 267.

EXAMPLE 4(121)

3-(N-((2-(2-((2-phenylethylamino)carbonyl)phenyl) phenyl)carbonyl)-N-(2-(pyridin-3-yl)ethyl)amino) propanoic acid HPLC measurement condition: A HPLC retention time: 3.16 minutes; MASS data (ESI, Pos., 20V): 522 (M+H)$^+$.

EXAMPLE 4(122)

3-(N-((2-(2-((1,2,3,4-tetrahydro-1-naphthylamino) carbonyl)phenyl)phenyl)carbonyl)-N-(2-(4-methylphenyl)ethyl)amino)propanoic acid HPLC measurement condition: A HPLC retention time: 4.08 minutes; MASS data (ESI, Pos., 20V): 561 (M+H)$^+$.

EXAMPLE 4(123)

3-(N-((2-(2-((N-benzyl-N-(2-hydroxyethyl)amino) carbonyl)phenyl)phenyl)carbonyl)-N-(2-(4-methylphenyl)ethyl)amino)propanoic acid HPLC measurement condition: A HPLC retention time: 3.77 minutes; MASS data (ESI, Pos., 20V): 565 (M+H)$^+$.

EXAMPLE 4(124)

3-(N-((2-(2-((1-indaneamino)carbonyl)phenyl)phenyl)carbonyl)-N-(2-(4-methylphenyl)ethyl)amino) propanoic acid HPLC measurement condition: A HPLC retention time: 4.00 minutes; MASS data (ESI, Pos., 20V): 547 (M+H)$^+$.

EXAMPLE 4(125)

3-(N-((2-(2-((1-naphthylmethylamino)carbonyl)phenyl)phenyl)carbonyl)-N-(2-(4-methylphenyl)ethyl) amino)propanoic acid HPLC measurement condition: A HPLC retention time: 4.08 minutes; MASS data (ESI, Pos., 20V): 571 (M+H)$^+$.

EXAMPLE 4(126)

3-(N-((2-(2-((pyridin-2-ylmethylamino)carbonyl) phenyl)phenyl)carbonyl)-N-(2-(4-methylphenyl) ethyl)amino)propanoic acid HPLC measurement condition: A HPLC retention time: 3.33 minutes; MASS data (ESI, Pos., 20V): 522 (M+H)$^+$.

EXAMPLE 4(127)

3-(N-((2-(2-((pyridin-3-ylmethylamino)carbonyl) phenyl)phenyl)carbonyl)-N-(2-(4-methylphenyl) ethyl)amino)propanoic acid HPLC measurement condition: A HPLC retention time: 3.27 minutes; MASS data (ESI, Pos., 20V): 522 (M+H)$^+$.

EXAMPLE 4(128)

3-(N-((2-(2-((1,2,3,4-tetrahydroisoquinolin-2-yl) carbonyl)phenyl)phenyl)carbonyl)-N-(2-(4-methylphenyl)ethyl)amino)propanoic acid HPLC measurement condition: A HPLC retention time: 3.95 minutes; MASS data (ESI, Pos., 20V): 547 (M+H)$^+$.

EXAMPLE 4(129)

3-(N-((2-(2-((α-methylbenzylamino)carbonyl)phenyl)phenyl)carbonyl)-N-(2-(4-methylphenyl)ethyl) amino)propanoic acid HPLC measurement condition: A HPLC retention time: 3.99 minutes; MASS data (ESI, Pos., 20V): 535 (M+H)$^+$.

EXAMPLE 4(130)

3-(N-((2-(2-((benzylamino)carbonyl)phenyl)phenyl) carbonyl)-N-(2-(4-methylphenyl)ethyl)amino)propanoic acid HPLC measurement condition: A HPLC retention time: 3.91 minutes; MASS data (ESI, Pos., 20V): 521 (M+H)$^+$.

EXAMPLE 4(131)

3-(N-((2-(2-((2-methoxybenzylamino)carbonyl)phenyl)phenyl)carbonyl)-N-(2-(4-methylphenyl)ethyl) amino)propanoic acid HPLC measurement condition: A HPLC retention time: 3.93 minutes; MASS data (ESI, Pos., 20V): 551 (M+H)$^+$.

EXAMPLE 4(132)

3-(N-((2-(2-((2-methylbenzylamino)carbonyl)phenyl)phenyl)carbonyl)-N-(2-(4-methylphenyl)ethyl) amino)propanoic acid HPLC measurement condition: A HPLC retention time: 4.00 minutes; MASS data (ESI, Pos., 20V): 535 (M+H)$^+$.

EXAMPLE 4(133)

3-(N-((2-(2-((3-methoxybenzylamino)carbonyl)phenyl)phenyl)carbonyl)-N-(2-(4-methylphenyl)ethyl)amino)propanoic acid HPLC measurement condition: A HPLC retention time: 3.91 minutes; MASS data (ESI, Pos., 20V): 551 (M+H)$^+$.

EXAMPLE 4(134)

3-(N-((2-(2-((4-chlorobenzylamino)carbonyl)phenyl)phenyl)carbonyl)-N-(2-(4-methylphenyl)ethyl)amino)propanoic acid HPLC measurement condition: A HPLC retention time: 4.04 minutes; MASS data (ESI, Pos., 20V): 555 (M+H)$^+$.

EXAMPLE 4(135)

3-(N-((2-(2-((4-methoxybenzylamino)carbonyl)phenyl)phenyl)carbonyl)-N-(2-(4-methylphenyl)ethyl)amino)propanoic acid HPLC measurement condition: A HPLC retention time: 3.88 minutes; MASS data (ESI, Pos., 20V): 551 (M+H)$^+$.

EXAMPLE 4(136)

3-(N-((2-(2-((4-methylbenzylamino)carbonyl)phenyl)phenyl)carbonyl)-N-(2-(4-methylphenyl)ethyl)amino)propanoic acid HPLC measurement condition: A HPLC retention time: 3.99 minutes; MASS data (ESI, Pos., 20V): 535 (M+H)$^+$.

EXAMPLE 4(137)

3-(N-((2-(2-((N-methyl-N-benzylamino)carbonyl)phenyl)phenyl)carbonyl)-N-(2-(4-methylphenyl)ethyl)amino)propanoic acid HPLC measurement condition: A HPLC retention time: 3.95 minutes; MASS data (ESI, Pos., 20V): 535 (M+H)$^+$.

EXAMPLE 4(138)

3-(N-((2-(2-((N-methyl-N-(6-methylpyridin-2-yl)methylamino)carbonyl)phenyl)phenyl)carbonyl)-N-(1-methyl-3-phenylpropyl)amino)propanoic acid HPLC measurement condition: A HPLC retention time: 3.34 minutes; MASS data (ESI, Pos., 20V): 564 (M+H)$^+$.

EXAMPLE 4(139)

3-(N-((2-(2-((N-ethyl-N-benzylamino)carbonyl)phenyl)phenyl)carbonyl)-N-(2-(4-methylphenyl)ethyl)amino)propanoic acid HPLC measurement condition: A HPLC retention time: 4.02 minutes; MASS data (ESI, Pos., 20V): 549 (M+H)$^+$.

EXAMPLE 4(140)

3-(N-((2-(2-((N-butyl-N-benzylamino)carbonyl)phenyl)phenyl)carbonyl)-N-(2-(4-methylphenyl)ethyl)amino)propanoic acid HPLC measurement condition: A HPLC retention time: 4.21 minutes; MASS data (ESI, Pos., 20V): 577 (M+H)$^+$.

EXAMPLE 4(141)

3-(N-((2-(2-((4-(tert-butyl)benzylamino)carbonyl)phenyl)phenyl)carbonyl)-N-(2-(4-methylphenyl)ethyl)amino)propanoic acid HPLC measurement condition: A HPLC retention time: 4.22 minutes; MASS data (ESI, Pos., 20V): 577 (M+H)$^+$.

EXAMPLE 4(142)

3-(N-((2-(2-(((5-methyl-2-furyl)methylamino)carbonyl)phenyl)phenyl)carbonyl)-N-(2-(4-methylphenyl)ethyl)amino)propanoic acid HPLC measurement condition: A HPLC retention time: 3.88 minutes; MASS data (ESI, Pos., 20V): 525 (M+H)$^+$.

EXAMPLE 4(143)

3-(N-((2-(2-((1-phenyl-3-trifluoroacetoxypropylamino)carbonyl)phenyl)phenyl)carbonyl)-N-(2-(4-methylphenyl)ethyl)amino)propanoic acid HPLC measurement condition: A HPLC retention time: 4.16 minutes; MASS data (ESI, Pos., 20V): 661 (M+H)$^+$.

EXAMPLE 4(144)

3-(N-((2-(2-((2-fluorobenzylamino)carbonyl)phenyl)phenyl)carbonyl)-N-(2-(4-methylphenyl)ethyl)amino)propanoic acid HPLC measurement condition: A HPLC retention time: 3.93 minutes; MASS data (ESI, Pos., 20V): 539 (M+H)$^+$.

EXAMPLE 4(145)

3-(N-((2-(2-((3-fluorobenzylamino)carbonyl)phenyl)phenyl)carbonyl)-N-(2-(4-methylphenyl)ethyl)amino)propanoic acid HPLC measurement condition: A HPLC retention time: 3.95 minutes; MASS data (ESI, Pos., 20V): 539 (M+H)$^+$.

EXAMPLE 4(146)

3-(N-((2-(2-((2,5-difluorobenzylamino)carbonyl)phenyl)phenyl)carbonyl)-N-(2-(4-methylphenyl)ethyl)amino)propanoic acid HPLC measurement condition: A HPLC retention time: 3.97 minutes; MASS data (ESI, Pos., 20V): 557 (M+H)$^+$.

EXAMPLE 4(147)

3-(N-((2-(2-(((1R)-1-phenyl-2-hydroxyethylamino)carbonyl)phenyl)phenyl)carbonyl)-N-(2-(4-methylphenyl)ethyl)amino)propanoic acid HPLC measurement condition: A HPLC retention time: 3.77 minutes; MASS data (ESI, Pos., 20V): 551 (M+H)$^+$.

EXAMPLE 4(148)

3-(N-((2-(2-((2-chlorobenzylamino)carbonyl)phenyl)phenyl)carbonyl)-N-(2-(4-methylphenyl)ethyl)amino)propanoic acid HPLC measurement condition: A HPLC retention time: 4.00 minutes; MASS data (ESI, Pos., 20V): 555 (M+H)$^+$.

EXAMPLE 4(149)

3-(N-((2-(2-((4-fluorobenzylamino)carbonyl)phenyl)phenyl)carbonyl)-N-(2-(4-methylphenyl)ethyl)amino)propanoic acid HPLC measurement condition: A HPLC retention time: 3.93 minutes; MASS data (ESI, Pos., 20V): 539 (M+H)$^+$.

EXAMPLE 4(150)

3-(N-((2-(2-((allylamino)carbonyl)phenyl)phenyl)carbonyl)-N-(2-(4-methylphenyl)ethyl)amino)propanoic acid HPLC measurement condition: A HPLC retention time: 3.75 minutes; MASS data (ESI, Pos., 20V): 471 (M+H)$^+$.

EXAMPLE 4(151)

3-(N-((2-(2-((2,6-difluorobenzylamino)carbonyl)phenyl)phenyl)carbonyl)-N-(2-(4-methylphenyl)ethyl)amino)propanoic acid HPLC measurement condition: A HPLC retention time: 3.89 minutes; MASS data (ESI, Pos., 20V): 557 (M+H)$^+$.

EXAMPLE 4(152)

3-(N-((2-(2-((3-chlorobenzylamino)carbonyl)phenyl)phenyl)carbonyl)-N-(2-(4-methylphenyl)ethyl)amino)propanoic acid HPLC measurement condition: A HPLC retention time: 4.04 minutes; MASS data (ESI, Pos., 20V): 555 (M+H)$^+$.

EXAMPLE 4(153)

3-(N-((2-(2-(((1S)-1-phenyl-2-hydroxyethylamino)carbonyl)phenyl)phenyl)carbonyl)-N-(2-(4-methylphenyl)ethyl)amino)propanoic acid HPLC measurement condition: A HPLC retention time: 3.75 minutes; MASS data (ESI, Pos., 20V): 551 (M+H)$^+$.

EXAMPLE 4(154)

3-(N-((2-(2-(((1R)-1-(4-methylphenyl)ethylamino)carbonyl)phenyl)phenyl)carbonyl)-N-(2-(4-methylphenyl)ethyl)amino)propanoic acid HPLC measurement condition: A HPLC retention time: 4.08 minutes; MASS data (ESI, Pos., 20V): 549 (M+H)$^+$.

EXAMPLE 4(155)

3-(N-((2-(2-((1-(4-fluorophenyl)ethylamino)carbonyl)phenyl)phenyl)carbonyl)-N-(2-(4-methylphenyl)ethyl)amino)propanoic acid HPLC measurement condition: A HPLC retention time: 4.02 minutes; MASS data (ESI, Pos., 20V): 553 (M+H)$^+$.

EXAMPLE 4(156)

3-(N-((2-(2-((2-thienylmethylamino)carbonyl)phenyl)phenyl)carbonyl)-N-(2-(4-methylphenyl)ethyl)amino)propanoic acid HPLC measurement condition: A HPLC retention time: 3.88 minutes; MASS data (ESI, Pos., 20V): 527 (M+H)$^+$.

EXAMPLE 4(157)

3-(N-((2-(2-(((3S)-3-hydroxymethyl-1,2,3,4-tetrahydroisoquinolin-2-yl)carbonyl)phenyl)phenyl)carbonyl)-N-(2-(4-methylphenyl)ethyl)amino)propanoic acid HPLC measurement condition: A HPLC retention time: 3.78 minutes; MASS data (ESI, Pos., 20V): 577 (M+H)$^+$.

EXAMPLE 4(158)

3-(N-((2-(2-((3-methylbenzylamino)carbonyl)phenyl)phenyl)carbonyl)-N-(2-(4-methylphenyl)ethyl)amino)propanoic acid HPLC measurement condition: A HPLC retention time: 4.00 minutes; MASS data (ESI, Pos., 20V): 535 (M+H)$^+$.

EXAMPLE 4(159)

3-(N-((2-(2-((3,5-difluorobenzylamino)carbonyl)phenyl)phenyl)carbonyl)-N-(2-(4-methylphenyl)ethyl)amino)propanoic acid HPLC measurement condition: A HPLC retention time: 4.00 minutes; MASS data (ESI, Pos., 20V): 557 (M+H)$^+$.

EXAMPLE 4(160)

3-(N-((2-(2-((N-methyl-N-(6-methylpyridin-2-yl)methylamino)carbonyl)phenyl)phenyl)carbonyl)-N-(2-(4-methylphenyl)ethyl)amino)propanoic acid HPLC measurement condition: A HPLC retention time: 3.33 minutes; MASS data (ESI, Pos., 20V): 550 (M+H)$^+$.

EXAMPLE 4(161)

3-(N-((2-(2-((N-(2-(N,N-dimethylamino)ethyl)-N-benzylamino)carbonyl)phenyl)phenyl)carbonyl)-N-(2-(4-methylphenyl)ethyl)amino)propanoic acid HPLC measurement condition: A HPLC retention time: 3.55 minutes; MASS data (ESI, Pos., 20V): 592 (M+H)+.

EXAMPLE 4(162)

3-(N-((2-(2-((2-phenylethylamino)carbonyl)phenyl)phenyl)carbonyl)-N-(2-(4-methylphenyl)ethyl)amino)propanoic acid HPLC measurement condition: A HPLC retention time: 3.99 minutes; MASS data (ESI, Pos., 20V): 535 (M+H)+.

EXAMPLE 4(163)

3-(N-((2-(2-((1,2,3,4-tetrahydro-1-naphthylamino)carbonyl)phenyl)phenyl)carbonyl)-N-(2-(3-methoxyphenyl)ethyl)amino)propanoic acid HPLC measurement condition: A HPLC retention time: 3.97 minutes; MASS data (ESI, Pos., 20V): 577 (M+H)+.

EXAMPLE 4(164)

3-(N-((2-(2-((N-benzyl-N-(2-hydroxyethyl)amino)carbonyl)phenyl)phenyl)carbonyl)-N-(2-(3-methoxyphenyl)ethyl)amino)propanoic acid HPLC measurement condition: A HPLC retention time: 3.66 minutes; MASS data (ESI, Pos., 20V): 581 (M+H)+.

EXAMPLE 4(165)

3-(N-((2-(2-((1-naphthylmethylamino)carbonyl)phenyl)phenyl)carbonyl)-N-(2-(3-methoxyphenyl)ethyl)amino)propanoic acid HPLC measurement condition: A HPLC retention time: 3.95 minutes; MASS data (ESI, Pos., 20V): 587 (M+H)+.

EXAMPLE 4(166)

3-(N-((2-(2-((α-methylbenzylamino)carbonyl)phenyl)phenyl)carbonyl)-N-(2-(3-methoxyphenyl)ethyl)amino)propanoic acid HPLC measurement condition: A HPLC retention time: 3.88 minutes; MASS data (ESI, Pos., 20V): 551 (M+H)+.

EXAMPLE 4(167)

3-(N-((2-(2-((2-methylbenzylamino)carbonyl)phenyl)phenyl)carbonyl)-N-(2-(3-methoxyphenyl)ethyl)amino)propanoic acid HPLC measurement condition: A HPLC retention time: 3.88 minutes; MASS data (ESI, Pos., 20V): 551 (M+H)+.

EXAMPLE 4(168)

3-(N-((2-(2-((4-chlorobenzylamino)carbonyl)phenyl)phenyl)carbonyl)-N-(2-(3-methoxyphenyl)ethyl)amino)propanoic acid HPLC measurement condition: A HPLC retention time: 3.91 minutes; MASS data (ESI, Pos., 20V): 571 (M+H)+.

EXAMPLE 4(169)

3-(N-((2-(2-((4-methoxybenzylamino)carbonyl)phenyl)phenyl)carbonyl)-N-(2-(3-methoxyphenyl)ethyl)amino)propanoic acid HPLC measurement condition: A HPLC retention time: 3.77 minutes; MASS data (ESI, Pos., 20V): 567 (M+H)+.

EXAMPLE 4(170)

3-(N-((2-(2-((N-(isopropyl)-N-benzylamino)carbonyl)phenyl)phenyl)carbonyl)-N-(2-(3-methoxyphenyl)ethyl)amino)propanoic acid HPLC measurement condition: A HPLC retention time: 3.97 minutes; MASS data (ESI, Pos., 20V): 579 (M+H)+, 571.

EXAMPLE 4(171)

3-(N-((2-(2-((N-ethyl-N-benzylamino)carbonyl)phenyl)phenyl)carbonyl)-N-(2-(3-methoxyphenyl)ethyl)amino)propanoic acid HPLC measurement condition: A HPLC retention time: 3.89 minutes; MASS data (ESI, Pos., 20V): 565 (M+H)+.

EXAMPLE 4(172)

3-(N-((2-(2-((N-butyl-N-benzylamino)carbonyl)phenyl)phenyl)carbonyl)-N-(2-(3-methoxyphenyl)ethyl)amino)propanoic acid HPLC measurement condition: A HPLC retention time: 4.10 minutes; MASS data (ESI, Pos., 20V): 593 (M+H)+.

EXAMPLE 4(173)

3-(N-((2-(2-((4-(tert-butyl)benzylamino)carbonyl)phenyl)phenyl)carbonyl)-N-(2-(3-methoxyphenyl)ethyl)amino)propanoic acid HPLC measurement condition: A HPLC retention time: 4.11 minutes; MASS data (ESI, Pos., 20V): 593 (M+H)+.

EXAMPLE 4(174)

3-(N-((2-(2-(((5-methyl-2-furyl)methylamino)carbonyl)phenyl)phenyl)carbonyl)-N-(2-(3-methoxyphenyl)ethyl)amino)propanoic acid HPLC measurement condition: A HPLC retention time: 3.78 minutes; MASS data (ESI, Pos., 20V): 541 (M+H)+.

EXAMPLE 4(175)

3-(N-((2-(2-((1-phenyl-3-trifluoroacetoxypropylamino)carbonyl)phenyl)phenyl)carbonyl)-N-(2-(3-methoxyphenyl)ethyl)amino)propanoic acid HPLC measurement condition: A HPLC retention time: 4.04 minutes; MASS data (ESI, Pos., 20V): 699 (M+Na)+, 677 (M+H)+.

EXAMPLE 4(176)

3-(N-((2-(2-((2,5-difluorobenzylamino)carbonyl)phenyl)phenyl)carbonyl)-N-(2-(3-methoxyphenyl)ethyl)amino)propanoic acid HPLC measurement condition: A HPLC retention time: 3.84 minutes; MASS data (ESI, Pos., 20V): 573 (M+H)+.

EXAMPLE 4(177)

3-(N-((2-(2-(((1R)-1-phenyl-2-hydroxyethylamino)carbonyl)phenyl)phenyl)carbonyl)-N-(2-(3-methoxyphenyl)ethyl)amino)propanoic acid HPLC measurement condition: A HPLC retention time: 3.62 minutes; MASS data (ESI, Pos., 20V): 567 (M+H)+.

EXAMPLE 4(178)

3-(N-((2-(2-((2-chlorobenzylamino)carbonyl)phenyl)phenyl)carbonyl)-N-(2-(3-methoxyphenyl)ethyl)amino)propanoic acid HPLC measurement condition: A HPLC retention time: 3.91 minutes; MASS data (ESI, Pos., 20V): 571 (M+H)+.

EXAMPLE 4(179)

3-(N-((2-(2-((4-fluorobenzylamino)carbonyl)phenyl)phenyl)carbonyl)-N-(2-(3-methoxyphenyl)ethyl)amino)propanoic acid HPLC measurement condition: A HPLC retention time: 3.82 minutes; MASS data (ESI, Pos., 20V): 555 (M+H)+.

EXAMPLE 4(180)

3-(N-((2-(2-((3-chlorobenzylamino)carbonyl)phenyl)phenyl)carbonyl)-N-(2-(3-methoxyphenyl)ethyl)amino)propanoic acid HPLC measurement condition: A HPLC retention time: 3.93 minutes; MASS data (ESI, Pos., 20V): 571 (M+H)+.

EXAMPLE 4(181)

3-(N-((2-(2-(((1S)-1-phenyl-2-hydroxyethylamino)carbonyl)phenyl)phenyl)carbonyl)-N-(2-(3-methoxyphenyl)ethyl)amino)propanoic acid HPLC measurement condition: A HPLC retention time: 3.62 minutes; MASS data (ESI, Pos., 20V): 567 (M+H)+.

EXAMPLE 4(182)

3-(N-((2-(2-(((1R)-1-(4-methylphenyl)ethylamino)carbonyl)phenyl)phenyl)carbonyl)-N-(2-(3-methoxyphenyl)ethyl)amino)propanoic acid HPLC measurement condition: A HPLC retention time: 3.95 minutes; MASS data (ESI, Pos., 20V): 565 (M+H)+.

EXAMPLE 4(183)

3-(N-((2-(2-((1-(4-fluorophenyl)ethylamino)carbonyl)phenyl)phenyl)carbonyl)-N-(2-(3-methoxyphenyl)ethyl)amino)propanoic acid HPLC measurement condition: A HPLC retention time: 3.89 minutes; MASS data (ESI, Pos., 20V): 569 (M+H)+.

EXAMPLE 4(184)

3-(N-((2-(2-(((3S)-3-hydroxymethyl-1,2,3,4-tetrahydroisoquinolin-2-yl)carbonyl)phenyl)phenyl)carbonyl)-N-(2-(3-methoxyphenyl)ethyl)amino)propanoic acid HPLC measurement condition: A HPLC retention time: 3.67 minutes; MASS data (ESI, Pos., 20V): 593 (M+H)+.

EXAMPLE 4(185)

3-(N-((2-(2-((3-methylbenzylamino)carbonyl)phenyl)phenyl)carbonyl)-N-(2-(3-methoxyphenyl)ethyl)amino)propanoic acid HPLC measurement condition: A HPLC retention time: 3.88 minutes; MASS data (ESI, Pos., 20V): 551 (M+H)+.

EXAMPLE 4(186)

3-(N-((2-(2-((3,5-difluorobenzylamino)carbonyl)phenylphenyl)carbonyl)-N-(2-(3-methoxyphenyl)ethyl)amino)propanoic acid HPLC measurement condition: A HPLC retention time: 3.88 minutes; MASS data (ESI, Pos., 20V): 573 (M+H)+.

EXAMPLE 4(187)

3-(N-((2-(2-((N-methyl-N-(6-methylpyridin-2-yl)methylamino)carbonyl)phenyl)phenyl)carbonyl)-N-(2-(3-methoxyphenyl)ethyl)amino)propanoic acid HPLC measurement condition: A HPLC retention time: 3.23 minutes; MASS data (ESI, Pos., 20V): 566 (M+H)+.

EXAMPLE 4(188)

3-(N-((2-(2-((N-(2-(N,N-dimethylamino)ethyl)-N-benzylamino)carbonyl)phenyl)phenyl)carbonyl)-N-(2-(3-methoxyphenyl)ethyl)amino)propanoic acid HPLC measurement condition: A HPLC retention time: 3.45 minutes; MASS data (ESI, Pos., 20V): 608 (M+H)+.

EXAMPLE 4(189)

3-(N-((2-(2-((2-phenylethylamino)carbonyl)phenyl)phenyl)carbonyl)-N-(2-(3-methoxyphenyl)ethyl)amino)propanoic acid HPLC measurement condition: A HPLC retention time: 3.86 minutes; MASS data (ESI, Pos., 20V): 551 (M+H)+.

EXAMPLE 4(190)

3-(N-((2-(2-((1,2,3,4-tetrahydro-1-naphthylamino)carbonyl)phenyl)phenyl)carbonyl)-N-(2-(2-thienyl)ethyl)amino)propanoic acid HPLC measurement condition: A HPLC retention time: 3.93 minutes; MASS data (ESI, Pos., 20V): 553 (M+H)+.

EXAMPLE 4(191)

3-(N-((2-(2-((N-benzyl-N-(2-hydroxyethyl)amino)carbonyl)phenyl)phenyl)carbonyl)-N-(2-(2-thienyl)ethyl)amino)propanoic acid HPLC measurement condition: A HPLC retention time: 3.62 minutes; MASS data (ESI, Pos., 20V): 557 (M+H)+.

EXAMPLE 4(192)

3-(N-((2-(2-((2-furylmethylamino)carbonyl)phenyl)phenyl)carbonyl)-N-(2-(2-thienyl)ethyl)amino)propanoic acid HPLC measurement condition: A HPLC retention time: 3.67 minutes; MASS data (ESI, Pos., 20V): 503 (M+H)+.

EXAMPLE 4(193)

3-(N-((2-(2-((1-indaneamino)carbonyl)phenyl)phenyl)carbonyl)-N-(2-(2-thienyl)ethyl)amino)propanoic acid HPLC measurement condition: A HPLC retention time: 3.86 minutes; MASS data (ESI, Pos., 20V): 539 (M+H)+.

EXAMPLE 4(194)

3-(N-((2-(2-((1-naphthylmethylamino)carbonyl)phenyl)phenyl)carbonyl)-N-(2-(2-thienyl)ethyl)amino)propanoic acid HPLC measurement condition: A HPLC retention time: 3.95 minutes; MASS data (ESI, Pos., 20V): 563 (M+H)+.

EXAMPLE 4(195)

3-(N-((2-(2-((pyridin-2-ylmethylamino)carbonyl)phenyl)phenyl)carbonyl)-N-(2-(2-thienyl)ethyl)amino)propanoic acid HPLC measurement condition: A HPLC retention time: 3.22 minutes; MASS data (ESI, Pos., 20V): 514 (M+H)+.

EXAMPLE 4(196)

3-(N-((2-(2-((pyridin-3-ylmethylamino)carbonyl)phenyl)phenyl)carbonyl)-N-(2-(2-thienyl)ethyl)amino)propanoic acid HPLC measurement condition: A HPLC retention time: 3.14 minutes; MASS data (ESI, Pos., 20V): 514 (M+H)+.

EXAMPLE 4(197)

3-(N-((2-(2-((1,2,3,4-tetrahydroisoquinolin-2-yl)carbonyl)phenyl)phenyl)carbonyl)-N-(2-(2-thienyl)ethyl)amino)propanoic acid HPLC measurement condition: A HPLC retention time: 3.82 minutes; MASS data (ESI, Pos., 20V): 539 (M+H)+.

EXAMPLE 4(198)

3-(N-((2-(2-((α-methylbenzylamino)carbonyl)phenyl)phenyl)carbonyl)-N-(2-(2-thienyl)ethyl)amino)propanoic acid HPLC measurement condition: A HPLC retention time: 3.86 minutes; MASS data (ESI, Pos., 20V): 527 (M+H)+.

EXAMPLE 4(199)

3-(N-((2-(2-((benzylamino)carbonyl)phenyl)phenyl)carbonyl)-N-(2-(2-thienyl)ethyl)amino)propanoic acid HPLC measurement condition: A HPLC retention time: 3.79 minutes; MASS data (ESI, Pos., 20V): 513 (M+H)+.

EXAMPLE 4(200)

3-(N-((2-(2-((2-methoxybenzylamino)carbonyl)phenyl)phenyl)carbonyl)-N-(2-(2-thienyl)ethyl)amino)propanoic acid HPLC measurement condition: A HPLC retention time: 3.78 minutes; MASS data (ESI, Pos., 20V): 543 (M+H)+.

EXAMPLE 4(201)

3-(N-((2-(2-((2-methylbenzylamino)carbonyl)phenyl)phenyl)carbonyl)-N-(2-(2-thienyl)ethyl)amino)propanoic acid HPLC measurement condition: A HPLC retention time: 3.84 minutes; MASS data (ESI, Pos., 20V): 527 (M+H)+.

EXAMPLE 4(202)

3-(N-((2-(2-((3-methoxybenzylamino)carbonyl)phenyl)phenyl)carbonyl)-N-(2-(2-thienyl)ethyl)amino)propanoic acid HPLC measurement condition: A HPLC retention time: 3.77 minutes; MASS data (ESI, Pos., 20V): 543 (M+H)+.

EXAMPLE 4(203)

3-(N-((2-(2-((4-chlorobenzylamino)carbonyl)phenyl)phenyl)carbonyl)-N-(2-(2-thienyl)ethyl)amino)propanoic acid HPLC measurement condition: A HPLC retention time: 3.89 minutes; MASS data (ESI, Pos., 20V): 547 (M+H)$^+$.

EXAMPLE 4(204)

3-(N-((2-(2-((4-methoxybenzylamino)carbonyl)phenyl)phenyl)carbonyl)-N-(2-(2-thienyl)ethyl)amino)propanoic acid HPLC measurement condition: A HPLC retention time: 3.73 minutes; MASS data (ESI, Pos., 20V): 543 (M+H)$^+$.

EXAMPLE 4(205)

3-(N-((2-(2-((4-methylbenzylamino)carbonyl)phenyl)phenyl)carbonyl)-N-(2-(2-thienyl)ethyl)amino)propanoic acid HPLC measurement condition: A HPLC retention time: 3.86 minutes; MASS data (ESI, Pos., 20V): 527 (M+H)$^+$.

EXAMPLE 4(206)

3-(N-((2-(2-((N-methyl-N-benzylamino)carbonyl)phenyl)phenyl)carbonyl)-N-(2-(2-thienyl)ethyl)amino)propanoic acid HPLC measurement condition: A HPLC retention time: 3.80 minutes; MASS data (ESI, Pos., 20V): 527 (M+H)$^+$.

EXAMPLE 4(207)

3-(N-((2-(2-((N-(isopropyl)-N-benzylamino)carbonyl)phenyl)phenyl)carbonyl)-N-(2-(2-thienyl)ethyl)amino)propanoic acid HPLC measurement condition: A HPLC retention time: 3.93 minutes; MASS data (ESI, Pos., 20V): 555 (M+H)$^+$.

EXAMPLE 4(208)

3-(N-((2-(2-((N-ethyl-N-benzylamino)carbonyl)phenyl)phenyl)carbonyl)-N-(2-(2-thienyl)ethyl)amino)propanoic acid HPLC measurement condition: A HPLC retention time: 3.88 minutes; MASS data (ESI, Pos., 20V): 541 (M+H)$^+$.

EXAMPLE 4(209)

3-(N-((2-(2-((N-butyl-N-benzylamino)carbonyl)phenyl)phenyl)carbonyl)-N-(2-(2-thienyl)ethyl)amino)propanoic acid HPLC measurement condition: A HPLC retention time: 4.08 minutes; MASS data (ESI, Pos., 20V): 569 (M+H)$^+$.

EXAMPLE 4(210)

3-(N-((2-(2-((4-(tert-butyl)benzylamino)carbonyl)phenyl)phenyl)carbonyl)-N-(2-(2-thienyl)ethyl)amino)propanoic acid HPLC measurement condition: A HPLC retention time: 4.10 minutes; MASS data (ESI, Pos., 20V): 569 (M+H)$^+$.

EXAMPLE 4(211)

3-(N-((2-(2-((1-phenyl-3-hydroxypropylamino)carbonyl)phenyl)phenyl)carbonyl)-N-(2-(2-thienyl)ethyl)amino)propanoic acid HPLC measurement condition: A HPLC retention time: 3.60 minutes; MASS data (ESI, Pos., 20V): 557 (M+H)$^+$.

EXAMPLE 4(212)

3-(N-((2-(2-((2-fluorobenzylamino)carbonyl)phenyl)phenyl)carbonyl)-N-(2-(2-thienyl)ethyl)amino)propanoic acid HPLC measurement condition: A HPLC retention time: 3.80 minutes; MASS data (ESI, Pos., 20V): 531 (M+H)$^+$.

EXAMPLE 4(213)

3-(N-((2-(2-((3-fluorobenzylamino)carbonyl)phenyl)phenyl)carbonyl)-N-(2-(2-thienyl)ethyl)amino)propanoic acid HPLC measurement condition: A HPLC retention time: 3.80 minutes; MASS data (ESI, Pos., 20V): 531 (M+H)$^+$.

EXAMPLE 4(214)

3-(N-((2-(2-((2,5-difluorobenzylamino)carbonyl)phenyl)phenyl)carbonyl)-N-(2-(2-thienyl)ethyl)amino)propanoic acid HPLC measurement condition: A HPLC retention time: 3.82 minutes; MASS data (ESI, Pos., 20V): 549 (M+H)$^+$.

EXAMPLE 4(215)

3-(N-((2-(2-(((1R)-1-phenyl-2-hydroxyethylamino)carbonyl)phenyl)phenyl)carbonyl)-N-(2-(2-thienyl)ethyl)amino)propanoic acid HPLC measurement condition: A HPLC retention time: 3.60 minutes; MASS data (ESI, Pos., 20V): 543 (M+H)$^+$.

EXAMPLE 4(216)

3-(N-((2-(2-((2-chlorobenzylamino)carbonyl)phenyl)phenyl)carbonyl)-N-(2-(2-thienyl)ethyl)amino)propanoic acid HPLC measurement condition: A HPLC retention time: 3.16 minutes; MASS data (ESI, Pos., 20V): 542 (M+H)$^+$.

EXAMPLE 4(217)

3-(N-((2-(2-((4-fluorobenzylamino)carbonyl)phenyl)phenyl)carbonyl)-N-(2-(2-thienyl)ethyl)amino)propanoic acid HPLC measurement condition: A HPLC retention time: 3.78 minutes; MASS data (ESI, Pos., 20V): 531 (M+H)$^+$, 156.

EXAMPLE 4(218)

3-(N-((2-(2-((allylamino)carbonyl)phenyl)phenyl)carbonyl)-N-(2-(2-thienyl)ethyl)amino)propanoic acid HPLC measurement condition: A HPLC retention time: 3.62 minutes; MASS data (ESI, Pos., 20V): 463 (M+H)$^+$.

EXAMPLE 4(219)

3-(N-((2-(2-((2,6-difluorobenzylamino)carbonyl)phenyl)phenyl)carbonyl)-N-(2-(2-thienyl)ethyl)amino)propanoic acid HPLC measurement condition: A HPLC retention time: 3.78 minutes; MASS data (ESI, Pos., 20V): 549 (M+H)$^+$.

EXAMPLE 4(220)

3-(N-((2-(2-((3-chlorobenzylamino)carbonyl)phenyl)phenyl)carbonyl)-N-(2-(2-thienyl)ethyl)amino)propanoic acid HPLC measurement condition: A HPLC retention time: 3.91 minutes; MASS data (ESI, Pos., 20V): 547 (M+H)$^+$.

EXAMPLE 4(221)

3-(N-((2-(2-(((1S)-1-phenyl-2-hydroxyethylamino)carbonyl)phenyl)phenyl)carbonyl)-N-(2-(2-thienyl)ethyl)amino)propanoic acid HPLC measurement condition: A HPLC retention time: 3.62 minutes; MASS data (ESI, Pos., 20V): 543 (M+H)$^+$.

EXAMPLE 4(222)

3-(N-((2-(2-(((1R)-1-(4-methylphenyl)ethylamino)carbonyl)phenyl)phenyl)carbonyl)-N-(2-(2-thienyl)ethyl)amino)propanoic acid HPLC measurement condition: A HPLC retention time: 3.93 minutes; MASS data (ESI, Pos., 20V): 541 (M+H)$^+$.

EXAMPLE 4(223)

3-(N-((2-(2-((1-(4-fluorophenyl)ethylamino)carbonyl)phenyl)phenyl)carbonyl)-N-(2-(2-thienyl)ethyl)amino)propanoic acid HPLC measurement condition: A HPLC retention time: 3.89 minutes; MASS data (ESI, Pos., 20V): 545 (M+H)$^+$.

EXAMPLE 4(224)

3-(N-((2-(2-((2-thienylmethylamino)carbonyl)phenyl)phenyl)carbonyl)-N-(2-(2-thienyl)ethyl)amino)propanoic acid HPLC measurement condition: A HPLC retention time: 3.75 minutes; MASS data (ESI, Pos., 20V): 519 (M+H)$^+$.

EXAMPLE 4(225)

3-(N-((2-(2-(((3S)-3-hydroxymethyl-1,2,3,4-tetrahydroisoquinolin-2-yl)carbonyl)phenyl)phenyl)carbonyl)-N-(2-(2-thienyl)ethyl)amino)propanoic acid HPLC measurement condition: A HPLC retention time: 3.63 minutes; MASS data (ESI, Pos., 20V): 569 (M+H)$^+$.

EXAMPLE 4(226)

3-(N-((2-(2-((3-methylbenzylamino)carbonyl)phenyl)phenyl)carbonyl)-N-(2-(2-thienyl)ethyl)amino)propanoic acid HPLC measurement condition: A HPLC retention time: 3.86 minutes; MASS data (ESI, Pos., 20V): 527 (M+H)$^+$.

EXAMPLE 4(227)

3-(N-((2-(2-((3,5-difluorobenzylamino)carbonyl)phenyl)phenyl)carbonyl)-N-(2-(2-thienyl)ethyl)amino)propanoic acid HPLC measurement condition: A HPLC retention time: 3.86 minutes; MASS data (ESI, Pos., 20V): 549 (M+H)$^+$.

EXAMPLE 4(228)

3-(N-((2-(2-((N-methyl-N-(6-methylpyridin-2-yl)methylamino)carbonyl)phenyl)phenyl)carbonyl)-N-(2-(2-thienyl)ethyl)amino)propanoic acid HPLC measurement condition: A HPLC retention time: 3.20 minutes; MASS data (ESI, Pos., 20V): 542 (M+H)$^+$.

EXAMPLE 4(229)

3-(N-((2-(2-((N-(2-(N,N-dimethylamino)ethyl)-N-benzylamino)carbonyl)phenyl)phenyl)carbonyl)-N-(2-(2-thienyl)ethyl)amino)propanoic acid HPLC measurement condition: A HPLC retention time: 3.44 minutes; MASS data (ESI, Pos., 20V): 584 (M+H)$^+$.

EXAMPLE 4(230)

3-(N-((2-(2-((2-phenylethylamino)carbonyl)phenyl)phenyl)carbonyl)-N-(2-(2-thienyl)ethyl)amino)propanoic acid HPLC measurement condition: A HPLC retention time: 3.86 minutes; MASS data (ESI, Pos., 20V): 527 (M+H)$^+$.

EXAMPLE 4(231)

3-(N-((2-(2-((1,2,3,4-tetrahydro-1-naphthylamino)carbonyl)phenyl)phenyl)carbonyl)-N-(pyridin-3-ylmethyl)amino)propanoic acid HPLC measurement condition: A HPLC retention time: 3.23 minutes; MASS data (ESI, Pos., 20V): 534 (M+H)$^+$.

EXAMPLE 4(232)

3-(N-((2-(2-((N-benzyl-N-(2-hydroxyethyl)amino)carbonyl)phenyl)phenyl)carbonyl)-N-(pyridin-3-ylmethyl)amino)propanoic acid HPLC measurement condition: A HPLC retention time: 3.07 minutes; MASS data (ESI, Pos., 20V): 538 (M+H)$^+$.

EXAMPLE 4(233)

3-(N-((2-(2-((1-naphthylmethylamino)carbonyl)phenyl)phenyl)carbonyl)-N-(pyridin-3-ylmethyl)amino)propanoic acid HPLC measurement condition: A HPLC retention time: 3.25 minutes; MASS data (ESI, Pos., 20V): 544 (M+H)$^+$.

EXAMPLE 4(234)

3-(N-((2-(2-((pyridin-2-ylmethylamino)carbonyl)phenyl)phenyl)carbonyl)-N-(pyridin-3-ylmethyl)amino)propanoic acid HPLC measurement condition: A HPLC retention time: 2.70 minutes; MASS data (ESI, Pos., 20V): 989 (2M+H)$^+$, 495 (M+H)$^+$, 248.

EXAMPLE 4(235)

3-(N-((2-(2-((pyridin-4-ylmethylamino)carbonyl)phenyl)phenyl)carbonyl)-N-(pyridin-3-ylmethyl)amino)propanoic acid HPLC measurement condition: A HPLC retention time: 2.70 minutes; MASS data (ESI, Pos., 20V): 989 (2M+H)$^+$, 495 (M+H)$^+$, 248.

EXAMPLE 4(236)

3-(N-((2-(2-((α-methylbenzylamino)carbonyl)phenyl)phenyl)carbonyl)-N-(pyridin-3-ylmethyl)amino)propanoic acid HPLC measurement condition: A HPLC retention time: 3.16 minutes; MASS data (ESI, Pos., 20V): 508 (M+H)$^+$.

EXAMPLE 4(237)

3-(N-((2-(2-((2-methylbenzylamino)carbonyl)phenyl)phenyl)carbonyl)-N-(pyridin-3-ylmethyl)amino)propanoic acid HPLC measurement condition: A HPLC retention time: 3.16 minutes; MASS data (ESI, Pos., 20V): 508 (M+H)$^+$.

EXAMPLE 4(238)

3-(N-((2-(2-((4-chlorobenzylamino)carbonyl)phenyl)phenyl)carbonyl)-N-(pyridin-3-ylmethyl)amino)propanoic acid HPLC measurement condition: A HPLC retention time: 3.23 minutes; MASS data (ESI, Pos., 20V): 528 (M+H)$^+$.

EXAMPLE 4(239)

3-(N-((2-(2-((N-ethyl-N-benzylamino)carbonyl)phenyl)phenyl)carbonyl)-N-(pyridin-3-ylmethyl)amino)propanoic acid HPLC measurement condition: A HPLC retention time: 3.25 minutes; MASS data (ESI, Pos., 20V): 522 (M+H)$^+$.

EXAMPLE 4(240)

3-(N-((2-(2-((N-butyl-N-benzylamino)carbonyl)phenyl)phenyl)carbonyl)-N-(pyridin-3-ylmethyl)amino)propanoic acid HPLC measurement condition: A HPLC retention time: 3.42 minutes; MASS data (ESI, Pos., 20V): 550 (M+H)$^+$.

EXAMPLE 4(241)

3-(N-((2-(2-((4-(tert-butyl)benzylamino)carbonyl)phenyl)phenyl)carbonyl)-N-(pyridin-3-ylmethyl)amino)propanoic acid HPLC measurement condition: A HPLC retention time: 3.42 minutes; MASS data (ESI, Pos., 20V): 550 (M+H)$^+$.

EXAMPLE 4(242)

3-(N-((2-(2-((1-phenyl-3-hydroxypropylamino)carbonyl)phenyl)phenyl)carbonyl)-N-(pyridin-3-ylmethyl)amino)propanoic acid HPLC measurement condition: A HPLC retention time: 3.01 minutes; MASS data (ESI, Pos., 20V): 538 (M+H)$^+$.

EXAMPLE 4(243)

3-(N-((2-(2-((2,5-difluorobenzylamino)carbonyl)phenyl)phenyl)carbonyl)-N-(pyridin-3-ylmethyl)amino)propanoic acid HPLC measurement condition: A HPLC retention time: 3.14 minutes; MASS data (ESI, Pos., 20V): 530 (M+H)$^+$.

EXAMPLE 4(244)

3-(N-((2-(2-(((1R)-1-phenyl-2-hydroxyethylamino)carbonyl)phenyl)phenyl)carbonyl)-N-(pyridin-3-ylmethyl)amino)propanoic acid HPLC measurement condition: A HPLC retention time: 3.00 minutes; MASS data (ESI, Pos., 20V): 524 (M+H)$^+$.

EXAMPLE 4(245)

3-(N-((2-(2-((2-chlorobenzylamino)carbonyl)phenyl)phenyl)carbonyl)-N-(pyridin-3-ylmethyl)amino)propanoic acid HPLC measurement condition: A HPLC retention time: 3.20 minutes; MASS data (ESI, Pos., 20V): 528 (M+H)+.

EXAMPLE 4(246)

3-(N-((2-(2-((3-chlorobenzylamino)carbonyl)phenyl)phenyl)carbonyl)-N-(pyridin-3-ylmethyl)amino)propanoic acid HPLC measurement condition: A HPLC retention time: 3.23 minutes; MASS data (ESI, Pos., 20V): 528 (M+H)+.

EXAMPLE 4(247)

3-(N-((2-(2-(((1S)-1-phenyl-2-hydroxyethylamino)carbonyl)phenyl)phenyl)carbonyl)-N-(pyridin-3-ylmethyl)amino)propanoic acid HPLC measurement condition: A HPLC retention time: 3.00 minutes; MASS data (ESI, Pos., 20V): 524 (M+H)+.

EXAMPLE 4(248)

3-(N-((2-(2-(((1R)-1-(4-methylphenyl)ethylamino)carbonyl)phenyl)phenyl)carbonyl)-N-(pyridin-3-ylmethyl)amino)propanoic acid HPLC measurement condition: A HPLC retention time: 3.23 minutes; MASS data (ESI, Pos., 20V): 522 (M+H)+.

EXAMPLE 4(249)

3-(N-((2-(2-((1-(4-fluorophenyl)ethylamino)carbonyl)phenyl)phenyl)carbonyl)-N-(pyridin-3-ylmethyl)amino)propanoic acid HPLC measurement condition: A HPLC retention time: 3.20 minutes; MASS data (ESI, Pos., 20V): 526 (M+H)+.

EXAMPLE 4(250)

3-(N-((2-(2-(((3S)-3-hydroxymethyl-1,2,3,4-tetrahydroisoquinolin-2-yl)carbonyl)phenyl)phenyl)carbonyl)-N-(pyridin-3-ylmethyl)amino)propanoic acid HPLC measurement condition: A HPLC retention time: 3.09 minutes; MASS data (ESI, Pos., 20V): 550 (M+H)+.

EXAMPLE 4(251)

3-(N-((2-(2-((3-methylbenzylamino)carbonyl)phenyl)phenyl)carbonyl)-N-(pyridin-3-ylmethyl)amino)propanoic acid HPLC measurement condition: A HPLC retention time: 3.17 minutes; MASS data (ESI, Pos., 20V): 508 (M+H)+.

EXAMPLE 4(252)

3-(N-((2-(2-((3,5-difluorobenzylamino)carbonyl)phenyl)phenyl)carbonyl)-N-(pyridin-3-ylmethyl)amino)propanoic acid HPLC measurement condition: A HPLC retention time: 3.20 minutes; MASS data (ESI, Pos., 20V): 530 (M+H)+.

EXAMPLE 4(253)

3-(N-((2-(2-((N-methyl-N-(6-methylpyridin-2-yl)methylamino)carbonyl)phenyl)phenyl)carbonyl)-N-(pyridin-3-ylmethyl)amino)propanoic acid HPLC measurement condition: A HPLC retention time: 2.76 minutes; MASS data (ESI, Pos., 20V): 523 (M+H)+, 262.

EXAMPLE 4(254)

3-(N-((2-(2-((N-(2-(N,N-dimethylamino)ethyl)-N-benzylamino)carbonyl)phenyl)phenyl)carbonyl)-N-(pyridin-3-ylmethyl)amino)propanoic acid HPLC measurement condition: A HPLC retention time: 2.94 minutes; MASS data (ESI, Pos., 20V): 565 (M+H)+, 283.

EXAMPLE 4(255)

3-(N-((2-(2-((2-phenylethylamino)carbonyl)phenyl)phenyl)carbonyl)-N-(pyridin-3-ylmethyl)amino)propanoic acid HPLC measurement condition: A HPLC retention time: 3.18 minutes; MASS data (ESI, Pos., 20V): 508 (M+H)+.

EXAMPLE 4(256)

3-(N-((2-(2-((1,2,3,4-tetrahydro-1-naphthylamino)carbonyl)phenyl)phenyl)carbonyl)-N-(2-phenylpropyl)amino)propanoic acid HPLC measurement condition: A HPLC retention time: 4.04 minutes; MASS data (ESI, Pos., 20V): 561 (M+H)+.

EXAMPLE 4(257)

3-(N-((2-(2-((N-benzyl-N-(2-hydroxyethyl)amino)carbonyl)phenyl)phenyl)carbonyl)-N-(2-phenylpropyl)amino)propanoic acid HPLC measurement condition: A HPLC retention time: 3.73 minutes; MASS data (ESI, Pos., 20V): 565 (M+H)+.

EXAMPLE 4(258)

3-(N-((2-(2-((2-furylmethylamino)carbonyl)phenyl)phenyl)carbonyl)-N-(2-phenylpropyl)amino)propanoic acid HPLC measurement condition: A HPLC retention time: 3.78 minutes; MASS data (ESI, Pos., 20V): 511 (M+H)+.

EXAMPLE 4(259)

3-(N-((2-(2-((1-indaneamino)carbonyl)phenyl)phenyl)carbonyl)-N-(2-phenylpropyl)amino)propanoic acid HPLC measurement condition: A HPLC retention time: 3.99 minutes; MASS data (ESI, Pos., 20V): 547 (M+H)$^+$.

EXAMPLE 4(260)

3-(N-((2-(2-((1-naphthylmethylamino)carbonyl)phenyl)phenyl)carbonyl)-N-(2-phenylpropyl)amino)propanoic acid HPLC measurement condition: A HPLC retention time: 4.06 minutes; MASS data (ESI, Pos., 20V): 571 (M+H)$^+$.

EXAMPLE 4(261)

3-(N-((2-(2-((pyridin-2-ylmethylamino)carbonyl)phenyl)phenyl)carbonyl)-N-(2-phenylpropyl)amino)propanoic acid HPLC measurement condition: A HPLC retention time: 3.29 minutes; MASS data (ESI, Pos., 20V): 522 (M+H)$^+$.

EXAMPLE 4(262)

3-(N-((2-(2-((pyridin-3-ylmethylamino)carbonyl)phenyl)phenyl)carbonyl)-N-(2-phenylpropyl)amino)propanoic acid HPLC measurement condition: A HPLC retention time: 3.23 minutes; MASS data (ESI, Pos., 20V): 522 (M+H)$^+$.

EXAMPLE 4(263)

3-(N-((2-(2-((1,2,3,4-tetrahydroisoquinolin-2-yl)carbonyl)phenyl)phenyl)carbonyl)-N-(2-phenylpropyl)amino)propanoic acid HPLC measurement condition: A HPLC retention time: 3.95 minutes; MASS data (ESI, Pos., 20V): 547 (M+H)$^+$.

EXAMPLE 4(264)

3-(N-((2-(2-((α-methylbenzylamino)carbonyl)phenyl)phenyl)carbonyl)-N-(2-phenylpropyl)amino)propanoic acid HPLC measurement condition: A HPLC retention time: 3.97 minutes; MASS data (ESI, Pos., 20V): 535 (M+H)$^+$.

EXAMPLE 4(265)

3-(N-((2-(2-((2-methoxybenzylamino)carbonyl)phenyl)phenyl)carbonyl)-N-(2-phenylpropyl)amino)propanoic acid HPLC measurement condition: A HPLC retention time: 3.89 minutes; MASS data (ESI, Pos., 20V): 551 (M+H)$^+$.

EXAMPLE 4(266)

3-(N-((2-(2-((2-methylbenzylamino)carbonyl)phenyl)phenyl)carbonyl)-N-(2-phenylpropyl)amino) propanoic acid HPLC measurement condition: A HPLC retention time: 3.95 minutes; MASS data (ESI, Pos., 20V): 535 (M+H)$^+$.

EXAMPLE 4(267)

3-(N-((2-(2-((3-methoxybenzylamino)carbonyl)phenyl)phenyl)carbonyl)-N-(2-phenylpropyl)amino) propanoic acid HPLC measurement condition: A HPLC retention time: 3.86 minutes; MASS data (ESI, Pos., 20V): 551 (M+H)$^+$.

EXAMPLE 4(268)

3-(N-((2-(2-((4-chlorobenzylamino)carbonyl)phenyl)phenyl)carbonyl)-N-(2-phenylpropyl)amino)propanoic acid HPLC measurement condition: A HPLC retention time: 4.01 minutes; MASS data (ESI, Pos., 20V): 555 (M+H)$^+$.

EXAMPLE 4(269)

3-(N-((2-(2-((4-methoxybenzylamino)carbonyl)phenyl)phenyl)carbonyl)-N-(2-phenylpropyl)amino) propanoic acid HPLC measurement condition: A HPLC retention time: 3.84 minutes; MASS data (ESI, Pos., 20V): 551 (M+H)$^+$.

EXAMPLE 4(270)

3-(N-((2-(2-((4-methylbenzylamino)carbonyl)phenyl)phenyl)carbonyl)-N-(2-phenylpropyl)amino) propanoic acid HPLC measurement condition: A HPLC retention time: 3.99 minutes; MASS data (ESI, Pos., 20V): 535 (M+H)$^+$.

EXAMPLE 4(271)

3-(N-((2-(2-((N-methyl-N-benzylamino)carbonyl)phenyl)phenyl)carbonyl)-N-(2-phenylpropyl)amino) propanoic acid HPLC measurement condition: A HPLC retention time: 3.93 minutes; MASS data (ESI, Pos., 20V): 535 (M+H)$^+$.

EXAMPLE 4(272)

3-(N-((2-(2-((N-ethyl-N-benzylamino)carbonyl)phenyl)phenyl)carbonyl)-N-(2-phenylpropyl)amino) propanoic acid HPLC measurement condition: A HPLC retention time: 4.00 minutes; MASS data (ESI, Pos., 20V): 549 (M+H)$^+$.

EXAMPLE 4(273)

3-(N-((2-(2-((N-butyl-N-benzylamino)carbonyl)phenyl)phenyl)carbonyl)-N-(2-phenylpropyl)amino)propanoic acid HPLC measurement condition: A HPLC retention time: 4.19 minutes; MASS data (ESI, Pos., 20V): 577 (M+H)$^+$.

EXAMPLE 4(274)

3-(N-((2-(2-((4-(tert-butyl)benzylamino)carbonyl)phenyl)phenyl)carbonyl)-N-(2-phenylpropyl)amino)propanoic acid HPLC measurement condition: A HPLC retention time: 4.22 minutes; MASS data (ESI, Pos., 20V): 577 (M+H)$^+$.

EXAMPLE 4(275)

3-(N-((2-(2-((1-phenyl-3-trifluoroacetoxypropylamino)carbonyl)phenyl)phenyl)carbonyl)-N-(2-phenylpropyl)amino)propanoic acid HPLC measurement condition: A HPLC retention time: 4.13 minutes; MASS data (ESI, Pos., 20V): 661 (M+H)$^+$.

EXAMPLE 4(276)

3-(N-((2-(2-((2-fluorobenzylamino)carbonyl)phenyl)phenyl)carbonyl)-N-(2-phenylpropyl)amino)propanoic acid HPLC measurement condition: A HPLC retention time: 3.91 minutes; MASS data (ESI, Pos., 20V): 539 (M+H)$^+$.

EXAMPLE 4(277)

3-(N-((2-(2-((3-fluorobenzylamino)carbonyl)phenyl)phenyl)carbonyl)-N-(2-phenylpropyl)amino)propanoic acid HPLC measurement condition: A HPLC retention time: 3.93 minutes; MASS data (ESI, Pos., 20V): 539 (M+H)$^+$.

EXAMPLE 4(278)

3-(N-((2-(2-((2,5-difluorobenzylamino)carbonyl)phenyl)phenyl)carbonyl)-N-(2-phenylpropyl)amino)propanoic acid HPLC measurement condition: A HPLC retention time: 3.93 minutes; MASS data (ESI, Pos., 20V): 557 (M+H)$^+$.

EXAMPLE 4(279)

3-(N-((2-(2-(((1R)-1-phenyl-2-hydroxyethylamino)carbonyl)phenyl)phenyl)carbonyl)-N-(2-phenylpropyl)amino)propanoic acid HPLC measurement condition: A HPLC retention time: 3.71 minutes; MASS data (ESI, Pos., 20V): 551 (M+H)$^+$.

EXAMPLE 4(280)

3-(N-((2-(2-((2-chlorobenzylamino)carbonyl)phenyl)phenyl)carbonyl)-N-(2-phenylpropyl)amino)propanoic acid HPLC measurement condition: A HPLC retention time: 4.00 minutes; MASS data (ESI, Pos., 20V): 555 (M+H)$^+$.

EXAMPLE 4(281)

3-(N-((2-(2-((4-fluorobenzylamino)carbonyl)phenyl)phenyl)carbonyl)-N-(2-phenylpropyl)amino)propanoic acid HPLC measurement condition: A HPLC retention time: 3.91 minutes; MASS data (ESI, Pos., 20V): 539 (M+H)$^+$.

EXAMPLE 4(282)

3-(N-((2-(2-((allylamino)carbonyl)phenyl)phenyl)carbonyl)-N-(2-phenylpropyl)amino)propanoic acid HPLC measurement condition: A HPLC retention time: 3.73 minutes; MASS data (ESI, Pos., 20V): 471 (M+H)$^+$.

EXAMPLE 4(283)

3-(N-((2-(2-((2,6-difluorobenzylamino)carbonyl)phenyl)phenyl)carbonyl)-N-(2-phenylpropyl)amino)propanoic acid HPLC measurement condition: A HPLC retention time: 3.88 minutes; MASS data (ESI, Pos., 20V): 557 (M+H)$^+$.

EXAMPLE 4(284)

3-(N-((2-(2-((3-chlorobenzylamino)carbonyl)phenyl)phenyl)carbonyl)-N-(2-phenylpropyl)amino)propanoic acid HPLC measurement condition: A HPLC retention time: 4.00 minutes; MASS data (ESI, Pos., 20V): 555 (M+H)$^+$.

EXAMPLE 4(285)

3-(N-((2-(2-(((1S)-1-phenyl-2-hydroxyethylamino)carbonyl)phenyl)phenyl)carbonyl)-N-(2-phenylpropyl)amino)propanoic acid HPLC measurement condition: A HPLC retention time: 3.71 minutes; MASS data (ESI, Pos., 20V): 551 (M+H)$^+$.

EXAMPLE 4(286)

3-(N-((2-(2-(((1R)-1-(4-methylphenyl)ethylamino)carbonyl)phenyl)phenyl)carbonyl)-N-(2-phenylpropyl)amino)propanoic acid HPLC measurement condition: A HPLC retention time: 4.04 minutes; MASS data (ESI, Pos., 20V): 549 (M+H)$^+$.

EXAMPLE 4(287)

3-(N-((2-(2-((1-(4-fluorophenyl)ethylamino)carbonyl)phenyl)phenyl)carbonyl)-N-(2-phenylpropyl)amino)propanoic acid HPLC measurement condition: A HPLC retention time: 3.97 minutes; MASS data (ESI, Pos., 20V): 553 (M+H)$^+$.

EXAMPLE 4(288)

3-(N-((2-(2-((2-thienylmethylamino)carbonyl)phenyl)phenyl)carbonyl)-N-(2-phenylpropyl)amino)propanoic acid HPLC measurement condition: A HPLC retention time: 3.86 minutes; MASS data (ESI, Pos., 20V): 527 (M+H)$^+$.

EXAMPLE 4(289)

3-(N-((2-(2-(((3S)-3-hydroxymethyl-1,2,3,4-tetrahydroisoquinolin-2-yl)carbonyl)phenyl)phenyl)carbonyl)-N-(2-phenylpropyl)amino)propanoic acid HPLC measurement condition: A HPLC retention time: 3.58 minutes; MASS data (ESI, Pos., 20V): 577 (M+H)$^+$; HPLC retention time: 3.75 minutes; MASS data (ESI, Pos., 20V): 577 (M+H)$^+$, 473.

EXAMPLE 4(290)

3-(N-((2-(2-((3-methylbenzylamino)carbonyl)phenyl)phenyl)carbonyl)-N-(2-phenylpropyl)amino)propanoic acid HPLC measurement condition: A HPLC retention time: 3.97 minutes; MASS data (ESI, Pos., 20V): 535 (M+H)$^+$.

EXAMPLE 4(291)

3-(N-((2-(2-((3,5-difluorobenzylamino)carbonyl)phenyl)phenyl)carbonyl)-N-(2-phenylpropyl)amino)propanoic acid HPLC measurement condition: A HPLC retention time: 3.97 minutes; MASS data (ESI, Pos., 20V): 557 (M+H)$^+$.

EXAMPLE 4(292)

3-(N-((2-(2-((N-methyl-N-(6-methylpyridin-2-yl)methylamino)carbonyl)phenyl)phenyl)carbonyl)-N-(2-phenylpropyl)amino)propanoic acid HPLC measurement condition: A HPLC retention time: 3.29 minutes; MASS data (ESI, Pos., 20V): 550 (M+H)$^+$.

EXAMPLE 4(293)

3-(N-((2-(2-((N-(2-(N,N-dimethylamino)ethyl)-N-benzylamino)carbonyl)phenyl)phenyl)carbonyl)-N-(2-phenylpropyl)amino)propanoic acid HPLC measurement condition: A HPLC retention time: 3.51 minutes; MASS data (ESI, Pos., 20V): 592 (M+H)$^+$.

EXAMPLE 4(294)

3-(N-((2-(2-((2-phenylethylamino)carbonyl)phenyl)phenyl)carbonyl)-N-(2-phenylpropyl)amino)propanoic acid HPLC measurement condition: A HPLC retention time: 3.95 minutes; MASS data (ESI, Pos., 20V): 535 (M+H)$^+$.

EXAMPLE 4(295)

3-(N-((2-(2-((1,2,3,4-tetrahydro-1-naphthylamino)carbonyl)phenyl)phenyl)carbonyl)-N-(2-(pyridin-2-yl)ethyl)amino)propanoic acid HPLC measurement condition: A HPLC retention time: 3.25 minutes; MASS data (ESI, Pos., 20V): 548 (M+H)$^+$.

EXAMPLE 4(296)

3-(N-((2-(2-((N-benzyl-N-(2-hydroxyethyl)amino)carbonyl)phenyl)phenyl)carbonyl)-N-(2-(pyridin-2-yl)ethyl)amino)propanoic acid HPLC measurement condition: A HPLC retention time: 3.07 minutes; MASS data (ESI, Pos., 20V): 552 (M+H)$^+$.

EXAMPLE 4(297)

3-(N-((2-(2-((1-naphthylmethylamino)carbonyl)phenyl)phenyl)carbonyl)-N-(2-(pyridin-2-yl)ethyl)amino)propanoic acid HPLC measurement condition: A HPLC retention time: 3.27 minutes; MASS data (ESI, Pos., 20V): 558 (M+H)$^+$.

EXAMPLE 4(298)

3-(N-((2-(2-((α-methylbenzylamino)carbonyl)phenyl)phenyl)carbonyl)-N-(2-(pyridin-2-yl)ethyl)amino)propanoic acid HPLC measurement condition: A HPLC retention time: 3.18 minutes; MASS data (ESI, Pos., 20V): 522 (M+H)$^+$.

EXAMPLE 4(299)

3-(N-((2-(2-((2-methylbenzylamino)carbonyl)phenyl)phenyl)carbonyl)-N-(2-(pyridin-2-yl)ethyl)amino)propanoic acid HPLC measurement condition: A HPLC retention time: 3.18 minutes; MASS data (ESI, Pos., 20V): 522 (M+H)$^+$.

EXAMPLE 4(300)

3-(N-((2-(2-((4-chlorobenzylamino)carbonyl)phenyl)phenyl)carbonyl)-N-(2-(pyridin-2-yl)ethyl)amino)propanoic acid HPLC measurement condition: A HPLC retention time: 3.23 minutes; MASS data (ESI, Pos., 20V): 542 (M+H)$^+$.

EXAMPLE 4(301)

3-(N-((2-(2-((N-ethyl-N-benzylamino)carbonyl)phenyl)phenyl)carbonyl)-N-(2-(pyridin-2-yl)ethyl)amino)propanoic acid HPLC measurement condition: A HPLC retention time: 3.29 minutes; MASS data (ESI, Pos., 20V): 536 (M+H)$^+$.

EXAMPLE 4(302)

3-(N-((2-(2-((N-butyl-N-benzylamino)carbonyl)phenyl)phenyl)carbonyl)-N-(2-(pyridin-2-yl)ethyl)amino)propanoic acid HPLC measurement condition: A HPLC retention time: 3.45 minutes; MASS data (ESI, Pos., 20V): 564 (M+H)$^+$.

EXAMPLE 4(303)

3-(N-((2-(2-((4-(tert-butyl)benzylamino)carbonyl)phenyl)phenyl)carbonyl)-N-(2-(pyridin-2-yl)ethyl)amino)propanoic acid HPLC measurement condition: A HPLC retention time: 3.42 minutes; MASS data (ESI, Pos., 20V): 564 (M+H)$^+$.

EXAMPLE 4(304)

3-(N-((2-(2-(((5-methyl-2-furyl)methylamino)carbonyl)phenyl)phenyl)carbonyl)-N-(2-(pyridin-2-yl)ethyl)amino)propanoic acid HPLC measurement condition: A HPLC retention time: 3.11 minutes; MASS data (ESI, Pos., 20V): 512 (M+H)$^+$.

EXAMPLE 4(305)

3-(N-((2-(2-((1-phenyl-3-hydroxypropylamino)carbonyl)phenyl)phenyl)carbonyl)-N-(2-(pyridin-2-yl)ethyl)amino)propanoic acid HPLC measurement condition: A HPLC retention time: 3.01 minutes; MASS data (ESI, Pos., 20V): 552 (M+H)$^+$.

EXAMPLE 4(306)

3-(N-((2-(2-((2,5-difluorobenzylamino)carbonyl)phenyl)phenyl)carbonyl)-N-(2-(pyridin-2-yl)ethyl)amino)propanoic acid HPLC measurement condition: A HPLC retention time: 3.16 minutes; MASS data (ESI, Pos., 20V): 544 (M+H)$^+$.

EXAMPLE 4(307)

3-(N-((2-(2-(((1R)-1-phenyl-2-hydroxyethylamino)carbonyl)phenyl)phenyl)carbonyl)-N-(2-(pyridin-2-yl)ethyl)amino)propanoic acid HPLC measurement condition: A HPLC retention time: 3.00 minutes; MASS data (ESI, Pos., 20V): 538 (M+H)$^+$.

EXAMPLE 4(308)

3-(N-((2-(2-((3-chlorobenzylamino)carbonyl)phenyl)phenyl)carbonyl)-N-(2-(pyridin-2-yl)ethyl)amino)propanoic acid HPLC measurement condition: A HPLC retention time: 3.22 minutes; MASS data (ESI, Pos., 20V): 542 (M+H)$^+$.

EXAMPLE 4(309)

3-(N-((2-(2-(((1S)-1-phenyl-2-hydroxyethylamino)carbonyl)phenyl)phenyl)carbonyl)-N-(2-(pyridin-2-yl)ethyl)amino)propanoic acid HPLC measurement condition: A HPLC retention time: 3.01 minutes; MASS data (ESI, Pos., 20V): 538 (M+H)$^+$.

EXAMPLE 4(310)

3-(N-((2-(2-(((1R)-1-(4-methylphenyl)ethylamino)carbonyl)phenyl)phenyl)carbonyl)-N-(2-(pyridin-2-yl)ethyl)amino)propanoic acid HPLC measurement condition: A HPLC retention time: 3.23 minutes; MASS data (ESI, Pos., 20V): 536 (M+H)$^+$.

EXAMPLE 4(311)

3-(N-((2-(2-((1-(4-fluorophenyl)ethylamino)carbonyl)phenyl)phenyl)carbonyl)-N-(2-(pyridin-2-yl)ethyl)amino)propanoic acid HPLC measurement condition: A HPLC retention time: 3.20 minutes; MASS data (ESI, Pos., 20V): 540 (M+H)$^+$.

EXAMPLE 4(312)

3-(N-((2-(2-(((3S)-3-hydroxymethyl-1,2,3,4-tetrahydroisoquinolin-2-yl)carbonyl)phenyl)phenyl)carbonyl)-N-(2-(pyridin-2-yl)ethyl)amino)propanoic acid HPLC measurement condition: A HPLC retention time: 2.96 minutes; MASS data (ESI, Pos., 20V): 564 (M+H)$^+$, 282; HPLC retention time: 3.08 minutes; MASS data (ESI, Pos., 20V): 564 (M+H)$^+$.

EXAMPLE 4(313)

3-(N-((2-(2-((3-methylbenzylamino)carbonyl)phenyl)phenyl)carbonyl)-N-(2-(pyridin-2-yl)ethyl)amino)propanoic acid HPLC measurement condition: A HPLC retention time: 3.20 minutes; MASS data (ESI, Pos., 20V): 522 (M+H)$^+$.

EXAMPLE 4(314)

3-(N-((2-(2-((N-methyl-N-(6-methylpyridin-2-yl)methylamino)carbonyl)phenyl)phenyl)carbonyl)-N-(2-(pyridin-2-yl)ethyl)amino)propanoic acid HPLC measurement condition: A HPLC retention time: 2.74 minutes; MASS data (ESI, Pos., 20V): 537 (M+H)$^+$, 432, 269.

EXAMPLE 4(315)

3-(N-((2-(2-((N-(2-(N,N-dimethylamino)ethyl)-N-benzylamino)carbonyl)phenyl)phenyl)carbonyl)-N-(2-(pyridin-2-yl)ethyl)amino)propanoic acid HPLC measurement condition: A HPLC retention time: 2.92 minutes; MASS data (ESI, Pos., 20V): 579 (M+H)$^+$, 290, 267.

EXAMPLE 4(316)

3-(N-((2-(2-((1,2,3,4-tetrahydro-1-naphthylamino)carbonyl)phenyl)phenyl)carbonyl)-N-(2-(3,4-dimethoxyphenyl)ethyl)amino)propanoic acid HPLC measurement condition: A HPLC retention time: 3.82 minutes; MASS data (ESI, Pos., 20V): 607 (M+H)$^+$.

EXAMPLE 4(317)

3-(N-((2-(2-((N-benzyl-N-(2-hydroxyethyl)amino)carbonyl)phenyl)phenyl)carbonyl)-N-(2-(3,4-dimethoxyphenyl)ethyl)amino)propanoic acid HPLC measurement condition: A HPLC retention time: 3.49 minutes; MASS data (ESI, Pos., 20V): 611 (M+H)$^+$.

EXAMPLE 4(318)

3-(N-((2-(2-((2-furylmethylamino)carbonyl)phenyl)phenyl)carbonyl)-N-(2-(3,4-dimethoxyphenyl)ethyl)amino)propanoic acid HPLC measurement condition: A HPLC retention time: 3.55 minutes; MASS data (ESI, Pos., 20V): 557 (M+H)$^+$.

EXAMPLE 4(319)

3-(N-((2-(2-((1-indaneamino)carbonyl)phenyl)phenyl)carbonyl)-N-(2-(3,4-dimethoxyphenyl)ethyl)amino)propanoic acid HPLC measurement condition: A HPLC retention time: 3.73 minutes; MASS data (ESI, Pos., 20V): 593 (M+H)$^+$.

EXAMPLE 4(320)

3-(N-((2-(2-((1-naphthylmethylamino)carbonyl)phenyl)phenyl)carbonyl)-N-(2-(3,4-dimethoxyphenyl)ethyl)amino)propanoic acid HPLC measurement condition: A HPLC retention time: 3.82 minutes; MASS data (ESI, Pos., 20V): 617 (M+H)$^+$.

EXAMPLE 4(321)

3-(N-((2-(2-((pyridin-2-ylmethylamino)carbonyl)phenyl)phenyl)carbonyl)-N-(2-(3,4-dimethoxyphenyl)ethyl)amino)propanoic acid HPLC measurement condition: A HPLC retention time: 3.14 minutes; MASS data (ESI, Pos., 20V): 568 (M+H)$^+$.

EXAMPLE 4(322)

3-(N-((2-(2-((pyridin-3-ylmethylamino)carbonyl)phenyl)phenyl)carbonyl)-N-(2-(3,4-dimethoxyphenyl)ethyl)amino)propanoic acid HPLC measurement condition: A HPLC retention time: 3.07 minutes; MASS data (ESI, Pos., 20V): 568 (M+H)$^+$.

EXAMPLE 4(323)

3-(N-((2-(2-((1,2,3,4-tetrahydroisoquinolin-2-yl)carbonyl)phenyl)phenyl)carbonyl)-N-(2-(3,4-dimethoxyphenyl)ethyl)amino)propanoic acid HPLC measurement condition: A HPLC retention time: 3.71 minutes; MASS data (ESI, Pos., 20V): 593 (M+H)$^+$, 358.

EXAMPLE 4(324)

3-(N-((2-(2-((α-methylbenzylamino)carbonyl)phenyl)phenyl)carbonyl)-N-(2-(3,4-dimethoxyphenyl)ethyl)amino)propanoic acid HPLC measurement condition: A HPLC retention time: 3.73 minutes; MASS data (ESI, Pos., 20V): 581 (M+H)$^+$.

EXAMPLE 4(325)

3-(N-((2-(2-((benzylamino)carbonyl)phenyl)phenyl)carbonyl)-N-(2-(3,4-dimethoxyphenyl)ethyl)amino)propanoic acid HPLC measurement condition: A HPLC retention time: 3.64 minutes; MASS data (ESI, Pos., 20V): 567 (M+H)$^+$.

EXAMPLE 4(326)

3-(N-((2-(2-((2-methoxybenzylamino)carbonyl)phenyl)phenyl)carbonyl)-N-(2-(3,4-dimethoxyphenyl)ethyl)amino)propanoic acid HPLC measurement condition: A HPLC retention time: 3.66 minutes; MASS data (ESI, Pos., 20V): 597 (M+H)$^+$.

EXAMPLE 4(327)

3-(N-((2-(2-((2-methylbenzylamino)carbonyl)phenyl)phenyl)carbonyl)-N-(2-(3,4-dimethoxyphenyl)ethyl)amino)propanoic acid HPLC measurement condition: A HPLC retention time: 3.73 minutes; MASS data (ESI, Pos., 20V): 581 (M+H)$^+$.

EXAMPLE 4(328)

3-(N-((2-(2-((3-methoxybenzylamino)carbonyl)phenyl)phenyl)carbonyl)-N-(2-(3,4-dimethoxyphenyl)ethyl)amino)propanoic acid HPLC measurement condition: A HPLC retention time: 3.66 minutes; MASS data (ESI, Pos., 20V): 597 (M+H)$^+$.

EXAMPLE 4(329)

3-(N-((2-(2-((4-chlorobenzylamino)carbonyl)phenyl)phenyl)carbonyl)-N-(2-(3,4-dimethoxyphenyl)ethyl)amino)propanoic acid HPLC measurement condition: A HPLC retention time: 3.79 minutes; MASS data (ESI, Pos., 20V): 601 (M+H)$^+$.

EXAMPLE 4(330)

3-(N-((2-(2-((4-methoxybenzylamino)carbonyl)phenyl)phenyl)carbonyl)-N-(2-(3,4-dimethoxyphenyl)ethyl)amino)propanoic acid HPLC measurement condition: A HPLC retention time: 3.62 minutes; MASS data (ESI, Pos., 20V): 597 (M+H)$^+$.

EXAMPLE 4(331)

3-(N-((2-(2-((4-methylbenzylamino)carbonyl)phenyl)phenyl)carbonyl)-N-(2-(3,4-dimethoxyphenyl)ethyl)amino)propanoic acid HPLC measurement condition: A HPLC retention time: 3.73 minutes; MASS data (ESI, Pos., 20V): 581 (M+H)$^+$.

EXAMPLE 4(332)

3-(N-((2-(2-((N-methyl-N-benzylamino)carbonyl)phenyl)phenyl)carbonyl)-N-(2-(3,4-dimethoxyphenyl)ethyl)amino)propanoic acid HPLC measurement condition: A HPLC retention time: 3.67 minutes; MASS data (ESI, Pos., 20V): 581 (M+H)$^+$, 346.

EXAMPLE 4(333)

3-(N-((2-(2-((N-ethyl-N-benzylamino)carbonyl)phenyl)phenyl)carbonyl)-N-(2-(3,4-dimethoxyphenyl)ethyl)amino)propanoic acid HPLC measurement condition: A HPLC retention time: 3.77 minutes; MASS data (ESI, Pos., 20V): 595 (M+H)$^+$, 360.

EXAMPLE 4(334)

3-(N-((2-(2-((N-butyl-N-benzylamino)carbonyl)phenyl)phenyl)carbonyl)-N-(2-(3,4-dimethoxyphenyl)ethyl)amino)propanoic acid HPLC measurement condition: A HPLC retention time: 3.97 minutes; MASS data (ESI, Pos., 20V): 623 (M+H)$^+$, 388.

EXAMPLE 4(335)

3-(N-((2-(2-((4-(tert-butyl)benzylamino)carbonyl)phenyl)phenyl)carbonyl)-N-(2-(3,4-dimethoxyphenyl)ethyl)amino)propanoic acid HPLC measurement condition: A HPLC retention time: 3.99 minutes; MASS data (ESI, Pos., 20V): 623 (M+H)$^+$, 388.

EXAMPLE 4(336)

3-(N-((2-(2-((1-phenyl-3-hydroxypropylamino)carbonyl)phenyl)phenyl)carbonyl)-N-(2-(3,4-dimethoxyphenyl)ethyl)amino)propanoic acid HPLC measurement condition: A HPLC retention time: 3.47 minutes; MASS data (ESI, Pos., 20V): 611 (M+H)$^+$.

EXAMPLE 4(337)

3-(N-((2-(2-((2-fluorobenzylamino)carbonyl)phenyl)phenyl)carbonyl)-N-(2-(3,4-dimethoxyphenyl)ethyl)amino)propanoic acid HPLC measurement condition: A HPLC retention time: 3.67 minutes; MASS data (ESI, Pos., 20V): 585 (M+H)$^+$.

EXAMPLE 4(338)

3-(N-((2-(2-((3-fluorobenzylamino)carbonyl)phenyl)phenyl)carbonyl)-N-(2-(3,4-dimethoxyphenyl)ethyl)amino)propanoic acid HPLC measurement condition: A HPLC retention time: 3.67 minutes; MASS data (ESI, Pos., 20V): 585 (M+H)$^+$.

EXAMPLE 4(339)

3-(N-((2-(2-((2,5-difluorobenzylamino)carbonyl)phenyl)phenyl)carbonyl)-N-(2-(3,4-dimethoxyphenyl)ethyl)amino)propanoic acid HPLC measurement condition: A HPLC retention time: 3.69 minutes; MASS data (ESI, Pos., 20V): 603 (M+H)$^+$.

EXAMPLE 4(340)

3-(N-((2-(2-(((1R)-1-phenyl-2-hydroxyethylamino)carbonyl)phenyl)phenyl)carbonyl)-N-(2-(3,4-dimethoxyphenyl)ethyl)amino)propanoic acid HPLC measurement condition: A HPLC retention time: 3.49 minutes; MASS data (ESI, Pos., 20V): 597 (M+H)$^+$.

EXAMPLE 4(341)

3-(N-((2-(2-((2-chlorobenzylamino)carbonyl)phenyl)phenyl)carbonyl)-N-(2-(3,4-dimethoxyphenyl)ethyl)amino)propanoic acid HPLC measurement condition: A HPLC retention time: 3.77 minutes; MASS data (ESI, Pos., 20V): 601 (M+H)$^+$.

EXAMPLE 4(342)

3-(N-((2-(2-((4-fluorobenzylamino)carbonyl)phenyl)phenyl)carbonyl)-N-(2-(3,4-dimethoxyphenyl)ethyl)amino)propanoic acid HPLC measurement condition: A HPLC retention time: 3.67 minutes; MASS data (ESI, Pos., 20V): 585 (M+H)$^+$.

EXAMPLE 4(343)

3-(N-((2-(2-((allylamino)carbonyl)phenyl)phenyl)carbonyl)-N-(2-(3,4-dimethoxyphenyl)ethyl)amino)propanoic acid HPLC measurement condition: A HPLC retention time: 3.47 minutes; MASS data (ESI, Pos., 20V): 517 (M+H)$^+$.

EXAMPLE 4(344)

3-(N-((2-(2-((2,6-difluorobenzylamino)carbonyl)phenyl)phenyl)carbonyl)-N-(2-(3,4-dimethoxyphenyl)ethyl)amino)propanoic acid HPLC measurement condition: A HPLC retention time: 3.66 minutes; MASS data (ESI, Pos., 20V): 603 (M+H)$^+$.

EXAMPLE 4(345)

3-(N-((2-(2-((3-chlorobenzylamino)carbonyl)phenyl)phenyl)carbonyl)-N-(2-(3,4-dimethoxyphenyl)ethyl)amino)propanoic acid HPLC measurement condition: A HPLC retention time: 3.79 minutes; MASS data (ESI, Pos., 20V): 601 (M+H)$^+$.

EXAMPLE 4(346)

3-(N-((2-(2-(((1S)-1-phenyl-2-hydroxyethylamino)carbonyl)phenyl)phenyl)carbonyl)-N-(2-(3,4-dimethoxyphenyl)ethyl)amino)propanoic acid HPLC measurement condition: A HPLC retention time: 3.49 minutes; MASS data (ESI, Pos., 20V): 597 (M+H)$^+$.

EXAMPLE 4(347)

3-(N-((2-(2-(((1R)-1-(4-methylphenyl)ethylamino)carbonyl)phenyl)phenyl)carbonyl)-N-(2-(3,4-dimethoxyphenyl)ethyl)amino)propanoic acid HPLC measurement condition: A HPLC retention time: 3.80 minutes; MASS data (ESI, Pos., 20V): 595 (M+H)$^+$.

EXAMPLE 4(348)

3-(N-((2-(2-((1-(4-fluorophenyl)ethylamino)carbonyl)phenyl)phenyl)carbonyl)-N-(2-(3,4-dimethoxyphenyl)ethyl)amino)propanoic acid HPLC measurement condition: A HPLC retention time: 3.77 minutes; MASS data (ESI, Pos., 20V): 599 (M+H)$^+$.

EXAMPLE 4(349)

3-(N-((2-(2-((2-thienylmethylamino)carbonyl)phenyl)phenyl)carbonyl)-N-(2-(3,4-dimethoxyphenyl)ethyl)amino)propanoic acid HPLC measurement condition: A HPLC retention time: 3.62 minutes; MASS data (ESI, Pos., 20V): 573 (M+H)$^+$.

EXAMPLE 4(350)

3-(N-((2-(2-(((3S)-3-hydroxymethyl-1,2,3,4-tetrahydroisoquinolin-2-yl)carbonyl)phenyl)phenyl)carbonyl)-N-(2-(3,4-dimethoxyphenyl)ethyl)amino)propanoic acid HPLC measurement condition: A HPLC retention time: 3.42 minutes; MASS data (ESI, Pos., 20V): 623 (M+H)$^+$, 388; HPLC retention time: 3.53 minutes; MASS data (ESI, Pos., 20V): 623 (M+H)$^+$, 519.

EXAMPLE 4(351)

3-(N-((2-(2-((3-methylbenzylamino)carbonyl)phenyl)phenyl)carbonyl)-N-(2-(3,4-dimethoxyphenyl)ethyl)amino)propanoic acid HPLC measurement condition: A HPLC retention time: 3.73 minutes; MASS data (ESI, Pos., 20V): 581 (M+H)$^+$.

EXAMPLE 4(352)

3-(N-((2-(2-((3,5-difluorobenzylamino)carbonyl)phenyl)phenyl)carbonyl)-N-(2-(3,4-dimethoxyphenyl)ethyl)amino)propanoic acid HPLC measurement condition: A HPLC retention time: 3.75 minutes; MASS data (ESI, Pos., 20V): 603 (M+H)$^+$.

EXAMPLE 4(353)

3-(N-((2-(2-((N-methyl-N-(6-methylpyridin-2-yl)methylamino)carbonyl)phenyl)phenyl)carbonyl)-N-(2-(3,4-dimethoxyphenyl)ethyl)amino)propanoic acid HPLC measurement condition: A HPLC retention time: 3.11 minutes; MASS data (ESI, Pos., 20V): 596 (M+H)$^+$.

EXAMPLE 4(354)

3-(N-((2-(2-((2-phenylethylamino)carbonyl)phenyl)phenyl)carbonyl)-N-(2-(3,4-dimethoxyphenyl)ethyl)amino)propanoic acid HPLC measurement condition: A HPLC retention time: 3.71 minutes; MASS data (ESI, Pos., 20V): 581 (M+H)$^+$.

EXAMPLE 4(355)

3-(N-((2-(2-((1,2,3,4-tetrahydro-1-naphthylamino)carbonyl)phenyl)phenyl)carbonyl)-N-(1-methyl-3-phenylpropyl)amino)propanoic acid HPLC measurement condition: A HPLC retention time: 4.08 minutes; MASS data (ESI, Pos., 20V): 575 (M+H)$^+$.

EXAMPLE 4(356)

3-(N-((2-(2-((N-benzyl-N-(2-hydroxyethyl)amino)carbonyl)phenyl)phenyl)carbonyl)-N-(1-methyl-3-phenylpropyl)amino)propanoic acid HPLC measurement condition: A HPLC retention time: 3.77 minutes; MASS data (ESI, Pos., 20V): 579 (M+H)$^+$.

EXAMPLE 4(357)

3-(N-((2-(2-((1-naphthylmethylamino)carbonyl)phenyl)phenyl)carbonyl)-N-(1-methyl-3-phenylpropyl)amino)propanoic acid HPLC measurement condition: A HPLC retention time: 4.10 minutes; MASS data (ESI, Pos., 20V): 585 (M+H)+.

EXAMPLE 4(358)

3-(N-((2-(2-((α-methylbenzylamino)carbonyl)phenyl)phenyl)carbonyl)-N-(1-methyl-3-phenylpropyl)amino)propanoic acid HPLC measurement condition: A HPLC retention time: 4.00 minutes; MASS data (ESI, Pos., 20V): 549 (M+H)+.

EXAMPLE 4(359)

3-(N-((2-(2-((2-methylbenzylamino)carbonyl)phenyl)phenyl)carbonyl)-N-(1-methyl-3-phenylpropyl)amino)propanoic acid HPLC measurement condition: A HPLC retention time: 4.00 minutes; MASS data (ESI, Pos., 20V): 549 (M+H)+.

EXAMPLE 4(360)

3-(N-((2-(2-((4-chlorobenzylamino)carbonyl)phenyl)phenyl)carbonyl)-N-(1-methyl-3-phenylpropyl)amino)propanoic acid HPLC measurement condition: A HPLC retention time: 4.06 minutes; MASS data (ESI, Pos., 20V): 569 (M+H)+.

EXAMPLE 4(361)

3-(N-((2-(2-((3-methoxybenzylamino)carbonyl)phenyl)phenyl)carbonyl)-N-(2-(pyridin-3-yl)ethyl)amino)propanoic acid HPLC measurement condition: A HPLC retention time: 3.11 minutes; MASS data (ESI, Pos., 20V): 538 (M+H)+.

EXAMPLE 4(362)

3-(N-((2-(2-((N-ethyl-N-benzylamino)carbonyl)phenyl)phenyl)carbonyl)-N-(1-methyl-3-phenylpropyl)amino)propanoic acid HPLC measurement condition: A HPLC retention time: 4.06 minutes; MASS data (ESI, Pos., 20V): 563 (M+H)+.

EXAMPLE 4(363)

3-(N-((2-(2-((N-butyl-N-benzylamino)carbonyl)phenyl)phenyl)carbonyl)-N-(1-methyl-3-phenylpropyl)amino)propanoic acid HPLC measurement condition: A HPLC retention time: 4.26 minutes; MASS data (ESI, Pos., 20V): 591 (M+H)+.

EXAMPLE 4(364)

3-(N-((2-(2-((4-(tert-butyl)benzylamino)carbonyl)phenyl)phenyl)carbonyl)-N-(1-methyl-3-phenylpropyl)amino)propanoic acid HPLC measurement condition: A HPLC retention time: 4.22 minutes; MASS data (ESI, Pos., 20V): 591 (M+H)+.

EXAMPLE 4(365)

3-(N-((2-(2-((1-phenyl-3-hydroxypropylamino)carbonyl)phenyl)phenyl)carbonyl)-N-(1-methyl-3-phenylpropyl)amino)propanoic acid HPLC measurement condition: A HPLC retention time: 3.77 minutes; MASS data (ESI, Pos., 20V): 579 (M+H)+.

EXAMPLE 4(366)

3-(N-((2-(2-((2-fluorobenzylamino)carbonyl)phenyl)phenyl)carbonyl)-N-(1-methyl-3-phenylpropyl)amino)propanoic acid HPLC measurement condition: A HPLC retention time: 3.95 minutes; MASS data (ESI, Pos., 20V): 553 (M+H)+.

EXAMPLE 4(367)

3-(N-((2-(2-((2,5-difluorobenzylamino)carbonyl)phenyl)phenyl)carbonyl)-N-(1-methyl-3-phenylpropyl)amino)propanoic acid HPLC measurement condition: A HPLC retention time: 3.99 minutes; MASS data (ESI, Pos., 20V): 571 (M+H)+.

EXAMPLE 4(368)

3-(N-((2-(2-(((1R)-1-phenyl-2-hydroxyethylamino)carbonyl)phenyl)phenyl)carbonyl)-N-(1-methyl-3-phenylpropyl)amino)propanoic acid HPLC measurement condition: A HPLC retention time: 3.78 minutes; MASS data (ESI, Pos., 20V): 565 (M+H)+.

EXAMPLE 4(369)

3-(N-((2-(2-((2-chlorobenzylamino)carbonyl)phenyl)phenyl)carbonyl)-N-(1-methyl-3-phenylpropyl)amino)propanoic acid HPLC measurement condition: A HPLC retention time: 4.02 minutes; MASS data (ESI, Pos., 20V): 569 (M+H)+.

EXAMPLE 4(370)

3-(N-((2-(2-((3-chlorobenzylamino)carbonyl)phenyl)phenyl)carbonyl)-N-(1-methyl-3-phenylpropyl)amino)propanoic acid HPLC measurement condition: A HPLC retention time: 4.06 minutes; MASS data (ESI, Pos., 20V): 569 (M+H)+.

EXAMPLE 4(371)

3-(N-((2-(2-(((1S)-1-phenyl-2-hydroxyethylamino)carbonyl)phenyl)phenyl)carbonyl)-N-(1-methyl-3-phenylpropyl)amino)propanoic acid HPLC measurement condition: A HPLC retention time: 3.75 minutes; MASS data (ESI, Pos., 20V): 565 (M+H)$^+$.

EXAMPLE 4(372)

3-(N-((2-(2-(((1R)-1-(4-methylphenyl)ethylamino)carbonyl)phenyl)phenyl)carbonyl)-N-(1-methyl-3-phenylpropyl)amino)propanoic acid HPLC measurement condition: A HPLC retention time: 4.08 minutes; MASS data ESI, Pos., 20V): 563 (M+H)$^+$.

EXAMPLE 4(373)

3-(N-((2-(2-((1-(4-fluorophenyl)ethylamino)carbonyl)phenyl)phenyl)carbonyl)-N-(1-methyl-3-phenylpropyl)amino)propanoic acid HPLC measurement condition: A HPLC retention time: 4.02 minutes; MASS data (ESI, Pos., 20V): 567 (M+H)$^+$.

EXAMPLE 4(374)

3-(N-((2-(2-(((3S)-3-hydroxymethyl-1,2,3,4-tetrahydroisoquinolin-2-yl)carbonyl)phenyl)phenyl)carbonyl)-N-(1-methyl-3-phenylpropyl)amino)propanoic acid HPLC measurement condition: A HPLC retention time: 3.69 minutes; MASS data (ESI, Pos., 20V): 591 (M+H)$^+$; HPLC retention time: 3.80 minutes; MASS data (ESI, Pos., 20V): 591 (M+H)$^+$, 487.

EXAMPLE 4(375)

3-(N-((2-(2-((3-methylbenzylamino)carbonyl)phenyl)phenyl)carbonyl)-N-(1-methyl-3-phenylpropyl)amino)propanoic acid HPLC measurement condition: A HPLC retention time: 4.02 minutes; MASS data (ESI, Pos., 20V): 549 (M+H)$^+$.

EXAMPLE 4(376)

3-(N-((2-(2-((3,5-difluorobenzylamino)carbonyl)phenyl)phenyl)carbonyl)-N-(1-methyl-3-phenylpropyl)amino)propanoic acid HPLC measurement condition: A HPLC retention time: 4.00 minutes; MASS data (ESI, Pos., 20V): 571 (M+H)$^+$.

EXAMPLE 4(377)

3-(N-((2-(2-((N-(2-(N,N-dimethylamino)ethyl)-N-benzylamino)carbonyl)phenyl)phenyl)carbonyl)-N-(1-methyl-3-phenylpropyl)amino)propanoic acid HPLC measurement condition: A HPLC retention time: 3.60 minutes; MASS data (ESI, Pos., 20V): 606 (M+H)$^+$.

EXAMPLE 4(378)

3-(N-((2-(2-((2-phenylethylamino)carbonyl)phenyl)phenyl)carbonyl)-N-(1-methyl-3-phenylpropyl)amino)propanoic acid HPLC measurement condition: A HPLC retention time: 3.99 minutes; MASS data (ESI, Pos., 20V): 549 (M+H)$^+$.

EXAMPLE 4(379)

3-(N-((2-(2-((1,2,3,4-tetrahydro-1-naphthylamino)carbonyl)phenyl)phenyl)carbonyl)-N-(2-(2-methoxyphenyl)ethyl)amino)propanoic acid HPLC measurement condition: A HPLC retention time: 4.00 minutes; MASS data (ESI, Pos., 20V): 577 (M+H)$^+$.

EXAMPLE 4(380)

3-(N-((2-(2-((N-benzyl-N-(2-hydroxyethyl)amino)carbonyl)phenyl)phenyl)carbonyl)-N-(2-(2-methoxyphenyl)ethyl)amino)propanoic acid HPLC measurement condition: A HPLC retention time: 3.67 minutes; MASS data (ESI, Pos., 20V): 581 (M+H)$^+$.

EXAMPLE 4(381)

3-(N-((2-(2-((1-indaneamino)carbonyl)phenyl)phenyl)carbonyl)-N-(2-(2-methoxyphenyl)ethyl)amino)propanoic acid HPLC measurement condition: A HPLC retention time: 3.97 minutes; MASS data (ESI, Pos., 20V): 563 (M+H)$^+$.

EXAMPLE 4(382)

3-(N-((2-(2-((1-naphthylmethylamino)carbonyl)phenyl)phenyl)carbonyl)-N-(2-(2-methoxyphenyl)ethyl)amino)propanoic acid HPLC measurement condition: A HPLC retention time: 4.02 minutes; MASS data (ESI, Pos., 20V): 587 (M+H)$^+$.

EXAMPLE 4(383)

3-(N-((2-(2-((pyridin-2-ylmethylamino)carbonyl)phenyl)phenyl)carbonyl)-N-(2-(2-methoxyphenyl)ethyl)amino)propanoic acid HPLC measurement condition: A HPLC retention time: 3.31 minutes; MASS data (ESI, Pos., 20V): 538 (M+H)$^+$.

EXAMPLE 4(384)

3-(N-((2-(2-((pyridin-3-ylmethylamino)carbonyl)phenyl)phenyl)carbonyl)-N-(2-(2-methoxyphenyl)ethyl)amino)propanoic acid HPLC measurement condition: A HPLC retention time: 3.22 minutes; MASS data (ESI, Pos., 20V): 538 (M+H)$^+$.

EXAMPLE 4(385)

3-(N-((2-(2-((1,2,3,4-tetrahydroisoquinolin-2-yl)carbonyl)phenyl)phenyl)carbonyl)-N-(2-(2-methoxyphenyl)ethyl)amino)propanoic acid HPLC measurement condition: A HPLC retention time: 3.89 minutes; MASS data (ESI, Pos., 20V): 563 (M+H)$^+$.

EXAMPLE 4(386)

3-(N-((2-(2-((α-methylbenzylamino)carbonyl)phenyl)phenyl)carbonyl)-N-(2-(2-methoxyphenyl)ethyl)amino)propanoic acid HPLC measurement condition: A HPLC retention time: 3.91 minutes; MASS data (ESI, Pos., 20V): 551 (M+H)$^+$.

EXAMPLE 4(387)

3-(N-((2-(2-((2-methylbenzylamino)carbonyl)phenyl)phenyl)carbonyl)-N-(2-(2-methoxyphenyl)ethyl)amino)propanoic acid HPLC measurement condition: A HPLC retention time: 3.93 minutes; MASS data (ESI, Pos., 20V): 551 (M+H)$^+$.

EXAMPLE 4(388)

3-(N-((2-(2-((4-chlorobenzylamino)carbonyl)phenyl)phenyl)carbonyl)-N-(2-(2-methoxyphenyl)ethyl)amino)propanoic acid HPLC measurement condition: A HPLC retention time: 3.99 minutes; MASS data (ESI, Pos., 20V): 571 (M+H)$^+$.

EXAMPLE 4(389)

3-(N-((2-(2-((N-ethyl-N-benzylamino)carbonyl)phenyl)phenyl)carbonyl)-N-(2-(2-methoxyphenyl)ethyl)amino)propanoic acid HPLC measurement condition: A HPLC retention time: 3.93 minutes; MASS data (ESI, Pos., 20V): 565 (M+H)$^+$.

EXAMPLE 4(390)

3-(N-((2-(2-((N-butyl-N-benzylamino)carbonyl)phenyl)phenyl)carbonyl)-N-(2-(2-methoxyphenyl)ethyl)amino)propanoic acid HPLC measurement condition: A HPLC retention time: 4.13 minutes; MASS data (ESI, Pos., 20V): 593 (M+H)$^+$.

EXAMPLE 4(391)

3-(N-((2-(2-((4-(tert-butyl)benzylamino)carbonyl)phenyl)phenyl)carbonyl)-N-(2-(2-methoxyphenyl)ethyl)amino)propanoic acid HPLC measurement condition: A HPLC retention time: 4.17 minutes; MASS data (ESI, Pos., 20V): 593 (M+H)$^+$.

EXAMPLE 4(392)

3-(N-((2-(2-((1-phenyl-3-hydroxypropylamino)carbonyl)phenyl)phenyl)carbonyl)-N-(2-(2-methoxyphenyl)ethyl)amino)propanoic acid HPLC measurement condition: A HPLC retention time: 3.67 minutes; MASS data (ESI, Pos., 20V): 581 (M+H)$^+$.

EXAMPLE 4(393)

3-(N-((2-(2-((2,5-difluorobenzylamino)carbonyl)phenyl)phenyl)carbonyl)-N-(2-(2-methoxyphenyl)ethyl)amino)propanoic acid HPLC measurement condition: A HPLC retention time: 3.89 minutes; MASS data (ESI, Pos., 20V): 573 (M+H)$^+$.

EXAMPLE 4(394)

3-(N-((2-(2-(((1R)-1-phenyl-2-hydroxyethylamino)carbonyl)phenyl)phenyl)carbonyl)-N-(2-(2-methoxyphenyl)ethyl)amino)propanoic acid HPLC measurement condition: A HPLC retention time: 3.67 minutes; MASS data (ESI, Pos., 20V): 567 (M+H)$^+$.

EXAMPLE 4(395)

3-(N-((2-(2-((2-chlorobenzylamino)carbonyl)phenyl)phenyl)carbonyl)-N-(2-(2-methoxyphenyl)ethyl)amino)propanoic acid HPLC measurement condition: A HPLC retention time: 3.97 minutes; MASS data (ESI, Pos., 20V): 571 (M+H)$^+$.

EXAMPLE 4(396)

3-(N-((2-(2-((4-fluorobenzylamino)carbonyl)phenyl)phenyl)carbonyl)-N-(2-(2-methoxyphenyl)ethyl)amino)propanoic acid HPLC measurement condition: A HPLC retention time: 3.86 minutes; MASS data (ESI, Pos., 20V): 555 (M+H)$^+$.

EXAMPLE 4(397)

3-(N-((2-(2-((2,6-difluorobenzylamino)carbonyl)phenyl)phenyl)carbonyl)-N-(2-(2-methoxyphenyl)ethyl)amino)propanoic acid HPLC measurement condition: A HPLC retention time: 3.84 minutes; MASS data (ESI, Pos., 20V): 573 (M+H)$^+$.

EXAMPLE 4(398)

3-(N-((2-(2-((3-chlorobenzylamino)carbonyl)phenyl)phenyl)carbonyl)-N-(2-(2-methoxyphenyl)ethyl)amino)propanoic acid HPLC measurement condition: A HPLC retention time: 3.99 minutes; MASS data (ESI, Pos., 20V): 571 (M+H)$^+$.

EXAMPLE 4(399)

3-(N-((2-(2-(((1S)-1-phenyl-2-hydroxyethylamino) carbonyl)phenyl)phenyl)carbonyl)-N-(2-(2-methoxyphenyl)ethyl)amino)propanoic acid HPLC measurement condition: A HPLC retention time: 3.69 minutes; MASS data (ESI, Pos., 20V): 567 (M+H)+.

EXAMPLE 4(400)

3-(N-((2-(2-(((1R)-1-(4-methylphenyl)ethylamino) carbonyl)phenyl)phenyl)carbonyl)-N-(2-(2-methoxyphenyl)ethyl)amino)propanoic acid HPLC measurement condition: A HPLC retention time: 4.02 minutes; MASS data (ESI, Pos., 20V): 565 (M+H)+.

EXAMPLE 4(401)

3-(N-((2-(2-((1-(4-fluorophenyl)ethylamino)carbonyl)phenyl)phenyl)carbonyl)-N-(2-(2-methoxyphenyl)ethyl)amino)propanoic acid HPLC measurement condition: A HPLC retention time: 3.95 minutes; MASS data (ESI, Pos., 20V): 569 (M+H)+.

EXAMPLE 4(402)

3-(N-((2-(2-((2-thienylmethylamino)carbonyl)phenyl)phenyl)carbonyl)-N-(2-(2-methoxyphenyl)ethyl) amino)propanoic acid HPLC measurement condition: A HPLC retention time: 3.82 minutes; MASS data (ESI, Pos., 20V): 543 (M+H)+.

EXAMPLE 4(403)

3-(N-((2-(2-(((3S)-3-hydroxymethyl-1,2,3,4-tetrahydroisoquinolin-2-yl)carbonyl)phenyl)phenyl)carbonyl)-N-(2-(2-methoxyphenyl)ethyl)amino)propanoic acid HPLC measurement condition: A HPLC retention time: 3.56 minutes; MASS data (ESI, Pos., 20V): 593 (M+H)+; HPLC retention time: 3.71 minutes; MASS data (ESI, Pos., 20V): 593 (M+H)+, 489.

EXAMPLE 4(404)

3-(N-((2-(2-((3-methylbenzylamino)carbonyl)phenyl)phenyl)carbonyl)-N-(2-(2-methoxyphenyl)ethyl) amino)propanoic acid HPLC measurement condition: A HPLC retention time: 3.95 minutes; MASS data (ESI, Pos., 20V): 551 (M+H)+.

EXAMPLE 4(405)

3-(N-((2-(2-((N-methyl-N-(6-methylpyridin-2-yl) methylamino)carbonyl)phenyl)phenyl)carbonyl)-N-(2-(2-methoxyphenyl)ethyl)amino)propanoic acid HPLC measurement condition: A HPLC retention time: 3.27 minutes; MASS data (ESI, Pos., 20V): 566 (M+H)+.

EXAMPLE 4(406)

3-(N-((2-(2-((N-(2-(N,N-dimethylamino)ethyl)-N-benzylamino)carbonyl)phenyl)phenyl)carbonyl)-N-(2-(2-methoxyphenyl)ethyl)amino)propanoic acid HPLC measurement condition: A HPLC retention time: 3.49 minutes; MASS data (ESI, Pos., 20V): 608 (M+H)+.

EXAMPLE 4(407)

3-(N-((2-(2-((1,2,3,4-tetrahydro-1-naphthylamino) carbonyl)phenyl)phenyl)carbonyl)-N-(4-methoxybenzyl)amino)propanoic acid HPLC measurement condition: A HPLC retention time: 3.89 minutes; MASS data (ESI, Pos., 20V): 563 (M+H)+.

EXAMPLE 4(408)

3-(N-((2-(2-((N-benzyl-N-(2-hydroxyethyl)amino) carbonyl)phenyl)phenyl)carbonyl)-N-(4-methoxybenzyl)amino)propanoic acid HPLC measurement condition: A HPLC retention time: 3.58 minutes; MASS data (ESI, Pos., 20V): 567 (M+H)+.

EXAMPLE 4(409)

3-(N-((2-(2-((1-indaneamino)carbonyl)phenyl)phenyl)carbonyl)-N-(4-methoxybenzyl)amino)propanoic acid HPLC measurement condition: A HPLC retention time: 3.82 minutes; MASS data (ESI, Pos., 20V): 549 (M+H)+.

EXAMPLE 4(410)

3-(N-((2-(2-((1-naphthylmethylamino)carbonyl)phenyl)phenyl)carbonyl)-N-(4-methoxybenzyl)amino) propanoic acid HPLC measurement condition: A HPLC retention time: 3.91 minutes; MASS data (ESI, Pos., 20V): 573 (M+H)+.

EXAMPLE 4(411)

3-(N-((2-(2-((pyridin-2-ylmethylamino)carbonyl) phenyl)phenyl)carbonyl)-N-(4-methoxybenzyl) amino)propanoic acid HPLC measurement condition: A HPLC retention time: 3.20 minutes; MASS data (ESI, Pos., 20V): 524 (M+H)+.

EXAMPLE 4(412)

3-(N-((2-(2-((pyridin-3-ylmethylamino)carbonyl) phenyl)phenyl)carbonyl)-N-(4-methoxybenzyl) amino)propanoic acid HPLC measurement condition: A HPLC retention time: 3.14 minutes; MASS data (ESI, Pos., 20V): 524 (M+H)+.

EXAMPLE 4(413)

3-(N-((2-(2-((1,2,3,4-tetrahydroisoquinolin-2-yl) carbonyl)phenyl)phenyl)carbonyl)-N-(4-methoxybenzyl)amino)propanoic acid HPLC measurement condition: A HPLC retention time: 3.78 minutes; MASS data (ESI, Pos., 20V): 549 (M+H)+.

EXAMPLE 4(414)

3-(N-((2-(2-((α-methylbenzylamino)carbonyl)phenyl)phenyl)carbonyl)-N-(4-methoxybenzyl)amino) propanoic acid HPLC measurement condition: A HPLC retention time: 3.80 minutes; MASS data (ESI, Pos., 20V): 537 (M+H)+.

EXAMPLE 4(415)

3-(N-((2-(2-((benzylamino)carbonyl)phenyl)phenyl) carbonyl)-N-(4-methoxybenzyl)amino)propanoic acid HPLC measurement condition: A HPLC retention time: 3.73 minutes; MASS data (ESI, Pos., 20V): 523 (M+H)+.

EXAMPLE 4(416)

3-(N-((2-(2-((2-methoxybenzylamino)carbonyl)phenyl)phenyl)carbonyl)-N-(4-methoxybenzyl)amino) propanoic acid HPLC measurement condition: A HPLC retention time: 3.73 minutes; MASS data (ESI, Pos., 20V): 553 (M+H)+.

EXAMPLE 4(417)

3-(N-((2-(2-((2-methylbenzylamino)carbonyl)phenyl)phenyl)carbonyl)-N-(4-methoxybenzyl)amino) propanoic acid HPLC measurement condition: A HPLC retention time: 3.82 minutes; MASS data (ESI, Pos., 20V): 537 (M+H)+.

EXAMPLE 4(418)

3-(N-((2-(2-((3-methoxybenzylamino)carbonyl)phenyl)phenyl)carbonyl)-N-(4-methoxybenzyl)amino) propanoic acid HPLC measurement condition: A HPLC retention time: 3.73 minutes; MASS data (ESI, Pos., 20V): 553 (M+H)+.

EXAMPLE 4(419)

3-(N-((2-(2-((4-chlorobenzylamino)carbonyl)phenyl) phenyl)carbonyl)-N-(4-methoxybenzyl)amino)propanoic acid HPLC measurement condition: A HPLC retention time: 3.88 minutes; MASS data (ESI, Pos., 20V): 557 (M+H)+.

EXAMPLE 4(420)

3-(N-((2-(2-((4-methoxybenzylamino)carbonyl)phenyl)phenyl)carbonyl)-N-(4-methoxybenzyl)amino) propanoic acid HPLC measurement condition: A HPLC retention time: 3.71 minutes; MASS data (ESI, Pos., 20V): 553 (M+H)+.

EXAMPLE 4(421)

3-(N-((2-(2-((4-methylbenzylamino)carbonyl)phenyl)phenyl)carbonyl)-N-(4-methoxybenzyl)amino) propanoic acid HPLC measurement condition: A HPLC retention time: 3.82 minutes; MASS data (ESI, Pos., 20V): 537 (M+H)+.

EXAMPLE 4(422)

3-(N-((2-(2-((N-methyl-N-benzylamino)carbonyl) phenyl)phenyl)carbonyl)-N-(4-methoxybenzyl) amino)propanoic acid HPLC measurement condition: A HPLC retention time: 3.77 minutes; MASS data (ESI, Pos., 20V): 537 (M+H)+.

EXAMPLE 4(423)

3-(N-((2-(2-((N-ethyl-N-benzylamino)carbonyl)phenyl)phenyl)carbonyl)-N-(4-methoxybenzyl)amino) propanoic acid HPLC measurement condition: A HPLC retention time: 3.83 minutes; MASS data (ESI, Pos., 20V): 551 (M+H)+.

EXAMPLE 4(424)

3-(N-((2-(2-((N-butyl-N-benzylamino)carbonyl) phenyl)phenyl)carbonyl)-N-(4-methoxybenzyl) amino)propanoic acid HPLC measurement condition: A HPLC retention time: 4.04 minutes; MASS data (ESI, Pos., 20V): 579 (M+H)+.

EXAMPLE 4(425)

3-(N-((2-(2-((4-(tert-butyl)benzylamino)carbonyl) phenyl)phenyl)carbonyl)-N-(4-methoxybenzyl) amino)propanoic acid HPLC measurement condition: A HPLC retention time: 4.06 minutes; MASS data (ESI, Pos., 20V): 579 (M+H)+.

EXAMPLE 4(426)

3-(N-((2-(2-((1-phenyl-3-hydroxypropylamino)carbonyl)phenyl)phenyl)carbonyl)-N-(4-methoxybenzyl)amino)propanoic acid HPLC measurement condition: A HPLC retention time: 3.56 minutes; MASS data (ESI, Pos., 20V): 567 (M+H)+.

EXAMPLE 4(427)

3-(N-((2-(2-((2-fluorobenzylamino)carbonyl)phenyl)phenyl)carbonyl)-N-(4-methoxybenzyl)amino)propanoic acid HPLC measurement condition: A HPLC retention time: 3.77 minutes; MASS data (ESI, Pos., 20V): 541 (M+H)$^+$.

EXAMPLE 4(428)

3-(N-((2-(2-((3-fluorobenzylamino)carbonyl)phenyl)phenyl)carbonyl)-N-(4-methoxybenzyl)amino)propanoic acid HPLC measurement condition: A HPLC retention time: 3.77 minutes; MASS data (ESI, Pos., 20V): 541 (M+H)$^+$.

EXAMPLE 4(429)

3-(N-((2-(2-((2,5-difluorobenzylamino)carbonyl)phenyl)phenyl)carbonyl)-N-(4-methoxybenzyl)amino)propanoic acid HPLC measurement condition: A HPLC retention time: 3.78 minutes; MASS data (ESI, Pos., 20V): 559 (M+H)$^+$.

EXAMPLE 4(430)

3-(N-((2-(2-(((1R)-1-phenyl-2-hydroxyethylamino)carbonyl)phenyl)phenyl)carbonyl)-N-(4-methoxybenzyl)amino)propanoic acid HPLC measurement condition: A HPLC retention time: 3.56 minutes; MASS data (ESI, Pos., 20V): 553 (M+H)$^+$.

EXAMPLE 4(431)

3-(N-((2-(2-((2-chlorobenzylamino)carbonyl)phenyl)phenyl)carbonyl)-N-(4-methoxybenzyl)amino)propanoic acid HPLC measurement condition: A HPLC retention time: 3.84 minutes; MASS data (ESI, Pos., 20V): 557 (M+H)$^+$.

EXAMPLE 4(432)

3-(N-((2-(2-((4-fluorobenzylamino)carbonyl)phenyl)phenyl)carbonyl)-N-(4-methoxybenzyl)amino)propanoic acid HPLC measurement condition: A HPLC retention time: 3.75 minutes; MASS data (ESI, Pos., 20V): 541 (M+H)$^+$.

EXAMPLE 4(433)

3-(N-((2-(2-((allylamino)carbonyl)phenyl)phenyl)carbonyl)-N-(4-methoxybenzyl)amino)propanoic acid HPLC measurement condition: A HPLC retention time: 3.56 minutes; MASS data (ESI, Pos., 20V): 473 (M+H)$^+$.

EXAMPLE 4(434)

3-(N-((2-(2-((2,6-difluorobenzylamino)carbonyl)phenyl)phenyl)carbonyl)-N-(4-methoxybenzyl)amino)propanoic acid HPLC measurement condition: A HPLC retention time: 3.73 minutes; MASS data (ESI, Pos., 20V): 559 (M+H)$^+$.

EXAMPLE 4(435)

3-(N-((2-(2-((3-chlorobenzylamino)carbonyl)phenyl)phenyl)carbonyl)-N-(4-methoxybenzyl)amino)propanoic acid HPLC measurement condition: A HPLC retention time: 3.85 minutes; MASS data (ESI, Pos., 20V): 557 (M+H)$^+$.

EXAMPLE 4(436)

3-(N-((2-(2-(((1S)-1-phenyl-2-hydroxyethylamino)carbonyl)phenyl)phenyl)carbonyl)-N-(4-methoxybenzyl)amino)propanoic acid HPLC measurement condition: A HPLC retention time: 3.55 minutes; MASS data (ESI, Pos., 20V): 553 (M+H)$^+$.

EXAMPLE 4(437)

3-(N-((2-(2-(((1R)-1-(4-methylphenyl)ethylamino)carbonyl)phenyl)phenyl)carbonyl)-N-(4-methoxybenzyl)amino)propanoic acid HPLC measurement condition: A HPLC retention time: 3.89 minutes; MASS data (ESI, Pos., 20V): 551 (M+H)$^+$.

EXAMPLE 4(438)

3-(N-((2-(2-((1-(4-fluorophenyl)ethylamino)carbonyl)phenyl)phenyl)carbonyl)-N-(4-methoxybenzyl)amino)propanoic acid HPLC measurement condition: A HPLC retention time: 3.84 minutes; MASS data (ESI, Pos., 20V): 555 (M+H)$^+$.

EXAMPLE 4(439)

3-(N-((2-(2-((2-thienylmethylamino)carbonyl)phenyl)phenyl)carbonyl)-N-(4-methoxybenzyl)amino)propanoic acid HPLC measurement condition: A HPLC retention time: 3.71 minutes; MASS data (ESI, Pos., 20V): 529 (M+H)$^+$.

EXAMPLE 4(440)

3-(N-((2-(2-(((3S)-3-hydroxymethyl-1,2,3,4-tetrahydroisoquinolin-2-yl)carbonyl)phenyl)phenyl)carbonyl)-N-(4-methoxybenzyl)amino)propanoic acid HPLC measurement condition: A HPLC retention time: 3.49 minutes; MASS data (ESI, Pos., 20V): 579 (M+H)$^+$; HPLC retention time: 3.62 minutes; MASS data (ESI, Pos., 20V): 579 (M+H)$^+$, 475.

EXAMPLE 4(441)

3-(N-((2-(2-((3-methylbenzylamino)carbonyl)phenyl)phenyl)carbonyl)-N-(4-methoxybenzyl)amino)propanoic acid HPLC measurement condition: A HPLC retention time: 3.84 minutes; MASS data (ESI, Pos., 20V): 537 (M+H)$^+$.

EXAMPLE 4(442)

3-(N-((2-(2-((3,5-difluorobenzylamino)carbonyl)phenyl)phenyl)carbonyl)-N-(4-methoxybenzyl)amino)propanoic acid HPLC measurement condition: A HPLC retention time: 3.84 minutes; MASS data (ESI, Pos., 20V): 559 (M+H)$^+$.

EXAMPLE 4(443)

3-(N-((2-(2-((N-methyl-N-(6-methylpyridin-2-yl)methylamino)carbonyl)phenyl)phenyl)carbonyl)-N-(4-methoxybenzyl)amino)propanoic acid HPLC measurement condition: A HPLC retention time: 3.18 minutes; MASS data (ESI, Pos., 20V): 552 (M+H)$^+$.

EXAMPLE 4(444)

3-(N-((2-(2-((N-(2-(N,N-dimethylamino)ethyl)-N-benzylamino)carbonyl)phenyl)phenyl)carbonyl)-N-(4-methoxybenzyl)amino)propanoic acid HPLC measurement condition: A HPLC retention time: 3.40 minutes; MASS data (ESI, Pos., 20V): 594 (M+H)$^+$.

EXAMPLE 4(445)

3-(N-((2-(2-((2-phenylethylamino)carbonyl)phenyl)phenyl)carbonyl)-N-(4-methoxybenzyl)amino)propanoic acid HPLC measurement condition: A HPLC retention time: 3.80 minutes; MASS data (ESI, Pos., 20V): 537 (M+H)$^+$.

EXAMPLE 4(446)

3-(N-((2-(2-((1,2,3,4-tetrahydro-1-naphthylamino)carbonyl)phenyl)phenyl)carbonyl)-N-(2-(pyridin-4-yl)ethyl)amino)propanoic acid HPLC measurement condition: A HPLC retention time: 3.22 minutes; MASS data (ESI, Pos., 20V): 548 (M+H)$^+$, 131.

EXAMPLE 4(447)

3-(N-((2-(2-((N-benzyl-N-(2-hydroxyethyl)amino)carbonyl)phenyl)phenyl)carbonyl)-N-(2-(pyridin-4-yl)ethyl)amino)propanoic acid HPLC measurement condition: A HPLC retention time: 3.03 minutes; MASS data (ESI, Pos., 20V): 552 (M+H)$^+$.

EXAMPLE 4(448)

3-(N-((2-(2-((1-naphthylmethylamino)carbonyl)phenyl)phenyl)carbonyl)-N-(2-(pyridin-4-yl)ethyl)amino)propanoic acid HPLC measurement condition: A HPLC retention time: 3.23 minutes; MASS data (ESI, Pos., 20V): 558 (M+H)$^+$.

EXAMPLE 4(449)

3-(N-((2-(2-((pyridin-2-ylmethylamino)carbonyl)phenyl)phenyl)carbonyl)-N-(2-(pyridin-4-yl)ethyl)amino)propanoic acid HPLC measurement condition: A HPLC retention time: 2.72 minutes; MASS data (ESI, Pos., 20V): 509 (M+H)$^+$, 255.

EXAMPLE 4(450)

3-(N-((2-(2-((α-methylbenzylamino)carbonyl)phenyl)phenyl)carbonyl)-N-(2-(pyridin-4-yl)ethyl)amino)propanoic acid HPLC measurement condition: A HPLC retention time: 3.14 minutes; MASS data (ESI, Pos., 20V): 522 (M+H)$^+$.

EXAMPLE 4(451)

3-(N-((2-(2-((benzylamino)carbonyl)phenyl)phenyl)carbonyl)-N-(2-(pyridin-4-yl)ethyl)amino)propanoic acid HPLC measurement condition: A HPLC retention time: 3.07 minutes; MASS data (ESI, Pos., 20V): 508 (M+H)$^+$.

EXAMPLE 4(452)

3-(N-((2-(2-((2-methylbenzylamino)carbonyl)phenyl)phenyl)carbonyl)-N-(2-(pyridin-4-yl)ethyl)amino)propanoic acid HPLC measurement condition: A HPLC retention time: 3.16 minutes; MASS data (ESI, Pos., 20V): 522 (M+H)$^+$.

EXAMPLE 4(453)

3-(N-((2-(2-((4-chlorobenzylamino)carbonyl)phenyl)phenyl)carbonyl)-N-(2-(pyridin-4-yl)ethyl)amino)propanoic acid HPLC measurement condition: A HPLC retention time: 3.20 minutes; MASS data (ESI, Pos., 20V): 542 (M+H)$^+$.

EXAMPLE 4(454)

3-(N-((2-(2-((N-ethyl-N-benzylamino)carbonyl)phenyl)phenyl)carbonyl)-N-(2-(pyridin-4-yl)ethyl)amino)propanoic acid HPLC measurement condition: A HPLC retention time: 3.22 minutes; MASS data (ESI, Pos., 20V): 536 (M+H)$^+$.

EXAMPLE 4(455)

3-(N-((2-(2-((N-butyl-N-benzylamino)carbonyl)phenyl)phenyl)carbonyl)-N-(2-(pyridin-4-yl)ethyl)amino)propanoic acid HPLC measurement condition: A HPLC retention time: 3.40 minutes; MASS data (ESI, Pos., 20V): 564 (M+H)+.

EXAMPLE 4(456)

3-(N-((2-(2-((4-(tert-butyl)benzylamino)carbonyl)phenyl)phenyl)carbonyl)-N-(2-(pyridin-4-yl)ethyl)amino)propanoic acid HPLC measurement condition: A HPLC retention time: 3.38 minutes; MASS data (ESI, Pos., 20V): 564 (M+H)+.

EXAMPLE 4(457)

3-(N-((2-(2-((1-phenyl-3-hydroxypropylamino)carbonyl)phenyl)phenyl)carbonyl)-N-(2-(pyridin-4-yl)ethyl)amino)propanoic acid HPLC measurement condition: A HPLC retention time: 2.98 minutes; MASS data (ESI, Pos., 20V): 552 (M+H)+.

EXAMPLE 4(458)

3-(N-((2-(2-((2-fluorobenzylamino)carbonyl)phenyl)phenyl)carbonyl)-N-(2-(pyridin-4-yl)ethyl)amino)propanoic acid HPLC measurement condition: A HPLC retention time: 3.11 minutes; MASS data (ESI, Pos., 20V): 526 (M+H)+.

EXAMPLE 4(459)

3-(N-((2-(2-((2,5-difluorobenzylamino)carbonyl)phenyl)phenyl)carbonyl)-N-(2-(pyridin-4-yl)ethyl)amino)propanoic acid HPLC measurement condition: A HPLC retention time: 3.14 minutes; MASS data (ESI, Pos., 20V): 544 (M+H)+.

EXAMPLE 4(460)

3-(N-((2-(2-(((1R)-1-phenyl-2-hydroxyethylamino)carbonyl)phenyl)phenyl)carbonyl)-N-(2-(pyridin-4-yl)ethyl)amino)propanoic acid HPLC measurement condition: A HPLC retention time: 3.00 minutes; MASS data (ESI, Pos., 20V): 538 (M+H)+, 201.

EXAMPLE 4(461)

3-(N-((2-(2-((2-chlorobenzylamino)carbonyl)phenyl)phenyl)carbonyl)-N-(2-(pyridin-4-yl)ethyl)amino)propanoic acid HPLC measurement condition: A HPLC retention time: 3.18 minutes; MASS data (ESI, Pos., 20V): 542 (M+H)+.

EXAMPLE 4(462)

3-(N-((2-(2-((4-fluorobenzylamino)carbonyl)phenyl)phenyl)carbonyl)-N-(2-(pyridin-4-yl)ethyl)amino)propanoic acid HPLC measurement condition: A HPLC retention time: 3.12 minutes; MASS data (ESI, Pos., 20V): 526 (M+H)+.

EXAMPLE 4(463)

3-(N-((2-(2-((3-chlorobenzylamino)carbonyl)phenyl)phenyl)carbonyl)-N-(2-(pyridin-4-yl)ethyl)amino)propanoic acid HPLC measurement condition: A HPLC retention time: 3.20 minutes; MASS data (ESI, Pos., 20V): 542 (M+H)+.

EXAMPLE 4(464)

3-(N-((2-(2-(((1S)-1-phenyl-2-hydroxyethylamino)carbonyl)phenyl)phenyl)carbonyl)-N-(2-(pyridin-4-yl)ethyl)amino)propanoic acid HPLC measurement condition: A HPLC retention time: 2.98 minutes; MASS data (ESI, Pos., 20V): 538 (M+H)+.

EXAMPLE 4(465)

3-(N-((2-(2-(((1R)-1-(4-methylphenyl)ethylamino)carbonyl)phenyl)phenyl)carbonyl)-N-(2-(pyridin-4-yl)ethyl)amino)propanoic acid HPLC measurement condition: A HPLC retention time: 3.22 minutes; MASS data (ESI, Pos., 20V): 536 (M+H)+.

EXAMPLE 4(466)

3-(N-((2-(2-((1-(4-fluorophenyl)ethylamino)carbonyl)phenyl)phenyl)carbonyl)-N-(2-(pyridin-4-yl)ethyl)amino)propanoic acid HPLC measurement condition: A HPLC retention time: 3.16 minutes; MASS data (ESI, Pos., 20V): 540 (M+H)+.

EXAMPLE 4(467)

3-(N-((2-(2-(((3S)-3-hydroxymethyl-1,2,3,4-tetrahydroisoquinolin-2-yl)carbonyl)phenyl)phenyl)carbonyl)-N-(2-(pyridin-4-yl)ethyl)amino)propanoic acid HPLC measurement condition: A HPLC retention time: 2.96 minutes; MASS data (ESI, Pos., 20V): 564 (M+H)+, 282; HPLC retention time: 3.07 minutes; MASS data (ESI, Pos., 20V): 564 (M+H)+, 482, 282.

EXAMPLE 4(468)

3-(N-((2-(2-((3-methylbenzylamino)carbonyl)phenyl)phenyl)carbonyl)-N-(2-(pyridin-4-yl)ethyl)amino)propanoic acid HPLC measurement condition: A HPLC retention time: 3.18 minutes; MASS data (ESI, Pos., 20V): 522 (M+H)+.

EXAMPLE 4(469)

3-(N-((2-(2-((N-methyl-N-(6-methylpyridin-2-yl)methylamino)carbonyl)phenyl)phenyl)carbonyl)-N-(2-(pyridin-4-yl)ethyl)amino)propanoic acid HPLC measurement condition: A HPLC retention time: 2.74 minutes; MASS data (ESI, Pos., 20V): 537 (M+H)$^+$, 432, 269.

EXAMPLE 4(470)

3-(N-((2-(2-((N-(2-(N,N-dimethylamino)ethyl)-N-benzylamino)carbonyl)phenyl)phenyl)carbonyl)-N-(2-(pyridin-4-yl)ethyl)amino)propanoic acid HPLC measurement condition: A HPLC retention time: 2.92 minutes; MASS data (ESI, Pos., 20V): 579 (M+H)$^+$, 290, 267.

EXAMPLE 4(471)

3-(N-((2-(2-((1,2,3,4-tetrahydro-1-naphthylamino)carbonyl)phenyl)phenyl)carbonyl)-N-(2-phenylethyl)amino)propanoic acid HPLC measurement condition: A HPLC retention time: 3.97 minutes; MASS data (ESI, Pos., 20V): 547 (M+H)$^+$.

EXAMPLE 4(472)

3-(N-((2-(2-((N-benzyl-N-(2-hydroxyethyl)amino)carbonyl)phenyl)phenyl)carbonyl)-N-(2-phenylethyl)amino)propanoic acid HPLC measurement condition: A HPLC retention time: 3.66 minutes; MASS data (ESI, Pos., 20V): 551 (M+H)$^+$.

EXAMPLE 4(473)

3-(N-((2-(2-((1-naphthylmethylamino)carbonyl)phenyl)phenyl)carbonyl)-N-(2-phenylethyl)amino)propanoic acid HPLC measurement condition: A HPLC retention time: 4.00 minutes; MASS data (ESI, Pos., 20V): 557 (M+H)$^+$.

EXAMPLE 4(474)

3-(N-((2-(2-((pyridin-2-ylmethylamino)carbonyl)phenyl)phenyl)carbonyl)-N-(2-phenylethyl)amino)propanoic acid HPLC measurement condition: A HPLC retention time: 3.23 minutes; MASS data (ESI, Pos., 20V): 508 (M+H)$^+$.

EXAMPLE 4(475)

3-(N-((2-(2-((α-methylbenzylamino)carbonyl)phenyl)phenyl)carbonyl)-N-(2-phenylethyl)amino)propanoic acid HPLC measurement condition: A HPLC retention time: 3.88 minutes; MASS data (ESI, Pos., 20V): 521 (M+H)$^+$.

EXAMPLE 4(476)

3-(N-((2-(2-((2-methylbenzylamino)carbonyl)phenyl)phenyl)carbonyl)-N-(2-phenylethyl)amino)propanoic acid HPLC measurement condition: A HPLC retention time: 3.88 minutes; MASS data (ESI, Pos., 20V): 521 (M+H)$^+$.

EXAMPLE 4(477)

3-(N-((2-(2-((4-chlorobenzylamino)carbonyl)phenyl)phenyl)carbonyl)-N-(2-phenylethyl)amino)propanoic acid HPLC measurement condition: A HPLC retention time: 3.95 minutes; MASS data (ESI, Pos., 20V): 541 (M+H)$^+$.

EXAMPLE 4(478)

3-(N-((2-(2-((N-ethyl-N-benzylamino)carbonyl)phenyl)phenyl)carbonyl)-N-(2-phenylethyl)amino)propanoic acid HPLC measurement condition: A HPLC retention time: 3.91 minutes; MASS data (ESI, Pos., 20V): 535 (M+H)$^+$.

EXAMPLE 4(479)

3-(N-((2-(2-((N-butyl-N-benzylamino)carbonyl)phenyl)phenyl)carbonyl)-N-(2-phenylethyl)amino)propanoic acid HPLC measurement condition: A HPLC retention time: 4.10 minutes; MASS data (ESI, Pos., 20V): 563 (M+H)$^+$.

EXAMPLE 4(480)

3-(N-((2-(2-((4-(tert-butyl)benzylamino)carbonyl)phenyl)phenyl)carbonyl)-N-(2-phenylethyl)amino)propanoic acid HPLC measurement condition: A HPLC retention time: 4.13 minutes; MASS data (ESI, Pos., 20V): 563 (M+H)$^+$.

EXAMPLE 4(481)

3-(N-((2-(2-((1-phenyl-3-hydroxypropylamino)carbonyl)phenyl)phenyl)carbonyl)-N-(2-phenylethyl)amino)propanoic acid HPLC measurement condition: A HPLC retention time: 3.66 minutes; MASS data (ESI, Pos., 20V): 551 (M+H)$^+$.

EXAMPLE 4(482)

3-(N-((2-(2-((2,5-difluorobenzylamino)carbonyl)phenyl)phenyl)carbonyl)-N-(2-phenylethyl)amino)propanoic acid HPLC measurement condition: A HPLC retention time: 3.86 minutes; MASS data (ESI, Pos., 20V): 543 (M+H)$^+$.

EXAMPLE 4(483)

3-(N-((2-(2-(((1R)-1-phenyl-2-hydroxyethylamino) carbonyl)phenyl)phenyl)carbonyl)-N-(2-phenylethyl)amino)propanoic acid HPLC measurement condition: A HPLC retention time: 3.64 minutes; MASS data (ESI, Pos., 20V): 537 (M+H)$^+$.

EXAMPLE 4(484)

3-(N-((2-(2-((2-chlorobenzylamino)carbonyl)phenyl) phenyl)carbonyl)-N-(2-phenylethyl)amino)propanoic acid HPLC measurement condition: A HPLC retention time: 3.93 minutes; MASS data (ESI, Pos., 20V): 541 (M+H)$^+$.

EXAMPLE 4(485)

3-(N-((2-(2-((3-chlorobenzylamino)carbonyl)phenyl) phenyl)carbonyl)-N-(2-phenylethyl)amino)propanoic acid HPLC measurement condition: A HPLC retention time: 3.95 minutes; MASS data (ESI, Pos., 20V): 541 (M+H)$^+$.

EXAMPLE 4(486)

3-(N-((2-(2-(((1S)-1-phenyl-2-hydroxyethylamino) carbonyl)phenyl)phenyl)carbonyl)-N-(2-phenylethyl)amino)propanoic acid HPLC measurement condition: A HPLC retention time: 3.66 minutes; MASS data (ESI, Pos., 20V): 537 (M+H)$^+$.

EXAMPLE 4(487)

3-(N-((2-(2-(((1R)-1-(4-methylphenyl)ethylamino) carbonyl)phenyl)phenyl)carbonyl)-N-(2-phenylethyl)amino)propanoic acid HPLC measurement condition: A HPLC retention time: 3.97 minutes; MASS data (ESI, Pos., 20V): 535 (M+H)$^+$.

EXAMPLE 4(488)

3-(N-((2-(2-((1-(4-fluorophenyl)ethylamino)carbonyl)phenyl)phenyl)carbonyl)-N-(2-phenylethyl) amino)propanoic acid HPLC measurement condition: A HPLC retention time: 3.91 minutes; MASS data (ESI, Pos., 20V): 539 (M+H)$^+$.

EXAMPLE 4(489)

3-(N-((2-(2-(((3S)-3-hydroxymethyl-1,2,3,4-tetrahydroisoquinolin-2-yl)carbonyl)phenyl)phenyl)carbonyl)-N-(2-phenylethyl)amino)propanoic acid HPLC measurement condition: A HPLC retention time: 3.55 minutes; MASS data (ESI, Pos., 20V): 563 (M+H)$^+$; HPLC retention time: 3.69 minutes; MASS data (ESI, Pos., 20V): 563 (M+H)$^+$, 459.

EXAMPLE 4(490)

3-(N-((2-(2-((3-methylbenzylamino)carbonyl)phenyl)phenyl)carbonyl)-N-(2-phenylethyl)amino)propanoic acid HPLC measurement condition: A HPLC retention time: 3.89 minutes; MASS data (ESI, Pos., 20V): 521 (M+H)$^+$.

EXAMPLE 4(491)

3-(N-((2-(2-((3,5-difluorobenzylamino)carbonyl) phenyl)phenyl)carbonyl)-N-(2-phenylethyl)amino) propanoic acid HPLC measurement condition: A HPLC retention time: 3.91 minutes; MASS data (ESI, Pos., 20V): 543 (M+H)$^+$.

EXAMPLE 4(492)

3-(N-((2-(2-((N-methyl-N-(6-methylpyridin-2-yl) methylamino)carbonyl)phenyl)phenyl)carbonyl)-N-(2-phenylethyl)amino)propanoic acid HPLC measurement condition: A HPLC retention time: 3.22 minutes; MASS data (ESI, Pos., 20V): 536 (M+H)$^+$.

EXAMPLE 4(493)

3-(N-((2-(2-((N-(2-(N,N-dimethylamino)ethyl)-N-benzylamino)carbonyl)phenyl)phenyl)carbonyl)-N-(2-phenylethyl)amino)propanoic acid HPLC measurement condition: A HPLC retention time: 3.44 minutes; MASS data (ESI, Pos., 20V): 578 (M+H)$^+$.

EXAMPLE 4(494)

3-(N-((2-(2-((2-phenylethylamino)carbonyl)phenyl) phenyl)carbonyl)-N-(2-phenylethyl)amino)propanoic acid HPLC measurement condition: A HPLC retention time: 3.88 minutes; MASS data (ESI, Pos., 20V): 521 (M+H)$^+$.

EXAMPLE 4(495)

3-(N-((2-(2-((1,2,3,4-tetrahydro-1-naphthylamino) carbonyl)phenyl)phenyl)carbonyl)-N-(2-(4-methoxyphenyl)ethyl)amino)propanoic acid HPLC measurement condition: A HPLC retention time: 3.95 minutes; MASS data (ESI, Pos., 20V): 577 (M+H)$^+$.

EXAMPLE 4(496)

3-(N-((2-(2-((N-benzyl-N-(2-hydroxyethyl)amino) carbonyl)phenyl)phenyl)carbonyl)-N-(2-(4-methoxyphenyl)ethyl)amino)propanoic acid HPLC measurement condition: A HPLC retention time: 3.64 minutes; MASS data (ESI, Pos., 20V): 581 (M+H)$^+$.

EXAMPLE 4(497)

3-(N-((2-(2-((2-furylmethylamino)carbonyl)phenyl)phenyl)carbonyl)-N-(2-(4-methoxyphenyl)ethyl)amino)propanoic acid HPLC measurement condition: A HPLC retention time: 3.67 minutes; MASS data (ESI, Pos., 20V): 527 (M+H)+.

EXAMPLE 4(498)

3-(N-((2-(2-((1-indaneamino)carbonyl)phenyl)phenyl)carbonyl)-N-(2-(4-methoxyphenyl)ethyl)amino)propanoic acid HPLC measurement condition: A HPLC retention time: 3.88 minutes; MASS data (ESI, Pos., 20V): 563 (M+H)+.

EXAMPLE 4(499)

3-(N-((2-(2-((1-naphthylmethylamino)carbonyl)phenyl)phenyl)carbonyl)-N-(2-(4-methoxyphenyl)ethyl)amino)propanoic acid HPLC measurement condition: A HPLC retention time: 3.95 minutes; MASS data (ESI, Pos., 20V): 587 (M+H)+.

EXAMPLE 4(500)

3-(N-((2-(2-((pyridin-2-ylmethylamino)carbonyl)phenyl)phenyl)carbonyl)-N-(2-(4-methoxyphenyl)ethyl)amino)propanoic acid HPLC measurement condition: A HPLC retention time: 3.23 minutes; MASS data (ESI, Pos., 20V): 538 (M+H)+.

EXAMPLE 4(501)

3-(N-((2-(2-((pyridin-3-ylmethylamino)carbonyl)phenyl)phenyl)carbonyl)-N-(2-(4-methoxyphenyl)ethyl)amino)propanoic acid HPLC measurement condition: A HPLC retention time: 3.16 minutes; MASS data (ESI, Pos., 20V): 538 (M+H)+.

EXAMPLE 4(502)

3-(N-((2-(2-((1,2,3,4-tetrahydroisoquinolin-2-yl)carbonyl)phenyl)phenyl)carbonyl)-N-(2-(4-methoxyphenyl)ethyl)amino)propanoic acid HPLC measurement condition: A HPLC retention time: 3.84 minutes; MASS data (ESI, Pos., 20V): 563 (M+H)+.

EXAMPLE 4(503)

3-(N-((2-(2-((α-methylbenzylamino)carbonyl)phenyl)phenyl)carbonyl)-N-(2-(4-methoxyphenyl)ethyl)amino)propanoic acid HPLC measurement condition: A HPLC retention time: 3.86 minutes; MASS data (ESI, Pos., 20V): 551 (M+H)+.

EXAMPLE 4(504)

3-(N-((2-(2-((benzylamino)carbonyl)phenyl)phenyl)carbonyl)-N-(2-(4-methoxyphenyl)ethyl)amino)propanoic acid HPLC measurement condition: A HPLC retention time: 3.78 minutes; MASS data (ESI, Pos., 20V): 537 (M+H)+.

EXAMPLE 4(505)

3-(N-((2-(2-((2-methylbenzylamino)carbonyl)phenyl)phenyl)carbonyl)-N-(2-(4-methoxyphenyl)ethyl)amino)propanoic acid HPLC measurement condition: A HPLC retention time: 3.84 minutes; MASS data (ESI, Pos., 20V): 551 (M+H)+.

EXAMPLE 4(506)

3-(N-((2-(2-((4-chlorobenzylamino)carbonyl)phenyl)phenyl)carbonyl)-N-(2-(4-methoxyphenyl)ethyl)amino)propanoic acid HPLC measurement condition: A HPLC retention time: 3.91 minutes; MASS data (ESI, Pos., 20V): 571 (M+H)+.

EXAMPLE 4(507)

3-(N-((2-(2-((N-ethyl-N-benzylamino)carbonyl)phenyl)phenyl)carbonyl)-N-(2-(4-methoxyphenyl)ethyl)amino)propanoic acid HPLC measurement condition: A HPLC retention time: 3.89 minutes; MASS data (ESI, Pos., 20V): 565 (M+H)+.

EXAMPLE 4(508)

3-(N-((2-(2-((N-butyl-N-benzylamino)carbonyl)phenyl)phenyl)carbonyl)-N-(2-(4-methoxyphenyl)ethyl)amino)propanoic acid HPLC measurement condition: A HPLC retention time: 4.08 minutes; MASS data (ESI, Pos., 20V): 593 (M+H)+.

EXAMPLE 4(509)

3-(N-((2-(2-((4-(tert-butyl)benzylamino)carbonyl)phenyl)phenyl)carbonyl)-N-(2-(4-methoxyphenyl)ethyl)amino)propanoic acid HPLC measurement condition: A HPLC retention time: 4.10 minutes; MASS data (ESI, Pos., 20V): 593 (M+H)+.

EXAMPLE 4(510)

3-(N-((2-(2-((1-phenyl-3-hydroxypropylamino)carbonyl)phenyl)phenyl)carbonyl)-N-(2-(4-methoxyphenyl)ethyl)amino)propanoic acid HPLC measurement condition: A HPLC retention time: 3.62 minutes; MASS data (ESI, Pos., 20V): 581 (M+H)+.

EXAMPLE 4(511)

3-(N-((2-(2-((2-fluorobenzylamino)carbonyl)phenyl)phenyl)carbonyl)-N-(2-(4-methoxyphenyl)ethyl)amino)propanoic acid HPLC measurement condition: A HPLC retention time: 3.80 minutes; MASS data (ESI, Pos., 20V): 555 (M+H)$^+$.

EXAMPLE 4(512)

3-(N-((2-(2-((2,5-difluorobenzylamino)carbonyl)phenyl)phenyl)carbonyl)-N-(2-(4-methoxyphenyl)ethyl)amino)propanoic acid HPLC measurement condition: A HPLC retention time: 3.84 minutes; MASS data (ESI, Pos., 20V): 573 (M+H)$^+$.

EXAMPLE 4(513)

3-(N-((2-(2-(((1R)-1-phenyl-2-hydroxyethylamino)carbonyl)phenyl)phenyl)carbonyl)-N-(2-(4-methoxyphenyl)ethyl)amino)propanoic acid HPLC measurement condition: A HPLC retention time: 3.62 minutes; MASS data (ESI, Pos., 20V): 567 (M+H)$^+$.

EXAMPLE 4(514)

3-(N-((2-(2-((2-chlorobenzylamino)carbonyl)phenyl)phenyl)carbonyl)-N-(2-(4-methoxyphenyl)ethyl)amino)propanoic acid HPLC measurement condition: A HPLC retention time: 3.88 minutes; MASS data (ESI, Pos., 20V): 571 (M+H)$^+$.

EXAMPLE 4(515)

3-(N-((2-(2-((4-fluorobenzylamino)carbonyl)phenyl)phenyl)carbonyl)-N-(2-(4-methoxyphenyl)ethyl)amino)propanoic acid HPLC measurement condition: A HPLC retention time: 3.80 minutes; MASS data (ESI, Pos., 20V): 555 (M+H)$^+$.

EXAMPLE 4(516)

3-(N-((2-(2-((2,6-difluorobenzylamino)carbonyl)phenyl)phenyl)carbonyl)-N-(2-(4-methoxyphenyl)ethyl)amino)propanoic acid HPLC measurement condition: A HPLC retention time: 3.78 minutes; MASS data (ESI, Pos., 20V): 573 (M+H)$^+$.

EXAMPLE 4(517)

3-(N-((2-(2-((3-chlorobenzylamino)carbonyl)phenyl)phenyl)carbonyl)-N-(2-(4-methoxyphenyl)ethyl)amino)propanoic acid HPLC measurement condition: A HPLC retention time: 3.91 minutes; MASS data (ESI, Pos., 20V): 571 (M+H)$^+$.

EXAMPLE 4(518)

3-(N-((2-(2-(((1S)-1-phenyl-2-hydroxyethylamino)carbonyl)phenyl)phenyl)carbonyl)-N-(2-(4-methoxyphenyl)ethyl)amino)propanoic acid HPLC measurement condition: A HPLC retention time: 3.62 minutes; MASS data (ESI, Pos., 20V): 567 (M+H)$^+$.

EXAMPLE 4(519)

3-(N-((2-(2-(((1R)-1-(4-methylphenyl)ethylamino)carbonyl)phenyl)phenyl)carbonyl)-N-(2-(4-methoxyphenyl)ethyl)amino)propanoic acid HPLC measurement condition: A HPLC retention time: 3.93 minutes; MASS data (ESI, Pos., 20V): 565 (M+H)$^+$.

EXAMPLE 4(520)

3-(N-((2-(2-((1-(4-fluorophenyl)ethylamino)carbonyl)phenyl)phenyl)carbonyl)-N-(2-(4-methoxyphenyl)ethyl)amino)propanoic acid HPLC measurement condition: A HPLC retention time: 3.89 minutes; MASS data (ESI, Pos., 20V): 569 (M+H)$^+$.

EXAMPLE 4(521)

3-(N-((2-(2-((2-thienylmethylamino)carbonyl)phenyl)phenyl)carbonyl)-N-(2-(4-methoxyphenyl)ethyl)amino)propanoic acid HPLC measurement condition: A HPLC retention time: 3.77 minutes; MASS data (ESI, Pos., 20V): 543 (M+H)$^+$.

EXAMPLE 4(522)

3-(N-((2-(2-(((3S)-3-hydroxymethyl-1,2,3,4-tetrahydroisoquinolin-2-yl)carbonyl)phenyl)phenyl)carbonyl)-N-(2-(4-methoxyphenyl)ethyl)amino)propanoic acid HPLC measurement condition: A HPLC retention time: 3.51 minutes; MASS data (ESI, Pos., 20V): 593 (M+H)$^+$; HPLC retention time: 3.66 minutes; MASS data (ESI, Pos., 20V): 593 (M+H)$^+$, 489.

EXAMPLE 4(523)

3-(N-((2-(2-((3-methylbenzylamino)carbonyl)phenyl)phenyl)carbonyl)-N-(2-(4-methoxyphenyl)ethyl)amino)propanoic acid HPLC measurement condition: A HPLC retention time: 3.86 minutes; MASS data (ESI, Pos., 20V): 551 (M+H)$^+$.

EXAMPLE 4(524)

3-(N-((2-(2-((3,5-difluorobenzylamino)carbonyl)phenyl)phenyl)carbonyl)-N-(2-(4-methoxyphenyl)ethyl)amino)propanoic acid HPLC measurement condition: A HPLC retention time: 3.88 minutes; MASS data (ESI, Pos., 20V): 573 (M+H)$^+$.

EXAMPLE 4(525)

3-(N-((2-(2-((N-methyl-N-(6-methylpyridin-2-yl)methylamino)carbonyl)phenyl)phenyl)carbonyl)-N-(2-(4-methoxyphenyl)ethyl)amino)propanoic acid HPLC measurement condition: A HPLC retention time: 3.20 minutes; MASS data (ESI, Pos., 20V): 566 (M+H)$^+$.

EXAMPLE 4(526)

3-(N-((2-(2-((N-(2-(N,N-dimethylamino)ethyl)-N-benzylamino)carbonyl)phenyl)phenyl)carbonyl)-N-(2-(4-methoxyphenyl)ethyl)amino)propanoic acid HPLC measurement condition: A HPLC retention time: 3.44 minutes; MASS data (ESI, Pos., 20V): 608 (M+H)$^+$.

EXAMPLE 4(527)

3-(N-((2-(2-((2-phenylethylamino)carbonyl)phenyl)phenyl)carbonyl)-N-(2-(4-methoxyphenyl)ethyl)amino)propanoic acid HPLC measurement condition: A HPLC retention time: 3.86 minutes; MASS data (ESI, Pos., 20V): 551 (M+H)$^+$.

EXAMPLE 4(528)

3-(N-((2-(2-((1,2,3,4-tetrahydro-1-naphthylamino)carbonyl)phenyl)phenyl)carbonyl)-N-(2-(4-aminosulfonylphenyl)ethyl)amino)propanoic acid HPLC measurement condition: A HPLC retention time: 3.60 minutes; MASS data (ESI, Pos., 20V): 626 (M+H)$^+$.

EXAMPLE 4(529)

3-(N-((2-(2-((N-benzyl-N-(2-hydroxyethyl)amino)carbonyl)phenyl)phenyl)carbonyl)-N-(2-(4-aminosulfonylphenyl)ethyl)amino)propanoic acid HPLC measurement condition: A HPLC retention time: 3.33 minutes; MASS data (ESI, Pos., 20V): 630 (M+H)$^+$.

EXAMPLE 4(530)

3-(N-((2-(2-((2-furylmethylamino)carbonyl)phenyl)phenyl)carbonyl)-N-(2-(4-aminosulfonylphenyl)ethyl)amino)propanoic acid HPLC measurement condition: A HPLC retention time: 3.34 minutes; MASS data (ESI, Pos., 20V): 576 (M+H)$^+$, 248.

EXAMPLE 4(531)

3-(N-((2-(2-((1-indaneamino)carbonyl)phenyl)phenyl)carbonyl)-N-(2-(4-aminosulfonylphenyl)ethyl)amino)propanoic acid HPLC measurement condition: A HPLC retention time: 3.53 minutes; MASS data (ESI, Pos., 20V): 612 (M+H)$^+$.

EXAMPLE 4(532)

3-(N-((2-(2-((1-naphthylmethylamino)carbonyl)phenyl)phenyl)carbonyl)-N-(2-(4-aminosulfonylphenyl)ethyl)amino)propanoic acid HPLC measurement condition: A HPLC retention time: 3.59 minutes; MASS data (ESI, Pos., 20V): 636 (M+H)$^+$.

EXAMPLE 4(533)

3-(N-((2-(2-((pyridin-2-ylmethylamino)carbonyl)phenyl)phenyl)carbonyl)-N-(2-(4-aminosulfonylphenyl)ethyl)amino)propanoic acid HPLC measurement condition: A HPLC retention time: 2.96 minutes; MASS data (ESI, Pos., 20V): 587 (M+H)$^+$.

EXAMPLE 4(534)

3-(N-((2-(2-((pyridin-3-ylmethylamino)carbonyl)phenyl)phenyl)carbonyl)-N-(2-(4-aminosulfonylphenyl)ethyl)amino)propanoic acid HPLC measurement condition: A HPLC retention time: 2.94 minutes; MASS data (ESI, Pos., 20V): 587 (M+H)$^+$.

EXAMPLE 4(535)

3-(N-((2-(2-((1,2,3,4-tetrahydroisoquinolin-2-yl)carbonyl)phenyl)phenyl)carbonyl)-N-(2-(4-aminosulfonylphenyl)ethyl)amino)propanoic acid HPLC measurement condition: A HPLC retention time: 3.53 minutes; MASS data (ESI, Pos., 20V): 612 (M+H)$^+$.

EXAMPLE 4(536)

3-(N-((2-(2-((α-methylbenzylamino)carbonyl)phenyl)phenyl)carbonyl)-N-(2-(4-aminosulfonylphenyl)ethyl)amino)propanoic acid HPLC measurement condition: A HPLC retention time: 3.51 minutes; MASS data (ESI, Pos., 20V): 600 (M+H)$^+$.

EXAMPLE 4(537)

3-(N-((2-(2-((benzylamino)carbonyl)phenyl)phenyl)carbonyl)-N-(2-(4-aminosulfonylphenyl)ethyl)amino)propanoic acid HPLC measurement condition: A HPLC retention time: 3.45 minutes; MASS data (ESI, Pos., 20V): 586 (M+H)$^+$.

EXAMPLE 4(538)

3-(N-((2-(2-((2-methoxybenzylamino)carbonyl)phenyl)phenyl)carbonyl)-N-(2-(4-aminosulfonylphenyl)ethyl)amino)propanoic acid HPLC measurement condition: A HPLC retention time: 3.47 minutes; MASS data (ESI, Pos., 20V): 616 (M+H)$^+$.

EXAMPLE 4(539)

3-(N-((2-(2-((2-methylbenzylamino)carbonyl)phenyl)phenyl)carbonyl)-N-(2-(4-aminosulfonylphenyl)ethyl)amino)propanoic acid HPLC measurement condition: A HPLC retention time: 3.49 minutes; MASS data (ESI, Pos., 20V): 600 (M+H)$^+$.

EXAMPLE 4(540)

3-(N-((2-(2-((3-methoxybenzylamino)carbonyl)phenyl)phenyl)carbonyl)-N-(2-(4-aminosulfonylphenyl)ethyl)amino)propanoic acid HPLC measurement condition: A HPLC retention time: 3.44 minutes; MASS data (ESI, Pos., 20V): 616 (M+H)$^+$.

EXAMPLE 4(541)

3-(N-((2-(2-((4-chlorobenzylamino)carbonyl)phenyl)phenyl)carbonyl)-N-(2-(4-aminosulfonylphenyl)ethyl)amino)propanoic acid HPLC measurement condition: A HPLC retention time: 3.56 minutes; MASS data (ESI, Pos., 20V): 620 (M+H)$^+$.

EXAMPLE 4(542)

3-(N-((2-(2-((4-methoxybenzylamino)carbonyl)phenyl)phenyl)carbonyl)-N-(2-(4-aminosulfonylphenyl)ethyl)amino)propanoic acid HPLC measurement condition: A HPLC retention time: 3.40 minutes; MASS data (ESI, Pos., 20V): 616 (M+H)$^+$.

EXAMPLE 4(543)

3-(N-((2-(2-((4-methylbenzylamino)carbonyl)phenyl)phenyl)carbonyl)-N-(2-(4-aminosulfonylphenyl)ethyl)amino)propanoic acid HPLC measurement condition: A HPLC retention time: 3.51 minutes; MASS data (ESI, Pos., 20V): 600 (M+H)$^+$.

EXAMPLE 4(544)

3-(N-((2-(2-((N-methyl-N-benzylamino)carbonyl)phenyl)phenyl)carbonyl)-N-(2-(4-aminosulfonylphenyl)ethyl)amino)propanoic acid HPLC measurement condition: A HPLC retention time: 3.49 minutes; MASS data (ESI, Pos., 20V): 600 (M+H)$^+$.

EXAMPLE 4(545)

3-(N-((2-(2-((N-ethyl-N-benzylamino)carbonyl)phenyl)phenyl)carbonyl)-N-(2-(4-aminosulfonylphenyl)ethyl)amino)propanoic acid HPLC measurement condition: A HPLC retention time: 3.56 minutes; MASS data (ESI, Pos., 20V): 614 (M+H)$^+$.

EXAMPLE 4(546)

3-(N-((2-(2-((N-butyl-N-benzylamino)carbonyl)phenyl)phenyl)carbonyl)-N-(2-(4-aminosulfonylphenyl)ethyl)amino)propanoic acid HPLC measurement condition: A HPLC retention time: 3.75 minutes; MASS data (ESI, Pos., 20V): 642 (M+H)$^+$.

EXAMPLE 4(547)

3-(N-((2-(2-((4-(tert-butyl)benzylamino)carbonyl)phenyl)phenyl)carbonyl)-N-(2-(4-aminosulfonylphenyl)ethyl)amino)propanoic acid HPLC measurement condition: A HPLC retention time: 3.73 minutes; MASS data (ESI, Pos., 20V): 642 (M+H)$^+$.

EXAMPLE 4(548)

3-(N-((2-(2-((1-phenyl-3-hydroxypropylamino)carbonyl)phenyl)phenyl)carbonyl)-N-(2-(4-aminosulfonylphenyl)ethyl)amino)propanoic acid HPLC measurement condition: A HPLC retention time: 3.29 minutes; MASS data (ESI, Pos., 20V): 630 (M+H)$^+$.

EXAMPLE 4(549)

3-(N-((2-(2-((2-fluorobenzylamino)carbonyl)phenyl)phenyl)carbonyl)-N-(2-(4-aminosulfonylphenyl)ethyl)amino)propanoic acid HPLC measurement condition: A HPLC retention time: 3.45 minutes; MASS data (ESI, Pos., 20V): 604 (M+H)$^+$.

EXAMPLE 4(550)

3-(N-((2-(2-((3-fluorobenzylamino)carbonyl)phenyl)phenyl)carbonyl)-N-(2-(4-aminosulfonylphenyl)ethyl)amino)propanoic acid HPLC measurement condition: A HPLC retention time: 3.45 minutes; MASS data (ESI, Pos., 20V): 604 (M+H)$^+$.

EXAMPLE 4(551)

3-(N-((2-(2-((2,5-difluorobenzylamino)carbonyl)phenyl)phenyl)carbonyl)-N-(2-(4-aminosulfonylphenyl)ethyl)amino)propanoic acid HPLC measurement condition: A HPLC retention time: 3.47 minutes; MASS data (ESI, Pos., 20V): 622 (M+H)$^+$.

EXAMPLE 4(552)

3-(N-((2-(2-(((1R)-1-phenyl-2-hydroxyethylamino)carbonyl)phenyl)phenyl)carbonyl)-N-(2-(4-aminosulfonylphenyl)ethyl)amino)propanoic acid HPLC measurement condition: A HPLC retention time: 3.27 minutes; MASS data (ESI, Pos., 20V): 616 (M+H)$^+$.

EXAMPLE 4(553)

3-(N-((2-(2-((2-chlorobenzylamino)carbonyl)phenyl)phenyl)carbonyl)-N-(2-(4-aminosulfonylphenyl)ethyl)amino)propanoic acid HPLC measurement condition: A HPLC retention time: 3.53 minutes; MASS data (ESI, Pos., 20V): 620 (M+H)$^+$.

EXAMPLE 4(554)

3-(N-((2-(2-((4-fluorobenzylamino)carbonyl)phenyl)phenyl)carbonyl)-N-(2-(4-aminosulfonylphenyl)ethyl)amino)propanoic acid HPLC measurement condition: A HPLC retention time: 3.47 minutes; MASS data (ESI, Pos., 20V): 604 (M+H)$^+$.

EXAMPLE 4(555)

3-(N-((2-(2-((allylamino)carbonyl)phenyl)phenyl)carbonyl)-N-(2-(4-aminosulfonylphenyl)ethyl)amino)propanoic acid HPLC measurement condition: A HPLC retention time: 3.25 minutes; MASS data (ESI, Pos., 20V): 536 (M+H)$^+$.

EXAMPLE 4(556)

3-(N-((2-(2-((2,6-difluorobenzylamino)carbonyl)phenyl)phenyl)carbonyl)-N-(2-(4-aminosulfonylphenyl)ethyl)amino)propanoic acid HPLC measurement condition: A HPLC retention time: 3.44 minutes; MASS data (ESI, Pos., 20V): 622 (M+H)$^+$.

EXAMPLE 4(557)

3-(N-((2-(2-((3-chlorobenzylamino)carbonyl)phenyl)phenyl)carbonyl)-N-(2-(4-aminosulfonylphenyl)ethyl)amino)propanoic acid HPLC measurement condition: A HPLC retention time: 3.55 minutes; MASS data (ESI, Pos., 20V): 620 (M+H)$^+$.

EXAMPLE 4(558)

3-(N-((2-(2-(((1S)-1-phenyl-2-hydroxyethylamino)carbonyl)phenyl)phenyl)carbonyl)-N-(2-(4-aminosulfonylphenyl)ethyl)amino)propanoic acid HPLC measurement condition: A HPLC retention time: 3.27 minutes; MASS data (ESI, Pos., 20V): 616 (M+H)$^+$.

EXAMPLE 4(559)

3-(N-((2-(2-(((1R)-1-(4-methylphenyl)ethylamino)carbonyl)phenyl)phenyl)carbonyl)-N-(2-(4-aminosulfonylphenyl)ethyl)amino)propanoic acid HPLC measurement condition: A HPLC retention time: 3.56 minutes; MASS data (ESI, Pos., 20V): 614 (M+H)$^+$.

EXAMPLE 4(560)

3-(N-((2-(2-((1-(4-fluorophenyl)ethylamino)carbonyl)phenyl)phenyl)carbonyl)-N-(2-(4-aminosulfonylphenyl)ethyl)amino)propanoic acid HPLC measurement condition: A HPLC retention time: 3.53 minutes; MASS data (ESI, Pos., 20V): 618 (M+H)$^+$.

EXAMPLE 4(561)

3-(N-((2-(2-((2-thienylmethylamino)carbonyl)phenyl)phenyl)carbonyl)-N-(2-(4-aminosulfonylphenyl)ethyl)amino)propanoic acid HPLC measurement condition: A HPLC retention time: 3.40 minutes; MASS data (ESI, Pos., 20V): 592 (M+H)$^+$.

EXAMPLE 4(562)

3-(N-((2-(2-(((3S)-3-hydroxymethyl-1,2,3,4-tetrahydroisoquinolin-2-yl)carbonyl)phenyl)phenyl)carbonyl)-N-(2-(4-aminosulfonylphenyl)ethyl)amino)propanoic acid HPLC measurement condition: A HPLC retention time: 3.23 minutes; MASS data (ESI, Pos., 20V): 642 (M+H)$^+$; HPLC retention time: 3.36 minutes; MASS data (ESI, Pos., 20V): 642 (M+H)$^+$.

EXAMPLE 4(563)

3-(N-((2-(2-((3-methylbenzylamino)carbonyl)phenyl)phenyl)carbonyl)-N-(2-(4-aminosulfonylphenyl)ethyl)amino)propanoic acid HPLC measurement condition: A HPLC retention time: 3.53 minutes; MASS data (ESI, Pos., 20V): 600 (M+H)$^+$.

EXAMPLE 4(564)

3-(N-((2-(2-((3,5-difluorobenzylamino)carbonyl)phenyl)phenyl)carbonyl)-N-(2-(4-aminosulfonylphenyl)ethyl)amino)propanoic acid HPLC measurement condition: A HPLC retention time: 3.51 minutes; MASS data (ESI, Pos., 20V): 622 (M+H)$^+$.

EXAMPLE 4(565)

3-(N-((2-(2-((N-methyl-N-(6-methylpyridin-2-yl)methylamino)carbonyl)phenyl)phenyl)carbonyl)-N-(2-(4-aminosulfonylphenyl)ethyl)amino)propanoic acid HPLC measurement condition: A HPLC retention time: 2.96 minutes; MASS data (ESI, Pos., 20V): 615 (M+H)$^+$, 361.

EXAMPLE 4(566)

3-(N-((2-(2-((N-(2-(N,N-dimethylamino)ethyl)-N-benzylamino)carbonyl)phenyl)phenyl)carbonyl)-N-(2-(4-aminosulfonylphenyl)ethyl)amino)propanoic acid HPLC measurement condition: A HPLC retention time: 3.18 minutes; MASS data (ESI, Pos., 20V): 657 (M+H)$^+$, 403.

EXAMPLE 4(567)

3-(N-((2-(2-((2-phenylethylamino)carbonyl)phenyl)phenyl)carbonyl)-N-(2-(4-aminosulfonylphenyl)ethyl)amino)propanoic acid HPLC measurement condition: A HPLC retention time: 3.49 minutes; MASS data (ESI, Pos., 20V): 600 (M+H)$^+$.

EXAMPLE 4(568)

3-(N-((2-(2-((1,2,3,4-tetrahydro-1-naphthylamino)carbonyl)phenyl)phenyl)carbonyl)-N-(2-(2,4-dichlorophenyl)ethyl)amino)propanoic acid HPLC measurement condition: A HPLC retention time: 4.21 minutes; MASS data (ESI, Pos., 20V): 615 (M+H)$^+$.

EXAMPLE 4(569)

3-(N-((2-(2-((N-benzyl-N-(2-hydroxyethyl)amino)carbonyl)phenyl)phenyl)carbonyl)-N-(2-(2,4-dichlorophenyl)ethyl)amino)propanoic acid HPLC measurement condition: A HPLC retention time: 3.88 minutes; MASS data (ESI, Pos., 20V): 619 (M+H)$^+$.

EXAMPLE 4(570)

3-(N-((2-(2-((1-naphthylmethylamino)carbonyl)phenyl)phenyl)carbonyl)-N-(2-(2,4-dichlorophenyl)ethyl)amino)propanoic acid HPLC measurement condition: A HPLC retention time: 4.21 minutes; MASS data (ESI, Pos., 20V): 625 (M+H)$^+$.

EXAMPLE 4(571)

3-(N-((2-(2-((pyridin-2-ylmethylamino)carbonyl)phenyl)phenyl)carbonyl)-N-(2-(2,4-dichlorophenyl)ethyl)amino)propanoic acid HPLC measurement condition: A HPLC retention time: 3.44 minutes; MASS data (ESI, Pos., 20V): 576 (M+H)$^+$.

EXAMPLE 4(572)

3-(N-((2-(2-((α-methylbenzylamino)carbonyl)phenyl)phenyl)carbonyl)-N-(2-(2,4-dichlorophenyl)ethyl)amino)propanoic acid HPLC measurement condition: A HPLC retention time: 4.11 minutes; MASS data (ESI, Pos., 20V): 589 (M+H)$^+$.

EXAMPLE 4(573)

3-(N-((2-(2-((benzylamino)carbonyl)phenyl)phenyl)carbonyl)-N-(2-(2,4-dichlorophenyl)ethyl)amino)propanoic acid HPLC measurement condition: A HPLC retention time: 4.04 minutes; MASS data (ESI, Pos., 20V): 575 (M+H)$^+$.

EXAMPLE 4(574)

3-(N-((2-(2-((2-methylbenzylamino)carbonyl)phenyl)phenyl)carbonyl)-N-(2-(2,4-dichlorophenyl)ethyl)amino)propanoic acid HPLC measurement condition: A HPLC retention time: 4.11 minutes; MASS data (ESI, Pos., 20V): 589 (M+H)$^+$.

EXAMPLE 4(575)

3-(N-((2-(2-((4-chlorobenzylamino)carbonyl)phenyl)phenyl)carbonyl)-N-(2-(2,4-dichlorophenyl)ethyl)amino)propanoic acid HPLC measurement condition: A HPLC retention time: 4.17 minutes; MASS data (ESI, Pos., 20V): 609 (M+H)$^+$.

EXAMPLE 4(576)

3-(N-((2-(2-((4-methoxybenzylamino)carbonyl)phenyl)phenyl)carbonyl)-N-(2-(2,4-dichlorophenyl)ethyl)amino)propanoic acid HPLC measurement condition: A HPLC retention time: 4.00 minutes; MASS data (ESI, Pos., 20V): 605 (M+H)$^+$.

EXAMPLE 4(577)

3-(N-((2-(2-((N-ethyl-N-benzylamino)carbonyl)phenyl)phenyl)carbonyl)-N-(2-(2,4-dichlorophenyl)ethyl)amino)propanoic acid HPLC measurement condition: A HPLC retention time: 4.17 minutes; MASS data (ESI, Pos., 20V): 603 (M+H)$^+$.

EXAMPLE 4(578)

3-(N-((2-(2-((N-butyl-N-benzylamino)carbonyl)phenyl)phenyl)carbonyl)-N-(2-(2,4-dichlorophenyl)ethyl)amino)propanoic acid HPLC measurement condition: A HPLC retention time: 4.34 minutes; MASS data (ESI, Pos., 20V): 631 (M+H)$^+$.

EXAMPLE 4(579)

3-(N-((2-(2-((4-(tert-butyl)benzylamino)carbonyl)phenyl)phenyl)carbonyl)-N-(2-(2,4-dichlorophenyl)ethyl)amino)propanoic acid HPLC measurement condition: A HPLC retention time: 4.35 minutes; MASS data (ESI, Pos., 20V): 631 (M+H)$^+$.

EXAMPLE 4(580)

3-(N-((2-(2-((1-phenyl-3-hydroxypropylamino)carbonyl)phenyl)phenyl)carbonyl)-N-(2-(2,4-dichlorophenyl)ethyl)amino)propanoic acid HPLC measurement condition: A HPLC retention time: 3.88 minutes; MASS data (ESI, Pos., 20V): 619 (M+H)$^+$.

EXAMPLE 4(581)

3-(N-((2-(2-((2-fluorobenzylamino)carbonyl)phenyl)phenyl)carbonyl)-N-(2-(2,4-dichlorophenyl)ethyl)amino)propanoic acid HPLC measurement condition: A HPLC retention time: 4.08 minutes; MASS data (ESI, Pos., 20V): 593 (M+H)$^+$.

EXAMPLE 4(582)

3-(N-((2-(2-((2,5-difluorobenzylamino)carbonyl)phenyl)phenyl)carbonyl)-N-(2-(2,4-dichlorophenyl)ethyl)amino)propanoic acid HPLC measurement condition: A HPLC retention time: 4.10 minutes; MASS data (ESI, Pos., 20V): 611 (M+H)$^+$.

EXAMPLE 4(583)

3-(N-((2-(2-(((1R)-1-phenyl-2-hydroxyethylamino)carbonyl)phenyl)phenyl)carbonyl)-N-(2-(2,4-dichlorophenyl)ethyl)amino)propanoic acid HPLC measurement condition: A HPLC retention time: 3.88 minutes; MASS data (ESI, Pos., 20V): 605 (M+H)$^+$.

EXAMPLE 4(584)

3-(N-((2-(2-((2-chlorobenzylamino)carbonyl)phenyl)phenyl)carbonyl)-N-(2-(2,4-dichlorophenyl)ethyl)amino)propanoic acid HPLC measurement condition: A HPLC retention time: 4.15 minutes; MASS data (ESI, Pos., 20V): 609 (M+H)$^+$.

EXAMPLE 4(585)

3-(N-((2-(2-((4-fluorobenzylamino)carbonyl)phenyl)phenyl)carbonyl)-N-(2-(2,4-dichlorophenyl)ethyl)amino)propanoic acid HPLC measurement condition: A HPLC retention time: 4.06 minutes; MASS data (ESI, Pos., 20V): 593 (M+H)$^+$.

EXAMPLE 4(586)

3-(N-((2-(2-((3-chlorobenzylamino)carbonyl)phenyl)phenyl)carbonyl)-N-(2-(2,4-dichlorophenyl)ethyl)amino)propanoic acid HPLC measurement condition: A HPLC retention time: 4.21 minutes; MASS data (ESI, Pos., 20V): 609 (M+H)$^+$.

EXAMPLE 4(587)

3-(N-((2-(2-(((1S)-1-phenyl-2-hydroxyethylamino)carbonyl)phenyl)phenyl)carbonyl)-N-(2-(2,4-dichlorophenyl)ethyl)amino)propanoic acid HPLC measurement condition: A HPLC retention time: 3.88 minutes; MASS data (ESI, Pos., 20V): 605 (M+H)$^+$.

EXAMPLE 4(588)

3-(N-((2-(2-(((1R)-1-(4-methylphenyl)ethylamino)carbonyl)phenyl)phenyl)carbonyl)-N-(2-(2,4-dichlorophenyl)ethyl)amino)propanoic acid HPLC measurement condition: A HPLC retention time: 4.22 minutes; MASS data (ESI, Pos., 20V): 603 (M+H)$^+$.

EXAMPLE 4(589)

3-(N-((2-(2-((1-(4-fluorophenyl)ethylamino)carbonyl)phenyl)phenyl)carbonyl)-N-(2-(2,4-dichlorophenyl)ethyl)amino)propanoic acid HPLC measurement condition: A HPLC retention time: 4.15 minutes; MASS data (ESI, Pos., 20V): 607 (M+H)$^+$.

EXAMPLE 4(590)

3-(N-((2-(2-(((3S)-3-hydroxymethyl-1,2,3,4-tetrahydroisoquinolin-2-yl)carbonyl)phenyl)phenyl)carbonyl)-N-(2-(2,4-dichlorophenyl)ethyl)amino)propanoic acid HPLC measurement condition: A HPLC retention time: 3.73 minutes; MASS data (ESI, Pos., 20V): 631 (M+H)$^+$; HPLC retention time: 3.93 minutes; MASS data (ESI, Pos., 20V): 631 (M+H)$^+$, 527.

EXAMPLE 4(591)

3-(N-((2-(2-((3-methylbenzylamino)carbonyl)phenyl)phenyl)carbonyl)-N-(2-(2,4-dichlorophenyl)ethyl)amino)propanoic acid HPLC measurement condition: A HPLC retention time: 4.15 minutes; MASS data (ESI, Pos., 20V): 589 (M+H)$^+$.

EXAMPLE 4(592)

3-(N-((2-(2-((3,5-difluorobenzylamino)carbonyl)phenyl)phenyl)carbonyl)-N-(2-(2,4-dichlorophenyl)ethyl)amino)propanoic acid HPLC measurement condition: A HPLC retention time: 4.13 minutes; MASS data (ESI, Pos., 20V): 611 (M+H)$^+$.

EXAMPLE 4(593)

3-(N-((2-(2-((N-methyl-N-(6-methylpyridin-2-yl)methylamino)carbonyl)phenyl)phenyl)carbonyl)-N-(2-(2,4-dichlorophenyl)ethyl)amino)propanoic acid HPLC measurement condition: A HPLC retention time: 3.40 minutes; MASS data (ESI, Pos., 20V): 604 (M+H)$^+$.

EXAMPLE 4(594)

3-(N-((2-(2-((N-(2-(N,N-dimethylamino)ethyl)-N-benzylamino)carbonyl)phenyl)phenyl)carbonyl)-N-(2-(2,4-dichlorophenyl)ethyl)amino)propanoic acid HPLC measurement condition: A HPLC retention time: 3.62 minutes; MASS data (ESI, Pos., 20V): 646 (M+H)+.

EXAMPLE 4(595)

3-(N-((2-(2-((2-phenylethylamino)carbonyl)phenyl)phenyl)carbonyl)-N-(2-(2,4-dichlorophenyl)ethyl)amino)propanoic acid HPLC measurement condition: A HPLC retention time: 4.13 minutes; MASS data (ESI, Pos., 20V): 589 (M+H)+.

EXAMPLE 4(596)

3-(N-((2-(2-((1,2,3,4-tetrahydro-1-naphthylamino)carbonyl)phenyl)phenyl)carbonyl)-N-(2-(4-ethoxyphenyl)ethyl)amino)propanoic acid HPLC measurement condition: A HPLC retention time: 4.01 minutes; MASS data (ESI, Pos., 20V): 591 (M+H)+.

EXAMPLE 4(597)

3-(N-((2-(2-((N-benzyl-N-(2-hydroxyethyl)amino)carbonyl)phenyl)phenyl)carbonyl)-N-(2-(4-ethoxyphenyl)ethyl)amino)propanoic acid HPLC measurement condition: A HPLC retention time: 3.71 minutes; MASS data (ESI, Pos., 20V): 595 (M+H)+.

EXAMPLE 4(598)

3-(N-((2-(2-((1-naphthylmethylamino)carbonyl)phenyl)phenyl)carbonyl)-N-(2-(4-ethoxyphenyl)ethyl)amino)propanoic acid HPLC measurement condition: A HPLC retention time: 4.06 minutes; MASS data (ESI, Pos., 20V): 601 (M+H)+.

EXAMPLE 4(599)

3-(N-((2-(2-((pyridin-2-ylmethylamino)carbonyl)phenyl)phenyl)carbonyl)-N-(2-(4-ethoxyphenyl)ethyl)amino)propanoic acid HPLC measurement condition: A HPLC retention time: 3.33 minutes; MASS data (ESI, Pos., 20V): 552 (M+H)+.

EXAMPLE 4(600)

3-(N-((2-(2-((pyridin-3-ylmethylamino)carbonyl)phenyl)phenyl)carbonyl)-N-(2-(4-ethoxyphenyl)ethyl)amino)propanoic acid HPLC measurement condition: A HPLC retention time: 3.25 minutes; MASS data (ESI, Pos., 20V): 552 (M+H)+.

EXAMPLE 4(601)

3-(N-((2-(2-((2-phenylethylamino)carbonyl)phenyl)phenyl)carbonyl)-N-(benzyl)amino)propanoic acid HPLC measurement condition: A HPLC retention time: 3.80 minutes; MASS data (ESI, Pos., 20V): 507 (M+H)+.

EXAMPLE 4(602)

3-(N-((2-(2-((α-methylbenzylamino)carbonyl)phenyl)phenyl)carbonyl)-N-(2-(4-ethoxyphenyl)ethyl)amino)propanoic acid HPLC measurement condition: A HPLC retention time: 3.95 minutes; MASS data (ESI, Pos., 20V): 565 (M+H)+.

EXAMPLE 4(603)

3-(N-((2-(2-((benzylamino)carbonyl)phenyl)phenyl)carbonyl)-N-(2-(4-ethoxyphenyl)ethyl)amino)propanoic acid HPLC measurement condition: A HPLC retention time: 3.89 minutes; MASS data (ESI, Pos., 20V): 551 (M+H)+.

EXAMPLE 4(604)

3-(N-((2-(2-((2-methylbenzylamino)carbonyl)phenyl)phenyl)carbonyl)-N-(2-(4-ethoxyphenyl)ethyl)amino)propanoic acid HPLC measurement condition: A HPLC retention time: 3.97 minutes; MASS data (ESI, Pos., 20V): 565 (M+H)+.

EXAMPLE 4(605)

3-(N-((2-(2-((4-chlorobenzylamino)carbonyl)phenyl)phenyl)carbonyl)-N-(2-(4-ethoxyphenyl)ethyl)amino)propanoic acid HPLC measurement condition: A HPLC retention time: 4.02 minutes; MASS data (ESI, Pos., 20V): 585 (M+H)+.

EXAMPLE 4(606)

3-(N-((2-((4-methoxybenzylamino)carbonyl)phenyl)phenyl)carbonyl)-N-(2-(4-ethoxyphenyl)ethyl)amino)propanoic acid HPLC measurement condition: A HPLC retention time: 3.86 minutes; MASS data (ESI, Pos., 20V): 581 (M+H)+.

EXAMPLE 4(607)

3-(N-((2-(2-((N-ethyl-N-benzylamino)carbonyl)phenyl)phenyl)carbonyl)-N-(2-(4-ethoxyphenyl)ethyl)amino)propanoic acid HPLC measurement condition: A HPLC retention time: 3.99 minutes; MASS data (ESI, Pos., 20V): 579 (M+H)+.

EXAMPLE 4(608)

3-(N-((2-(2-((N-butyl-N-benzylamino)carbonyl)phenyl)phenyl)carbonyl)-N-(2-(4-ethoxyphenyl)ethyl)amino)propanoic acid HPLC measurement condition: A HPLC retention time: 4.15 minutes; MASS data (ESI, Pos., 20V): 607 (M+H)$^+$.

EXAMPLE 4(609)

3-(N-((2-(2-((4-(tert-butyl)benzylamino)carbonyl)phenyl)phenyl)carbonyl)-N-(2-(4-ethoxyphenyl)ethyl)amino)propanoic acid HPLC measurement condition: A HPLC retention time: 4.19 minutes; MASS data (ESI, Pos., 20V): 607 (M+H)$^+$.

EXAMPLE 4(610)

3-(N-((2-(2-((1-phenyl-3-hydroxypropylamino)carbonyl)phenyl)phenyl)carbonyl)-N-(2-(4-ethoxyphenyl)ethyl)amino)propanoic acid HPLC measurement condition: A HPLC retention time: 3.71 minutes; MASS data (ESI, Pos., 20V): 595 (M+H)$^+$.

EXAMPLE 4(611)

3-(N-((2-(2-((2,5-difluorobenzylamino)carbonyl)phenyl)phenyl)carbonyl)-N-(2-(4-ethoxyphenyl)ethyl)amino)propanoic acid HPLC measurement condition: A HPLC retention time: 3.95 minutes; MASS data (ESI, Pos., 20V): 587 (M+H)$^+$.

EXAMPLE 4(612)

3-(N-((2-(2-(((1R)-1-phenyl-2-hydroxyethylamino)carbonyl)phenyl)phenyl)carbonyl)-N-(2-(4-ethoxyphenyl)ethyl)amino)propanoic acid HPLC measurement condition: A HPLC retention time: 3.73 minutes; MASS data (ESI, Pos., 20V): 581 (M+H)$^+$.

EXAMPLE 4(613)

3-(N-((2-(2-((2-chlorobenzylamino)carbonyl)phenyl)phenyl)carbonyl)-N-(2-(4-ethoxyphenyl)ethyl)amino)propanoic acid HPLC measurement condition: A HPLC retention time: 3.99 minutes; MASS data (ESI, Pos., 20V): 585 (M+H)$^+$.

EXAMPLE 4(614)

3-(N-((2-(2-((3-chlorobenzylamino)carbonyl)phenyl)phenyl)carbonyl)-N-(2-(4-ethoxyphenyl)ethyl)amino)propanoic acid HPLC measurement condition: A HPLC retention time: 4.00 minutes; MASS data (ESI, Pos., 20V): 585 (M+H)$^+$.

EXAMPLE 4(615)

3-(N-((2-(2-(((1S)-1-phenyl-2-hydroxyethylamino)carbonyl)phenyl)phenyl)carbonyl)-N-(2-(4-ethoxyphenyl)ethyl)amino)propanoic acid HPLC measurement condition: A HPLC retention time: 3.71 minutes; MASS data (ESI, Pos., 20V): 581 (M+H)$^+$.

EXAMPLE 4(616)

3-(N-((2-(2-(((1R)-1-(4-methylphenyl)ethylamino)carbonyl)phenyl)phenyl)carbonyl)-N-(2-(4-ethoxyphenyl)ethyl)amino)propanoic acid HPLC measurement condition: A HPLC retention time: 4.04 minutes; MASS data (ESI, Pos., 20V): 579 (M+H)$^+$.

EXAMPLE 4(617)

3-(N-((2-(2-((1-(4-fluorophenyl)ethylamino)carbonyl)phenyl)phenyl)carbonyl)-N-(2-(4-ethoxyphenyl)ethyl)amino)propanoic acid HPLC measurement condition: A HPLC retention time: 3.99 minutes; MASS data (ESI, Pos., 20V): 583 (M+H)$^+$.

EXAMPLE 4(618)

3-(N-((2-(2-(((3S)-3-hydroxymethyl-1,2,3,4-tetrahydroisoquinolin-2-yl)carbonyl)phenyl)phenyl)carbonyl)-N-(2-(4-ethoxyphenyl)ethyl)amino)propanoic acid HPLC measurement condition: A HPLC retention time: 3.60 minutes; MASS data (ESI Pos., 20V): 607 (M+H)$^+$; HPLC retention time: 3.78 minutes; MASS data (ESI, Pos., 20V): 607 (M+H)$^+$, 503.

EXAMPLE 4(619)

3-(N-((2-(2-((3-methylbenzylamino)carbonyl)phenyl)phenyl)carbonyl)-N-(2-(4-ethoxyphenyl)ethyl)amino)propanoic acid HPLC measurement condition: A HPLC retention time: 3.97 minutes; MASS data (ESI, Pos., 20V): 565 (M+H)$^+$.

EXAMPLE 4(620)

3-(N-((2-(2-((3,5-difluorobenzylamino)carbonyl)phenyl)phenyl)carbonyl)-N-(2-(4-ethoxyphenyl)ethyl)amino)propanoic acid HPLC measurement condition: A HPLC retention time: 3.96 minutes; MASS data (ESI, Pos., 20V): 587 (M+H)$^+$.

EXAMPLE 4(621)

3-(N-((2-(2-((N-methyl-N-(6-methylpyridin-2-yl)methylamino)carbonyl)phenyl)phenyl)carbonyl)-N-(2-(4-ethoxyphenyl)ethyl)amino)propanoic acid HPLC measurement condition: A HPLC retention time: 3.29 minutes; MASS data (ESI, Pos., 20V): 580 (M+H)$^+$.

EXAMPLE 4(622)

3-(N-((2-(2-((N-(2-(N,N-dimethylamino)ethyl)-N-benzylamino)carbonyl)phenyl)phenyl)carbonyl)-N-(2-(4-ethoxyphenyl)ethyl)amino)propanoic acid HPLC measurement condition: A HPLC retention time: 3.51 minutes; MASS data (ESI, Pos., 20V): 622 (M+H)$^+$.

EXAMPLE 4(623)

3-(N-((2-(2-((2-phenylethylamino)carbonyl)phenyl)phenyl)carbonyl)-N-(2-(4-ethoxyphenyl)ethyl)amino)propanoic acid HPLC measurement condition: A HPLC retention time: 3.97 minutes; MASS data (ESI, Pos., 20V): 565 (M+H)$^+$.

EXAMPLE 4(624)

3-(N-((2-(2-((1,2,3,4-tetrahydro-1-naphthylamino)carbonyl)phenyl)phenyl)carbonyl)-N-(4-fluorobenzyl)amino)propanoic acid HPLC measurement condition: A HPLC retention time: 3.95 minutes; MASS data (ESI, Pos., 20V): 551 (M+H)$^+$.

EXAMPLE 4(625)

3-(N-((2-(2-((N-benzyl-N-(2-hydroxyethyl)amino)carbonyl)phenyl)phenyl)carbonyl)-N-(4-fluorobenzyl)amino)propanoic acid HPLC measurement condition: A HPLC retention time: 3.64 minutes; MASS data (ESI, Pos., 20V): 555 (M+H)$^+$.

EXAMPLE 4(626)

3-(N-((2-(2-((1-indaneamino)carbonyl)phenyl)phenyl)carbonyl)-N-(4-fluorobenzyl)amino)propanoic acid HPLC measurement condition: A HPLC retention time: 3.88 minutes; MASS data (ESI, Pos., 20V): 537 (M+H)$^+$.

EXAMPLE 4(627)

3-(N-((2-(2-((1-naphthylmethylamino)carbonyl)phenyl)phenyl)carbonyl)-N-(4-fluorobenzyl)amino)propanoic acid HPLC measurement condition: A HPLC retention time: 3.95 minutes; MASS data (ESI, Pos., 20V): 561 (M+H)$^+$.

EXAMPLE 4(628)

3-(N-((2-(2-((pyridin-2-ylmethylamino)carbonyl)phenyl)phenyl)carbonyl)-N-(4-fluorobenzyl)amino)propanoic acid HPLC measurement condition: A HPLC retention time: 3.20 minutes; MASS data (ESI, Pos., 20V): 512 (M+H)$^+$.

EXAMPLE 4(629)

3-(N-((2-(2-((pyridin-3-ylmethylamino)carbonyl)phenyl)phenyl)carbonyl)-N-(4-fluorobenzyl)amino)propanoic acid HPLC measurement condition: A HPLC retention time: 3.14 minutes; MASS data (ESI, Pos., 20V): 512 (M+H)$^+$.

EXAMPLE 4(630)

3-(N-((2-(2-((1,2,3,4-tetrahydroisoquinolin-2-yl)carbonyl)phenyl)phenyl)carbonyl)-N-(4-fluorobenzyl)amino)propanoic acid HPLC measurement condition: A HPLC retention time: 3.86 minutes; MASS data (ESI, Pos., 20V): 537 (M+H)$^+$.

EXAMPLE 4(631)

3-(N-((2-(2-((α-methylbenzylamino)carbonyl)phenyl)phenyl)carbonyl)-N-(4-fluorobenzyl)amino)propanoic acid HPLC measurement condition: A HPLC retention time: 3.86 minutes; MASS data (ESI, Pos., 20V): 525 (M+H)$^+$.

EXAMPLE 4(632)

3-(N-((2-(2-((benzylamino)carbonyl)phenyl)phenyl)carbonyl)-N-(4-fluorobenzyl)amino)propanoic acid HPLC measurement condition: A HPLC retention time: 3.78 minutes; MASS data (ESI, Pos., 20V): 511 (M+H)$^+$.

EXAMPLE 4(633)

3-(N-((2-(2-((2-methoxybenzylamino)carbonyl)phenyl)phenyl)carbonyl)-N-(4-fluorobenzyl)amino)propanoic acid HPLC measurement condition: A HPLC retention time: 3.78 minutes; MASS data (ESI, Pos., 20V): 541 (M+H)$^+$.

EXAMPLE 4(634)

3-(N-((2-(2-((2-methylbenzylamino)carbonyl)phenyl)phenyl)carbonyl)-N-(4-fluorobenzyl)amino)propanoic acid HPLC measurement condition: A HPLC retention time: 3.86 minutes; MASS data (ESI, Pos., 20V): 525 (M+H)$^+$.

EXAMPLE 4(635)

3-(N-((2-(2-((3-methylbenzylamino)carbonyl)phenyl)phenyl)carbonyl)-N-(4fluorobenzyl)amino)propanoic acid HPLC measurement condition: A HPLC retention time: 3.77 minutes; MASS data (ESI, Pos., 20V): 541 (M+H)$^+$.

EXAMPLE 4(636)

3-(N-((2-(2-((4-chlorobenzylamino)carbonyl)phenyl)phenyl)carbonyl)-N-(4-fluorobenzyl)amino)propanoic acid HPLC measurement condition: A HPLC retention time: 3.91 minutes; MASS data (ESI, Pos., 20V): 545 (M+H)+.

EXAMPLE 4(637)

3-(N-((2-(2-((4-methoxybenzylamino)carbonyl)phenyl)phenyl)carbonyl)-N-(4-fluorobenzyl)amino)propanoic acid HPLC measurement condition: A HPLC retention time: 3.73 minutes; MASS data (ESI, Pos., 20V): 541 (M+H)+.

EXAMPLE 4(638)

3-(N-((2-(2-((4-methylbenzylamino)carbonyl)phenyl)phenyl)carbonyl)-N-(4-fluorobenzyl)amino)propanoic acid HPLC measurement condition: A HPLC retention time: 3.86 minutes; MASS data (ESI, Pos., 20V): 525 (M+H)+.

EXAMPLE 4(639)

3-(N-((2-(2-((N-methyl-N-benzylamino)carbonyl)phenyl)phenyl)carbonyl)-N-(4-fluorobenzyl)amino)propanoic acid HPLC measurement condition: A HPLC retention time: 3.84 minutes; MASS data (ESI, Pos., 20V): 525 (M+H)+.

EXAMPLE 4(640)

3-(N-((2-(2-((N-ethyl-N-benzylamino)carbonyl)phenyl)phenyl)carbonyl)-N-(4-fluorobenzyl)amino)propanoic acid HPLC measurement condition: A HPLC retention time: 3.91 minutes; MASS data (ESI, Pos., 20V): 539 (M+H)+.

EXAMPLE 4(641)

3-(N-((2-(2-((N-butyl-N-benzylamino)carbonyl)phenyl)phenyl)carbonyl)-N-(4-fluorobenzyl)amino)propanoic acid HPLC measurement condition: A HPLC retention time: 4.06 minutes; MASS data (ESI, Pos., 20V): 567 (M+H)+.

EXAMPLE 4(642)

3-(N-((2-(2-((4-(tert-butyl)benzylamino)carbonyl)phenyl)phenyl)carbonyl)-N-(4-fluorobenzyl)amino)propanoic acid HPLC measurement condition: A HPLC retention time: 4.10 minutes; MASS data (ESI, Pos., 20V): 567 (M+H)+.

EXAMPLE 4(643)

3-(N-((2-(2-((1-phenyl-3-hydroxypropylamino)carbonyl)phenyl)phenyl)carbonyl)-N-(4-fluorobenzyl)amino)propanoic acid HPLC measurement condition: A HPLC retention time: 3.62 minutes; MASS data (ESI, Pos., 20V): 555 (M+H)+.

EXAMPLE 4(644)

3-(N-((2-(2-((2-fluorobenzylamino)carbonyl)phenyl)phenyl)carbonyl)-N-(4-fluorobenzyl)amino)propanoic acid HPLC measurement condition: A HPLC retention time: 3.80 minutes; MASS data (ESI, Pos., 20V): 529 (M+H)+.

EXAMPLE 4(645)

3-(N-((2-(2-((3-fluorobenzylamino)carbonyl)phenyl)phenyl)carbonyl)-N-(4-fluorobenzyl)amino)propanoic acid HPLC measurement condition: A HPLC retention time: 3.82 minutes; MASS data (ESI, Pos., 20V): 529 (M+H)+.

EXAMPLE 4(646)

3-(N-((2-(2-((2,5-difluorobenzylamino)carbonyl)phenyl)phenyl)carbonyl)-N-(4-fluorobenzyl)amino)propanoic acid HPLC measurement condition: A HPLC retention time: 3.82 minutes; MASS data (ESI, Pos., 20V): 547 (M+H)+.

EXAMPLE 4(647)

3-(N-((2-(2-(((1R)-1-phenyl-2-hydroxyethylamino)carbonyl)phenyl)phenyl)carbonyl)-N-(4-fluorobenzyl)amino)propanoic acid HPLC measurement condition: A HPLC retention time: 3.60 minutes; MASS data (ESI, Pos., 20V): 541 (M+H)+.

EXAMPLE 4(648)

3-(N-((2-(2-((2-chlorobenzylamino)carbonyl)phenyl)phenyl)carbonyl)-N-(4-fluorobenzyl)amino)propanoic acid HPLC measurement condition: A HPLC retention time: 3.89 minutes; MASS data (ESI, Pos., 20V): 545 (M+H)+.

EXAMPLE 4(649)

3-(N-((2-(2-((4-fluorobenzylamino)carbonyl)phenyl)phenyl)carbonyl)-N-(4-fluorobenzyl)amino)propanoic acid HPLC measurement condition: A HPLC retention time: 3.78 minutes; MASS data (ESI, Pos., 20V): 529 (M+H)+.

EXAMPLE 4(650)

3-(N-((2-(2-((allylamino)carbonyl)phenyl)phenyl)carbonyl)-N-(4-fluorobenzyl)amino)propanoic acid HPLC measurement condition: A HPLC retention time: 3.62 minutes; MASS data (ESI, Pos., 20V): 461 (M+H)$^+$.

EXAMPLE 4(651)

3-(N-((2-(2-((2,6-difluorobenzylamino)carbonyl)phenyl)phenyl)carbonyl)-N-(4-fluorobenzyl)amino)propanoic acid HPLC measurement condition: A HPLC retention time: 3.78 minutes; MASS data (ESI, Pos., 20V): 547 (M+H)$^+$.

EXAMPLE 4(652)

3-(N-((2-(2-((3-chlorobenzylamino)carbonyl)phenyl)phenyl)carbonyl)-N-(4-fluorobenzyl)amino)propanoic acid HPLC measurement condition: A HPLC retention time: 3.91 minutes; MASS data (ESI, Pos., 20V): 545 (M+H)$^+$.

EXAMPLE 4(653)

3-(N-((2-(2-(((1S)-1-phenyl-2-hydroxyethylamino)carbonyl)phenyl)phenyl)carbonyl)-N-(4-fluorobenzyl)amino)propanoic acid HPLC measurement condition: A HPLC retention time: 3.60 minutes; MASS data (ESI, Pos., 20V): 541 (M+H)$^+$.

EXAMPLE 4(654)

3-(N-((2-(2-(((1R)-1-(4-methylphenyl)ethylamino)carbonyl)phenyl)phenyl)carbonyl)-N-(4-fluorobenzyl)amino)propanoic acid HPLC measurement condition: A HPLC retention time: 3.95 minutes; MASS data (ESI, Pos., 20V): 539 (M+H)$^+$.

EXAMPLE 4(655)

3-(N-((2-(2-((1-(4-fluorophenyl)ethylamino)carbonyl)phenyl)phenyl)carbonyl)-N-(4-fluorobenzyl)amino)propanoic acid HPLC measurement condition: A HPLC retention time: 3.88 minutes; MASS data (ESI, Pos., 20V): 543 (M+H)$^+$.

EXAMPLE 4(656)

3-(N-((2-(2-((2-thienylmethylamino)carbonyl)phenyl)phenyl)carbonyl)-N-(4-fluorobenzyl)amino)propanoic acid HPLC measurement condition: A HPLC retention time: 3.73 minutes; MASS data (ESI, Pos., 20V): 517 (M+H)$^+$.

EXAMPLE 4(657)

3-(N-((2-(2-(((3S)-3-hydroxymethyl-1,2,3,4-tetrahydroisoquinolin-2-yl)carbonyl)phenyl)phenyl)carbonyl)-N-(4-fluorobenzyl)amino)propanoic acid HPLC measurement condition: A HPLC retention time: 3.49 minutes; MASS data (ESI, Pos., 20V): 567 (M+H)$^+$; HPLC retention time: 3.66 minutes; MASS data (ESI, Pos., 20V): 567 (M+H)$^+$.

EXAMPLE 4(658)

3-(N-((2-(2-((3-methylbenzylamino)carbonyl)phenyl)phenyl)carbonyl)-N-(4-fluorobenzyl)amino)propanoic acid HPLC measurement condition: A HPLC retention time: 3.86 minutes; MASS data (ESI, Pos., 20V): 525 (M+H)$^+$.

EXAMPLE 4(659)

3-(N-((2-(2-((3,5-difluorobenzylamino)carbonyl)phenyl)phenyl)carbonyl)-N-(4-fluorobenzyl)amino)propanoic acid HPLC measurement condition: A HPLC retention time: 3.86 minutes; MASS data (ESI, Pos., 20V): 547 (M+H)$^+$.

EXAMPLE 4(660)

3-(N-((2-(2-((N-methyl-N-(6-methylpyridin-2-yl)methylamino)carbonyl)phenyl)phenyl)carbonyl)-N-(4-fluorobenzyl)amino)propanoic acid HPLC measurement condition: A HPLC retention time: 3.18 minutes; MASS data (ESI, Pos., 20V): 540 (M+H)$^+$.

EXAMPLE 4(661)

3-(N-((2-(2-((N-(2-(N,N-dimethylamino)ethyl)-N-benzylamino)carbonyl)phenyl)phenyl)carbonyl)-N-(4-fluorobenzyl)amino)propanoic acid HPLC measurement condition: A HPLC retention time: 3.40 minutes; MASS data (ESI, Pos., 20V): 582 (M+H)$^+$.

EXAMPLE 4(662)

3-(N-((2-(2-((2-phenylethylamino)carbonyl)phenyl)phenyl)carbonyl)-N-(4-fluorobenzyl)amino)propanoic acid HPLC measurement condition: A HPLC retention time: 3.84 minutes; MASS data (ESI, Pos., 20V): 525 (M+H)$^+$.

EXAMPLE 4(663)

3-(N-((2-(2-((1,2,3,4-tetrahydro-1-naphthylamino)carbonyl)phenyl)phenyl)carbonyl)-N-(2-(2-methylphenyl)ethyl)amino)propanoic acid HPLC measurement condition: A HPLC retention time: 4.06 minutes; MASS data (ESI, Pos., 20V): 561 (M+H)$^+$.

EXAMPLE 4(664)

3-(N-((2-(2-((N-benzyl-N-(2-hydroxyethyl)amino)carbonyl)phenyl)phenyl)carbonyl)-N-(2-(2-methylphenyl)ethyl)amino)propanoic acid HPLC measurement condition: A HPLC retention time: 3.75 minutes; MASS data (ESI, Pos., 20V): 565 (M+H)$^+$.

EXAMPLE 4(665)

3-(N-((2-(2-((1-indaneamino)carbonyl)phenyl)phenyl)carbonyl)-N-(2-(2-methylphenyl)ethyl)amino)propanoic acid HPLC measurement condition: A HPLC retention time: 4.01 minutes; MASS data (ESI, Pos., 20V): 547 (M+H)$^+$.

EXAMPLE 4(666)

3-(N-((2-(2-((1-naphthylmethylamino)carbonyl)phenyl)phenyl)carbonyl)-N-(2-(2-methylphenyl)ethyl)amino)propanoic acid HPLC measurement condition: A HPLC retention time: 4.06 minutes; MASS data (ESI, Pos., 20V): 571 (M+H)$^+$.

EXAMPLE 4(667)

3-(N-((2-(2-((pyridin-2-ylmethylamino)carbonyl)phenyl)phenyl)carbonyl)-N-(2-(2-methylphenyl)ethyl)amino)propanoic acid HPLC measurement condition: A HPLC retention time: 3.29 minutes; MASS data (ESI, Pos., 20V): 522 (M+H)$^+$.

EXAMPLE 4(668)

3-(N-((2-(2-((pyridin-3-ylmethylamino)carbonyl)phenyl)phenyl)carbonyl)-N-(2-(2-methylphenyl)ethyl)amino)propanoic acid HPLC measurement condition: A HPLC retention time: 3.25 minutes; MASS data (ESI, Pos., 20V): 522 (M+H)$^+$.

EXAMPLE 4(669)

3-(N-((2-(2-((1,2,3,4-tetrahydroisoquinolin-2-yl)carbonyl)phenyl)phenyl)carbonyl)-N-(2-(2-methylphenyl)ethyl)amino)propanoic acid HPLC measurement condition: A HPLC retention time: 3.97 minutes; MASS data (ESI, Pos., 20V): 547 (M+H)$^+$.

EXAMPLE 4(670)

3-(N-((2-(2-((α-methylbenzylamino)carbonyl)phenyl)phenyl)carbonyl)-N-(2-(2-methylphenyl)ethyl)amino)propanoic acid HPLC measurement condition: A HPLC retention time: 3.99 minutes; MASS data (ESI, Pos., 20V): 535 (M+H)$^+$.

EXAMPLE 4(671)

3-(N-((2-(2-((benzylamino)carbonyl)phenyl)phenyl)carbonyl)-N-(2-(2-methylphenyl)ethyl)amino)propanoic acid HPLC measurement condition: A HPLC retention time: 3.91 minutes; MASS data (ESI, Pos., 20V): 521 (M+H)$^+$.

EXAMPLE 4(672)

3-(N-((2-(2-((2-methoxybenzylamino)carbonyl)phenyl)phenyl)carbonyl)-N-(2-(2-methylphenyl)ethyl)amino)propanoic acid HPLC measurement condition: A HPLC retention time: 3.91 minutes; MASS data (ESI, Pos., 20V): 551 (M+H)$^+$.

EXAMPLE 4(673)

3-(N-((2-(2-((2-methylbenzylamino)carbonyl)phenyl)phenyl)carbonyl)-N-(2-(2-methylphenyl)ethyl)amino)propanoic acid HPLC measurement condition: A HPLC retention time: 3.99 minutes; MASS data (ESI, Pos., 20V): 535 (M+H)$^+$.

EXAMPLE 4(674)

3-(N-((2-(2-((3-methoxybenzylamino)carbonyl)phenyl)phenyl)carbonyl)-N-(2-(2-methylphenyl)ethyl)amino)propanoic acid HPLC measurement condition: A HPLC retention time: 3.89 minutes; MASS data (ESI, Pos., 20V): 551 (M+H)$^+$.

EXAMPLE 4(675)

3-(N-((2-(2-((4-chlorobenzylamino)carbonyl)phenyl)phenyl)carbonyl)-N-(2-(2-methylphenyl)ethyl)amino)propanoic acid HPLC measurement condition: A HPLC retention time: 4.02 minutes; MASS data (ESI, Pos., 20V): 555 (M+H)$^+$.

EXAMPLE 4(676)

3-(N-((2-(2-((4-methoxybenzylamino)carbonyl)phenyl)phenyl)carbonyl)-N-(2-(2-methylphenyl)ethyl)amino)propanoic acid HPLC measurement condition: A HPLC retention time: 3.88 minutes; MASS data (ESI, Pos., 20V): 551 (M+H)$^+$.

EXAMPLE 4(677)

3-(N-((2-(2-((4-methylbenzylamino)carbonyl)phenyl)phenyl)carbonyl)-N-(2-(2-methylphenyl)ethyl)amino)propanoic acid HPLC measurement condition: A HPLC retention time: 3.99 minutes; MASS data (ESI, Pos., 20V): 535 (M+H)$^+$.

EXAMPLE 4(678)

3-(N-((2-(2-((N-methyl-N-benzylamino)carbonyl)phenyl)phenyl)carbonyl)-N-(2-(2-methylphenyl)ethyl)amino)propanoic acid HPLC measurement condition: A HPLC retention time: 3.93 minutes; MASS data (ESI, Pos., 20V): 535 (M+H)$^+$.

EXAMPLE 4(679)

3-(N-((2-(2-((N-ethyl-N-benzylamino)carbonyl)phenyl)phenyl)carbonyl)-N-(2-(2-methylphenyl)ethyl)amino)propanoic acid HPLC measurement condition: A HPLC retention time: 4.02 minutes; MASS data (ESI, Pos., 20V): 549 (M+H)$^+$.

EXAMPLE 4(680)

3-(N-((2-(2-((N-butyl-N-benzylamino)carbonyl)phenyl)phenyl)carbonyl)-N-(2-(2-methylphenyl)ethyl)amino)propanoic acid HPLC measurement condition: A HPLC retention time: 4.21 minutes; MASS data (ESI, Pos., 20V): 577 (M+H)$^+$.

EXAMPLE 4(681)

3-(N-((2-(2-((4-(tert-butyl)benzylamino)carbonyl)phenyl)phenyl)carbonyl)-N-(2-(2-methylphenyl)ethyl)amino)propanoic acid HPLC measurement condition: A HPLC retention time: 4.22 minutes; MASS data (ESI, Pos., 20V): 577 (M+H)$^+$.

EXAMPLE 4(682)

3-(N-((2-(2-((1-phenyl-3-hydroxypropylamino)carbonyl)phenyl)phenyl)carbonyl)-N-(2-(2-methylphenyl)ethyl)amino)propanoic acid HPLC measurement condition: A HPLC retention time: 3.73 minutes; MASS data (ESI, Pos., 20V): 565 (M+H)$^+$.

EXAMPLE 4(683)

3-(N-((2-(2-((2-fluorobenzylamino)carbonyl)phenyl)phenyl)carbonyl)-N-(2-(2-methylphenyl)ethyl)amino)propanoic acid HPLC measurement condition: A HPLC retention time: 3.91 minutes; MASS data (ESI, Pos., 20V): 539 (M+H)$^+$.

EXAMPLE 4(684)

3-(N-((2-(2-((3-fluorobenzylamino)carbonyl)phenyl)phenyl)carbonyl)-N-(2-(2-methylphenyl)ethyl)amino)propanoic acid HPLC measurement condition: A HPLC retention time: 3.95 minutes; MASS data (ESI, Pos., 20V): 539 (M+H)$^+$.

EXAMPLE 4(685)

3-(N-((2-(2-((2,5-difluorobenzylamino)carbonyl)phenyl)phenyl)carbonyl)-N-(2-(2-methylphenyl)ethyl)amino)propanoic acid HPLC measurement condition: A HPLC retention time: 3.93 minutes; MASS data (ESI, Pos., 20V): 557 (M+H)$^+$.

EXAMPLE 4(686)

3-(N-((2-(2-(((1R)-1-phenyl-2-hydroxyethylamino)carbonyl)phenyl)phenyl)carbonyl)-N-(2-(2-methylphenyl)ethyl)amino)propanoic acid HPLC measurement condition: A HPLC retention time: 3.73 minutes; MASS data (ESI, Pos., 20V): 551 (M+H)$^+$.

EXAMPLE 4(687)

3-(N-((2-(2-((2-chlorobenzylamino)carbonyl)phenyl)phenyl)carbonyl)-N-(2-(2-methylphenyl)ethyl)amino)propanoic acid HPLC measurement condition: A HPLC retention time: 4.00 minutes; MASS data (ESI, Pos., 20V): 555 (M+H)$^+$.

EXAMPLE 4(688)

3-(N-((2-(2-((4-fluorobenzylamino)carbonyl)phenyl)phenyl)carbonyl)-N-(2-(2-methylphenyl)ethyl)amino)propanoic acid HPLC measurement condition: A HPLC retention time: 3.91 minutes; MASS data (ESI, Pos., 20V): 539 (M+H)$^+$.

EXAMPLE 4(689)

3-(N-((2-(2-((allylamino)carbonyl)phenyl)phenyl)carbonyl)-N-(2-(2-methylphenyl)ethyl)amino)propanoic acid HPLC measurement condition: A HPLC retention time: 3.73 minutes; MASS data (ESI, Pos., 20V): 471 (M+H)$^+$.

EXAMPLE 4(690)

3-(N-((2-(2-((2,6-difluorobenzylamino)carbonyl)phenyl)phenyl)carbonyl)-N-(2-(2-methylphenyl)ethyl)amino)propanoic acid HPLC measurement condition: A HPLC retention time: 3.88 minutes; MASS data (ESI, Pos., 20V): 557 (M+H)$^+$.

EXAMPLE 4(691)

3-(N-((2-(2-((3-chlorobenzylamino)carbonyl)phenyl)phenyl)carbonyl)-N-(2-(2-methylphenyl)ethyl)amino)propanoic acid HPLC measurement condition: A HPLC retention time: 4.02 minutes; MASS data (ESI, Pos., 20V): 555 (M+H)$^+$.

EXAMPLE 4(692)

3-(N-((2-(2-(((1S)-1-phenyl-2-hydroxyethylamino)carbonyl)phenyl)phenyl)carbonyl)-N-(2-(2-methylphenyl)ethyl)amino)propanoic acid HPLC measurement condition: A HPLC retention time: 3.73 minutes; MASS data (ESI, Pos., 20V): 551 (M+H)$^+$.

EXAMPLE 4(693)

3-(N-((2-(2-(((1R)-1-(4-methylphenyl)ethylamino)carbonyl)phenyl)phenyl)carbonyl)-N-(2-(2-methylphenyl)ethyl)amino)propanoic acid HPLC measurement condition: A HPLC retention time: 4.06 minutes; MASS data (ESI, Pos., 20V): 549 (M+H)$^+$.

EXAMPLE 4(694)

3-(N-((2-(2-((1-(4-fluorophenyl)ethylamino)carbonyl)phenyl)phenyl)carbonyl)-N-(2-(2-methylphenyl)ethyl)amino)propanoic acid HPLC measurement condition: A HPLC retention time: 4.02 minutes; MASS data (ESI, Pos., 20V): 553 (M+H)$^+$.

EXAMPLE 4(695)

3-(N-((2-(2-((2-thienylmethylamino)carbonyl)phenyl)phenyl)carbonyl)-N-(2-(2-methylphenyl)ethyl)amino)propanoic acid HPLC measurement condition: A HPLC retention time: 3.89 minutes; MASS data (ESI, Pos., 20V): 527 (M+H)$^+$.

EXAMPLE 4(696)

3-(N-((2-(2-(((3S)-3-hydroxymethyl-1,2,3,4-tetrahydroisoquinolin-2-yl)carbonyl)phenyl)phenyl)carbonyl)-N-(2-(2-methylphenyl)ethyl)amino)propanoic acid HPLC measurement condition: A HPLC retention time: 3.60 minutes; MASS data (ESI, Pos., 20V): 577 (M+H)$^+$; HPLC retention time: 3.77 minutes; MASS data (ESI, Pos., 20V): 577 (M+H)$^+$.

EXAMPLE 4(697)

3-(N-((2-(2-((3-methylbenzylamino)carbonyl)phenyl)phenyl)carbonyl)-N-(2-(2-methylphenyl)ethyl)amino)propanoic acid HPLC measurement condition: A HPLC retention time: 3.96 minutes; MASS data (ESI, Pos., 20V): 535 (M+H)$^+$.

EXAMPLE 4(698)

3-(N-((2-(2-((3,5-difluorobenzylamino)carbonyl)phenyl)phenyl)carbonyl)-N-(2-(2-methylphenyl)ethyl)amino)propanoic acid HPLC measurement condition: A HPLC retention time: 3.99 minutes; MASS data (ESI, Pos., 20V): 557 (M+H)$^+$.

EXAMPLE 4(699)

3-(N-((2-(2-((N-methyl-N-(6-methylpyridin-2-yl)methylamino)carbonyl)phenyl)phenyl)carbonyl)-N-(2-(2-methylphenyl)ethyl)amino)propanoic acid HPLC measurement condition: A HPLC retention time: 3.27 minutes; MASS data (ESI, Pos., 20V): 550 (M+H)$^+$.

EXAMPLE 4(700)

3-(N-((2-(2-((N-(2-(N,N-dimethylamino)ethyl)-N-benzylamino)carbonyl)phenyl)phenyl)carbonyl)-N-(2-(2-methylphenyl)ethyl)amino)propanoic acid HPLC measurement condition: A HPLC retention time: 3.51 minutes; MASS data (ESI, Pos., 20V): 592 (M+H)$^+$.

EXAMPLE 4(701)

3-(N-((2-(2-((2-phenylethylamino)carbonyl)phenyl)phenyl)carbonyl)-N-(2-(2-methylphenyl)ethyl)amino)propanoic acid HPLC measurement condition: A HPLC retention time: 3.97 minutes; MASS data (ESI, Pos., 20V): 535 (M+H)$^+$.

EXAMPLE 4(702)

3-(N-((2-(2-((1,2,3,4-tetrahydro-1-naphthylamino)carbonyl)phenyl)phenyl)carbonyl)-N-(2-(2,5-dimethoxyphenyl)ethyl)amino)propanoic acid HPLC measurement condition: A HPLC retention time: 3.99 minutes; MASS data (ESI, Pos., 20V): 607 (M+H)$^+$.

EXAMPLE 4(703)

3-(N-((2-(2-((N-benzyl-N-(2-hydroxyethyl)amino)carbonyl)phenyl)phenyl)carbonyl)-N-(2-(2,5-dimethoxyphenyl)ethyl)amino)propanoic acid HPLC measurement condition: A HPLC retention time: 3.66 minutes; MASS data (ESI, Pos., 20V): 611 (M+H)$^+$.

EXAMPLE 4(704)

3-(N-((2-(2-((2-furylmethylamino)carbonyl)phenyl)phenyl)carbonyl)-N-(2-(2,5-dimethoxyphenyl)ethyl)amino)propanoic acid HPLC measurement condition: A HPLC retention time: 3.73 minutes; MASS data (ESI, Pos., 20V): 557 (M+H)$^+$.

EXAMPLE 4(705)

3-(N-((2-(2-((1-indaneamino)carbonyl)phenyl)phenyl)carbonyl)-N-(2-(2,5-dimethoxyphenyl)ethyl)amino)propanoic acid HPLC measurement condition: A HPLC retention time: 3.93 minutes; MASS data (ESI, Pos., 20V): 593 (M+H)$^+$.

EXAMPLE 4(706)

3-(N-((2-(2-((1-naphthylmethylamino)carbonyl)phenyl)phenyl)carbonyl)-N-(2-(2,5-dimethoxyphenyl)ethyl)amino)propanoic acid HPLC measurement condition: A HPLC retention time: 4.00 minutes; MASS data (ESI, Pos., 20V): 617 (M+H)+.

EXAMPLE 4(707)

3-(N-((2-(2-((pyridin-2-ylmethylamino)carbonyl)phenyl)phenyl)carbonyl)-N-(2-(2,5-dimethoxyphenyl)ethyl)amino)propanoic acid HPLC measurement condition: A HPLC retention time: 3.27 minutes; MASS data (ESI, Pos., 20V): 568 (M+H)+.

EXAMPLE 4(708)

3-(N-((2-(2-((pyridin-3-ylmethylamino)carbonyl)phenyl)phenyl)carbonyl)-N-(2-(2,5-dimethoxyphenyl)ethyl)amino)propanoic acid HPLC measurement condition: A HPLC retention time: 3.20 minutes; MASS data (ESI, Pos., 20V): 568 (M+H)+.

EXAMPLE 4(709)

3-(N-((2-(2-((1,2,3,4-tetrahydroisoquinolin-2-yl)carbonyl)phenyl)phenyl)carbonyl)-N-(2-(2,5-dimethoxyphenyl)ethyl)amino)propanoic acid HPLC measurement condition: A HPLC retention time: 3.86 minutes; MASS data (ESI, Pos., 20V): 593 (M+H)+.

EXAMPLE 4(710)

3-(N-((2-(2-((α-methylbenzylamino)carbonyl)phenyl)phenyl)carbonyl)-N-(2-(2,5-dimethoxyphenyl)ethyl)amino)propanoic acid HPLC measurement condition: A HPLC retention time: 3.89 minutes; MASS data (ESI, Pos., 20V): 581 (M+H)+.

EXAMPLE 4(711)

3-(N-((2-(2-((benzylamino)carbonyl)phenyl)phenyl)carbonyl)-N-(2-(2,5-dimethoxyphenyl)ethyl)amino)propanoic acid HPLC measurement condition: A HPLC retention time: 3.82 minutes; MASS data (ESI, Pos., 20V): 567 (M+H)+.

EXAMPLE 4(712)

3-(N-((2-(2-((2-methoxybenzylamino)carbonyl)phenyl)phenyl)carbonyl)-N-(2-(2,5-dimethoxyphenyl)ethyl)amino)propanoic acid HPLC measurement condition: A HPLC retention time: 3.84 minutes; MASS data (ESI, Pos., 20V): 597 (M+H)+.

EXAMPLE 4(713)

3-(N-((2-(2-((2-methylbenzylamino)carbonyl)phenyl)phenyl)carbonyl)-N-(2-(2,5-dimethoxyphenyl)ethyl)amino)propanoic acid HPLC measurement condition: A HPLC retention time: 3.89 minutes; MASS data (ESI, Pos., 20V): 581 (M+H)+.

EXAMPLE 4(714)

3-(N-((2-(2-((3-methoxybenzylamino)carbonyl)phenyl)phenyl)carbonyl)-N-(2-(2,5-dimethoxyphenyl)ethyl)amino)propanoic acid HPLC measurement condition: A HPLC retention time: 3.82 minutes; MASS data (ESI, Pos., 20V): 597 (M+H)+.

EXAMPLE 4(715)

3-(N-((2-(2-((4-chlorobenzylamino)carbonyl)phenyl)phenyl)carbonyl)-N-(2-(2,5-dimethoxyphenyl)ethyl)amino)propanoic acid HPLC measurement condition: A HPLC retention time: 3.97 minutes; MASS data (ESI, Pos., 20V): 601 (M+H)+.

EXAMPLE 4(716)

3-(N-((2-(2-((4-methoxybenzylamino)carbonyl)phenyl)phenyl)carbonyl)-N-(2-(2,5-dimethoxyphenyl)ethyl)amino)propanoic acid HPLC measurement condition: A HPLC retention time: 3.80 minutes; MASS data (ESI, Pos., 20V): 597 (M+H)+.

EXAMPLE 4(717)

3-(N-((2-(2-((4-methylbenzylamino)carbonyl)phenyl)phenyl)carbonyl)-N-(2-(2,5-dimethoxyphenyl)ethyl)amino)propanoic acid HPLC measurement condition: A HPLC retention time: 3.91 minutes; MASS data (ESI, Pos., 20V): 581 (M+H)+.

EXAMPLE 4(718)

3-(N-((2-(2-((N-methyl-N-benzylamino)carbonyl)phenyl)phenyl)carbonyl)-N-(2-(2,5-dimethoxyphenyl)ethyl)amino)propanoic acid HPLC measurement condition: A HPLC retention time: 3.84 minutes; MASS data (ESI, Pos., 20V): 581 (M+H)+.

EXAMPLE 4(719)

3-(N-((2-(2-((N-isopropyl-N-benzylamino)carbonyl)phenyl)phenyl)carbonyl)-N-(2-(2,5-dimethoxyphenyl)ethyl)amino)propanoic acid HPLC measurement condition: A HPLC retention time: 3.97 minutes; MASS data (ESI, Pos., 20V): 609 (M+H)+.

EXAMPLE 4(720)

3-(N-((2-(2-((N-ethyl-N-benzylamino)carbonyl)phenyl)phenyl)carbonyl)-N-(2-(2,5-dimethoxyphenyl)ethyl)amino)propanoic acid HPLC measurement condition: A HPLC retention time: 3.91 minutes; MASS data (ESI, Pos., 20V): 595 (M+H)$^+$.

EXAMPLE 4(721)

3-(N-((2-(2-((N-butyl-N-benzylamino)carbonyl)phenyl)phenyl)carbonyl)-N-(2-(2,5-dimethoxyphenyl)ethyl)amino)propanoic acid HPLC measurement condition: A HPLC retention time: 4.11 minutes; MASS data (ESI, Pos., 20V): 623 (M+H)$^+$.

EXAMPLE 4(722)

3-(N-((2-(2-((4-(tert-butyl)benzylamino)carbonyl)phenyl)phenyl)carbonyl)-N-(2-(2,5-dimethoxyphenyl)ethyl)amino)propanoic acid HPLC measurement condition: A HPLC retention time: 4.13 minutes; MASS data (ESI, Pos., 20V): 623 (M+H)$^+$.

EXAMPLE 4(723)

3-(N-((2-(2-((1-phenyl-3-hydroxypropylamino)carbonyl)phenyl)phenyl)carbonyl)-N-(2-(2,5-dimethoxyphenyl)ethyl)amino)propanoic acid HPLC measurement condition: A HPLC retention time: 3.64 minutes; MASS data (ESI, Pos., 20V): 611 (M+H)$^+$.

EXAMPLE 4(724)

3-(N-((2-(2-((2-fluorobenzylamino)carbonyl)phenyl)phenyl)carbonyl)-N-(2-(2,5-dimethoxyphenyl)ethyl)amino)propanoic acid HPLC measurement condition: A HPLC retention time: 3.84 minutes; MASS data (ESI, Pos., 20V): 585 (M+H)$^+$.

EXAMPLE 4(725)

3-(N-((2-(2-((3-fluorobenzylamino)carbonyl)phenyl)phenyl)carbonyl)-N-(2-(2,5-dimethoxyphenyl)ethyl)amino)propanoic acid HPLC measurement condition: A HPLC retention time: 3.84 minutes; MASS data (ESI, Pos., 20V): 585 (M+H)$^+$.

EXAMPLE 4(726)

3-(N-((2-(2-((2,5-difluorobenzylamino)carbonyl)phenyl)phenyl)carbonyl)-N-(2-(2,5-dimethoxyphenyl)ethyl)amino)propanoic acid HPLC measurement condition: A HPLC retention time: 3.88 minutes; MASS data (ESI, Pos., 20V): 603 (M+H)$^+$.

EXAMPLE 4(727)

3-(N-((2-(2-(((1R)-1-phenyl-2-hydroxyethylamino)carbonyl)phenyl)phenyl)carbonyl)-N-(2-(2,5-dimethoxyphenyl)ethyl)amino)propanoic acid HPLC measurement condition: A HPLC retention time: 3.66 minutes; MASS data (ESI, Pos., 20V): 597 (M+H)$^+$.

EXAMPLE 4(728)

3-(N-((2-(2-((2-chlorobenzylamino)carbonyl)phenyl)phenyl)carbonyl)-N-(2-(2,5-dimethoxyphenyl)ethyl)amino)propanoic acid HPLC measurement condition: A HPLC retention time: 3.93 minutes; MASS data (ESI, Pos., 20V): 601 (M+H)$^+$.

EXAMPLE 4(729)

3-(N-((2-(2-((4-fluorobenzylamino)carbonyl)phenyl)phenyl)carbonyl)-N-(2-(2,5-dimethoxyphenyl)ethyl)amino)propanoic acid HPLC measurement condition: A HPLC retention time: 3.84 minutes; MASS data (ESI, Pos., 20V): 585 (M+H)$^+$.

EXAMPLE 4(730)

3-(N-((2-(2-((allylamino)carbonyl)phenyl)phenyl)carbonyl)-N-(2-(2,5-dimethoxyphenyl)ethyl)amino)propanoic acid HPLC measurement condition: A HPLC retention time: 3.66 minutes; MASS data (ESI, Pos., 20V): 517 (M+H)$^+$.

EXAMPLE 4(731)

3-(N-((2-(2-((2,6-difluorobenzylamino)carbonyl)phenyl)phenyl)carbonyl)-N-(2-(2,5-dimethoxyphenyl)ethyl)amino)propanoic acid HPLC measurement condition: A HPLC retention time: 3.80 minutes; MASS data (ESI, Pos., 20V): 603 (M+H)$^+$.

EXAMPLE 4(732)

3-(N-((2-(2-((3-chlorobenzylamino)carbonyl)phenyl)phenyl)carbonyl)-N-(2-(2,5-dimethoxyphenyl)ethyl)amino)propanoic acid HPLC measurement condition: A HPLC retention time: 3.95 minutes; MASS data (ESI, Pos., 20V): 601 (M+H)$^+$.

EXAMPLE 4(733)

3-(N-((2-(2-(((1S)-1-phenyl-2-hydroxyethylamino)carbonyl)phenyl)phenyl)carbonyl)-N-(2-(2,5-dimethoxyphenyl)ethyl)amino)propanoic acid HPLC measurement condition: A HPLC retention time: 3.66 minutes; MASS data (ESI, Pos., 20V): 597 (M+H)$^+$.

EXAMPLE 4(734)

3-(N-((2-(2-(((1R)-1-(4-methylphenyl)ethylamino)carbonyl)phenyl)phenyl)carbonyl)-N-(2-(2,5-dimethoxyphenyl)ethyl)amino)propanoic acid HPLC measurement condition: A HPLC retention time: 3.97 minutes; MASS data (ESI, Pos., 20V): 595 (M+H)$^+$.

EXAMPLE 4(735)

3-(N-((2-(2-((1-(4-fluorophenyl)ethylamino)carbonyl)phenyl)phenyl)carbonyl)-N-(2-(2,5-dimethoxyphenyl)ethyl)amino)propanoic acid HPLC measurement condition: A HPLC retention time: 3.93 minutes; MASS data (ESI, Pos., 20V): 599 (M+H)$^+$.

EXAMPLE 4(736)

3-(N-((2-(2-((2-thienylmethylamino)carbonyl)phenyl)phenyl)carbonyl)-N-(2-(2,5-dimethoxyphenyl)ethyl)amino)propanoic acid HPLC measurement condition: A HPLC retention time: 3.80 minutes; MASS data (ESI, Pos., 20V): 573 (M+H)$^+$.

EXAMPLE 4(737)

3-(N-((2-(2-(((3S)-3-hydroxymethyl-1,2,3,4-tetrahydroisoquinolin-2-yl)carbonyl)phenyl)phenyl)carbonyl)-N-(2-(2,5-dimethoxyphenyl)ethyl)amino)propanoic acid HPLC measurement condition: A HPLC retention time: 3.55 minutes; MASS data (ESI, Pos., 20V): 623 (M+H)$^+$; HPLC retention time: 3.71 minutes; MASS data (ESI, Pos., 20V): 623 (M+H)$^+$.

EXAMPLE 4(738)

3-(N-((2-(2-((3-methylbenzylamino)carbonyl)phenyl)phenyl)carbonyl)-N-(2-(2,5-dimethoxyphenyl)ethyl)amino)propanoic acid HPLC measurement condition: A HPLC retention time: 3.89 minutes; MASS data (ESI, Pos., 20V): 581 (M+H)$^+$.

EXAMPLE 4(739)

3-(N-((2-(2-((3,5-difluorobenzylamino)carbonyl)phenyl)phenyl)carbonyl)-N-(2-(2,5-dimethoxyphenyl)ethyl)amino)propanoic acid HPLC measurement condition: A HPLC retention time: 3.91 minutes; MASS data (ESI, Pos., 20V): 603 (M+H)$^+$.

EXAMPLE 4(740)

3-(N-((2-(2-((N-methyl-N-(6-methylpyridin-2-yl)methylamino)carbonyl)phenyl)phenyl)carbonyl)-N-(2-(2,5-dimethoxyphenyl)ethyl)amino)propanoic acid HPLC measurement condition: A HPLC retention time: 3.25 minutes; MASS data (ESI, Pos., 20V): 596 (M+H)$^+$.

EXAMPLE 4(741)

3-(N-((2-(2-((N-(2-(N,N-dimethylamino)ethyl)-N-benzylamino)carbonyl)phenyl)phenyl)carbonyl)-N-(2-(2,5-dimethoxyphenyl)ethyl)amino)propanoic acid HPLC measurement condition: A HPLC retention time: 3.47 minutes; MASS data (ESI, Pos., 20V): 638 (M+H)$^+$.

EXAMPLE 4(742)

3-(N-((2-(2-((2-phenylethylamino)carbonyl)phenyl)phenyl)carbonyl)-N-(2-(2,5-dimethoxyphenyl)ethyl)amino)propanoic acid HPLC measurement condition: A HPLC retention time: 3.89 minutes; MASS data (ESI, Pos., 20V): 581 (M+H)$^+$.

EXAMPLE 4(743)

3-(N-((2-(2-((1,2,3,4-tetrahydro-1-naphthylamino)carbonyl)phenyl)phenyl)carbonyl)-N-(2-(3-ethoxy-4-methoxyphenyl)ethyl)amino)propanoic acid HPLC measurement condition: A HPLC retention time: 3.91 minutes; MASS data (ESI, Pos., 20V): 621 (M+H)$^+$.

EXAMPLE 4(744)

3-(N-((2-(2-((N-benzyl-N-(2-hydroxyethyl)amino)carbonyl)phenyl)phenyl)carbonyl)-N-(2-(3-ethoxy-4-methoxyphenyl)ethyl)amino)propanoic acid HPLC measurement condition: A HPLC retention time: 3.60 minutes; MASS data (ESI, Pos., 20V): 625 (M+H)$^+$.

EXAMPLE 4(745)

3-(N-((2-(2-((2-furylmethylamino)carbonyl)phenyl)phenyl)carbonyl)-N-(2-(3-ethoxy-4-methoxyphenyl)ethyl)amino)propanoic acid HPLC measurement condition: A HPLC retention time: 3.63 minutes; MASS data (ESI, Pos., 20V): 571 (M+H)$^+$.

EXAMPLE 4(746)

3-(N-((2-(2-((1-indaneamino)carbonyl)phenyl)phenyl)carbonyl)-N-(2-(3-ethoxy-4-methoxyphenyl)ethyl)amino)propanoic acid HPLC measurement condition: A HPLC retention time: 3.86 minutes; MASS data (ESI, Pos., 20V): 607 (M+H)$^+$.

EXAMPLE 4(747)

3-(N-((2-(2-((1-naphthylmethylamino)carbonyl)phenyl)phenyl)carbonyl)-N-(2-(3-ethoxy-4-methoxyphenyl)ethyl)amino)propanoic acid HPLC measurement condition: A HPLC retention time: 3.91 minutes; MASS data (ESI, Pos., 20V): 631 (M+H)$^+$.

EXAMPLE 4(748)

3-(N-((2-(2-((pyridin-2-ylmethylamino)carbonyl)
phenyl)phenyl)carbonyl)-N-(2-(3-ethoxy-4-methox-
yphenyl)ethyl)amino)propanoic acid HPLC measurement condition: A HPLC retention time: 3.20 minutes; MASS data (ESI, Pos., 20V): 582 (M+H)$^+$.

EXAMPLE 4(749)

3-(N-((2-(2-((pyridin-3-ylmethylamino)carbonyl)
phenyl)phenyl)carbonyl)-N-(2-(3-ethoxy-4-methox-
yphenyl)ethyl)amino)propanoic acid HPLC measurement condition: A HPLC retention time: 3.14 minutes; MASS data (ESI, Pos., 20V): 582 (M+H)$^+$.

EXAMPLE 4(750)

3-(N-((2-(2-((1,2,3,4-tetrahydroisoquinolin-2-yl)
carbonyl)phenyl)phenyl)carbonyl)-N-(2-(3-ethoxy-
4-methoxyphenyl)ethyl)amino)propanoic acid HPLC measurement condition: A HPLC retention time: 3.80 minutes; MASS data (ESI, Pos., 20V): 607 (M+H)$^+$.

EXAMPLE 4(751)

3-(N-((2-(2-((α-methylbenzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.80 minutes; MASS data (ESI, Pos., 20V): 595 (M+H)$^+$.

EXAMPLE 4(752)

3-(N-((2-(2-((benzylamino)carbonyl)phenyl)phenyl)
carbonyl)-N-(2-(3-ethoxy-4-methoxyphenyl)ethyl)
amino)propanoic acid HPLC measurement condition: A HPLC retention time: 3.75 minutes; MASS data (ESI, Pos., 20V): 581 (M+H)$^+$.

EXAMPLE 4(753)

3-(N-((2-(2-((2-methoxybenzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.75 minutes; MASS data (ESI, Pos., 20V): 611 (M+H)$^+$.

EXAMPLE 4(754)

3-(N-((2-(2-((2-methylbenzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.82 minutes; MASS data (ESI, Pos., 20V): 595 (M+H)$^+$.

EXAMPLE 4(755)

3-(N-((2-(2-((3-methoxybenzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.73 minutes; MASS data (ESI, Pos., 20V): 611 (M+H)$^+$.

EXAMPLE 4(756)

3-(N-((2-(2-((4-chlorobenzylamino)carbonyl)phenyl)
phenyl)carbonyl)-N-2-(3-ethoxy-4-methoxyphenyl)
ethyl)amino)propanoic acid HPLC measurement condition: A HPLC retention time: 3.88 minutes; MASS data (ESI, Pos., 20V): 615 (M+H)$^+$.

EXAMPLE 4(757)

3-(N-((2-(2-((4-methoxybenzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.71 minutes; MASS data (ESI, Pos., 20V): 611 (M+H)$^+$.

EXAMPLE 4(758)

3-(N-((2-(2-((4-methylbenzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.82 minutes; MASS data (ESI, Pos., 20V): 595 (M+H)$^+$.

EXAMPLE 4(759)

3-(N-((2-(2-((N-methyl-N-benzylamino)carbonyl)
phenyl)phenyl)carbonyl)-N-(2-(3-ethoxy-4-methox-
yphenyl)ethyl)amino)propanoic acid HPLC measurement condition: A HPLC retention time: 3.77 minutes; MASS data (ESI, Pos., 20V): 595 (M+H)$^+$.

EXAMPLE 4(760)

3-(N-((2-(2-((N-isopropyl-N-benzylamino)carbonyl)
phenyl)phenyl)carbonyl)-N-(2-(3-ethoxy-4-methox-
yphenyl)ethyl)amino)propanoic acid HPLC measurement condition: A HPLC retention time: 3.91 minutes; MASS data (ESI, Pos., 20V): 623 (M+H)$^+$.

EXAMPLE 4(761)

3-(N-((2-(2-((N-ethyl-N-benzylamino)carbonyl)phe-
nyl)phenyl)carbonyl)-N-(2-(3-ethoxy-4-methox-
yphenyl)ethyl)amino)propanoic acid HPLC measurement condition: A HPLC retention time: 3.86 minutes; MASS data (ESI, Pos., 20V): 609 (M+H)$^+$.

EXAMPLE 4(762)

3-(N-((2-(2-((N-butyl-N-benzylamino)carbonyl)phenyl)phenyl)carbonyl)-N-(2-(3-ethoxy-4-methoxyphenyl)ethyl)amino)propanoic acid HPLC measurement condition: A HPLC retention time: 4.06 minutes; MASS data (ESI, Pos., 20V): 637 (M+H)$^+$, 388.

EXAMPLE 4(763)

3-(N-((2-(2-((4-(tert-butyl)benzylamino)carbonyl)phenyl)phenyl)carbonyl)-N-(2-(3-ethoxy-4-methoxyphenyl)ethyl)amino)propanoic acid HPLC measurement condition: A HPLC retention time: 4.06 minutes; MASS data (ESI, Pos., 20V): 637 (M+H)$^+$.

EXAMPLE 4(764)

3-(N-((2-(2-((1-phenyl-3-hydroxypropylamino)carbonyl)phenyl)phenyl)carbonyl)-N-(2-(3-ethoxy-4-methoxyphenyl)ethyl)amino)propanoic acid HPLC measurement condition: A HPLC retention time: 3.56 minutes; MASS data (ESI, Pos., 20V): 625 (M+H)$^+$.

EXAMPLE 4(765)

3-(N-((2-(2-((2-fluorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.75 minutes; MASS data (ESI, Pos., 20V): 599 (M+H)$^+$.

EXAMPLE 4(766)

3-(N-((2-(2-((3-fluorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.78 minutes; MASS data (ESI, Pos., 20V): 599 (M+H)$^+$.

EXAMPLE 4(767)

3-(N-((2-(2-((2,5-difluorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.80 minutes; MASS data (ESI, Pos., 20V): 617 (M+H)$^+$.

EXAMPLE 4(768)

3-(N-((2-(2-(((1R)-1-phenyl-2-hydroxyethylamino)carbonyl)phenyl)phenyl)carbonyl)-N-(2-(3-ethoxy-4-methoxyphenyl)ethyl)amino)propanoic acid HPLC measurement condition: A HPLC retention time: 3.58 minutes; MASS data (ESI, Pos., 20V): 611 (M+H)$^+$.

EXAMPLE 4(769)

3-(N-((2-(2-((2-chlorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.86 minutes; MASS data (ESI, Pos., 20V): 615 (M+H)$^+$.

EXAMPLE 4(770)

3-(N-((2-(2-((4-fluorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.77 minutes; MASS data (ESI, Pos., 20V): 599 (M+H)$^+$.

EXAMPLE 4(771)

3-(N-((2-(2-((allylamino)carbonyl)phenyl)phenyl)carbonyl)-N-(2-(3-ethoxy-4-methoxyphenyl)ethyl)amino)propanoic acid HPLC measurement condition: A HPLC retention time: 3.58 minutes; MASS data (ESI, Pos., 20V): 531 (M+H)$^+$.

EXAMPLE 4(772)

3-(N-((2-(2-((2,6-difluorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.75 minutes; MASS data (ESI, Pos., 20V): 617 (M+H)$^+$.

EXAMPLE 4(773)

3-(N-((2-(2-((3-chlorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.88 minutes; MASS data (ESI, Pos., 20V): 615 (M+H)$^+$.

EXAMPLE 4(774)

3-(N-((2-(2-(((1S)-1-phenyl-2-hydroxyethylamino)carbonyl)phenyl)phenyl)carbonyl)-N-(2-(3-ethoxy-4-methoxyphenyl)ethyl)amino)propanoic acid HPLC measurement condition: A HPLC retention time: 3.58 minutes; MASS data (ESI, Pos., 20V): 611 (M+H)$^+$.

EXAMPLE 4(775)

3-(N-((2-(2-(((1R)-1-(4-methylphenyl)ethylamino)carbonyl)phenyl)phenyl)carbonyl)-N-(2-(3-ethoxy-4-methoxyphenyl)ethyl)amino)propanoic acid HPLC measurement condition: A HPLC retention time: 3.91 minutes; MASS data (ESI, Pos., 20V): 609 (M+H)$^+$.

EXAMPLE 4(776)

3-(N-((2-(2-((1-(4-fluorophenyl)ethylamino)carbonyl)phenyl)phenyl)carbonyl)-N-(2-(3-ethoxy-4-methoxyphenyl)ethyl)amino)propanoic acid HPLC measurement condition: A HPLC retention time: 3.84 minutes; MASS data (ESI, Pos., 20V): 613 (M+H)$^+$.

EXAMPLE 4(777)

3-(N-((2-(2-((2-thienylmethylamino)carbonyl)phenyl)phenyl)carbonyl)-N-(2-(3-ethoxy-4-methoxyphenyl)ethyl)amino)propanoic acid HPLC measurement condition: A HPLC retention time: 3.71 minutes; MASS data (ESI, Pos., 20V): 587 (M+H)$^+$.

EXAMPLE 4(778)

3-(N-((2-(2-(((3S)-3-hydroxymethyl-1,2,3,4-tetrahydroisoquinolin-2-yl)carbonyl)phenyl)phenyl)carbonyl)-N-(2-(3-ethoxy-4-methoxyphenyl)ethyl)amino)propanoic acid HPLC measurement condition: A HPLC retention time: 3.47 minutes; MASS data (ESI, Pos., 20V): 637 (M+H)$^+$; HPLC retention time: 3.62 minutes; MASS data (ESI, Pos., 20V): 637 (M+H)$^+$, 533.

EXAMPLE 4(779)

3-(N-((2-(2-((3-methylbenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.82 minutes; MASS data (ESI, Pos., 20V): 595 (M+H)$^+$.

EXAMPLE 4(780)

3-(N-((2-(2-((3,5-difluorobenzylamino)carbonyl)phenyl)phenyl)carbonyl)-N-(2-(3-ethoxy-4-methoxyphenyl)ethyl)amino)propanoic acid HPLC measurement condition: A HPLC retention time: 3.84 minutes; MASS data (ESI, Pos., 20V): 617 (M+H)$^+$.

EXAMPLE 4(781)

3-(N-((2-(2-((N-methyl-N-(6-methylpyridin-2-yl)methylamino)carbonyl)phenyl)phenyl)carbonyl)-N-(2-(3-ethoxy-4-methoxyphenyl)ethyl)amino)propanoic acid HPLC measurement condition: A HPLC retention time: 3.18 minutes; MASS data (ESI, Pos., 20V): 610 (M+H)$^+$, 596.

EXAMPLE 4(782)

3-(N-((2-(2-((N-(2-(N,N-dimethylamino)ethyl)-N-benzylamino)carbonyl)phenyl)phenyl)carbonyl)-N-(2-(3-ethoxy-4-methoxyphenyl)ethyl)amino)propanoic acid HPLC measurement condition: A HPLC retention time: 3.40 minutes; MASS data (ESI, Pos., 20V): 652 (M+H)$^+$.

EXAMPLE 4(783)

3-(N-((2-(2-((2-phenylethylamino)carbonyl)phenyl)phenyl)carbonyl)-N-(2-(3-ethoxy-4-methoxyphenyl)ethyl)amino)propanoic acid HPLC measurement condition: A HPLC retention time: 3.82 minutes; MASS data (ESI, Pos., 20V): 595 (M+H)$^+$.

EXAMPLE 4(784)

3-(N-((2-(2-((1,2,3,4-tetrahydro-1-naphthylamino)carbonyl)phenyl)phenyl)carbonyl)-N-(2-(3-methoxy-4-ethoxyphenyl)ethyl)amino)propanoic acid HPLC measurement condition: A HPLC retention time: 3.93 minutes; MASS data (ESI, Pos., 20V): 621 (M+H)$^+$.

EXAMPLE 4(785)

3-(N-((2-(2-((N-benzyl-N-(2-hydroxyethyl)amino)carbonyl)phenyl)phenyl)carbonyl)-N-(2-(3-methoxy-4-ethoxyphenyl)ethyl)amino)propanoic acid HPLC measurement condition: A HPLC retention time: 3.62 minutes; MASS data (ESI, Pos., 20V): 625 (M+H)$^+$.

EXAMPLE 4(786)

3-(N-((2-(2-((2-furylmethylamino)carbonyl)phenyl)phenyl)carbonyl)-N-(2-(3-methoxy-4-ethoxyphenyl)ethyl)amino)propanoic acid HPLC measurement condition: A HPLC retention time: 3.67 minutes; MASS data (ESI, Pos., 20V): 571 (M+H)$^+$.

EXAMPLE 4(787)

3-(N-((2-(2-((1-indaneamino)carbonyl)phenyl)phenyl)carbonyl)-N-(2-(3-methoxy-4-ethoxyphenyl)ethyl)amino)propanoic acid HPLC measurement condition: A HPLC retention time: 3.86 minutes; MASS data (ESI, Pos., 20V): 607 (M+H)$^+$.

EXAMPLE 4(788)

3-(N-((2-(2-((1-naphthylmethylamino)carbonyl)phenyl)phenyl)carbonyl)-N-(2-(3-methoxy-4-ethoxyphenyl)ethyl)amino)propanoic acid HPLC measurement condition: A HPLC retention time: 3.95 minutes; MASS data (ESI, Pos., 20V): 631 (M+H)$^+$.

EXAMPLE 4(789)

3-(N-((2-(2-((pyridin-2-ylmethylamino)carbonyl)
phenyl)phenyl)carbonyl)-N-(2-(3-methoxy-4-ethox-
yphenyl)ethyl)amino)propanoic acid HPLC measurement condition: A HPLC retention time:
3.22 minutes; MASS data (ESI, Pos., 20V): 582 (M+H)$^+$.

EXAMPLE 4(790)

3-(N-((2-(2-((pyridin-3-ylmethylamino)carbonyl)
phenyl)phenyl)carbonyl)-N-(2-(3-methoxy-4-ethox-
yphenyl)ethyl)amino)propanoic acid HPLC measurement condition: A HPLC retention time:
3.16 minutes; MASS data (ESI, Pos., 20V): 582 (M+H)$^+$.

EXAMPLE 4(791)

3-(N-((2-(2-((1,2,3,4-tetrahydroisoquinolin-2-yl)
carbonyl)phenyl)phenyl)carbonyl)-N-(2-(3-methoxy-
4-ethoxyphenyl)ethyl)amino)propanoic acid HPLC measurement condition: A HPLC retention time:
3.82 minutes; MASS data (ESI, Pos., 20V): 607 (M+H)$^+$.

EXAMPLE 4(792)

3-(N-((2-(2-((α-methylbenzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.84 minutes; MASS data (ESI, Pos., 20V): 595 (M+H)$^+$.

EXAMPLE 4(793)

3-(N-((2-(2-((benzylamino)carbonyl)phenyl)phenyl)
carbonyl)-N-(2-(3-methoxy-4-ethoxyphenyl)ethyl)
amino)propanoic acid HPLC measurement condition: A HPLC retention time:
3.77 minutes; MASS data (ESI, Pos., 20V): 581 (M+H)$^+$.

EXAMPLE 4(794)

3-(N-((2-(2-((2-methoxybenzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.78 minutes; MASS data (ESI, Pos., 20V): 611 (M+H)$^+$.

EXAMPLE 4(795)

3-(N-((2-(2-((2-methylbenzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.84 minutes; MASS data (ESI, Pos., 20V): 595 (M+H)$^+$.

EXAMPLE 4(796)

3-(N-((2-(2-((3-methoxybenzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.75 minutes; MASS data (ESI, Pos., 20V): 611 (M+H)$^+$.

EXAMPLE 4(797)

3-(N-((2-(2-((4-chlorobenzylamino)carbonyl)phenyl)
phenyl)carbonyl)-N-(2-(3-methoxy-4-ethoxyphenyl)
ethyl)amino)propanoic acid HPLC measurement condition: A HPLC retention time:
3.89 minutes; MASS data (ESI, Pos., 20V): 615 (M+H)$^+$.

EXAMPLE 4(798)

3-(N-((2-(2-((4-methoxybenzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.75 minutes; MASS data (ESI, Pos., 20V): 611 (M+H)$^+$.

EXAMPLE 4(799)

3-(N-((2-(2-((4-methylbenzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.86 minutes; MASS data (ESI, Pos., 20V): 595 (M+H)$^+$.

EXAMPLE 4(800)

3-(N-((2-(2-((N-methyl-N-benzylamino)carbonyl)
phenyl)phenyl)carbonyl)-N-(2-(3-methoxy-4-ethox-
yphenyl)ethyl)amino)propanoic acid HPLC measurement condition: A HPLC retention time:
3.80 minutes; MASS data (ESI, Pos., 20V): 595 (M+H)$^+$.

EXAMPLE 4(801)

3-(N-((2-(2-((N-ethyl-N-benzylamino)carbonyl)phe-
nyl)phenyl)carbonyl)-N-(2-(3-methoxy-4-ethox-
yphenyl)ethyl)amino)propanoic acid HPLC measurement condition: A HPLC retention time:
3.88 minutes; MASS data (ESI, Pos., 20V): 609 (M+H)$^+$.

EXAMPLE 4(802)

3-(N-((2-(2-((N-butyl-N-benzylamino)carbonyl)
phenyl)phenyl)carbonyl)-N-(2-(3-methoxy-4-ethox-
yphenyl)ethyl)amino)propanoic acid HPLC measurement condition: A HPLC retention time:
4.06 minutes; MASS data (ESI, Pos., 20V): 637 (M+H)$^+$, 388.

EXAMPLE 4(803)

3-(N-((2-(2-((4-(tert-butyl)benzylamino)carbonyl)phenyl)phenyl)carbonyl)-N-(2-(3-methoxy-4-ethoxyphenyl)ethyl)amino)propanoic acid HPLC measurement condition: A HPLC retention time: 4.10 minutes; MASS data (ESI, Pos., 20V): 637 (M+H)$^+$.

EXAMPLE 4(804)

3-(N-((2-(2-((1-phenyl-3-hydroxypropylamino)carbonyl)phenyl)phenyl)carbonyl)-N-(2-(3-methoxy-4-ethoxyphenyl)ethyl)amino)propanoic acid HPLC measurement condition: A HPLC retention time: 3.58 minutes; MASS data (ESI, Pos., 20V): 625 (M+H)$^+$.

EXAMPLE 4(805)

3-(N-((2-(2-((2-fluorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.78 minutes; MASS data (ESI, Pos., 20V): 599 (M+H)$^+$.

EXAMPLE 4(806)

3-(N-((2-(2-((3-fluorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.80 minutes; MASS data (ESI, Pos., 20V): 599 (M+H)$^+$.

EXAMPLE 4(807)

3-(N-((2-(2-((2,5-difluorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.80 minutes; MASS data (ESI, Pos., 20V): 617 (M+H)$^+$.

EXAMPLE 4(808)

3-(N-((2-(2-(((1R)-1-phenyl-2-hydroxyethylamino)carbonyl)phenyl)phenyl)carbonyl)-N-(2-(3-methoxy-4-ethoxyphenyl)ethyl)amino)propanoic acid HPLC measurement condition: A HPLC retention time: 3.58 minutes; MASS data (ESI, Pos., 20V): 611 (M+H)$^+$.

EXAMPLE 4(809)

3-(N-((2-(2-((2-chlorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.89 minutes; MASS data (ESI, Pos., 20V): 615 (M+H)$^+$.

EXAMPLE 4(810)

3-(N-((2-(2-((4-fluorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.78 minutes; MASS data (ESI, Pos., 20V): 599 (M+H)$^+$.

EXAMPLE 4(811)

3-(N-((2-(2-((allylamino)carbonyl)phenyl)phenyl)carbonyl)-N-(2-(3-methoxy-4-ethoxyphenyl)ethyl)amino)propanoic acid HPLC measurement condition: A HPLC retention time: 3.60 minutes; MASS data (ESI, Pos., 20V): 531 (M+H)$^+$.

EXAMPLE 4(812)

3-(N-((2-(2-((2,6-difluorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.77 minutes; MASS data (ESI, Pos., 20V): 617 (M+H)$^+$.

EXAMPLE 4(813)

3-(N-((2-(2-((3-chlorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.88 minutes; MASS data (ESI, Pos., 20V): 615 (M+H)$^+$.

EXAMPLE 4(814)

3-(N-((2-(2-(((1S)-1-phenyl-2-hydroxyethylamino)carbonyl)phenyl)phenyl)carbonyl)-N-(2-(3-methoxy-4-ethoxyphenyl)ethyl)amino)propanoic acid HPLC measurement condition: A HPLC retention time: 3.58 minutes; MASS data (ESI, Pos., 20V): 611 (M+H)$^+$.

EXAMPLE 4(815)

3-(N-((2-(2-(((1R)-1-(4-methylphenyl)ethylamino)carbonyl)phenyl)phenyl)carbonyl)-N-(2-(3-methoxy-4-ethoxyphenyl)ethyl)amino)propanoic acid HPLC measurement condition: A HPLC retention time: 3.91 minutes; MASS data (ESI, Pos., 20V): 609 (M+H)$^+$.

EXAMPLE 4(816)

3-(N-((2-(2-((1-(4-fluorophenyl)ethylamino)carbonyl)phenyl)phenyl)carbonyl)-N-(2-(3-methoxy-4-ethoxyphenyl)ethyl)amino)propanoic acid HPLC measurement condition: A HPLC retention time: 3.86 minutes; MASS data (ESI, Pos., 20V): 613 (M+H)$^+$.

EXAMPLE 4(817)

3-(N-((2-(2-((2-thienylmethylamino)carbonyl)phenyl)phenyl)carbonyl)-N-(2-(3-methoxy-4-ethoxyphenyl)ethyl)amino)propanoic acid HPLC measurement condition: A HPLC retention time: 3.73 minutes; MASS data (ESI, Pos., 20V): 587 (M+H)$^+$.

EXAMPLE 4(818)

3-(N-((2-(2-(((3S)-3-hydroxymethyl-1,2,3,4-tetrahydroisoquinolin-2-yl)carbonyl)phenyl)phenyl)carbonyl)-N-(2-(3-methoxy-4-ethoxyphenyl)ethyl)amino)propanoic acid HPLC measurement condition: A HPLC retention time: 3.51 minutes; MASS data (ESI, Pos., 20V): 637 (M+H)$^+$; HPLC retention time: 3.66 minutes; MASS data (ESI, Pos., 20V): 637 (M+H)$^+$, 533.

EXAMPLE 4(819)

3-(N-((2-(2-((3-methylbenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.84 minutes; MASS data (ESI, Pos., 20V): 595 (M+H)$^+$.

EXAMPLE 4(820)

3-(N-((2-(2-((3,5-difluorobenzylamino)carbonyl)phenyl)phenyl)carbonyl)-N-(2-(3-methoxy-4-ethoxyphenyl)ethyl)amino)propanoic acid HPLC measurement condition: A HPLC retention time: 3.84 minutes; MASS data (ESI, Pos., 20V): 617 (M+H)$^+$.

EXAMPLE 4(821)

3-(N-((2-(2-((N-methyl-N-(6-methylpyridin-2-yl)methylamino)carbonyl)phenyl)phenyl)carbonyl)-N-(2-(3-methoxy-4-ethoxyphenyl)ethyl)amino)propanoic acid HPLC measurement condition: A HPLC retention time: 3.20 minutes; MASS data (ESI, Pos., 20V): 610 (M+H)$^+$.

EXAMPLE 4(822)

3-(N-((2-(2-((N-(2-(N,N-dimethylamino)ethyl)-N-benzylamino)carbonyl)phenyl)phenyl)carbonyl)-N-(2-(3-methoxy-4-ethoxyphenyl)ethyl)amino)propanoic acid HPLC measurement condition: A HPLC retention time: 3.42 minutes; MASS data (ESI, Pos., 20V): 652 (M+H)$^+$.

EXAMPLE 4(823)

3-(N-((2-(2-((2-phenylethylamino)carbonyl)phenyl)phenyl)carbonyl)-N-(2-(3-methoxy-4-ethoxyphenyl)ethyl)amino)propanoic acid HPLC measurement condition: A HPLC retention time: 3.84 minutes; MASS data (ESI, Pos., 20V): 595 (M+H)$^+$.

EXAMPLE 4(824)

3-(N-((2-(2-((1,2,3,4-tetrahydro-1-naphthylamino)carbonyl)phenyl)phenyl)carbonyl)-N-(2-(3,5-dimethoxyphenyl)ethyl)amino)propanoic acid HPLC measurement condition: A HPLC retention time: 3.97 minutes; MASS data (ESI, Pos., 20V): 607 (M+H)$^+$.

EXAMPLE 4(825)

3-(N-((2-(2-((N-benzyl-N-(2-hydroxyethyl)amino)carbonyl)phenyl)phenyl)carbonyl)-N-(2-(3,5-dimethoxyphenyl)ethyl)amino)propanoic acid HPLC measurement condition: A HPLC retention time: 3.66 minutes; MASS data (ESI, Pos., 20V): 611 (M+H)$^+$.

EXAMPLE 4(826)

3-(N-((2-(2-((2-furylmethylamino)carbonyl)phenyl)phenyl)carbonyl)-N-(2-(3,5-dimethoxyphenyl)ethyl)amino)propanoic acid HPLC measurement condition: A HPLC retention time: 3.69 minutes; MASS data (ESI, Pos., 20V): 557 (M+H)$^+$.

EXAMPLE 4(827)

3-(N-((2-(2-((1-indaneamino)carbonyl)phenyl)phenyl)carbonyl)-N-(2-(3,5-dimethoxyphenyl)ethyl)amino)propanoic acid HPLC measurement condition: A HPLC retention time: 3.89 minutes; MASS data (ESI, Pos., 20V): 593 (M+H)$^+$.

EXAMPLE 4(828)

3-(N-((2-(2-((1-naphthylmethylamino)carbonyl)phenyl)phenyl)carbonyl)-N-(2-(3,5-dimethoxyphenyl)ethyl)amino)propanoic acid HPLC measurement condition: A HPLC retention time: 3.97 minutes; MASS data (ESI, Pos., 20V): 617 (M+H)$^+$.

EXAMPLE 4(829)

3-(N-((2-(2-((pyridin-2-ylmethylamino)carbonyl)phenyl)phenyl)carbonyl)-N-(2-(3,5-dimethoxyphenyl)ethyl)amino)propanoic acid HPLC measurement condition: A HPLC retention time: 3.25 minutes; MASS data (ESI, Pos., 20V): 568 (M+H)$^+$.

EXAMPLE 4(830)

3-(N-((2-(2-((pyridin-3-ylmethylamino)carbonyl)phenyl)phenyl)carbonyl)-N-(2-(3,5-dimethoxyphenyl)ethyl)amino)propanoic acid HPLC measurement condition: A HPLC retention time: 3.20 minutes; MASS data (ESI, Pos., 20V): 568 (M+H)$^+$.

EXAMPLE 4(831)

3-(N-((2-(2-((1,2,3,4-tetrahydroisoquinolin-2-yl)carbonyl)phenyl)phenyl)carbonyl)-N-(2-(3,5-dimethoxyphenyl)ethyl)amino)propanoic acid HPLC measurement condition: A HPLC retention time: 3.86 minutes; MASS data (ESI, Pos., 20V): 593 (M+H)$^+$.

EXAMPLE 4(832)

3-(N-((2-(2-((α-methylbenzylamino)carbonyl)phenyl)phenyl)carbonyl)-N-(2-(3,5-dimethoxyphenyl)ethyl)amino)propanoic acid HPLC measurement condition: A HPLC retention time: 3.86 minutes; MASS data (ESI, Pos., 20V): 581 (M+H)$^+$.

EXAMPLE 4(833)

3-(N-((2-(2-((benzylamino)carbonyl)phenyl)phenyl)carbonyl)-N-(2-(3,5-dimethoxyphenyl)ethyl)amino)propanoic acid HPLC measurement condition: A HPLC retention time: 3.80 minutes; MASS data (ESI, Pos., 20V): 567 (M+H)$^+$.

EXAMPLE 4(834)

3-(N-((2-(2-((2-methoxybenzylamino)carbonyl)phenyl)phenyl)carbonyl)-N-(2-(3,5-dimethoxyphenyl)ethyl)amino)propanoic acid HPLC measurement condition: A HPLC retention time: 3.82 minutes; MASS data (ESI, Pos., 20V): 597 (M+H)$^+$.

EXAMPLE 4(835)

3-(N-((2-(2-((2-methylbenzylamino)carbonyl)phenyl)phenyl)carbonyl)-N-(2-(3,5-dimethoxyphenyl)ethyl)amino)propanoic acid HPLC measurement condition: A HPLC retention time: 3.88 minutes; MASS data (ESI, Pos., 20V): 581 (M+H)$^+$.

EXAMPLE 4(836)

3-(N-((2-(2-((3-methoxybenzylamino)carbonyl)phenyl)phenyl)carbonyl)-N-(2-(3,5-dimethoxyphenyl)ethyl)amino)propanoic acid HPLC measurement condition: A HPLC retention time: 3.78 minutes; MASS data (ESI, Pos., 20V): 597 (M+H)$^+$.

EXAMPLE 4(837)

3-(N-((2-(2-((4-chlorobenzylamino)carbonyl)phenyl)phenyl)carbonyl)-N-(2-(3,5-dimethoxyphenyl)ethyl)amino)propanoic acid HPLC measurement condition: A HPLC retention time: 3.93 minutes; MASS data (ESI, Pos., 20V): 601 (M+H)$^+$.

EXAMPLE 4(838)

3-(N-((2-(2-((4-methoxybenzylamino)carbonyl)phenyl)phenyl)carbonyl)-N-(2-(3,5-dimethoxyphenyl)ethyl)amino)propanoic acid HPLC measurement condition: A HPLC retention time: 3.77 minutes; MASS data (ESI, Pos., 20V): 597 (M+H)$^+$.

EXAMPLE 4(839)

3-(N-((2-(2-((4-methylbenzylamino)carbonyl)phenyl)phenyl)carbonyl)-N-(2-(3,5-dimethoxyphenyl)ethyl)amino)propanoic acid HPLC measurement condition: A HPLC retention time: 3.88 minutes; MASS data (ESI, Pos., 20V): 581 (M+H)$^+$.

EXAMPLE 4(840)

3-(N-((2-(2-((N-methyl-N-benzylamino)carbonyl)phenyl)phenyl)carbonyl)-N-(2-(3,5-dimethoxyphenyl)ethyl)amino)propanoic acid HPLC measurement condition: A HPLC retention time: 3.84 minutes; MASS data (ESI, Pos., 20V): 581 (M+H)$^+$.

EXAMPLE 4(841)

3-(N-((2-(2-((N-ethyl-N-benzylamino)carbonyl)phenylphenyl)carbonyl)-N-(2-(3,5-dimethoxyphenyl)ethyl)amino)propanoic acid HPLC measurement condition: A HPLC retention time: 3.91 minutes; MASS data (ESI, Pos., 20V): 595 (M+H)$^+$.

EXAMPLE 4(842)

3-(N-((2-(2-((N-butyl-N-benzylamino)carbonyl)phenyl)phenyl)carbonyl)-N-(2-(3,5-dimethoxyphenyl)ethyl)amino)propanoic acid HPLC measurement condition: A HPLC retention time: 4.10 minutes; MASS data (ESI, Pos., 20V): 623 (M+H)$^+$.

EXAMPLE 4(843)

3-(N-((2-(2-((4-(tert-butyl)benzylamino)carbonyl)phenyl)phenyl)carbonyl)-N-(2-(3,5-dimethoxyphenyl)ethyl)amino)propanoic acid HPLC measurement condition: A HPLC retention time: 4.11 minutes; MASS data (ESI, Pos., 20V): 623 (M+H)$^+$.

EXAMPLE 4(844)

3-(N-((2-(2-((1-phenyl-3-hydroxypropylamino)carbonyl)phenyl)phenyl)carbonyl)-N-(2-(3,5-dimethoxyphenyl)ethyl)amino)propanoic acid HPLC measurement condition: A HPLC retention time: 3.62 minutes; MASS data (ESI, Pos., 20V): 611 (M+H)+.

EXAMPLE 4(845)

3-(N-((2-(2-((2-fluorobenzylamino)carbonyl)phenyl)phenyl)carbonyl)-N-(2-(3,5-dimethoxyphenyl)ethyl)amino)propanoic acid HPLC measurement condition: A HPLC retention time: 3.82 minutes; MASS data (ESI, Pos., 20V): 585 (M+H)+.

EXAMPLE 4(846)

3-(N-((2-(2-((3-fluorobenzylamino)carbonyl)phenyl)phenyl)carbonyl)-N-(2-(3,5-dimethoxyphenyl)ethyl)amino)propanoic acid HPLC measurement condition: A HPLC retention time: 3.82 minutes; MASS data (ESI, Pos., 20V): 585 (M+H)+.

EXAMPLE 4(847)

3-(N-((2-(2-((2,5-difluorobenzylamino)carbonyl)phenyl)phenyl)carbonyl)-N-(2-(3,5-dimethoxyphenyl)ethyl)amino)propanoic acid HPLC measurement condition: A HPLC retention time: 3.84 minutes; MASS data (ESI, Pos., 20V): 603 (M+H)+.

EXAMPLE 4(848)

3-(N-((2-(2-(((1R)-1-phenyl-2-hydroxyethylamino)carbonyl)phenyl)phenyl)carbonyl)-N-(2-(3,5-dimethoxyphenyl)ethyl)amino)propanoic acid HPLC measurement condition: A HPLC retention time: 3.64 minutes; MASS data (ESI, Pos., 20V): 597 (M+H)+.

EXAMPLE 4(849)

3-(N-((2-(2-((2-chlorobenzylamino)carbonyl)phenyl)phenyl)carbonyl)-N-(2-(3,5-dimethoxyphenyl)ethyl)amino)propanoic acid HPLC measurement condition: A HPLC retention time: 3.89 minutes; MASS data (ESI, Pos., 20V): 601 (M+H)+.

EXAMPLE 4(850)

3-(N-((2-(2-((4-fluorobenzylamino)carbonyl)phenyl)phenyl)carbonyl)-N-(2-(3,5-dimethoxyphenyl)ethyl)amino)propanoic acid HPLC measurement condition: A HPLC retention time: 3.82 minutes; MASS data (ESI, Pos., 20V): 585 (M+H)+.

EXAMPLE 4(851)

3-(N-((2-(2-((allylamino)carbonyl)phenyl)phenyl)carbonyl)-N-(2-(3,5-dimethoxyphenyl)ethyl)amino)propanoic acid HPLC measurement condition: A HPLC retention time: 3.64 minutes; MASS data (ESI, Pos., 20V): 517 (M+H)+.

EXAMPLE 4(852)

3-(N-((2-(2-((2,6-difluorobenzylamino)carbonyl)phenyl)phenyl)carbonyl)-N-(2-(3,5-dimethoxyphenyl)ethyl)amino)propanoic acid HPLC measurement condition: A HPLC retention time: 3.80 minutes; MASS data (ESI, Pos., 20V): 603 (M+H)+.

EXAMPLE 4(853)

3-(N-((2-(2-((3-chlorobenzylamino)carbonyl)phenyl)phenyl)carbonyl)-N-(2-(3,5-dimethoxyphenyl)ethyl)amino)propanoic acid HPLC measurement condition: A HPLC retention time: 3.93 minutes; MASS data (ESI, Pos., 20V): 601 (M+H)+.

EXAMPLE 4(854)

3-(N-((2-(2-(((1S)-1-phenyl-2-hydroxyethylamino)carbonyl)phenyl)phenyl)carbonyl)-N-(2-(3,5-dimethoxyphenyl)ethyl)amino)propanoic acid HPLC measurement condition: A HPLC retention time: 3.62 minutes; MASS data (ESI, Pos., 20V): 597 (M+H)+.

EXAMPLE 4(855)

3-(N-((2-(2-(((1R)-1-(4-methylphenyl)ethylamino)carbonyl)phenyl)phenyl)carbonyl)-N-(2-(3,5-dimethoxyphenyl)ethyl)amino)propanoic acid HPLC measurement condition: A HPLC retention time: 3.95 minutes; MASS data (ESI, Pos., 20V): 595 (M+H)+.

EXAMPLE 4(856)

3-(N-((2-(2-((1-(4-fluorophenyl)ethylamino)carbonyl)phenyl)phenyl)carbonyl)-N-(2-(3,5-dimethoxyphenyl)ethyl)amino)propanoic acid HPLC measurement condition: A HPLC retention time: 3.89 minutes; MASS data (ESI, Pos., 20V): 599 (M+H)+.

EXAMPLE 4(857)

3-(N-((2-(2-((2-thienylmethylamino)carbonyl)phenyl)phenyl)carbonyl)-N-(2-(3,5-dimethoxyphenyl)ethyl)amino)propanoic acid HPLC measurement condition: A HPLC retention time: 3.75 minutes; MASS data (ESI, Pos., 20V): 573 (M+H)+.

EXAMPLE 4(858)

3-(N-((2-(2-(((3S)-3-hydroxymethyl-1,2,3,4-tetrahydroisoquinolin-2-yl)carbonyl)phenyl)phenyl)carbonyl)-N-(2-(3,5-dimethoxyphenyl)ethyl)amino)propanoic acid HPLC measurement condition: A HPLC retention time: 3.53 minutes; MASS data (ESI, Pos., 20V): 623 (M+H)$^+$; HPLC retention time: 3.67 minutes; MASS data (ESI, Pos., 20V): 623 (M+H)$^+$, 519.

EXAMPLE 4(859)

3-(N-((2-(2-((3-methylbenzylamino)carbonyl)phenyl)phenyl)carbonyl)-N-(2-(3,5-dimethoxyphenyl)ethyl)amino)propanoic acid HPLC measurement condition: A HPLC retention time: 3.88 minutes; MASS data (ESI, Pos., 20V): 581 (M+H)$^+$.

EXAMPLE 4(860)

3-(N-((2-(2-((3,5-difluorobenzylamino)carbonyl)phenyl)phenyl)carbonyl)-N-(2-(3,5-dimethoxyphenyl)ethyl)amino)propanoic acid HPLC measurement condition: A HPLC retention time: 3.88 minutes; MASS data (ESI, Pos., 20V): 603 (M+H)$^+$.

EXAMPLE 4(861)

3-(N-((2-(2-((N-methyl-N-(6-methylpyridin-2-yl)methylamino)carbonyl)phenyl)phenyl)carbonyl)-N-(2-(3,5-dimethoxyphenyl)ethyl)amino)propanoic acid HPLC measurement condition: A HPLC retention time: 3.23 minutes; MASS data (ESI, Pos., 20V): 596 (M+H)$^+$.

EXAMPLE 4(862)

3-(N-((2-(2-((N-(2-(N,N-dimethylamino)ethyl)-N-benzylamino)carbonyl)phenyl)phenyl)carbonyl)-N-(2-(3,5-dimethoxyphenyl)ethyl)amino)propanoic acid HPLC measurement condition: A HPLC retention time: 3.47 minutes; MASS data (ESI, Pos., 20V): 638 (M+H)$^+$.

EXAMPLE 4(863)

3-(N-((2-(2-((2-phenylethylamino)carbonyl)phenyl)phenyl)carbonyl)-N-(2-(3,5-dimethoxyphenyl)ethyl)amino)propanoic acid HPLC measurement condition: A HPLC retention time: 3.86 minutes; MASS data (ESI, Pos., 20V): 581 (M+H)$^+$.

EXAMPLE 4(864)

3-(N-((2-(2-((1,2,3,4-tetrahydro-1-naphthylamino)carbonyl)phenyl)phenyl)carbonyl)-N-(2-(2-ethoxyphenyl)ethyl)amino)propanoic acid HPLC measurement condition: A HPLC retention time: 4.13 minutes; MASS data (ESI, Pos., 20V): 591 (M+H)$^+$.

EXAMPLE 4(865)

3-(N-((2-(2-((N-benzyl-N-(2-hydroxyethyl)amino)carbonyl)phenyl)phenyl)carbonyl)-N-(2-(2-ethoxyphenyl)ethyl)amino)propanoic acid HPLC measurement condition: A HPLC retention time: 3.78 minutes; MASS data (ESI, Pos., 20V): 595 (M+H)$^+$.

EXAMPLE 4(866)

3-(N-((2-(2-((2-furylmethylamino)carbonyl)phenyl)phenyl)carbonyl)-N-(2-(2-ethoxyphenyl)ethyl)amino)propanoic acid HPLC measurement condition: A HPLC retention time: 3.86 minutes; MASS data (ESI, Pos., 20V): 541 (M+H)$^+$, 489.

EXAMPLE 4(867)

3-(N-((2-(2-((1-indaneamino)carbonyl)phenyl)phenyl)carbonyl)-N-(2-(2-ethoxyphenyl)ethyl)amino)propanoic acid HPLC measurement condition: A HPLC retention time: 4.06 minutes; MASS data (ESI, Pos., 20V): 577 (M+H)$^+$.

EXAMPLE 4(868)

3-(N-((2-(2-((1-naphthylmethylamino)carbonyl)phenyl)phenyl)carbonyl)-N-(2-(2-ethoxyphenyl)ethyl)amino)propanoic acid HPLC measurement condition: A HPLC retention time: 4.13 minutes; MASS data (ESI, Pos., 20V): 601 (M+H)$^+$.

EXAMPLE 4(869)

3-(N-((2-(2-((pyridin-2-ylmethylamino)carbonyl)phenyl)phenyl)carbonyl)-N-(2-(2-ethoxyphenyl)ethyl)amino)propanoic acid HPLC measurement condition: A HPLC retention time: 3.36 minutes; MASS data (ESI, Pos., 20V): 552 (M+H)$^+$.

EXAMPLE 4(870)

3-(N-((2-(2-((pyridin-3-ylmethylamino)carbonyl)phenyl)phenyl)carbonyl)-N-(2-(2-ethoxyphenyl)ethyl)amino)propanoic acid HPLC measurement condition: A HPLC retention time: 3.31 minutes; MASS data (ESI, Pos., 20V): 552 (M+H)$^+$.

EXAMPLE 4(871)

3-(N-((2-(2-((1,2,3,4-tetrahydroisoquinolin-2-yl)carbonyl)phenyl)phenyl)carbonyl)-N-(2-(2-ethoxyphenyl)ethyl)amino)propanoic acid HPLC measurement condition: A HPLC retention time: 4.00 minutes; MASS data (ESI, Pos., 20V): 577 (M+H)$^+$.

EXAMPLE 4(872)

3-(N-((2-(2-((α-methylbenzylamino)carbonyl)phenyl)phenyl)carbonyl)-N-(2-(2-ethoxyphenyl)ethyl)amino)propanoic acid HPLC measurement condition: A HPLC retention time: 4.02 minutes; MASS data (ESI, Pos., 20V): 565 (M+H)$^+$.

EXAMPLE 4(873)

3-(N-((2-(2-((benzylamino)carbonyl)phenyl)phenyl)carbonyl)-N-(2-(2-ethoxyphenyl)ethyl)amino)propanoic acid HPLC measurement condition: A HPLC retention time: 3.97 minutes; MASS data (ESI, Pos., 20V): 551 (M+H)$^+$.

EXAMPLE 4(874)

3-(N-((2-(2-((2-methoxybenzylamino)carbonyl)phenyl)phenyl)carbonyl)-N-(2-(2-ethoxyphenyl)ethyl)amino)propanoic acid HPLC measurement condition: A HPLC retention time: 3.99 minutes; MASS data (ESI, Pos., 20V): 581 (M+H)$^+$.

EXAMPLE 4(875)

3-(N-((2-(2-((2-methylbenzylamino)carbonyl)phenyl)phenyl)carbonyl)-N-(2-(2-ethoxyphenyl)ethyl)amino)propanoic acid HPLC measurement condition: A HPLC retention time: 4.04 minutes; MASS data (ESI, Pos., 20V): 565 (M+H)$^+$.

EXAMPLE 4(876)

3-(N-((2-(2-((3-methoxybenzylamino)carbonyl)phenyl)phenyl)carbonyl)-N-(2-(2-ethoxyphenyl)ethyl)amino)propanoic acid HPLC measurement condition: A HPLC retention time: 3.93 minutes; MASS data (ESI, Pos., 20V): 581 (M+H)$^+$.

EXAMPLE 4(877)

3-(N-((2-(2-((4-chlorobenzylamino)carbonyl)phenyl)phenyl)carbonyl)-N-(2-(2-ethoxyphenyl)ethyl)amino)propanoic acid HPLC measurement condition: A HPLC retention time: 4.10 minutes; MASS data (ESI, Pos., 20V): 585 (M+H)$^+$.

EXAMPLE 4(878)

3-(N-((2-(2-((4-methoxybenzylamino)carbonyl)phenyl)phenyl)carbonyl)-N-(2-(2-ethoxyphenyl)ethyl)amino)propanoic acid HPLC measurement condition: A HPLC retention time: 3.91 minutes; MASS data (ESI, Pos., 20V): 581 (M+H)$^+$.

EXAMPLE 4(879)

3-(N-((2-(2-((4-methylbenzylamino)carbonyl)phenyl)phenyl)carbonyl)-N-(2-(2-ethoxyphenyl)ethyl)amino)propanoic acid HPLC measurement condition: A HPLC retention time: 4.04 minutes; MASS data (ESI, Pos., 20V): 565 (M+H)$^+$.

EXAMPLE 4(880)

3-(N-((2-(2-((N-methyl-N-benzylamino)carbonyl)phenyl)phenyl)carbonyl)-N-(2-(2-ethoxyphenyl)ethyl)amino)propanoic acid HPLC measurement condition: A HPLC retention time: 3.99 minutes; MASS data (ESI, Pos., 20V): 565 (M+H)$^+$.

EXAMPLE 4(881)

3-(N-((2-(2-((N-ethyl-N-benzylamino)carbonyl)phenyl)phenyl)carbonyl)-N-(2-(2-ethoxyphenyl)ethyl)amino)propanoic acid HPLC measurement condition: A HPLC retention time: 4.04 minutes; MASS data (ESI, Pos., 20V): 579 (M+H)$^+$.

EXAMPLE 4(882)

3-(N-((2-(2-((N-butyl-N-benzylamino)carbonyl)phenyl)phenyl)carbonyl)-N-(2-(2-ethoxyphenyl)ethyl)amino)propanoic acid HPLC measurement condition: A HPLC retention time: 4.24 minutes; MASS data (ESI, Pos., 20V): 607 (M+H)$^+$.

EXAMPLE 4(883)

3-(N-((2-(2-((4-(tert-butyl)benzylamino)carbonyl)phenyl)phenyl)carbonyl)-N-(2-(2-ethoxyphenyl)ethyl)amino)propanoic acid HPLC measurement condition: A HPLC retention time: 4.28 minutes; MASS data (ESI, Pos., 20V): 607 (M+H)$^+$.

EXAMPLE 4(884)

3-(N-((2-(2-((1-phenyl-3-hydroxypropylamino)carbonyl)phenyl)phenyl)carbonyl)-N-(2-(2-ethoxyphenyl)ethyl)amino)propanoic acid HPLC measurement condition: A HPLC retention time: 3.79 minutes; MASS data (ESI, Pos., 20V): 595 (M+H)$^+$.

EXAMPLE 4(885)

3-(N-((2-(2-((2-fluorobenzylamino)carbonyl)phenyl)phenyl)carbonyl)-N-(2-(2-ethoxyphenyl)ethyl)amino)propanoic acid HPLC measurement condition: A HPLC retention time: 3.97 minutes; MASS data (ESI, Pos., 20V): 569 (M+H)$^+$.

EXAMPLE 4(886)

3-(N-((2-(2-((3-fluorobenzylamino)carbonyl)phenyl)phenyl)carbonyl)-N-(2-(2-ethoxyphenyl)ethyl)amino)propanoic acid HPLC measurement condition: A HPLC retention time: 3.99 minutes; MASS data (ESI, Pos., 20V): 569 (M+H)$^+$.

EXAMPLE 4(887)

3-(N-((2-(2-((2,5-difluorobenzylamino)carbonyl)phenyl)phenyl)carbonyl)-N-(2-(2-ethoxyphenyl)ethyl)amino)propanoic acid HPLC measurement condition: A HPLC retention time: 4.00 minutes; MASS data (ESI, Pos., 20V): 587 (M+H)$^+$.

EXAMPLE 4(888)

3-(N-((2-(2-(((1R)-1-phenyl-2-hydroxyethylamino)carbonyl)phenyl)phenyl)carbonyl)-N-(2-(2-ethoxyphenyl)ethyl)amino)propanoic acid HPLC measurement condition: A HPLC retention time: 3.78 minutes; MASS data (ESI, Pos., 20V): 581 (M+H)$^+$.

EXAMPLE 4(889)

3-(N-((2-(2-((2-chlorobenzylamino)carbonyl)phenyl)phenyl)carbonyl)-N-(2-(2-ethoxyphenyl)ethyl)amino)propanoic acid HPLC measurement condition: A HPLC retention time: 4.06 minutes; MASS data (ESI, Pos., 20V): 585 (M+H)$^+$.

EXAMPLE 4(890)

3-(N-((2-(2-((4-fluorobenzylamino)carbonyl)phenyl)phenyl)carbonyl)-N-(2-(2-ethoxyphenyl)ethyl)amino)propanoic acid HPLC measurement condition: A HPLC retention time: 3.97 minutes; MASS data (ESI, Pos., 20V): 569 (M+H)$^+$.

EXAMPLE 4(891)

3-(N-((2-(2-((allylamino)carbonyl)phenyl)phenyl)carbonyl)-N-(2-(2-ethoxyphenyl)ethyl)amino)propanoic acid HPLC measurement condition: A HPLC retention time: 3.80 minutes; MASS data (ESI, Pos., 20V): 501 (M+H)$^+$.

EXAMPLE 4(892)

3-(N-((2-(2-((2,6-difluorobenzylamino)carbonyl)phenyl)phenyl)carbonyl)-N-(2-(2-ethoxyphenyl)ethyl)amino)propanoic acid HPLC measurement condition: A HPLC retention time: 3.95 minutes; MASS data (ESI, Pos., 20V): 587 (M+H)$^+$.

EXAMPLE 4(893)

3-(N-((2-(2-((3-chlorobenzylamino)carbonyl)phenyl)phenyl)carbonyl)-N-(2-(2-ethoxyphenyl)ethyl)amino)propanoic acid HPLC measurement condition: A HPLC retention time: 4.10 minutes; MASS data (ESI, Pos., 20V): 585 (M+H)$^+$.

EXAMPLE 4(894)

3-(N-((2-(2-(((1S)-1-phenyl-2-hydroxyethylamino)carbonyl)phenyl)phenyl)carbonyl)-N-(2-(2-ethoxyphenyl)ethyl)amino)propanoic acid HPLC measurement condition: A HPLC retention time: 3.80 minutes; MASS data (ESI, Pos., 20V): 581 (M+H)$^+$.

EXAMPLE 4(895)

3-(N-((2-(2-(((1R)-1-(4-methylphenyl)ethylamino)carbonyl)phenyl)phenyl)carbonyl)-N-(2-(2-ethoxyphenyl)ethyl)amino)propanoic acid HPLC measurement condition: A HPLC retention time: 4.10 minutes; MASS data (ESI, Pos., 20V): 579 (M+H)$^+$.

EXAMPLE 4(896)

3-(N-((2-(2-((1-(4-fluorophenyl)ethylamino)carbonyl)phenyl)phenyl)carbonyl)-N-(2-(2-ethoxyphenyl)ethyl)amino)propanoic acid HPLC measurement condition: A HPLC retention time: 4.06 minutes; MASS data (ESI, Pos., 20V): 583 (M+H)$^+$.

EXAMPLE 4(897)

3-(N-((2-(2-((2-thienylmethylamino)carbonyl)phenyl)phenyl)carbonyl)-N-(2-(2-ethoxyphenyl)ethyl)amino)propanoic acid HPLC measurement condition: A HPLC retention time: 3.95 minutes; MASS data (ESI, Pos., 20V): 557 (M+H)$^+$.

EXAMPLE 4(898)

3-(N-((2-(2-(((3S)-3-hydroxymethyl-1,2,3,4-tetrahydroisoquinolin-2-yl)carbonyl)phenyl)phenyl)carbonyl)-N-(2-(2-ethoxyphenyl)ethyl)amino)propanoic acid HPLC measurement condition: A HPLC retention time: 3.66 minutes; MASS data (ESI, Pos., 20V): 607 (M+H)$^+$; HPLC retention time: 3.82 minutes; MASS data (ESI, Pos., 20V): 607 (M+H)$^+$.

EXAMPLE 4(899)

3-(N-((2-(2-((3-methylbenzylamino)carbonyl)phenyl)phenyl)carbonyl)-N-(2-(2-ethoxyphenyl)ethyl)amino)propanoic acid HPLC measurement condition: A HPLC retention time: 4.04 minutes; MASS data (ESI, Pos., 20V): 565 (M+H)$^+$.

EXAMPLE 4(900)

3-(N-((2-(2-((3,5-difluorobenzylamino)carbonyl)phenyl)phenyl)carbonyl)-N-(2-(2-ethoxyphenyl)ethyl)amino)propanoic acid HPLC measurement condition: A HPLC retention time: 4.04 minutes; MASS data (ESI, Pos., 20V): 587 (M+H)$^+$.

EXAMPLE 4(901)

3-(N-((2-(2-((N-methyl-N-(6-methylpyridin-2-yl)methylamino)carbonyl)phenyl)phenyl)carbonyl)-N-(2-(2-ethoxyphenyl)ethyl)amino)propanoic acid HPLC measurement condition: A HPLC retention time: 3.36 minutes; MASS data (ESI, Pos., 20V): 580 (M+H)$^+$.

EXAMPLE 4(902)

3-(N-((2-(2-((N-(2-(N,N-dimethylamino)ethyl)-N-benzylamino)carbonyl)phenyl)phenyl)carbonyl)-N-(2-(2-ethoxyphenyl)ethyl)amino)propanoic acid HPLC measurement condition: A HPLC retention time: 3.58 minutes; MASS data (ESI, Pos., 20V): 622 (M+H)$^+$.

EXAMPLE 4(903)

3-(N-((2-(2-((2-phenylethylamino)carbonyl)phenyl)phenyl)carbonyl)-N-(2-(2-ethoxyphenyl)ethyl)amino)propanoic acid HPLC measurement condition: A HPLC retention time: 4.04 minutes; MASS data (ESI, Pos., 20V): 565 (M+H)$^+$.

EXAMPLE 4(904)

3-(N-((2-(2-((1,2,3,4-tetrahydro-1-naphthylamino)carbonyl)phenyl)phenyl)carbonyl)-N-(2-(3-ethoxyphenyl)ethyl)amino)propanoic acid HPLC measurement condition: A HPLC retention time: 4.08 minutes; MASS data (ESI, Pos., 20V): 591 (M+H)$^+$.

EXAMPLE 4(905)

3-(N-((2-(2-((N-benzyl-N-(2-hydroxyethyl)amino)carbonyl)phenyl)phenyl)carbonyl)-N-(2-(3-ethoxyphenyl)ethyl)amino)propanoic acid HPLC measurement condition: A HPLC retention time: 3.75 minutes; MASS data (ESI, Pos., 20V): 595 (M+H)$^+$.

EXAMPLE 4(906)

3-(N-((2-(2-((2-furylmethylamino)carbonyl)phenyl)phenyl)carbonyl)-N-(2-(3-ethoxyphenyl)ethyl)amino)propanoic acid HPLC measurement condition: A HPLC retention time: 3.80 minutes; MASS data (ESI, Pos., 20V): 541 (M+H)$^+$.

EXAMPLE 4(907)

3-(N-((2-(2-((1-indaneamino)carbonyl)phenyl)phenyl)carbonyl)-N-(2-(3-ethoxyphenyl)ethyl)amino)propanoic acid HPLC measurement condition: A HPLC retention time: 4.00 minutes; MASS data (ESI, Pos., 20V): 577 (M+H)$^+$.

EXAMPLE 4(908)

3-(N-((2-(2-((1-naphthylmethylamino)carbonyl)phenyl)phenyl)carbonyl)-N-(2-(3-ethoxyphenyl)ethyl)amino)propanoic acid HPLC measurement condition: A HPLC retention time: 4.08 minutes; MASS data (ESI, Pos., 20V): 601 (M+H)$^+$.

EXAMPLE 4(909)

3-(N-((2-(2-((pyridin-2-ylmethylamino)carbonyl)phenyl)phenyl)carbonyl)-N-(2-(3-ethoxyphenyl)ethyl)amino)propanoic acid HPLC measurement condition: A HPLC retention time: 3.33 minutes; MASS data (ESI, Pos., 20V): 552 (M+H)$^+$.

EXAMPLE 4(910)

3-(N-((2-(2-((pyridin-3-ylmethylamino)carbonyl)phenyl)phenyl)carbonyl)-N-(2-(3-ethoxyphenyl)ethyl)amino)propanoic acid HPLC measurement condition: A HPLC retention time: 3.25 minutes; MASS data (ESI, Pos., 20V): 552 (M+H)$^+$.

EXAMPLE 4(911)

3-(N-((2-(2-((1,2,3,4-tetrahydroisoquinolin-2-yl)carbonyl)phenyl)phenyl)carbonyl)-N-(2-(3-ethoxyphenyl)ethyl)amino)propanoic acid HPLC measurement condition: A HPLC retention time: 3.97 minutes; MASS data (ESI, Pos., 20V): 577 (M+H)$^+$.

EXAMPLE 4(912)

3-(N-((2-(2-((α-methylbenzylamino)carbonyl)phenyl)phenyl)carbonyl)-N-(2-(3-ethoxyphenyl)ethyl)amino)propanoic acid HPLC measurement condition: A HPLC retention time: 3.99 minutes; MASS data (ESI, Pos., 20V): 565 (M+H)$^+$.

EXAMPLE 4(913)

3-(N-((2-(2-((benzylamino)carbonyl)phenyl)phenyl)carbonyl)-N-(2-(3-ethoxyphenyl)ethyl)amino)propanoic acid HPLC measurement condition: A HPLC retention time: 3.91 minutes; MASS data (ESI, Pos., 20V): 551 (M+H)$^+$.

EXAMPLE 4(914)

3-(N-((2-(2-((2-methoxybenzylamino)carbonyl)phenyl)phenyl)carbonyl)-N-(2-(3-ethoxyphenyl)ethyl)amino)propanoic acid HPLC measurement condition: A HPLC retention time: 3.91 minutes; MASS data (ESI, Pos., 20V): 581 (M+H)$^+$.

EXAMPLE 4(915)

3-(N-((2-(2-((2-methylbenzylamino)carbonyl)phenyl)phenyl)carbonyl)-N-(2-(3-ethoxyphenyl)ethyl)amino)propanoic acid HPLC measurement condition: A HPLC retention time: 3.97 minutes; MASS data (ESI, Pos., 20V): 565 (M+H)$^+$.

EXAMPLE 4(916)

3-(N-((2-(2-((3-methoxybenzylamino)carbonyl)phenyl)phenyl)carbonyl)-N-(2-(3-ethoxyphenyl)ethyl)amino)propanoic acid HPLC measurement condition: A HPLC retention time: 3.88 minutes; MASS data (ESI, Pos., 20V): 581 (M+H)$^+$.

EXAMPLE 4(917)

3-(N-((2-(2-((4-chlorobenzylamino)carbonyl)phenyl)phenyl)carbonyl)-N-(2-(3-ethoxyphenyl)ethyl)amino)propanoic acid HPLC measurement condition: A HPLC retention time: 4.04 minutes; MASS data (ESI, Pos., 20V): 585 (M+H)$^+$.

EXAMPLE 4(918)

3-(N-((2-(2-((4-methoxybenzylamino)carbonyl)phenyl)phenyl)carbonyl)-N-(2-(3-ethoxyphenyl)ethyl)amino)propanoic acid HPLC measurement condition: A HPLC retention time: 3.88 minutes; MASS data (ESI, Pos., 20V): 581 (M+H)$^+$.

EXAMPLE 4(919)

3-(N-((2-(2-((4-methylbenzylamino)carbonyl)phenyl)phenyl)carbonyl)-N-(2-(3-ethoxyphenyl)ethyl)amino)propanoic acid HPLC measurement condition: A HPLC retention time: 3.99 minutes; MASS data (ESI, Pos., 20V): 565 (M+H)$^+$.

EXAMPLE 4(920)

3-(N-((2-(2-((N-methyl-N-benzylamino)carbonyl)phenyl)phenyl)carbonyl)-N-(2-(3-ethoxyphenyl)ethyl)amino)propanoic acid HPLC measurement condition: A HPLC retention time: 3.93 minutes; MASS data (ESI, Pos., 20V): 565 (M+H)$^+$.

EXAMPLE 4(921)

3-(N-((2-(2-((N-ethyl-N-benzylamino)carbonyl)phenyl)phenyl)carbonyl)-N-(2-(3-ethoxyphenyl)ethyl)amino)propanoic acid HPLC measurement condition: A HPLC retention time: 4.00 minutes; MASS data (ESI, Pos., 20V): 579 (M+H)$^+$.

EXAMPLE 4(922)

3-(N-((2-(2-((N-butyl-N-benzylamino)carbonyl)phenyl)phenyl)carbonyl)-N-(2-(3-ethoxyphenyl)ethyl)amino)propanoic acid HPLC measurement condition: A HPLC retention time: 4.19 minutes; MASS data (ESI, Pos., 20V): 607 (M+H)$^+$.

EXAMPLE 4(923)

3-(N-((2-(2-((4-(tert-butyl)benzylamino)carbonyl)phenyl)phenyl)carbonyl)-N-(2-(3-ethoxyphenyl)ethyl)amino)propanoic acid HPLC measurement condition: A HPLC retention time: 4.22 minutes; MASS data (ESI, Pos., 20V): 607 (M+H)$^+$.

EXAMPLE 4(924)

3-(N-((2-(2-((1-phenyl-3-hydroxypropylamino)carbonyl)phenyl)phenyl)carbonyl)-N-(2-(3-ethoxyphenyl)ethyl)amino)propanoic acid HPLC measurement condition: A HPLC retention time: 3.71 minutes; MASS data (ESI, Pos., 20V): 595 (M+H)$^+$.

EXAMPLE 4(925)

3-(N-((2-(2-((2-fluorobenzylamino)carbonyl)phenyl)phenyl)carbonyl)-N-(2-(3-ethoxyphenyl)ethyl)amino)propanoic acid HPLC measurement condition: A HPLC retention time: 3.91 minutes; MASS data (ESI, Pos., 20V): 569 (M+H)$^+$.

EXAMPLE 4(926)

3-(N-((2-(2-((3-fluorobenzylamino)carbonyl)phenyl)phenyl)carbonyl)-N-(2-(3-ethoxyphenyl)ethyl)amino)propanoic acid HPLC measurement condition: A HPLC retention time: 3.93 minutes; MASS data (ESI, Pos., 20V): 569 (M+H)$^+$.

EXAMPLE 4(927)

3-(N-((2-(2-((2,5-difluorobenzylamino)carbonyl)phenyl)phenyl)carbonyl)-N-(2-(3-ethoxyphenyl)ethyl)amino)propanoic acid HPLC measurement condition: A HPLC retention time: 3.95 minutes; MASS data (ESI, Pos., 20V): 587 (M+H)+.

EXAMPLE 4(928)

3-(N-((2-(2-(((1R)-1-phenyl-2-hydroxyethylamino)carbonyl)phenyl)phenyl)carbonyl)-N-(2-(3-ethoxyphenyl)ethyl)amino)propanoic acid HPLC measurement condition: A HPLC retention time: 3.73 minutes; MASS data (ESI, Pos., 20V): 581 (M+H)+.

EXAMPLE 4(929)

3-(N-((2-(2-((2-chlorobenzylamino)carbonyl)phenyl)phenyl)carbonyl)-N-(2-(3-ethoxyphenyl)ethyl)amino)propanoic acid HPLC measurement condition: A HPLC retention time: 4.00 minutes; MASS data (ESI, Pos., 20V): 585 (M+H)+.

EXAMPLE 4(930)

3-(N-((2-(2-((4-fluorobenzylamino)carbonyl)phenyl)phenyl)carbonyl)-N-(2-(3-ethoxyphenyl)ethyl)amino)propanoic acid HPLC measurement condition: A HPLC retention time: 3.91 minutes; MASS data (ESI, Pos., 20V): 569 (M+H)+.

EXAMPLE 4(931)

3-(N-((2-(2-((allylamino)carbonyl)phenyl)phenyl)carbonyl)-N-(2-(3-ethoxyphenyl)ethyl)amino)propanoic acid HPLC measurement condition: A HPLC retention time: 3.75 minutes; MASS data (ESI, Pos., 20V): 501 (M+H)+.

EXAMPLE 4(932)

3-(N-((2-(2-((2,6-difluorobenzylamino)carbonyl)phenyl)phenyl)carbonyl)-N-(2-(3-ethoxyphenyl)ethyl)amino)propanoic acid HPLC measurement condition: A HPLC retention time: 3.89 minutes; MASS data (ESI, Pos., 20V): 587 (M+H)+.

EXAMPLE 4(933)

3-(N-((2-(2-((3-chlorobenzylamino)carbonyl)phenyl)phenyl)carbonyl)-N-(2-(3-ethoxyphenyl)ethyl)amino)propanoic acid HPLC measurement condition: A HPLC retention time: 4.04 minutes; MASS data (ESI, Pos., 20V): 585 (M+H)+.

EXAMPLE 4(934)

3-(N-((2-(2-(((1S)-1-phenyl-2-hydroxyethylamino)carbonyl)phenyl)phenyl)carbonyl)-N-(2-(3-ethoxyphenyl)ethyl)amino)propanoic acid HPLC measurement condition: A HPLC retention time: 3.73 minutes; MASS data (ESI, Pos., 20V): 581 (M+H)+.

EXAMPLE 4(935)

3-(N-((2-(2-(((1R)-1-(4-methylphenyl)ethylamino)carbonyl)phenyl)phenyl)carbonyl)-N-(2-(3-ethoxyphenyl)ethyl)amino)propanoic acid HPLC measurement condition: A HPLC retention time: 4.06 minutes; MASS data (ESI, Pos., 20V): 579 (M+H)+.

EXAMPLE 4(936)

3-(N-((2-(2-((1-(4-fluorophenyl)ethylamino)carbonyl)phenyl)phenyl)carbonyl)-N-(2-(3-ethoxyphenyl)ethyl)amino)propanoic acid HPLC measurement condition: A HPLC retention time: 3.99 minutes; MASS data (ESI, Pos., 20V): 583 (M+H)+.

EXAMPLE 4(937)

3-(N-((2-(2-((2-thienyl methylamino)carbonyl)phenyl)phenyl)carbonyl)-N-(2-(3-ethoxyphenyl)ethyl)amino)propanoic acid HPLC measurement condition: A HPLC retention time: 3.88 minutes; MASS data (ESI, Pos., 20V): 557 (M+H)+.

EXAMPLE 4(938)

3-(N-((2-(2-(((3S)-3-hydroxymethyl-1,2,3,4-tetrahydroisoquinolin-2-yl)carbonyl)phenyl)phenyl)carbonyl)-N-(2-(3-ethoxyphenyl)ethyl)amino)propanoic acid HPLC measurement condition: A HPLC retention time: 3.62 minutes; MASS data (ESI, Pos., 20V): 607 (M+H)+; HPLC retention time: 3.77 minutes; MASS data (ESI, Pos., 20V): 607 (M+H)+.

EXAMPLE 4(939)

3-(N-((2-(2-((3-methylbenzylamino)carbonyl)phenyl)phenyl)carbonyl)-N-(2-(3-ethoxyphenyl)ethyl)amino)propanoic acid HPLC measurement condition: A HPLC retention time: 3.97 minutes; MASS data (ESI, Pos., 20V): 565 (M+H)+.

EXAMPLE 4(940)

3-(N-((2-(2-((3,5-difluorobenzylamino)carbonyl)phenyl)phenyl)carbonyl)-N-(2-(3-ethoxyphenyl)ethyl)amino)propanoic acid HPLC measurement condition: A HPLC retention time: 3.97 minutes; MASS data (ESI, Pos., 20V): 587 (M+H)+.

EXAMPLE 4(941)

3-(N-((2-(2-((N-methyl-N-(6-methylpyridin-2-yl)methylamino)carbonyl)phenyl)phenyl)carbonyl)-N-(2-(3-ethoxyphenyl)ethyl)amino)propanoic acid HPLC measurement condition: A HPLC retention time: 3.33 minutes; MASS data (ESI, Pos., 20V): 580 (M+H)$^+$.

EXAMPLE 4(942)

3-(N-((2-(2-((N-(2-(N,N-dimethylamino)ethyl)-N-benzylamino)carbonyl)phenyl)phenyl)carbonyl)-N-(2-(3-ethoxyphenyl)ethyl)amino)propanoic acid HPLC measurement condition: A HPLC retention time: 3.53 minutes; MASS data (ESI, Pos., 20V): 622 (M+H)$^+$.

EXAMPLE 4(943)

3-(N-((2-(2-((2-phenylethylamino)carbonyl)phenyl)phenyl)carbonyl)-N-(2-(3-ethoxyphenyl)ethyl)amino)propanoic acid HPLC measurement condition: A HPLC retention time: 3.97 minutes; MASS data (ESI, Pos., 20V): 565 (M+H)$^+$.

EXAMPLE 4(944)

3-(N-((2-(2-((1,2,3,4-tetrahydro-1-naphthylamino)carbonyl)phenyl)phenyl)carbonyl)-N-(3-phenylpropyl)amino)propanoic acid HPLC measurement condition: A HPLC retention time: 4.06 minutes; MASS data (ESI, Pos., 20V): 561 (M+H)$^+$.

EXAMPLE 4(945)

3-(N-((2-(2-((N-benzyl-N-(2-hydroxyethyl)amino)carbonyl)phenyl)phenyl)carbonyl)-N-(3-phenylpropyl)amino)propanoic acid HPLC measurement condition: A HPLC retention time: 3.73 minutes; MASS data (ESI, Pos., 20V): 565 (M+H)$^+$.

EXAMPLE 4(946)

3-(N-((2-(2-((1-naphthylmethylamino)carbonyl)phenyl)phenyl)carbonyl)-N-(3-phenylpropyl)amino)propanoic acid HPLC measurement condition: A HPLC retention time: 4.04 minutes; MASS data (ESI, Pos., 20V): 571 (M+H)$^+$.

EXAMPLE 4(947)

3-(N-((2-(2-((pyridin-2-ylmethylamino)carbonyl)phenyl)phenyl)carbonyl)-N-(3-phenylpropyl)amino)propanoic acid HPLC measurement condition: A HPLC retention time: 3.33 minutes; MASS data (ESI, Pos., 20V): 522 (M+H)$^+$.

EXAMPLE 4(948)

3-(N-((2-(2-((α-methylbenzylamino)carbonyl)phenyl)phenyl)carbonyl)-N-(3-phenylpropyl)amino)propanoic acid HPLC measurement condition: A HPLC retention time: 3.97 minutes; MASS data (ESI, Pos., 20V): 535 (M+H)$^+$.

EXAMPLE 4(949)

3-(N-((2-(2-((2-methylbenzylamino)carbonyl)phenyl)phenyl)carbonyl)-N-(3-phenylpropyl)amino)propanoic acid HPLC measurement condition: A HPLC retention time: 3.97 minutes; MASS data (ESI, Pos., 20V): 535 (M+H)$^+$.

EXAMPLE 4(950)

3-(N-((2-(2-((4-chlorobenzylamino)carbonyl)phenyl)phenyl)carbonyl)-N-(3-phenylpropyl)amino)propanoic acid HPLC measurement condition: A HPLC retention time: 4.02 minutes; MASS data (ESI, Pos., 20V): 555 (M+H)$^+$.

EXAMPLE 4(951)

3-(N-((2-(2-((N-isopropyl-N-benzylamino)carbonyl)phenyl)phenyl)carbonyl)-N-(3-phenylpropyl)amino)propanoic acid HPLC measurement condition: A HPLC retention time: 4.06 minutes; MASS data (ESI, Pos., 20V): 563 (M+H)$^+$.

EXAMPLE 4(952)

3-(N-((2-(2-((N-ethyl-N-benzylamino)carbonyl)phenyl)phenyl)carbonyl)-N-(3-phenylpropyl)amino)propanoic acid HPLC measurement condition: A HPLC retention time: 3.99 minutes; MASS data (ESI, Pos., 20V): 549 (M+H)$^+$.

EXAMPLE 4(953)

3-(N-((2-(2-((N-butyl-N-benzylamino)carbonyl)phenyl)phenyl)carbonyl)-N-(3-phenylpropyl)amino)propanoic acid HPLC measurement condition: A HPLC retention time: 4.19 minutes; MASS data (ESI, Pos., 20V): 577 (M+H)$^+$.

EXAMPLE 4(954)

3-(N-((2-(2-((4-(tert-butyl)benzylamino)carbonyl)phenyl)phenyl)carbonyl)-N-(3-phenylpropyl)amino)propanoic acid HPLC measurement condition: A HPLC retention time: 4.19 minutes; MASS data (ESI, Pos., 20V): 577 (M+H)$^+$.

EXAMPLE 4(955)

3-(N-((2-(2-((1-phenyl-3-hydroxypropylamino)carbonyl)phenyl)phenyl)carbonyl)-N-(3-phenylpropyl)amino)propanoic acid HPLC measurement condition: A HPLC retention time: 3.73 minutes; MASS data (ESI, Pos., 20V): 565 (M+H)+.

EXAMPLE 4(956)

3-(N-((2-(2-((2,5-difluorobenzylamino)carbonyl)phenyl)phenyl)carbonyl)-N-(3-phenylpropyl)amino)propanoic acid HPLC measurement condition: A HPLC retention time: 3.93 minutes; MASS data (ESI, Pos., 20V): 557 (M+H)+.

EXAMPLE 4(957)

3-(N-((2-(2-(((1R)-1-phenyl-2-hydroxyethylamino)carbonyl)phenyl)phenyl)carbonyl)-N-(3-phenylpropyl)amino)propanoic acid HPLC measurement condition: A HPLC retention time: 3.73 minutes; MASS data (ESI, Pos., 20V): 551 (M+H)+.

EXAMPLE 4(958)

3-(N-((2-(2-((2-chlorobenzylamino)carbonyl)phenyl)phenyl)carbonyl)-N-(3-phenylpropyl)amino)propanoic acid HPLC measurement condition: A HPLC retention time: 3.99 minutes; MASS data (ESI, Pos., 20V): 555 (M+H)+.

EXAMPLE 4(959)

3-(N-((2-(2-((3-chlorobenzylamino)carbonyl)phenyl)phenyl)carbonyl)-N-(3-phenylpropyl)amino)propanoic acid HPLC measurement condition: A HPLC retention time: 4.02 minutes; MASS data (ESI, Pos., 20V): 555 (M+H)+.

EXAMPLE 4(960)

3-(N-((2-(2-(((1S)-1-phenyl-2-hydroxyethylamino)carbonyl)phenyl)phenyl)carbonyl)-N-(3-phenylpropyl)amino)propanoic acid HPLC measurement condition: A HPLC retention time: 3.73 minutes; MASS data (ESI, Pos., 20V): 551 (M+H)+.

EXAMPLE 4(961)

3-(N-((2-(2-(((1R)-1-(4-methylphenyl)ethylamino)carbonyl)phenyl)phenyl)carbonyl)-N-(3-phenylpropyl)amino)propanoic acid HPLC measurement condition: A HPLC retention time: 4.06 minutes; MASS data (ESI, Pos., 20V): 549 (M+H)+.

EXAMPLE 4(962)

3-(N-((2-(2-((1-(4-fluorophenyl)ethylamino)carbonyl)phenyl)phenyl)carbonyl)-N-(3-phenylpropyl)amino)propanoic acid HPLC measurement condition: A HPLC retention time: 3.99 minutes; MASS data (ESI, Pos., 20V): 553 (M+H)+.

EXAMPLE 4(963)

3-(N-((2-(2-(((3S)-3-hydroxymethyl-1,2,3,4-tetrahydroisoquinolin-2-yl)carbonyl)phenyl)phenyl)carbonyl)-N-(3-phenylpropyl)amino)propanoic acid HPLC measurement condition: A HPLC retention time: 3.62 minutes; MASS data (ESI, Pos., 20V): 577 (M+H)+; HPLC retention time: 3.75 minutes; MASS data (ESI, Pos., 20V): 577 (M+H)+, 473.

EXAMPLE 4(964)

3-(N-((2-(2-((3-methylbenzylamino)carbonyl)phenyl)phenyl)carbonyl)-N-(3-phenylpropyl)amino)propanoic acid HPLC measurement condition: A HPLC retention time: 3.97 minutes; MASS data (ESI, Pos., 20V): 535 (M+H)+.

EXAMPLE 4(965)

3-(N-((2-(2-((N-methyl-N-(6-methylpyridin-2-yl)methylamino)carbonyl)phenyl)phenyl)carbonyl)-N-(3-phenylpropyl)amino)propanoic acid HPLC measurement condition: A HPLC retention time: 3.31 minutes; MASS data (ESI, Pos., 20V): 550 (M+H)+.

EXAMPLE 4(966)

3-(N-((2-(2-((N-(2-(N,N-dimethylamino)ethyl)-N-benzylamino)carbonyl)phenyl)phenyl)carbonyl)-N-(3-phenylpropyl)amino)propanoic acid HPLC measurement condition: A HPLC retention time: 3.55 minutes; MASS data (ESI, Pos., 20V): 592 (M+H)+.

EXAMPLE 4(967)

3-(N-((2-(2-((1,2,3,4-tetrahydro-1-naphthylamino)carbonyl)phenyl)phenyl)carbonyl)-N-(benzyl)amino)propanoic acid HPLC measurement condition: A HPLC retention time: 3.93 minutes; MASS data (ESI, Pos., 20V): 533 (M+H)+.

EXAMPLE 4(968)

3-(N-((2-(2-((N-benzyl-N-(2-hydroxyethyl)amino)carbonyl)phenyl)phenyl)carbonyl)-N-(benzyl)amino)propanoic acid HPLC measurement condition: A HPLC retention time: 3.60 minutes; MASS data (ESI, Pos., 20V): 537 (M+H)+.

EXAMPLE 4(969)

3-(N-((2-(2-((1-naphthylmethylamino)carbonyl)phenyl)phenyl)carbonyl)-N-(benzyl)amino)propanoic acid HPLC measurement condition: A HPLC retention time: 3.93 minutes; MASS data (ESI, Pos., 20V): 543 (M+H)$^+$.

EXAMPLE 4(970)

3-(N-((2-(2-((α-methylbenzylamino)carbonyl)phenyl)phenyl)carbonyl)-N-(benzyl)amino)propanoic acid HPLC measurement condition: A HPLC retention time: 3.84 minutes; MASS data (ESI, Pos., 20V): 507 (M+H)$^+$.

EXAMPLE 4(971)

3-(N-((2-(2-((2-methylbenzylamino)carbonyl)phenyl)phenyl)carbonyl)-N-(benzyl)amino)propanoic acid HPLC measurement condition: A HPLC retention time: 3.82 minutes; MASS data (ESI, Pos., 20V): 507 (M+H)$^+$.

EXAMPLE 4(972)

3-(N-((2-(2-((4-chlorobenzylamino)carbonyl)phenyl)phenyl)carbonyl)-N-(benzyl)amino)propanoic acid HPLC measurement condition: A HPLC retention time: 3.89 minutes; MASS data (ESI, Pos., 20V): 527 (M+H)$^+$.

EXAMPLE 4(973)

3-(N-((2-(2-((N-ethyl-N-benzylamino)carbonyl)phenyl)phenyl)carbonyl)-N-(benzyl)amino)propanoic acid HPLC measurement condition: A HPLC retention time: 3.86 minutes; MASS data (ESI, Pos., 20V): 521 (M+H)$^+$.

EXAMPLE 4(974)

3-(N-((2-(2-((N-butyl-N-benzylamino)carbonyl)phenyl)phenyl)carbonyl)-N-(benzyl)amino)propanoic acid HPLC measurement condition: A HPLC retention time: 4.08 minutes; MASS data (ESI, Pos., 20V): 549 (M+H)$^+$.

EXAMPLE 4(975)

3-(N-((2-(2-((4-(tert-butyl)benzylamino)carbonyl)phenyl)phenyl)carbonyl)-N-(benzyl)amino)propanoic acid HPLC measurement condition: A HPLC retention time: 4.10 minutes; MASS data (ESI, Pos., 20V): 549 (M+H)$^+$.

EXAMPLE 4(976)

3-(N-((2-(2-((1-phenyl-3-hydroxypropylamino)carbonyl)phenyl)phenyl)carbonyl)-N-(benzyl)amino)propanoic acid HPLC measurement condition: A HPLC retention time: 3.60 minutes; MASS data (ESI, Pos., 20V): 537 (M+H)$^+$.

EXAMPLE 4(977)

3-(N-((2-(2-((2,5-difluorobenzylamino)carbonyl)phenyl)phenyl)carbonyl)-N-(benzyl)amino)propanoic acid HPLC measurement condition: A HPLC retention time: 3.80 minutes; MASS data (ESI, Pos., 20V): 529 (M+H)$^+$.

EXAMPLE 4(978)

3-(N-((2-(2-(((1R)-1-phenyl-2-hydroxyethylamino)carbonyl)phenyl)carbonyl)-N-(benzyl)amino)propanoic acid HPLC measurement condition: A HPLC retention time: 3.56 minutes; MASS data (ESI, Pos., 20V): 523 (M+H)$^+$.

EXAMPLE 4(979)

3-(N-((2-(2-((2-chlorobenzylamino)carbonyl)phenyl)phenyl)carbonyl)-N-(benzyl)amino)propanoic acid HPLC measurement condition: A HPLC retention time: 3.88 minutes; MASS data (ESI, Pos., 20V): 527 (M+H)$^+$.

EXAMPLE 4(980)

3-(N-((2-(2-((3-chlorobenzylamino)carbonyl)phenyl)phenyl)carbonyl)-N-(benzyl)amino)propanoic acid HPLC measurement condition: A HPLC retention time: 3.89 minutes; MASS data (ESI, Pos., 20V): 527 (M+H)$^+$.

EXAMPLE 4(981)

3-(N-((2-(2-(((1S)-1-phenyl-2-hydroxyethylamino)carbonyl)phenyl)carbonyl)-N-(benzyl)amino)propanoic acid HPLC measurement condition: A HPLC retention time: 3.58 minutes; MASS data (ESI, Pos., 20V): 523 (M+H)$^+$.

EXAMPLE 4(982)

3-(N-((2-(2-(((1R)-1-(4-methylphenyl)ethylamino)carbonyl)phenyl)carbonyl)-N-(benzyl)amino)propanoic acid HPLC measurement condition: A HPLC retention time: 3.93 minutes; MASS data (ESI, Pos., 20V): 521 (M+H)$^+$.

EXAMPLE 4(983)

3-(N-((2-(2-((1-(4-fluorophenyl)ethylamino)carbonyl)phenyl)phenyl)carbonyl)-N-(benzyl)amino)propanoic acid HPLC measurement condition: A HPLC retention time: 3.86 minutes; MASS data (ESI, Pos., 20V): 525 (M+H)+.

EXAMPLE 4(984)

3-(N-((2-(2-(((3S)-3-hydroxymethyl-1,2,3,4-tetrahydroisoquinolin-2-yl)carbonyl)phenyl)phenyl)carbonyl)-N-(benzyl)amino)propanoic acid HPLC measurement condition: A HPLC retention time: 3.49 minutes; MASS data (ESI, Pos., 20V): 549 (M+H)+; HPLC retention time: 3.62 minutes; MASS data (ESI, Pos., 20V): 549 (M+H)+, 445.

EXAMPLE 4(985)

3-(N-((2-(2-((N-methyl-N-(6-methylpyridin-2-yl)methylamino)carbonyl)phenyl)phenyl)carbonyl)-N-(benzyl)amino)propanoic acid HPLC measurement condition: A HPLC retention time: 3.16 minutes; MASS data (ESI, Pos., 20V): 522 (M+H)+, 508.

EXAMPLE 4(986)

3-(N-((2-(2-((N-(2-(N,N-dimethylamino)ethyl)-N-benzylamino)carbonyl)phenyl)phenyl)carbonyl)-N-(benzyl)amino)propanoic acid HPLC measurement condition: A HPLC retention time: 3.40 minutes; MASS data (ESI, Pos., 20V): 564 (M+H)+.

EXAMPLE 4(987)

3-(N-((2-(2-((pyridin-3-ylmethylamino)carbonyl)-4-methylphenyl)-5-methylphenyl)carbonyl)-N-(2-(4-ethoxyphenyl)ethyl)amino)propanoic acid HPLC measurement condition: B HPLC retention time: 3.59 minutes; MASS data (ESI, Pos.): 580 (M+H)+, 472.

EXAMPLE 4(988)

3-(N-((2-(2-((1-methyl-3-phenylpropylamino)carbonyl)phenyl)phenyl)carbonyl)-N-(2-(3-methoxyphenyl)ethyl)amino)propanoic acid HPLC measurement condition: A HPLC retention time: 3.99 minutes; MASS data (ESI, Pos., 20V): 579 (M+H)+.

EXAMPLE 4(989)

3-(N-((2-(2-((4-fluorobenzylamino)carbonyl)-4-methylphenyl)-5-methylphenyl)carbonyl)-N-(2-(4-ethoxyphenyl)ethyl)amino)propanoic acid HPLC measurement condition: B HPLC retention time: 4.53 minutes; MASS data (ESI, Pos.): 597 (M+H)+, 525.

EXAMPLE 4(990)

3-(N-((2-(2-((1-methyl-3-phenylpropylamino)carbonyl)phenyl)phenyl)carbonyl)-N-(2-phenylethyl)amino)propanoic acid HPLC measurement condition: A HPLC retention time: 4.00 minutes; MASS data (ESI, Pos., 20V): 549 (M+H)+.

EXAMPLE 4(991)

3-(N-((2-(2-((2-furylmethylamino)carbonyl)phenyl)phenyl)carbonyl)-N-(2-(3-methoxyphenyl)ethyl)amino)propanoic acid HPLC measurement condition: A HPLC retention time: 3.69 minutes; MASS data (ESI, Pos., 20V): 527 (M+H)+.

EXAMPLE 4(992)

3-(N-((2-(2-((1-indaneamino)carbonyl)phenyl)phenyl)carbonyl)-N-(2-(3-methoxyphenyl)ethyl)amino)propanoic acid HPLC measurement condition: A HPLC retention time: 3.89 minutes; MASS data (ESI, Pos., 20V): 563 (M+H)+.

EXAMPLE 4(993)

3-(N-((2-(2-((pyridin-2-ylmethylamino)carbonyl)phenyl)phenyl)carbonyl)-N-(2-(3-methoxyphenyl)ethyl)amino)propanoic acid HPLC measurement condition: A HPLC retention time: 3.23 minutes; MASS data (ESI, Pos., 20V): 538 (M+H)+.

EXAMPLE 4(994)

3-(N-((2-(2-((pyridin-3-ylmethylamino)carbonyl)phenyl)phenyl)carbonyl)-N-(2-(3-methoxyphenyl)ethyl)amino)propanoic acid HPLC measurement condition: A HPLC retention time: 3.18 minutes; MASS data (ESI, Pos., 20V): 538 (M+H)+.

EXAMPLE 4(995)

3-(N-((2-(2-((pyridin-4-ylmethylamino)carbonyl)phenyl)phenyl)carbonyl)-N-(2-(3-methoxyphenyl)ethyl)amino)propanoic acid HPLC measurement condition: A HPLC retention time: 3.2 minutes; MASS data (ESI, Pos., 20V): 538 (M+H)+.

EXAMPLE 4(996)

3-(N-((2-(2-((1,2,3,4-tetrahydroisoquinolin-2-yl)carbonyl)phenyl)phenyl)carbonyl)-N-(2-(3-methoxyphenyl)ethyl)amino)propanoic acid HPLC measurement condition: A HPLC retention time: 3.84 minutes; MASS data (ESI, Pos., 20V): 563 (M+H)+.

EXAMPLE 4(997)

3-(N-((2-(2-((benzylamino)carbonyl)phenyl)phenyl)carbonyl)-N-(2-(3-methoxyphenyl)ethyl)amino)propanoic acid HPLC measurement condition: A HPLC retention time: 3.8 minutes; MASS data (ESI, Pos., 20V): 537 (M+H)$^+$.

EXAMPLE 4(998)

3-(N-((2-(2-((2-methoxybenzylamino)carbonyl)phenyl)phenyl)carbonyl)-N-(2-(3-methoxyphenyl)ethyl)amino)propanoic acid HPLC measurement condition: A HPLC retention time: 3.82 minutes; MASS data (ESI, Pos., 20V): 567 (M+H)$^+$.

EXAMPLE 4(999)

3-(N-((2-(2-((3-methoxybenzylamino)carbonyl)phenyl)phenyl)carbonyl)-N-(2-(3-methoxyphenyl)ethyl)amino)propanoic acid HPLC measurement condition: A HPLC retention time: 3.78 minutes; MASS data (ESI, Pos., 20V): 567 (M+H)$^+$.

EXAMPLE 4(1000)

3-(N-((2-(2-((4-methylbenzylamino)carbonyl)phenyl)phenyl)carbonyl)-N-(2-(3-methoxyphenyl)ethyl)amino)propanoic acid HPLC measurement condition: A HPLC retention time: 3.88 minutes; MASS data (ESI, Pos., 20V): 551 (+H)$^+$.

EXAMPLE 4(1001)

3-(N-((2-(2-((N-methyl-N-benzylamino)carbonyl)phenyl)phenyl)carbonyl)-N-(2-(3-methoxyphenyl)ethyl)amino)propanoic acid HPLC measurement condition: A HPLC retention time: 3.82 minutes; MASS data (ESI, Pos., 20V): 551 (M+H)$^+$.

EXAMPLE 4(1002)

3-(N-((2-(2-((2-fluorobenzylamino)carbonyl)phenyl)phenyl)carbonyl)-N-(2-(3-methoxyphenyl)ethyl)amino)propanoic acid HPLC measurement condition: A HPLC retention time: 3.80 minutes; MASS data (ESI, Pos., 20V): 555 (M+H)$^+$.

EXAMPLE 4(1003)

3-(N-((2-(2-((3-fluorobenzylamino)carbonyl)phenyl)phenyl)carbonyl)-N-(2-(3-methoxyphenyl)ethyl)amino)propanoic acid HPLC measurement condition: A HPLC retention time: 3.82 minutes; MASS data (ESI, Pos., 20V): 555 (M+H)$^+$.

EXAMPLE 4(1004)

3-(N-((2-(2-((allylamino)carbonyl)phenyl)phenyl)carbonyl)-N-(2-(3-methoxyphenyl)ethyl)amino)propanoic acid HPLC measurement condition: A HPLC retention time: 3.64 minutes; MASS data (ESI, Pos., 20V): 995 (2M+Na)$^+$, 487 (M+H)$^+$.

EXAMPLE 4(1005)

3-(N-((2-(2-((2,6-difluorobenzylamino)carbonyl)phenyl)phenyl)carbonyl)-N-(2-(3-methoxyphenyl)ethyl)amino)propanoic acid HPLC measurement condition: A HPLC retention time: 3.78 minutes; MASS data (ESI, Pos., 20V): 573 (M+H)$^+$.

EXAMPLE 4(1006)

3-(N-((2-(2-((2-thienylmethylamino)carbonyl)phenyl)phenyl)carbonyl)-N-(2-(3-methoxyphenyl)ethyl)amino)propanoic acid HPLC measurement condition: A HPLC retention time: 3.78 minutes; MASS data (ESI, Pos., 20V): 543 (M+H)$^+$.

EXAMPLE 4(1007)

3-(N-((2-(2-((2-furylmethylamino)carbonyl)phenyl)phenyl)carbonyl)-N-(pyridin-3-ylmethyl)amino)propanoic acid HPLC measurement condition: A HPLC retention time: 3.03 minutes; MASS data (ESI, Pos., 20V): 967 (2M+H)$^+$, 484 (M+H)$^+$.

EXAMPLE 4(1008)

3-(N-((2-(2-((1-indaneamino)carbonyl)phenyl)phenyl)carbonyl)-N-(pyridin-3-ylmethyl)amino)propanoic acid HPLC measurement condition: A HPLC retention time: 3.20 minutes; MASS data (ESI, Pos., 20V): 520 (M+H)$^+$.

EXAMPLE 4(1009)

3-(N-((2-(2-((1,2,3,4-tetrahydroisoquinolin-2-yl)carbonyl)phenyl)phenyl)carbonyl)-N-(pyridin-3-ylmethyl)amino)propanoic acid HPLC measurement condition: A HPLC retention time: 3.21 minutes; MASS data (ESI, Pos., 20V): 520 (M+H)$^+$.

EXAMPLE 4(1010)

3-(N-((2-(2-((2-methoxybenzylamino)carbonyl)phenyl)phenyl)carbonyl)-N-(pyridin-3-ylmethyl)amino)propanoic acid HPLC measurement condition: A HPLC retention time: 3.14 minutes; MASS data (ESI, Pos., 20V): 524 (M+H)$^+$.

EXAMPLE 4(1011)

3-(N-((2-(2-((3-methoxybenzylamino)carbonyl)phenyl)phenyl)carbonyl)-N-(pyridin-3-ylmethyl)amino)propanoic acid HPLC measurement condition: A HPLC retention time: 3.11 minutes; MASS data (ESI, Pos., 20V): 524 (M+H)$^+$.

EXAMPLE 4(1012)

3-(N-((2-(2-((4-methoxybenzylamino)carbonyl)phenyl)phenyl)carbonyl)-N-(pyridin-3-ylmethyl)amino)propanoic acid HPLC measurement condition: A HPLC retention time: 3.09 minutes; MASS data (ESI, Pos., 20V): 524 (M+H)$^+$.

EXAMPLE 4(1013)

3-(N-((2-(2-((4-methylbenzylamino)carbonyl)phenyl)phenyl)carbonyl)-N-(pyridin-3-ylmethyl)amino)propanoic acid HPLC measurement condition: A HPLC retention time: 3.18 minutes; MASS data (ESI, Pos., 20V): 508 (M+H)$^+$.

EXAMPLE 4(1014)

3-(N-((2-(2-((N-methyl-N-benzylamino)carbonyl)phenyl)phenyl)carbonyl)-N-(pyridin-3-ylmethyl)amino)propanoic acid HPLC measurement condition: A HPLC retention time: 3.20 minutes; MASS data (ESI, Pos., 20V): 508 (M+H)$^+$.

EXAMPLE 4(1015)

3-(N-((2-(2-((2-fluorobenzylamino)carbonyl)phenyl)phenyl)carbonyl)-N-(pyridin-3-ylmethyl)amino)propanoic acid HPLC measurement condition: A HPLC retention time: 3.10 minutes; MASS data (ESI, Pos., 20V): 512 (M+H)$^+$.

EXAMPLE 4(1016)

3-(N-((2-(2-((3-fluorobenzylamino)carbonyl)phenyl)phenyl)carbonyl)-N-(pyridin-3-ylmethyl)amino)propanoic acid HPLC measurement condition: A HPLC retention time: 3.14 minutes; MASS data (ESI, Pos., 20V): 512 (M+H)$^+$.

EXAMPLE 4(1017)

3-(N-((2-(2-((4-fluorobenzylamino)carbonyl)phenyl)phenyl)carbonyl)-N-(pyridin-3-ylmethyl)amino)propanoic acid HPLC measurement condition: A HPLC retention time: 3.12 minutes; MASS data (ESI, Pos., 20V): 512 (M+H)$^+$.

EXAMPLE 4(1018)

3-(N-((2-(2-((allylamino)carbonyl)phenyl)phenyl)carbonyl)-N-(pyridin-3-ylmethyl)amino)propanoic acid HPLC measurement condition: A HPLC retention time: 2.94 minutes; MASS data (ESI, Pos., 20V): 887 (2M+H)$^+$, 444 (M+H)$^+$.

EXAMPLE 4(1019)

3-(N-((2-(2-((2,6-difluorobenzylamino)carbonyl)phenyl)phenyl)carbonyl)-N-(pyridin-3-ylmethyl)amino)propanoic acid HPLC measurement condition: A HPLC retention time: 3.11 minutes; MASS data (ESI, Pos., 20V): 530 (M+H)$^+$.

EXAMPLE 4(1020)

3-(N-((2-(2-((2-thienylmethylamino)carbonyl)phenyl)phenyl)carbonyl)-N-(pyridin-3-ylmethyl)amino)propanoic acid HPLC measurement condition: A HPLC retention time: 3.09 minutes; MASS data (ESI, Pos., 20V): 500 (M+H)$^+$.

EXAMPLE 4(1021)

3-(N-((2-(2-((1-indaneamino)carbonyl)phenyl)phenyl)carbonyl)-N-(2-(pyridin-2-yl)ethyl)amino)propanoic acid HPLC measurement condition: A HPLC retention time: 3.20 minutes; MASS data (ESI, Pos., 20V): 534 (M+H)$^+$.

EXAMPLE 4(1022)

3-(N-((2-(2-((pyridin-2-ylmethylamino)carbonyl)phenyl)phenyl)carbonyl)-N-(2-(pyridin-2-yl)ethyl)amino)propanoic acid HPLC measurement condition: A HPLC retention time: 2.72 minutes; MASS data (ESI, Pos., 20V): 509 (M+H)$^+$, 255.

EXAMPLE 4(1023)

3-(N-((2-(2-((pyridin-3-ylmethylamino)carbonyl)phenyl)phenyl)carbonyl)-N-(2-(pyridin-2-yl)ethyl)amino)propanoic acid HPLC measurement condition: A HPLC retention time: 2.72 minutes; MASS data (ESI, Pos., 20V): 509 (M+H)$^+$, 255.

EXAMPLE 4(1024)

3-(N-((2-(2-((1,2,3,4-tetrahydroisoquinolin-2-yl)carbonyl)phenyl)phenyl)carbonyl)-N-(2-(pyridin-2-yl)ethyl)amino)propanoic acid HPLC measurement condition: A HPLC retention time: 3.25 minutes; MASS data (ESI, Pos., 20V): 534 (M+H)$^+$.

EXAMPLE 4(1025)

3-(N-((2-(2-((2-methoxybenzylamino)carbonyl)phenyl)phenyl)carbonyl)-N-(2-(pyridin-2-yl)ethyl)amino)propanoic acid HPLC measurement condition: A HPLC retention time: 3.13 minutes; MASS data (ESI, Pos., 20V): 538 (M+H)$^+$.

EXAMPLE 4(1026)

3-(N-((2-(2-((3-methoxybenzylamino)carbonyl)phenyl)phenyl)carbonyl)-N-(2-(pyridin-2-yl)ethyl)amino)propanoic acid HPLC measurement condition: A HPLC retention time: 3.11 minutes; MASS data (ESI, Pos., 20V): 538 (M+H)$^+$.

EXAMPLE 4(1027)

3-(N-((2-(2-((4-methoxybenzylamino)carbonyl)phenyl)phenyl)carbonyl)-N-(2-(pyridin-2-yl)ethyl)amino)propanoic acid HPLC measurement condition: A HPLC retention time: 3.11 minutes; MASS data (ESI, Pos., 20V): 538 (M+H)$^+$.

EXAMPLE 4(1028)

3-(N-((2-(2-((4-methylbenzylamino)carbonyl)phenyl)phenyl)carbonyl)-N-(2-(pyridin-2-yl)ethyl)amino)propanoic acid HPLC measurement condition: A HPLC retention time: 3.20 minutes; MASS data (ESI, Pos., 20V): 522 (M+H)$^+$.

EXAMPLE 4(1029)

3-(N-((2-(2-((N-methyl-N-benzylamino)carbonyl)phenyl)phenyl)carbonyl)-N-(2-(pyridin-2-yl)ethyl)amino)propanoic acid HPLC measurement condition: A HPLC retention time: 3.22 minutes; MASS data (ESI, Pos., 20V): 522 (M+H)$^+$.

EXAMPLE 4(1030)

3-(N-((2-(2-((2-fluorobenzylamino)carbonyl)phenyl)phenyl)carbonyl)-N-(2-(pyridin-2-yl)ethyl)amino)propanoic acid HPLC measurement condition: A HPLC retention time: 3.12 minutes; MASS data (ESI, Pos., 20V): 526 (M+H)$^+$.

EXAMPLE 4(1031)

3-(N-((2-(2-((3-fluorobenzylamino)carbonyl)phenyl)phenyl)carbonyl)-N-(2-(pyridin-2-yl)ethyl)amino)propanoic acid HPLC measurement condition: A HPLC retention time: 3.14 minutes; MASS data (ESI, Pos., 20V): 526 (M+H)$^+$.

EXAMPLE 4(1032)

3-(N-((2-(2-((4-fluorobenzylamino)carbonyl)phenyl)phenyl)carbonyl)-N-(2-(pyridin-2-yl)ethyl)amino)propanoic acid HPLC measurement condition: A HPLC retention time: 3.14 minutes; MASS data (ESI, Pos., 20V): 526 (M+H)$^+$.

EXAMPLE 4(1033)

3-(N-((2-(2-((allylamino)carbonyl)phenyl)phenyl)carbonyl)-N-(2-(pyridin-2-yl)ethyl)amino)propanoic acid HPLC measurement condition: A HPLC retention time: 2.94 minutes; MASS data (ESI, Pos., 20V): 458 (M+H)$^+$.

EXAMPLE 4(1034)

3-(N-((2-(2-((2,6-difluorobenzylamino)carbonyl)phenyl)phenyl)carbonyl)-N-(2-(pyridin-2-yl)ethyl)amino)propanoic acid HPLC measurement condition: A HPLC retention time: 3.11 minutes; MASS data (ESI, Pos., 20V): 544 (M+H)$^+$.

EXAMPLE 4(1035)

3-(N-((2-(2-((2-thienylmethylamino)carbonyl)phenyl)phenyl)carbonyl)-N-(2-(pyridin-2-yl)ethyl)amino)propanoic acid HPLC measurement condition: A HPLC retention time: 3.09 minutes; MASS data (ESI, Pos., 20V): 514 (M+H)$^+$.

EXAMPLE 4(1036)

3-(N-((2-(2-((3,5-difluorobenzylamino)carbonyl)phenyl)phenyl)carbonyl)-N-(2-(pyridin-2-yl)ethyl)amino)propanoic acid HPLC measurement condition: A HPLC retention time: 3.18 minutes; MASS data (ESI, Pos., 20V): 544 (M+H)$^+$.

EXAMPLE 4(1037)

3-(N-((2-(2-((2-phenylethylamino)carbonyl)phenyl)phenyl)carbonyl)-N-(2-(pyridin-2-yl)ethyl)amino)propanoic acid HPLC measurement condition: A HPLC retention time: 3.16 minutes; MASS data (ESI, Pos., 20V): 522 (M+H)$^+$.

EXAMPLE 4(1038)

3-(N-((2-(2-((2-furylmethylamino)carbonyl)phenyl)phenyl)carbonyl)-N-(1-methyl-3-phenylpropyl)amino)propanoic acid HPLC measurement condition: A HPLC retention time: 3.84 minutes; MASS data (ESI, Pos., 20V): 525 (M+H)$^+$.

EXAMPLE 4(1039)

3-(N-((2-(2-((1-indaneamino)carbonyl)phenyl)phenyl)carbonyl)-N-(1-methyl-3-phenylpropyl)amino)propanoic acid HPLC measurement condition: A HPLC retention time: 4.02 minutes; MASS data (ESI, Pos., 20V): 561 (M+H)$^+$.

EXAMPLE 4(1040)

3-(N-((2-(2-((pyridin-2-ylmethylamino)carbonyl)phenyl)phenyl)carbonyl)-N-(1-methyl-3-phenylpropyl)amino)propanoic acid HPLC measurement condition: A HPLC retention time: 3.38 minutes; MASS data (ESI, Pos., 20V): 536 (M+H)$^+$.

EXAMPLE 4(1041)

3-(N-((2-(2-((pyridin-3-ylmethylamino)carbonyl)phenyl)phenyl)carbonyl)-N-(1-methyl-3-phenylpropyl)amino)propanoic acid HPLC measurement condition: A HPLC retention time: 3.27 minutes; MASS data (ESI, Pos., 20V): 536 (M+H)$^+$.

EXAMPLE 4(1042)

3-(N-((2-(2-((1,2,3,4-tetrahydroisoquinolin-2-yl)carbonyl)phenyl)phenyl)carbonyl)-N-(1-methyl-3-phenylpropyl)amino)propanoic acid HPLC measurement condition: A HPLC retention time: 4.00 minutes; MASS data (ESI, Pos., 20V): 561 (M+H)$^+$.

EXAMPLE 4(1043)

3-(N-((2-(2-((benzylamino)carbonyl)phenyl)phenyl)carbonyl)-N-(1-methyl-3-phenylpropyl)amino)propanoic acid HPLC measurement condition: A HPLC retention time: 3.93 minutes; MASS data (ESI, Pos., 20V): 535 (M+H)$^+$.

EXAMPLE 4(1044)

3-(N-((2-(2-((2-methoxybenzylamino)carbonyl)phenyl)phenyl)carbonyl)-N-(1-methyl-3-phenylpropyl)amino)propanoic acid HPLC measurement condition: A HPLC retention time: 3.95 minutes; MASS data (ESI, Pos., 20V): 565 (M+H)$^+$.

EXAMPLE 4(1045?

3-(N-((2-(2-((3-methoxybenzylamino)carbonyl)phenyl)phenyl)carbonyl)-N-(1-methyl-3-phenylpropyl)amino)propanoic acid HPLC measurement condition: A HPLC retention time: 3.91 minutes; MASS data (ESI, Pos., 20V): 565 (M+H)$^+$.

EXAMPLE 4(1046)

3-(N-((2-(2-((4-methoxybenzylamino)carbonyl)phenyl)phenyl)carbonyl)-N-(1-methyl-3-phenylpropyl)amino)propanoic acid HPLC measurement condition: A HPLC retention time: 3.89 minutes; MASS data (ESI, Pos., 20V): 565 (M+H)$^+$.

EXAMPLE 4(1047)

3-(N-((2-(2-((4-methylbenzylamino)carbonyl)phenyl)phenyl)carbonyl)-N-(1-methyl-3-phenylpropyl)amino)propanoic acid HPLC measurement condition: A HPLC retention time: 4.00 minutes; MASS data (ESI, Pos., 20V): 549 (M+H)$^+$.

EXAMPLE 4(1048)

3-(N-((2-(2-((N-methyl-N-benzylamino)carbonyl)phenyl)phenyl)carbonyl)-N-(1-methyl-3-phenylpropyl)amino)propanoic acid HPLC measurement condition: A HPLC retention time: 3.99 minutes; MASS data (ESI, Pos., 20V): 549 (M+H)$^+$.

EXAMPLE 4(1049)

3-(N-((2-(2-((3-fluorobenzylamino)carbonyl)phenyl)phenyl)carbonyl)-N-(1-methyl-3-phenylpropyl)amino)propanoic acid HPLC measurement condition: A HPLC retention time: 3.97 minutes; MASS data (ESI, Pos., 20V): 553 (M+H)$^+$.

EXAMPLE 4(1050)

3-(N-((2-(2-((4-fluorobenzylamino)carbonyl)phenyl)phenyl)carbonyl)-N-(1-methyl-3-phenylpropyl)amino)propanoic acid HPLC measurement condition: A HPLC retention time: 3.95 minutes; MASS data (ESI, Pos., 20V): 553 (M+H)$^+$.

EXAMPLE 4(1051)

3-(N-((2-(2-((allylamino)carbonyl)phenyl)phenyl)carbonyl)-N-(1-methyl-3-phenylpropyl)amino)propanoic acid HPLC measurement condition: A HPLC retention time: 3.78 minutes; MASS data (ESI, Pos., 20V): 485 (M+H)$^+$.

EXAMPLE 4(1052)

3-(N-((2-(2-((2,6-difluorobenzylamino)carbonyl)phenyl)phenyl)carbonyl)-N-(1-methyl-3-phenylpropyl)amino)propanoic acid HPLC measurement condition: A HPLC retention time: 3.93 minutes; MASS data (ESI, Pos., 20V): 571 (M+H)$^+$.

EXAMPLE 4(1053)

3-(N-((2-(2-((2-thienylmethylamino)carbonyl)phenyl)phenyl)carbonyl)-N-(1-methyl-3-phenylpropyl)amino)propanoic acid HPLC measurement condition: A HPLC retention time: 3.89 minutes; MASS data (ESI, Pos., 20V): 541 (M+H)$^+$.

EXAMPLE 4(1054)

3-(N-((2-(2-((2-methoxybenzylamino)carbonyl)phenyl)phenyl)carbonyl)-N-(2-(2-methoxyphenyl)ethyl)amino)propanoic acid HPLC measurement condition: A HPLC retention time: 3.86 minutes; MASS data (ESI, Pos., 20V): 567 (M+H)$^+$.

EXAMPLE 4(1055)

3-(N-((2-(2-((3-methoxybenzylamino)carbonyl)phenyl)phenyl)carbonyl)-N-(2-(2-methoxyphenyl)ethyl)amino)propanoic acid HPLC measurement condition: A HPLC retention time: 3.84 minutes; MASS data (ESI, Pos., 20V): 567 (M+H)$^+$.

EXAMPLE 4(1056)

3-(N-((2-(2-((4-methoxybenzylamino)carbonyl)phenyl)phenyl)carbonyl)-N-(2-(2-methoxyphenyl)ethyl)amino)propanoic acid HPLC measurement condition: A HPLC retention time: 3.82 minutes; MASS data (ESI, Pos., 20V): 567 (M+H)$^+$.

EXAMPLE 4(1057)

3-(N-((2-(2-((4-methylbenzylamino)carbonyl)phenyl)phenyl)carbonyl)-N-(2-(2-methoxyphenyl)ethyl)amino)propanoic acid HPLC measurement condition: A HPLC retention time: 3.93 minutes; MASS data (ESI, Pos., 20V): 551 (M+H)$^+$.

EXAMPLE 4(1058)

3-(N-((2-(2-((N-methyl-N-benzylamino)carbonyl)phenyl)phenyl)carbonyl)-N-(2-(2-methoxyphenyl)ethyl)amino)propanoic acid HPLC measurement condition: A HPLC retention time: 3.86 minutes; MASS data (ESI, Pos., 20V): 551 (M+H)$^+$, 537.

EXAMPLE 4(1059)

3-(N-((2-(2-((2-fluorobenzylamino)carbonyl)phenyl)phenyl)carbonyl)-N-(2-(2-methoxyphenyl)ethyl)amino)propanoic acid HPLC measurement condition: A HPLC retention time: 3.86 minutes; MASS data (ESI, Pos., 20V): 555 (M+H)$^+$.

EXAMPLE 4(1060)

3-(N-((2-(2-((3-fluorobenzylamino)carbonyl)phenyl)phenyl)carbonyl)-N-(2-(2-methoxyphenyl)ethyl)amino)propanoic acid HPLC measurement condition: A HPLC retention time: 3.89 minutes; MASS data (ESI, Pos., 20V): 555 (M+H)$^+$.

EXAMPLE 4(1061)

3-(N-((2-(2-((allylamino)carbonyl)phenyl)phenyl)carbonyl)-N-(2-(2-methoxyphenyl)ethyl)amino)propanoic acid HPLC measurement condition: A HPLC retention time: 3.69 minutes; MASS data (ESI, Pos., 20V): 487 (M+H)$^+$.

EXAMPLE 4(1062)

3-(N-((2-(2-((3,5-difluorobenzylamino)carbonyl)phenyl)phenyl)carbonyl)-N-(2-(2-methoxyphenyl)ethyl)amino)propanoic acid HPLC measurement condition: A HPLC retention time: 3.95 minutes; MASS data (ESI, Pos., 20V): 573 (M+H)$^+$.

EXAMPLE 4(1063)

3-(N-((2-(2-((2-phenylethylamino)carbonyl)phenyl)phenyl)carbonyl)-N-(2-(2-methoxyphenyl)ethyl)amino)propanoic acid HPLC measurement condition: A HPLC retention time: 3.91 minutes; MASS data (ESI, Pos., 20V): 551 (M+H)$^+$.

EXAMPLE 4(1064)

3-(N-((2-(2-((2-furylmethylamino)carbonyl)phenyl)phenyl)carbonyl)-N-(2-(pyridin-4-yl)ethyl)amino)propanoic acid HPLC measurement condition: A HPLC retention time: 3.01 minutes; MASS data (ESI, Pos., 20V): 498 (M+H)$^+$.

EXAMPLE 4(1065)

3-(N-((2-(2-((1-indaneamino)carbonyl)phenyl)phenyl)carbonyl)-N-(2-(pyridin-4-yl)ethyl)amino)propanoic acid HPLC measurement condition: A HPLC retention time: 3.18 minutes; MASS data (ESI, Pos., 20V): 534 (M+H)$^+$, 418.

EXAMPLE 4(1066)

3-(N-((2-(2-((pyridin-3-ylmethylamino)carbonyl)phenyl)phenyl)carbonyl)-N-(2-(pyridin-4-yl)ethyl)amino)propanoic acid HPLC measurement condition: A HPLC retention time: 2.70 minutes; MASS data (ESI, Pos., 20V): 509 (M+H)$^+$, 255.

EXAMPLE 4(1067)

3-(N-((2-(2-((1,2,3,4-tetrahydroisoquinolin-2-yl)carbonyl)phenyl)phenyl)carbonyl)-N-(2-(pyridin-4-yl)ethyl)amino)propanoic acid HPLC measurement condition: A HPLC retention time: 3.20 minutes; MASS data (ESI, Pos., 20V): 534 (M+H)$^+$.

EXAMPLE 4(1068)

3-(N-((2-(2-((2-methoxybenzylamino)carbonyl)phenyl)phenyl)carbonyl)-N-(2-(pyridin-4-yl)ethyl)amino)propanoic acid HPLC measurement condition: A HPLC retention time: 3.12 minutes; MASS data (ESI, Pos., 20V): 538 (M+H)$^+$.

EXAMPLE 4(1069)

3-(N-((2-(2-((3-methoxybenzylamino)carbonyl)phenyl)phenyl)carbonyl)-N-(2-(pyridin-4-yl)ethyl)amino)propanoic acid HPLC measurement condition: A HPLC retention time: 3.11 minutes; MASS data (ESI, Pos., 20V): 538 (M+H)$^+$.

EXAMPLE 4(1070)

3-(N-((2-(2-((4-methoxybenzylamino)carbonyl)phenyl)phenyl)carbonyl)-N-(2-(pyridin-4-yl)ethyl)amino)propanoic acid HPLC measurement condition: A HPLC retention time: 3.09 minutes; MASS data (ESI, Pos., 20V): 538 (M+H)$^+$.

EXAMPLE 4(1071)

3-(N-((2-(2-((4-methylbenzylamino)carbonyl)phenyl)phenyl)carbonyl)-N-(2-(pyridin-4-yl)ethyl)amino)propanoic acid HPLC measurement condition: A HPLC retention time: 3.16 minutes; MASS data (ESI, Pos., 20V): 522 (M+H)$^+$.

EXAMPLE 4(1072)

3-(N-((2-(2-((N-methyl-N-benzylamino)carbonyl)phenyl)phenyl)carbonyl)-N-(2-(pyridin-4-yl)ethyl)amino)propanoic acid HPLC measurement condition: A HPLC retention time: 3.16 minutes; MASS data (ESI, Pos., 20V): 522 (M+H)$^+$.

EXAMPLE 4(1073)

3-(N-((2-(2-((allylamino)carbonyl)phenyl)phenyl)carbonyl)-N-(2-(pyridin-4-yl)ethyl)amino)propanoic acid HPLC measurement condition: A HPLC retention time: 2.92 minutes; MASS data (ESI, Pos., 20V): 915 (2M+H)$^+$, 458 (M+H)$^+$.

EXAMPLE 4(1074)

3-(N-((2-(2-((2,6-difluorobenzylamino)carbonyl)phenyl)phenyl)carbonyl)-N-(2-(pyridin-4-yl)ethyl)amino)propanoic acid HPLC measurement condition: A HPLC retention time: 3.09 minutes; MASS data (ESI, Pos., 20V): 544 (M+H)$^+$, 272.

EXAMPLE 4(1075)

3-(N-((2-(2-((3,5-difluorobenzylamino)carbonyl)phenyl)phenyl)carbonyl)-N-(2-(pyridin-4-yl)ethyl)amino)propanoic acid HPLC measurement condition: A HPLC retention time: 3.18 minutes; MASS data (ESI, Pos., 20V): 544 (M+H)$^+$.

EXAMPLE 4(1076)

3-(N-((2-(2-((2-phenylethylamino)carbonyl)phenyl)phenyl)carbonyl)-N-(2-(pyridin-4-yl)ethyl)amino)propanoic acid HPLC measurement condition: A HPLC retention time: 3.14 minutes; MASS data (ESI, Pos., 20V): 522 (M+H)$^+$, 261.

EXAMPLE 4(1077)

3-(N-((2-(2-((1-indaneamino)carbonyl)phenyl)phenyl)carbonyl)-N-(2-phenylethyl)amino)propanoic acid HPLC measurement condition: A HPLC retention time: 3.89 minutes; MASS data (ESI, Pos., 20V): 533 (M+H)$^+$.

EXAMPLE 4(1078)

3-(N-((2-(2-((pyridin-3-ylmethylamino)carbonyl)phenyl)phenyl)carbonyl)-N-(2-phenylethyl)amino)propanoic acid HPLC measurement condition: A HPLC retention time: 3.18 minutes; MASS data (ESI, Pos., 20V): 508 (M+H)$^+$.

EXAMPLE 4(1079)

3-(N-((2-(2-((1,2,3,4-tetrahydroisoquinolin-2-yl)carbonyl)phenyl)phenyl)carbonyl)-N-(2-phenylethyl)amino)propanoic acid HPLC measurement condition: A HPLC retention time: 3.86 minutes; MASS data (ESI, Pos., 20V): 533 (M+H)$^+$.

EXAMPLE 4(1080)

3-(N-((2-(2-((2-methoxybenzylamino)carbonyl)phenyl)phenyl)carbonyl)-N-(2-phenylethyl)amino)propanoic acid HPLC measurement condition: A HPLC retention time: 3.84 minutes; MASS data (ESI, Pos., 20V): 537 (M+H)$^+$.

EXAMPLE 4(1081)

3-(N-((2-(2-((3-methoxybenzylamino)carbonyl)phenyl)phenyl)carbonyl)-N-(2-phenylethyl)amino)propanoic acid HPLC measurement condition: A HPLC retention time: 3.80 minutes; MASS data (ESI, Pos., 20V): 537 (M+H)$^+$.

EXAMPLE 4(1082)

3-(N-((2-(2-((4-methoxybenzylamino)carbonyl)phenyl)phenyl)carbonyl)-N-(2-phenylethyl)amino)propanoic acid HPLC measurement condition: A HPLC retention time: 3.78 minutes; MASS data (ESI, Pos., 20V): 537 (M+H)$^+$.

EXAMPLE 4(1083)

3-(N-((2-(2-((4-methylbenzylamino)carbonyl)phenyl)phenyl)carbonyl)-N-(2-phenylethyl)amino)propanoic acid HPLC measurement condition: A HPLC retention time: 3.91 minutes; MASS data (ESI, Pos., 20V): 521 (M+H)$^+$.

EXAMPLE 4(1084)

3-(N-((2-(2-((N-methyl-N-benzylamino)carbonyl)phenyl)phenylcarbonyl)-N-(2-phenylethyl)amino)propanoic acid HPLC measurement condition: A HPLC retention time: 3.84 minutes; MASS data (ESI, Pos., 20V): 521 (M+H)$^+$.

EXAMPLE 4(1085)

3-(N-((2-(2-((3-fluorobenzylamino)carbonyl)phenyl)phenyl)carbonyl)-N-(2-phenylethyl)amino)propanoic acid HPLC measurement condition: A HPLC retention time: 3.86 minutes; MASS data (ESI, Pos., 20V): 525 (M+H)$^+$.

EXAMPLE 4(1086)

3-(N-((2-(2-((4-fluorobenzylamino)carbonyl)phenyl)phenyl)carbonyl)-N-(2-phenylethyl)amino)propanoic acid HPLC measurement condition: A HPLC retention time: 3.84 minutes; MASS data (ESI, Pos., 20V): 525 (M+H)$^+$.

EXAMPLE 4(1087)

3-(N-((2-(2-((allylamino)carbonyl)phenyl)phenyl)carbonyl)-N-(2-phenylethyl)amino)propanoic acid HPLC measurement condition: A HPLC retention time: 3.62 minutes; MASS data (ESI, Pos., 20V): 457 (M+H)$^+$.

EXAMPLE 4(1088)

3-(N-((2-(2-((2,6-difluorobenzylamino)carbonyl)phenyl)phenyl)carbonyl)-N-(2-phenylethyl)amino)propanoic acid HPLC measurement condition: A HPLC retention time: 3.80 minutes; MASS data (ESI, Pos., 20V): 543 (M+H)$^+$.

EXAMPLE 4(1089)

3-(N-((2-(2-((2-thienylmethylamino)carbonyl)phenyl)phenyl)carbonyl)-N-(2-phenylethyl)amino)propanoic acid HPLC measurement condition: A HPLC retention time: 3.78 minutes; MASS data (ESI, Pos., 20V): 513 (M+H)$^+$.

EXAMPLE 4(1090)

3-(N-((2-(2-((2-methoxybenzylamino)carbonyl)phenyl)phenyl)carbonyl)-N-(2-(4-methoxyphenyl)ethyl)amino)propanoic acid HPLC measurement condition: A HPLC retention time: 3.80 minutes; MASS data (ESI, Pos., 20V): 567 (M+H)$^+$.

EXAMPLE 4(1091)

3-(N-((2-(2-((3-methoxybenzylamino)carbonyl)phenyl)phenyl)carbonyl)-N-(2-(4-methoxyphenyl)ethyl)amino)propanoic acid HPLC measurement condition: A HPLC retention time: 3.77 minutes; MASS data (ESI, Pos., 20V): 567 (M+H)$^+$.

EXAMPLE 4(1092)

3-(N-((2-(2-((4-methoxybenzylamino)carbonyl)phenyl)phenyl)carbonyl)-N-(2-(4-methoxyphenyl)ethyl)amino)propanoic acid HPLC measurement condition: A HPLC retention time: 3.75 minutes; MASS data (ESI, Pos., 20V): 567 (M+H)$^+$.

EXAMPLE 4(1093)

3-(N-((2-(2-((4-methylbenzylamino)carbonyl)phenyl)phenyl)carbonyl)-N-(2-(4-methoxyphenyl)ethyl)amino)propanoic acid HPLC measurement condition: A HPLC retention time: 3.86 minutes; MASS data (ESI, Pos., 20V): 551 (M+H)$^+$.

EXAMPLE 4(1094)

3-(N-((2-(2-((N-methyl-N-benzylamino)carbonyl)phenyl)phenyl)carbonyl)-N-(2-(4-methoxyphenyl)ethyl)amino)propanoic acid HPLC measurement condition: A HPLC retention time: 3.80 minutes; MASS data (ESI, Pos., 20V): 551 (M+H)$^+$.

EXAMPLE 4(1095)

3-(N-((2-(2-((3-fluorobenzylamino)carbonyl)phenyl)phenyl)carbonyl)-N-(2-(4-methoxyphenyl)ethyl)amino)propanoic acid HPLC measurement condition: A HPLC retention time: 3.80 minutes; MASS data (ESI, Pos., 20V): 555 (M+H)$^+$.

EXAMPLE 4(1096)

3-(N-((2-(2-((allylamino)carbonyl)phenyl)phenyl)carbonyl)-N-(2-(4-methoxyphenyl)ethyl)amino)propanoic acid HPLC measurement condition: A HPLC retention time: 3.60 minutes; MASS data (ESI, Pos., 20V): 487 (M+H)$^+$.

EXAMPLE 4(1097)

3-(N-((2-(2-((1-indaneamino)carbonyl)phenyl)phenyl)carbonyl)-N-(2-(2,4-dichlorophenyl)ethyl)amino)propanoic acid HPLC measurement condition: A HPLC retention time: 4.15 minutes; MASS data (ESI, Pos., 20V): 601 (M+H)$^+$.

EXAMPLE 4(1098)

3-(N-((2-(2-((pyridin-3-ylmethylamino)carbonyl)phenyl)phenyl)carbonyl)-N-(2-(2,4-dichlorophenyl)ethyl)amino)propanoic acid HPLC measurement condition: A HPLC retention time: 3.34 minutes; MASS data (ESI, Pos., 20V): 576 (M+H)$^+$.

EXAMPLE 4(1099)

3-(N-((2-(2-((1,2,3,4-tetrahydroisoquinolin-2-yl)carbonyl)phenyl)phenyl)carbonyl)-N-(2-(2,4-dichlorophenyl)ethyl)amino)propanoic acid HPLC measurement condition: A HPLC retention time: 4.10 minutes; MASS data (ESI, Pos., 20V): 601 (M+H)$^+$.

EXAMPLE 4(1100)

3-(N-((2-(2-((2-methoxybenzylamino)carbonyl)phenyl)phenyl)carbonyl)-N-(2-(2,4-dichlorophenyl)ethyl)amino)propanoic acid HPLC measurement condition: A HPLC retention time: 4.08 minutes; MASS data (ESI, Pos., 20V): 605 (M+H)$^+$.

EXAMPLE 4(1101)

3-(N-((2-(2-((3-methoxybenzylamino)carbonyl)phenyl)phenyl)carbonyl)-N-(2-(2,4-dichlorophenyl)ethyl)amino)propanoic acid HPLC measurement condition: A HPLC retention time: 4.06 minutes; MASS data (ESI, Pos., 20V): 605 (M+H)$^+$.

EXAMPLE 4(1102)

3-(N-((2-(2-((4-methylbenzylamino)carbonyl)phenyl)phenyl)carbonyl)-N-(2-(2,4-dichlorophenyl)ethyl)amino)propanoic acid HPLC measurement condition: A HPLC retention time: 4.13 minutes; MASS data (ESI, Pos., 20V): 589 (M+H)$^+$.

EXAMPLE 4(1103)

3-(N-((2-(2-((N-methyl-N-benzylamino)carbonyl)phenyl)phenyl)carbonyl)-N-(2-(2,4-dichlorophenyl)ethyl)amino)propanoic acid HPLC measurement condition: A HPLC retention time: 4.08 minutes; MASS data (ESI, Pos., 20V): 589 (M+H)$^+$.

EXAMPLE 4(1104)

3-(N-((2-(2-((3-fluorobenzylamino)carbonyl)phenyl)phenyl)carbonyl)-N-(2-(2,4-dichlorophenyl)ethyl)amino)propanoic acid HPLC measurement condition: A HPLC retention time: 4.06 minutes; MASS data (ESI, Pos., 20V): 593 (M+H)$^+$.

EXAMPLE 4(1105)

3-(N-((2-(2-((allylamino)carbonyl)phenyl)phenyl)carbonyl)-N-(2-(2,4-dichlorophenyl)ethyl)amino)propanoic acid HPLC measurement condition: A HPLC retention time: 3.88 minutes; MASS data (ESI, Pos., 20V): 525 (M+H)$^+$.

EXAMPLE 4(1106)

3-(N-((2-(2-((2,6-difluorobenzylamino)carbonyl)phenyl)phenyl)carbonyl)-N-(2-(2,4-dichlorophenyl)ethyl)amino)propanoic acid HPLC measurement condition: A HPLC retention time: 4.04 minutes; MASS data (ESI, Pos., 20V): 611 (M+H)$^+$.

EXAMPLE 4(1107)

3-(N-((2-(2-((2-thienylmethylamino)carbonyl)phenyl)phenyl)carbonyl)-N-(2-(2,4-dichlorophenyl)ethyl)amino)propanoic acid HPLC measurement condition: A HPLC retention time: 4.04 minutes; MASS data (ESI, Pos., 20V): 581 (M+H)$^+$.

EXAMPLE 4(1108)

3-(N-((2-(2-((2-furylmethylamino)carbonyl)phenyl)phenyl)carbonyl)-N-(2-(4-ethoxyphenyl)ethyl)amino)propanoic acid HPLC measurement condition: A HPLC retention time: 3.80 minutes; MASS data (ESI, Pos., 20V): 541 (M+H)$^+$.

EXAMPLE 4(1109)

3-(N-((2-(2-((1-indaneamino)carbonyl)phenyl)phenyl)carbonyl)-N-(2-(4-ethoxyphenyl)ethyl)amino)propanoic acid HPLC measurement condition: A HPLC retention time: 3.99 minutes; MASS data (ESI, Pos., 20V): 577 (M+H)$^+$.

EXAMPLE 4(1110)

3-(N-((2-(2-((1,2,3,4-tetrahydroisoquinolin-2-yl)carbonyl)phenyl)phenyl)carbonyl)-N-(2-(4-ethoxyphenyl)ethyl)amino)propanoic acid HPLC measurement condition: A HPLC retention time: 3.93 minutes; MASS data (ESI, Pos., 20V): 577 (M+H)$^+$.

EXAMPLE 4(1111)

3-(N-((2-(2-((2-methoxybenzylamino)carbonyl)phenyl)phenyl)carbonyl)-N-(2-(4-ethoxyphenyl)ethyl)amino)propanoic acid HPLC measurement condition: A HPLC retention time: 3.91 minutes; MASS data (ESI, Pos., 20V): 581 (M+H)$^+$.

EXAMPLE 4(1112)

3-(N-((2-(2-((3-methoxybenzylamino)carbonyl)phenyl)phenyl)carbonyl)-N-(2-(4-ethoxyphenyl)ethyl)amino)propanoic acid HPLC measurement condition: A HPLC retention time: 3.87 minutes; MASS data (ESI, Pos., 20V): 581 (M+H)$^+$.

EXAMPLE 4(1113)

3-(N-((2-(2-((4-methylbenzylamino)carbonyl)phenyl)phenyl)carbonyl)-N-(2-(4-ethoxyphenyl)ethyl)amino)propanoic acid HPLC measurement condition: A HPLC retention time: 3.99 minutes; MASS data (ESI, Pos., 20V): 565 (M+H)$^+$.

EXAMPLE 4(1114)

3-(N-((2-(2-((N-methyl-N-benzylamino)carbonyl)phenyl)phenyl)carbonyl)-N-(2-(4-ethoxyphenyl)ethyl)amino)propanoic acid HPLC measurement condition: A HPLC retention time: 3.91 minutes; MASS data (ESI, Pos., 20V): 565 (M+H)$^+$.

EXAMPLE 4(1115)

3-(N-((2-(2-((2-fluorobenzylamino)carbonyl)phenyl)phenyl)carbonyl)-N-(2-(4-ethoxyphenyl)ethyl)amino)propanoic acid HPLC measurement condition: A HPLC retention time: 3.91 minutes; MASS data (ESI, Pos., 20V): 569 (M+H)$^+$.

EXAMPLE 4(1116)

3-(N-((2-(2-((3-fluorobenzylamino)carbonyl)phenyl)phenyl)carbonyl)-N-(2-(4-ethoxyphenyl)ethyl)amino)propanoic acid HPLC measurement condition: A HPLC retention time: 3.93 minutes; MASS data (ESI, Pos., 20V): 569 (M+H)$^+$.

EXAMPLE 4(1117)

3-(N-((2-(2-((4-fluorobenzylamino)carbonyl)phenyl)phenyl)carbonyl)-N-(2-(4-ethoxyphenyl)ethyl)amino)propanoic acid HPLC measurement condition: A HPLC retention time: 3.89 minutes; MASS data (ESI, Pos., 20V): 569 (M+H)$^+$.

EXAMPLE 4(1118)

3-(N-((2-(2-((allylamino)carbonyl)phenyl)phenyl)carbonyl)-N-(2-(4-ethoxyphenyl)ethyl)amino)propanoic acid HPLC measurement condition: A HPLC retention time: 3.73 minutes; MASS data (ESI, Pos., 20V): 501 (M+H)$^+$.

EXAMPLE 4(1119)

3-(N-((2-(2-((2,6-difluorobenzylamino)carbonyl)phenyl)phenyl)carbonyl)-N-(2-(4-ethoxyphenyl)ethyl)amino)propanoic acid HPLC measurement condition: A HPLC retention time: 3.88 minutes; MASS data (ESI, Pos., 20V): 587 (M+H)$^+$.

EXAMPLE 4(1120)

3-(N-((2-(2-((2-thienylmethylamino)carbonyl)phenyl)phenyl)carbonyl)-N-(2-(4-ethoxyphenyl)ethyl)amino)propanoic acid HPLC measurement condition: A HPLC retention time: 3.86 minutes; MASS data (ESI, Pos., 20V): 557 (M+H)$^+$.

EXAMPLE 4(1121)

3-(N-((2-(2-((1-indaneamino)carbonyl)phenyl)phenyl)carbonyl)-N-(3-phenylpropyl)amino)propanoic acid HPLC measurement condition: A HPLC retention time: 3.99 minutes; MASS data (ESI, Pos., 20V): 547 (M+H)$^+$.

EXAMPLE 4(1122)

3-(N-((2-(2-((pyridin-3-ylmethylamino)carbonyl)phenyl)phenyl)carbonyl)-N-(3-phenylpropyl)amino)propanoic acid HPLC measurement condition: A HPLC retention time: 3.25 minutes; MASS data (ESI, Pos., 20V): 522 (M+H)$^+$.

EXAMPLE 4(1123)

3-(N-((2-(2-((1,2,3,4-tetrahydroisoquinolin-2-yl)carbonyl)phenyl)phenyl)carbonyl)-N-(3-phenylpropyl)amino)propanoic acid HPLC measurement condition: A HPLC retention time: 3.95 minutes; MASS data (ESI, Pos., 20V): 547 (M+H)$^+$.

EXAMPLE 4(1124)

3-(N-((2-(2-((benzylamino)carbonyl)phenyl)phenyl)carbonyl)-N-(3-phenylpropyl)amino)propanoic acid HPLC measurement condition: A HPLC retention time: 3.89 minutes; MASS data (ESI, Pos., 20V): 521 (M+H)$^+$.

EXAMPLE 4(1125)

3-(N-((2-(2-((2-methoxybenzylamino)carbonyl)phenyl)phenyl)carbonyl)-N-(3-phenylpropyl)amino)propanoic acid HPLC measurement condition: A HPLC retention time: 3.89 minutes; MASS data (ESI, Pos., 20V): 551 (M+H)$^+$.

EXAMPLE 4(1126)

3-(N-((2-(2-((3-methoxybenzylamino)carbonyl)phenyl)phenyl)carbonyl)-N-(3-phenylpropyl)amino)propanoic acid HPLC measurement condition: A HPLC retention time: 3.88 minutes; MASS data (ESI, Pos., 20V): 551 (M+H)$^+$.

EXAMPLE 4(1127)

3-(N-((2-(2-((4-methoxybenzylamino)carbonyl)phenyl)phenyl)carbonyl)-N-(3-phenylpropyl)amino)propanoic acid HPLC measurement condition: A HPLC retention time: 3.86 minutes; MASS data (ESI, Pos., 20V): 551 (M+H)$^+$.

EXAMPLE 4(1128)

3-(N-((2-(2-((4-methylbenzylamino)carbonyl)phenyl)phenyl)carbonyl)-N-(3-phenylpropyl)amino)propanoic acid HPLC measurement condition: A HPLC retention time: 3.99 minutes; MASS data (ESI, Pos., 20V): 535 (M+H)$^+$.

EXAMPLE 4(1129)

3-(N-((2-(2-((N-methyl-N-benzylamino)carbonyl)phenyl)phenyl)carbonyl)-N-(3-phenylpropyl)amino)propanoic acid HPLC measurement condition: A HPLC retention time: 3.93 minutes; MASS data (ESI, Pos., 20V): 535 (M+H)$^+$.

EXAMPLE 4(1130)

3-(N-((2-(2-((2-fluorobenzylamino)carbonyl)phenyl)phenyl)carbonyl)-N-(3-phenylpropyl)amino)propanoic acid HPLC measurement condition: A HPLC retention time: 3.89 minutes; MASS data (ESI, Pos., 20V): 539 (M+H)$^+$.

EXAMPLE 4(1131)

3-(N-((2-(2-((3-fluorobenzylamino)carbonyl)phenyl)phenyl)carbonyl)-N-(3-phenylpropyl)amino)propanoic acid HPLC measurement condition: A HPLC retention time: 3.93 minutes; MASS data (ESI, Pos., 20V): 539 (M+H)$^+$.

EXAMPLE 4(1132)

3-(N-((2-(2-((4-fluorobenzylamino)carbonyl)phenyl)phenyl)carbonyl)-N-(3-phenylpropyl)amino)propanoic acid HPLC measurement condition: A HPLC retention time: 3.91 minutes; MASS data (ESI, Pos., 20V): 539 (M+H)$^+$.

EXAMPLE 4(1133)

3-(N-((2-(2-((allylamino)carbonyl)phenyl)phenyl)carbonyl)-N-(3-phenylpropyl)amino)propanoic acid HPLC measurement condition: A HPLC retention time: 3.73 minutes; MASS data (ESI, Pos., 20V): 963 (2M+Na)$^+$, 471 (M+H)$^+$.

EXAMPLE 4(1134)

3-(N-((2-(2-((2,6-difluorobenzylamino)carbonyl)phenyl)phenyl)carbonyl)-N-(3-phenylpropyl)amino)propanoic acid HPLC measurement condition: A HPLC retention time: 3.88 minutes; MASS data (ESI, Pos., 20V): 557 (M+H)$^+$.

EXAMPLE 4(1135)

3-(N-((2-(2-((2-thienylmethylamino)carbonyl)phenyl)phenyl)carbonyl)-N-(3-phenylpropyl)amino)propanoic acid HPLC measurement condition: A HPLC retention time: 3.86 minutes; MASS data (ESI, Pos., 20V): 527 (M+H)$^+$.

EXAMPLE 4(1136)

3-(N-((2-(2-((3,5-difluorobenzylamino)carbonyl)phenyl)phenyl)carbonyl)-N-(3-phenylpropyl)amino)propanoic acid HPLC measurement condition: A HPLC retention time: 3.99 minutes; MASS data (ESI, Pos., 20V): 557 (M+H)$^+$.

EXAMPLE 4(1137)

3-(N-((2-(2-((2-phenylethylamino)carbonyl)phenyl)phenyl)carbonyl)-N-(3-phenylpropyl)amino)propanoic acid HPLC measurement condition: A HPLC retention time: 3.95 minutes; MASS data (ESI, Pos., 20V): 535 (M+H)$^+$.

EXAMPLE 4(1138)

3-(N-((2-(2-((1-indaneamino)carbonyl)phenyl)phenyl)carbonyl)-N-(benzyl)amino)propanoic acid HPLC measurement condition: A HPLC retention time: 3.86 minutes; MASS data (ESI, Pos., 20V): 519 (M+H)$^+$.

EXAMPLE 4(1139)

3-(N-((2-(2-((pyridin-2-ylmethylamino)carbonyl)phenyl)phenyl)carbonyl)-N-(benzyl)amino)propanoic acid HPLC measurement condition: A HPLC retention time: 3.18 minutes; MASS data (ESI, Pos., 20V): 987 (2M+H)$^+$, 494 (M+H)$^+$.

EXAMPLE 4(1140)

3-(N-((2-(2-((pyridin-3-ylmethylamino)carbonyl)phenyl)phenyl)carbonyl)-N-(benzyl)amino)propanoic acid HPLC measurement condition: A HPLC retention time: 3.12 minutes; MASS data (ESI, Pos., 20V): 987 (2M+H)$^+$, 494 (M+H)$^+$.

EXAMPLE 4(1141)

3-(N-((2-(2-((1,2,3,4-tetrahydroisoquinolin-2-yl)carbonyl)phenyl)phenyl)carbonyl)-N-(benzyl)amino)propanoic acid HPLC measurement condition: A HPLC retention time: 3.82 minutes; MASS data (ESI, Pos., 20V): 519 (M+H)$^+$.

EXAMPLE 4(1142)

3-(N-((2-(2-((benzylamino)carbonyl)phenyl)phenyl)carbonyl)-N-(benzyl)amino)propanoic acid HPLC measurement condition: A HPLC retention time: 3.77 minutes; MASS data (ESI, Pos., 20V): 985 (2M+H)$^+$, 493 (M+H)$^+$.

EXAMPLE 4(1143)

3-(N-((2-(2-((2-methoxybenzylamino)carbonyl)phenyl)phenyl)carbonyl)-N-(benzyl)amino)propanoic acid HPLC measurement condition: A HPLC retention time: 3.77 minutes; MASS data (ESI, Pos., 20V): 523 (M+H)$^+$.

EXAMPLE 4(1144)

3-(N-((2-(2-((3-methoxybenzylamino)carbonyl)phenyl)phenyl)carbonyl)-N-(benzyl)amino)propanoic acid HPLC measurement condition: A HPLC retention time: 3.73 minutes; MASS data (ESI, Pos., 20V): 523 (M+H)$^+$.

EXAMPLE 4(1145)

3-(N-((2-(2-((4-methoxybenzylamino)carbonyl)phenyl)phenyl)carbonyl)-N-(benzyl)amino)propanoic acid HPLC measurement condition: A HPLC retention time: 3.73 minutes; MASS data (ESI, Pos., 20V): 523 (M+H)$^+$.

EXAMPLE 4(1146)

3-(N-((2-(2-((4-methylbenzylamino)carbonyl)phenyl)phenyl)carbonyl)-N-(benzyl)amino)propanoic acid HPLC measurement condition: A HPLC retention time: 3.84 minutes; MASS data (ESI, Pos., 20V): 507 (M+H)$^+$.

EXAMPLE 4(1147)

3-(N-((2-(2-((N-methyl-N-benzylamino)carbonyl)phenyl)phenyl)carbonyl)-N-(benzyl)amino)propanoic acid HPLC measurement condition: A HPLC retention time: 3.78 minutes; MASS data (ESI, Pos., 20V): 507 (M+H)$^+$, 493.

EXAMPLE 4(1148)

3-(N-((2-(2-((2-fluorobenzylamino)carbonyl)phenyl)phenyl)carbonyl)-N-(benzyl)amino)propanoic acid HPLC measurement condition: A HPLC retention time: 3.77 minutes; MASS data (ESI, Pos., 20V): 511 (+H)$^+$.

EXAMPLE 4(1149)

3-(N-((2-(2-((3-fluorobenzylamino)carbonyl)phenyl)phenyl)carbonyl)-N-(benzyl)amino)propanoic acid HPLC measurement condition: A HPLC retention time: 3.78 minutes; MASS data (ESI, Pos., 20V): 511 (M+H)$^+$.

EXAMPLE 4(1150)

3-(N-((2-(2-((4-fluorobenzylamino)carbonyl)phenyl)phenyl)carbonyl)-N-(benzyl)amino)propanoic acid HPLC measurement condition: A HPLC retention time: 3.77 minutes; MASS data (ESI, Pos., 20V): 511 (M+H)$^+$.

EXAMPLE 4(1151)

3-(N-((2-(2-((allylamino)carbonyl)phenyl)phenyl)carbonyl)-N-(benzyl)amino)propanoic acid HPLC measurement condition: A HPLC retention time: 3.58 minutes; MASS data (ESI, Pos., 20V): 907 (2M+Na)$^+$, 443 (M+H)$^+$.

EXAMPLE 4(1152)

3-(N-((2-(2-((2,6-difluorobenzylamino)carbonyl)phenyl)phenyl)carbonyl)-N-(benzyl)amino)propanoic acid HPLC measurement condition: A HPLC retention time: 3.73 minutes; MASS data (ESI, Pos., 20V): 529 (M+H)$^+$.

EXAMPLE 4(1153)

3-(N-((2-(2-((2-thienylmethylamino)carbonyl)phenyl)phenyl)carbonyl)-N-(benzyl)amino)propanoic acid HPLC measurement condition: A HPLC retention time: 3.73 minutes; MASS data (ESI, Pos., 20V): 997 (2M+H)$^+$, 499 (M+H)$^+$.

EXAMPLE 4(1154)

3-(N-((2-(2-((3,5-difluorobenzylamino)carbonyl)phenyl)phenyl)carbonyl)-N-(benzyl)amino)propanoic acid HPLC measurement condition: A HPLC retention time: 3.86 minutes; MASS data (ESI, Pos., 20V): 529 (M+H)$^+$.

BIOLOGICAL EXAMPLE

The antagonistic activity of the compound against LPA receptor in the present invention was proved by experiment shown in the following. For example, the antagonistic activity of the compounds against EDG-2 was proved by experiment shown in the following.

A series of the procedure is based on the basic gene manipuration technique, that is gene overexpressed cells are prepared and a conventional method was utilized. In addition, the method for the evaluation of compounds in the present invention is improved on the usual method making enhancement of measurement precision and/or measurement sensitivity as follows. A detailed method of the experiment was shown in the following clause.

Evaluation of EDG-2 Antagonistic Activity by Monitoring the Change of Intracellular Calcium Ion Concentration Evaluation of EDG-2 antagonistic activity was carried out by using Chinese hamster ovary (CHO) cells which overexpressed human EDG-2 gene. Those cells were cultured with Ham's F12 medium (GIBCO BRL company No.11765-047) containing 10% FBS (fetal bovine serum), penicillin/streptomycin and blasticidin (5 µg/ml). At first in order to uptake Fura2-AM (Dojindo company No.348-05831) into the cells cells, cells were incubated for 60 minutes at 37 degrees in Fura2-AM (5 µM) solution [Ham's F12 medium containing 10% FBS, 20 mM HEPES buffer (pH 7.4) and 2.5 mM probenecid (Sigma company No.P-8761)]. Next, it was washed with Hanks solution containing HEPES buffer (20 mM, pH 7.4) and probenecid (2.5 mM) once, and immersed into the Hanks solution. Plates were set in fluorescent drug screening system (Hamamatsu photonics company, FDSS-2000) and intracellular calcium ion concentration was measured for 30 seconds with no stimulation and then solution of the compound of the present invention represented by formula (I) was added. Five minutes after adding thereto LPA (final concentration: 100 nM) was added, the increase of intracellular calcium ion concentrations before and after the addition of LPA (excitation wave length: 340 nM and 380 nM; fluorescent wave length: 500 nm) were measured every 3 seconds. The compound of the present invention represented by the formula (I) was dissolved in dimethyl sulfoxide (DMSO), and it was added so that the final concentration became 1 nM to 10 µM. 1-linolenoyl (18:3)-LPA was used as LPA. 1-linolenoyl (18:3)-LPA was synthesized from (18:3)-LPC (linolenoyl (18:3)-lysophosphatidylcholine) (Sedary company) by PLD (phospholipase D).

EDG-2 antagonistic activity was calculated as an inhibition rate (%) by the following equation, wherein the peak value of LPA (final concentration: 100 nM) in a well into which DMSO containing no test compound represented by the formula (I) was added was regarded as a control value (A), and in the cells treated with the test compound the difference (B) between the value before addition of the test compound and that after the addition was obtained and compared with the control value.

$$\text{Inhibition rate}(\%) = [(A-B)/A] \times 100$$

The IC$_{50}$ value was calculated as a concentration of the compound to be tested which showed 50% inhibition.

Experimental result for the compound of the present invention in Example 3 and Example 3(1) are shown in table 1.

TABLE 1

| Example number | IC$_{50}$ (µmol/L) |
|---|---|
| Example 3 | 0.41 |
| Example 3(1) | 0.78 |

FORMULATION EXAMPLE 1

The following components were admixed in a conventional manner, punched out to give 100 tablets each containing 50 mg of active ingredient.

| | |
|---|---|
| 3-(N-((2-(2-((4-chlorobenzylamino)carbonyl)phenyl)phenyl)carbonyl)-N-(2-(2,5-dimethoxyphenyl)ethyl)amino)propanoic acid | 5.0 g |
| carcium carboxymethyl cellulose (disintegrant) | 0.2 g |
| magnesium stearate (lubricant) | 0.1 g |
| microcrystalline cellulose | 4.7 g |

FORMULATION EXAMPLE 2

The following components were admixed in a conventional technique. The solution was sterilized in a conventional technique, filled in ampoules 5 ml each and freeze-dried over in a conventional technique to give 100 ampoules each containing 20 mg of active ingredient.

| | |
|---|---|
| 3-(N-((2-(2-((4-chlorobenzylamino)carbonyl)phenyl)phenyl)-carbonyl)-N-(2-(2,5-dimethoxyphenyl)ethyl)amino)propanoic acid | 2.0 g |
| mannitol | 20 g |
| distilled water | 1000 mL |

What is claimed is:

1. A β-alanine derivative represented by formula (I):

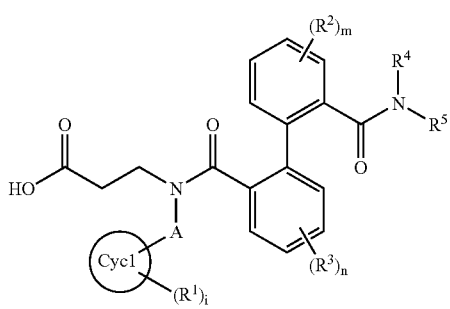

wherein A represents (1) C1~6 alkylene, (2) C2~6 alkenylene, or (3) C2~6 alkynylene wherein A may be substituted by 1-3 of C1~4 alkyl;

represents (1) C3~15 carbocyclic ring, or (2) 3-15 membered heterocyclic ring containing 1-4 of nitrogen atom(s), 1-2 of oxygen atom(s) and/or 1-2 of sulfur atom(s);

$R^1$ represents (1) C1~4 alkyl, (2) a halogen atom, (3) cyano, (4) trihalomethyl, (5) —$OR^6$, (6) —$SR^7$, (7) —$NR^8R^9$, (8) nitro, (9) —$COOR^{10}$, (10) —$CONR^{11}R^{12}$, (11) —$NR^{13}COR^{14}$, (12) —$SO_2NR^{15}R^{16}$, (13) —$NR^{17}SO_2R^{18}$, (14) —$S(O)R^{19}$ or (15) —$SO_2R^{20}$;

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ each independently represents (1) a hydrogen atom or (2) C1~4 alkyl;

$R^2$ and $R^3$ each independently represents (1) C1~4 alkyl, (2) C1~4 alkoxy or (3) a halogen atom;

$R^4$ and $R^5$ each independently represents (1) a hydrogen atom, (2) C1~4 alkyl, (3) C2~4 alkenyl, (4) C2~4 alkynyl, (5) C1~4 alkyl substituted by —$OR^{21}$, (6) C1~4 alkyl substituted by —$NR^{22}R^{23}$ or (7)

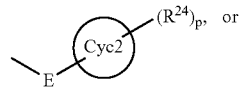

$R^4$ and $R^5$ taken together with nitrogen atom to which they are attached represents 3-15 membered mono-, bi- or tricyclic heterocyclic ring wherein the heterocyclic ring contains at least one nitrogen atom and may be substituted by C1~4 alkyl substituted by —$OR^{25}$;

$R^{21}$, $R^{22}$, $R^{23}$ and $R^{25}$ each independently represents (1) a hydrogen atom, (2) C1~4 alkyl (3) C2~6 acyl or (4) trihaloacetyl;

E represents (1) single bond, (2) C1~6 alkylene, (3) C2~6 alkenylene or (4) C2~6 alkynylene wherein E may be substituted by C1~4 alkyl substituted by 1-3 of group(s) selected from (1) C1~4 alkyl and (2) —$OR^{26}$;

$R^{26}$ represents (1) a hydrogen atom, (2) C1~4 alkyl, (3) C2~6 acyl or (4) trihaloacetyl;

Cyc2 represents (1) C3~15 carbocyclic ring or (2) 3-15 membered heterocyclic ring containing 1-4 of nitrogen atom(s), 1-2 of oxygen atom(s) and/or 1-2 of sulfur atom(s);

$R^{24}$ represents (1) C1~4 alkyl, (2) a halogen atom, (3) cyano, (4) trihalomethyl, (5) —$OR^{27}$, (6) —$SR^{28}$, (7) —$NR^{29}R^{30}$, (8) nitro, (9) —$COOR^{31}$, (10) —$CONR^{32}R^{33}$, (11) —$NR^{34}COR^{35}$, (12) —$SO_2NR^{36}R^{37}$, (13) —$R^{38}SO_2R^{39}$, (14) —$S(O)R^{40}$ or (15) —$SO_2R^{41}$;

$R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$ and $R^{41}$ each independently represents (1) a hydrogen atom or (2) C1~4 alkyl;

i represents 0 or an integer of 1~5;
m represents 0 or an integer of 1~4;
n represents 0 or an integer of 1~4;
p represents 0 or an integer of 1~5;

wherein when i is 2 or more, plural $R^1$ are the same or different; when m is 2 or more, plural $R^2$ are the same or different; when n is 2 or more, plural $R^3$ are the same or different; when p is 2 or more, plural $R^{24}$ are the same or different, or a prodrug thereof or a salt thereof;

wherein said prodrug is selected from the group consisting of the compound of formulas (IA), (IB) and (IC):

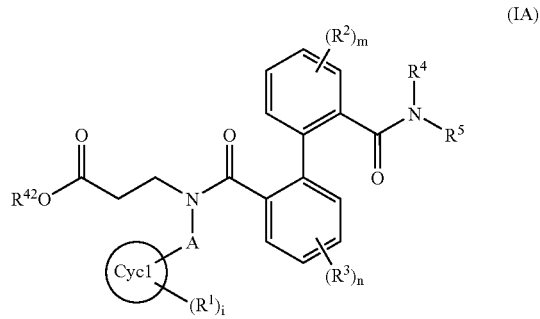

wherein $R^{42}$ represents (1) C1~8 alkyl or (2) C1~8 alkyl substituted by 1-2 of hydroxyl or amino;

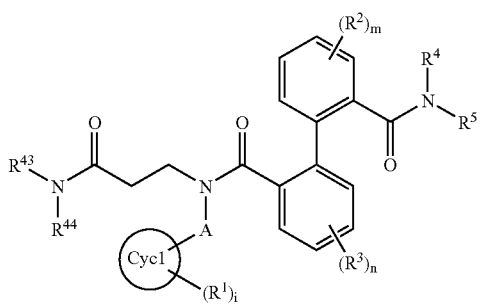

(IB)

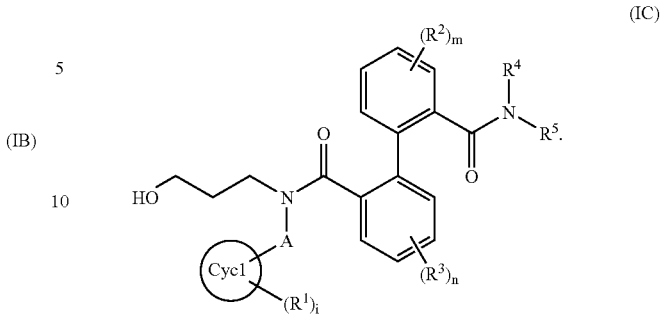

(IC)

wherein $R^{43}$ and $R^{44}$ each independently represents (1) a hydrogen atom, (2) C1~8 alkyl or (3) C1~8 alkyl substituted by 1-2 of hydroxyl or amino;

2. The prodrug according to claim 1, which is represented by the formula (IA).

3. The prodrug according to claim 1, which is represented by the formula (IB).

4. The prodrug according to claim 1, which is represented by the formula (IC).

5. A pharmaceutical composition comprising the compounds according to claim 1, or the prodrug thereof or the salt thereof and a pharmaceutically acceptable carrier.

* * * * *